United States Patent
Lei

(10) Patent No.: US 11,077,158 B2
(45) Date of Patent: Aug. 3, 2021

(54) OMEGA-3 FATTY ACID ENRICHMENT OF POULTRY PRODUCTS WITH DEFATTED MICROALGAE ANIMAL FEED

(71) Applicant: CORNELL UNIVERSITY, Ithaca, NY (US)

(72) Inventor: Xingen Lei, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 615 days.

(21) Appl. No.: 15/326,837

(22) PCT Filed: Jul. 17, 2015

(86) PCT No.: PCT/US2015/041000
§ 371 (c)(1),
(2) Date: Jan. 17, 2017

(87) PCT Pub. No.: WO2016/011410
PCT Pub. Date: Jan. 21, 2016

(65) Prior Publication Data
US 2017/0202894 A1    Jul. 20, 2017

Related U.S. Application Data

(60) Provisional application No. 62/025,779, filed on Jul. 17, 2014.

(51) Int. Cl.
| | |
|---|---|
| A61K 36/05 | (2006.01) |
| A23L 33/115 | (2016.01) |
| A23L 15/00 | (2016.01) |
| A23K 10/16 | (2016.01) |
| A23K 50/75 | (2016.01) |
| A23L 33/00 | (2016.01) |
| A61K 35/57 | (2015.01) |
| A61K 36/02 | (2006.01) |
| A61K 36/55 | (2006.01) |

(52) U.S. Cl.
CPC .............. *A61K 36/05* (2013.01); *A23K 10/16* (2016.05); *A23K 50/75* (2016.05); *A23L 15/20* (2016.08); *A23L 33/115* (2016.08); *A23L 33/30* (2016.08); *A61K 35/57* (2013.01); *A61K 36/02* (2013.01); *A61K 36/55* (2013.01); *A23V 2002/00* (2013.01)

(58) Field of Classification Search
CPC .................................. A61K 36/02; A23K 50/75
See application file for complete search history.

(56) References Cited

U.S. PATENT DOCUMENTS

| | | |
|---|---|---|
| 4,218,437 A | 8/1980 | Hiller |
| 6,248,938 B1 | 6/2001 | Austin-Phillips et al. |
| 8,486,675 B2 | 7/2013 | Tang |
| 2002/0192731 A1 | 12/2002 | Shih |
| 2003/0206913 A1 | 11/2003 | Webel et al. |
| 2005/0186282 A1 | 8/2005 | Rosenberg et al. |
| 2005/0271788 A1 | 12/2005 | Lanter et al. |
| 2006/0198928 A1 | 9/2006 | Jobe et al. |
| 2007/0172514 A1 | 7/2007 | Chi et al. |
| 2010/0190744 A1 | 7/2010 | Remmereit |
| 2010/0239712 A1 | 9/2010 | Brooks et al. |
| 2010/0303990 A1 | 12/2010 | Brooks et al. |
| 2011/0200705 A1 | 8/2011 | Tricarico et al. |
| 2011/0256170 A1 | 10/2011 | Spencer et al. |
| 2011/0256282 A1 | 10/2011 | Piechocki et al. |
| 2015/0201649 A1 | 7/2015 | Lei |
| 2015/0202224 A1 | 7/2015 | Bregman et al. |
| 2016/0150809 A1 | 6/2016 | Lei |
| 2017/0119018 A1 | 5/2017 | Lei |

FOREIGN PATENT DOCUMENTS

| | | | |
|---|---|---|---|
| CN | 1965676 B | | 6/2010 |
| CN | 101766259 A | | 7/2010 |
| CN | 102326687 A | | 1/2012 |
| CN | 102415504 A | * | 4/2012 |
| CN | 102423000 A | | 4/2012 |
| CN | 102597255 A | | 7/2012 |
| CN | 103889219 A | | 6/2014 |
| CN | 104470369 A | | 3/2015 |
| JP | 09135665 A | * | 5/1997 |
| JP | 2001286262 A | | 10/2001 |
| JP | 2011068741 A | | 4/2011 |
| RU | 2108102 C1 | | 4/1998 |
| WO | 1998/018345 A1 | | 5/1998 |
| WO | 2006/065675 A2 | | 6/2006 |

(Continued)

OTHER PUBLICATIONS

Nitsan et al. J. Agric. Food Chem. 1999, 47, 5127-5132. (Year: 1999).*
Petrukhin, "Primenenie Kimicheskikh I Biologicheskikh Veschestv V Kormlinii Ptitsy," M 86-7, 96-7, 121-23, 170-73 (1972).
A4feed, "Microalgae in Feeds," http://www.algae4feed.org/brief/microalgae-in-feeds/57, 7 pages (2013).
Pienkos et al., "The Promise and Challenges of Microalgal-Derived Biofuels," Biofuels, Bioprod. Bioref. 3:431-440 (2009).
Levine, Ira A. Ph.D., "Algal-Based Biofuels & Biofeeds: Economic Development, A Northeastern Perspective," Fulbright New Century Scholar, Burlington, VT, 37 pages (2010).

(Continued)

*Primary Examiner* — Amy L Clark
(74) *Attorney, Agent, or Firm* — Troutman Pepper Hamilton Sanders LLP

(57) ABSTRACT

The present invention relates to omega-3 fatty acid enrichment, and n-6 to n-3 fatty acid ratio improvement, of poultry products using animal feed supplemented with defatted microalgae, and treatment methods involving such poultry products. One aspect of the present invention relates to a method of producing poultry eggs with elevated amounts of n-3 fatty acids. This method involves feeding poultry an amount of defatted microalgae under conditions effective for the poultry to produce an egg comprising about 300 mg to about 550 mg of n-3 fatty acids.

10 Claims, 18 Drawing Sheets
Specification includes a Sequence Listing.

(56) References Cited

FOREIGN PATENT DOCUMENTS

| WO | 2010107422 A1 | 9/2010 |
| WO | 2010/120923 A1 | 10/2010 |
| WO | 2014015000 A1 | 1/2014 |
| WO | 2015/006541 A2 | 1/2015 |
| WO | 2015/168136 A1 | 11/2015 |

OTHER PUBLICATIONS

International Search Report and Written Opinion for corresponding application No. PCT/US2013/050827, dated Oct. 31, 2013.
International Search Report and Written Opinion for corresponding Application No. PCT/US2015/028009, dated Jul. 13, 2015.
CN 1024230008 [Google machine translation from on-line website https://www.google.com/patents/CN1 02423000B?cl=en&dq=CN102423000&hl=en&sa=X&ved=OahUKEwjXhaWPwunLAhWC0h4KHeTmAykQ6AEIHTAA (last visit, Mar. 30, 2016)]. Waybackmachine evidence for Microalgae in Feeds (http://web.archive.org/web/20110101000000*/http://www.algae4feed.org/), last visit Mar. 30, 2016.
Nagasaki et al., "Previously unknown virus infects marine diatom", Appl Environ Microbiol. 71(7):3528-3535 (2005 ).
Shields et al., "Algae for Aquaculture and Animal Feeds," Technikfolgenabschatzung—Theorie und Praxis 21(1):23-37 (2012).
Kim et al., "Potential of a Defatted Green Microalgal Biomass as an Iron Source for Hemoglobin Repletion," FASEB J. 28(1):Suupl. 828.8 (pp. 1-2) (2014).
Third Office Action in CN Application No. 201380037726.6 (dated Sep. 19, 2017).
Office Action for U.S. Appl. No. 14/415,013 (dated Dec. 15, 2015).
Office Action for U.S. Appl. No. 14/415,013 (dated Apr. 7, 2016).
Office Action for U.S. Appl. No. 14/415,013 (dated Nov. 15, 2016).
Office Action and Search Report in CN Application No. 201380037726.6 (dated May 18, 2016).
Office Action for U.S. Appl. No. 14/415,013 (dated Mar. 10, 2017).
Egg Products Reference Guide, American Egg Board, 1-8 (2006).
Second Office Action in CN Application No. 201380037726.6 (dated Feb. 17, 2017).
Shi et al., "Experiment on Using Seaweed Meal to Replace Equivalent Bran in Laying Hen Diets," Poultry Husbandry and Disease Control, Issue 2:16 (2004).
Silo et al., "Exploitation and Utilization of Seaweed Feed," Guangxi Journal of Animal Husbandry & Veterinary Medicine 15(3):41-42 (1999).
Wang et al., "Influence of Adding Kelp Slag Residue in Diets of Growing Pig Productivity," Feed Review (Technology), Issue 6:40 (2009).
Office Action for U.S. Appl. No. 14/415,013 (dated Jul. 26, 2017).
Labtestonline, ([retrieved from on-line website: https://web.archive.org/web/20110911181709/https://labtestsonline.org/understanding/analytes/phosphorus/tab/sample/], on-line published on Sep. 11, 2011]).
International Search Report and Written Opinion corresponding to International Application No. PCT/US2014/046121, filed Jul. 10, 2014 (dated Oct. 24, 2014).
Restriction Requirement for U.S. Appl. No. 14/904,295 (dated Dec. 29, 2017).
Herber et al., "Dietary Marine Algae Promotes Efficient Deposition of n-3 Fatty Acids for the Production of Enriched Shell Eggs," Poultry Science 75:1501-1507 (1996).
Lum et al., "Dual Potential of Microalgae as a Sustainable Biofuel Feedstock and Animal Feed," Journal of Animal Science and Biotechnology 4(53):1-7 (2013).
Lenihan-Geels et al., "Alternative Sources of Omega-3 Fats: Can We Find a Sustainable Substitute for Fish?" Nutrients 5:1301-1315 (2013).
PCT International Search Report and Written Opinion corresponding to PCT/US2015/041000, filed Jul. 17, 2015 (dated Oct. 13, 2015).
Office Action for U.S. Appl. No. 14/415,013 (dated Oct. 22, 2018).
Office Action for U.S. Appl. No. 14/904,295 (dated Oct. 16, 2018).
Cacoufal, downloaded by the U.S. Patent and Trademark Office from https://animalscience.tamu.edu/2012/08/29/study-focusses-on-feeding-beef-cattle-algae-co-products/dated Aug. 29, 2012 (Year: 2012).
AllaboutFeed, "Alage as Sustainable Protein Alternative for Animal Feed," downloaded by the U.S. Patent and Trademark Office from https://web.archive.org/web/20130111092412/https://www.allaboutfeed.net/Nutrition/Raw-Materials/2012/1/Algae-as-sustainable-protein-alternative-for-animal-feed, (Year: 2012).
Patarra et al., "Nutritional Value of Selected Macroalgae," J. Appl. Phycol. 23:205-208 (2011).
Skrede et al., "Evaluation of Microalgae as Sources of Digestible Nutrients for Monogastric Animals," Journal of Animal and Feed Sciences 20:131-142 (2011).
Office Action for U.S. Appl. No. 15/307,418 (dated Jan. 18, 2019).
Garcia-Casal et al., "High Iron Content and Bioavailability in Humans from Four Species of Marine Algae," J. Nutrition 137:2691-2695 (2007).
Priyadarshani et al., "Commercial and Industrial Applications of Micro Algae—A Review," J. Algal Biomass 3:89-100 (2012).
Office Action for U.S. Appl. No. 14/904,295 (dated Feb. 23, 2018).
Fourth Office Action for Chinese Application No. 201380037726.6, dated May 28, 2018.
Austic et al., "Potential and Limitation of a New Defatted Diatom Microalgal Biomass in Replacing Soybean Meal and Corn in Diets for Broiler Chickens," J. Agric. Food Chem. 61(30):7341-8 (2013).
Office Action for U.S. Appl. No. 15/307,418 (dated Apr. 27, 2018).
Office Action for U.S. Appl. No. 14/415,013 (dated Mar. 19, 2018).
First Office Action for CN Patent Application Serial No. 201580048692.X (dated Sep. 3, 2019).
First Office Action for CN Patent Application Serial No. 201480049809.1 (dated Mar. 5, 2019).
First Office Action for CN Patent Application Serial No. 201480049809.1 (dated Aug. 30, 2019).
Third Office Action for CN Patent Application Serial No. 201580048692.X (dated Mar. 26, 2021) (Machine Translation).

\* cited by examiner

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggatagggct gctttcaaca                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ctccagggaa cacgtaggaa                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcagggaaaa ttctgtggaa                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cagcggtcaa caacaacatc                                              20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ccaccataca ttcccctacg                                              20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cgctcttgtg actcccatct                                              20

<210> SEQ ID NO 7
<211> LENGTH: 20
<212> TYPE: DNA
<213> ORGANISM: Artificial Sequence

```
<220> FEATURE:
<223> OTHER INFORMATION: primer

<400> SEQUENCE: 7
cgcattcagc agatgagtct                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gccgtaggtg tcctcattgt                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cacaatgtac cctggcattg                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tccggattca tcgtactcct                                               20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
cacaatgtac cctggcattg                                               20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
tccggattca tcgtactcct                                               20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gttccaggag gaccaaacaa                                               20
```

```
<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
tctcctaaag cccacattgc                                                   20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
gcagggaaaa ttctgtggaa                                                   20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
cagcggtcaa caacaacatc                                                   20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
agctttgaac ccagcaagaa                                                   20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
agcaacgcag agaagaggaa                                                   20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
cgcattcagc agatgagtct                                                   20

<210> SEQ ID NO 20
<211> LENGTH: 20
<212> TYPE: DNA
<213> ORGANISM: Artificial
<220> FEATURE:
<223> OTHER INFORMATION: primer
```

-continued

<400> SEQUENCE: 20
gccgtaggtg tcctcattgt                                           20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
ccaccataca ttcccctacg                                           20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
cgctcttgtg actcccatct                                           20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
cttgggatta cgctgctctc                                           20

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
tctggctgct tttcttcctc                                           20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
ggatgaggtc tgccttttca                                           20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
aaaagttccc ctttccctca                                           20

<210> SEQ ID NO 27

```
<211> LENGTH: 20
<212> TYPE: DNA
<213> ORGANISM: Artificial
<220> FEATURE:
<223> OTHER INFORMATION: primer

<400> SEQUENCE: 27
ttcactttgt ggtggattgg                                            20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
tggccaatag tcacatggaa                                            20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
ccaaagtaca tgcggaacaa                                            20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
ccaccagagg acacgtatga                                            20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
gccatcatct ggtgagaggt                                            20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
gatttcggtt ttgctgccta                                            20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
```

```
ggatagggct gctttcaaca                                              20
```

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34

```
ctccagggaa cacgtaggaa                                              20
```

OMEGA-3 FATTY ACID ENRICHMENT OF POULTRY PRODUCTS WITH DEFATTED MICROALGAE ANIMAL FEED

This application is a national stage application under 35 U.S.C. § 371 of PCT Application No. PCT/US2015/041000, filed Jul. 17, 2015, which claims the priority benefit of U.S. Provisional Patent Application Ser. No. 62/025,779, filed Jul. 17, 2014, which is hereby incorporated by reference in its entirety.

This invention was made with government support under 2011-10006-30361 awarded by USDA. The government has certain rights in the invention.

FIELD OF THE INVENTION

The present invention relates to omega-3 fatty acid enrichment of poultry products using animal feed supplemented with defatted microalgae.

BACKGROUND OF THE INVENTION

Flaxseed, flaxseed oil, and canola have been incorporated into laying hen diets to produce omega-3 (also referred to herein as n-3) fatty acid-fortified eggs. These ingredients contain high amounts of α-linolenic acid (C18:3n3, "ALA") compared with other oil seeds. Desaturation and elongation can turn ALA into eicosapentanoic acid (C20:5n3, "EPA") or docosahexanoic acid (C22:6n3, "DHA"). Due to low efficiencies of such conversions in vivo, supplementing diets for laying hens with ALA rarely produces eggs containing more than 80 mg of DHA (Carrillo et al., "Potential Use of Seaweeds in the Laying Hen Ration to Improve the Quality of n-3 Fatty Acid Enriched Eggs," In *Nineteenth International Seaweed Symposium*, Borowitzka, M.; Critchley, A.; Kraan, S.; Peters, A.; Sjøtun, K.; Notoya, M., Eds. Springer Netherlands: 2:271-278 (2009); Van Elswyk, "Comparison of n-3 Fatty Acid Sources in Laying Hen Rations for Improvement of Whole Egg Nutritional Quality: A Review," *British Journal of Nutrition* 78: S61-S69 (1997)). Also, inclusion of flaxseed into the diets at levels >10% decreases egg production due to its anti-nutritional factors and high amount of poly unsaturated fatty acids ("PUFA") (Leeson et al., "Response of Layers to Dietary Flaxseed According to Body Weight Classification at Maturitym," *The Journal of Applied Poultry Research* 9:297-302 (2000)). Dietary supplementation of fish meal or oil high in DHA and EPA is effective in enriching eggs with these unsaturated fatty acids, but it has proven very hard to produce eggs with over 100 mg of DHA per egg without palatability problems (Leskanich et al., "Manipulation of the n-3 Polyunsaturated Fatty Acid Composition of Avian Eggs and Meat," *World's Poultry Science Journal* 53:155-183 (1997)). Using flaxseed meal or oil alone for producing n-3 fatty acids-fortified eggs has limitations on egg production, DHA and EPA contents, hen longevity, and sensory perception of eggs. Likewise, use of omega-3 fatty acids rich ingredients, such as flaxseed oil, flaxseed meal, fish oil, and fish meal, in laying hen diets results in the development of off-flavored or off-colored eggs. The use of novel feed ingredients in diet of laying hens to fortify n-3 fatty acids must be weighed against potential challenges to the sensory attributes of eggs. There is no advantage to enhancing the nutrient value of eggs if the resultant product is unacceptable to consumers.

An additional alternative source of n-3 fatty acids is marine microalgae. Microalgae contain a superior fatty acid profile to traditional animal feed protein sources and tend to contain a greater abundance of EPA and DHA (Fredriksson et al., "Fatty Acid and Carotenoid Composition of Egg Yolk as an Effect of Microalgae Addition to Feed Formula for Laying Hens," *Food Chemistry* 99:530-537 (2006); Kalogeropoulos et al., "Nutritional Evaluation and Bioactive Microconstituents (Carotenoids, Tocopherols, Sterols and Squalene) of Raw and Roasted Chicken Fed on DHA-Rich Microalgae," *Food Res. Int.* 43:2006-2013 (2010); Guschina et al., "Lipids and Lipid Metabolism in Eukaryotic Algae," *Prog. Lipid Res.* 45:160-186 (2006)). Microalgae also contain moderate to high amounts of crude protein (Becker, "Micro-Algae as a Source of Protein," *Biotechnol. Adv.* 25:207-210 (2007)), essential amino acids (Gatrell et al., "Nonruminant Nutrition Symposium: Potential of Defatted Microalgae from the Biofuel Industry as an Ingredient to Replace Corn and Soybean Meal in Swine and Poultry Diets," *J. Anim. Sci.* 92:1306-1314 (2014)) and carotenoids (Spolaore et al., "Commercial Applications of Microalgae," *J. Biosci. Bioeng.* 101:87-96 (2006)), and supplementation to poultry diets has improved the overall n-3 fatty acid status in egg yolk (Fredriksson et al., "Fatty Acid and Carotenoid Composition of Egg Yolk as an Effect of Microalgae Addition to Feed Formula for Laying Hens," *Food Chemistry* 99:530-537 (2006)) and breast muscle (Mooney et al., "Lipid and Flavour Quality of Stored Breast Meat from Broilers Fed Marine Algae," *J. Sci. Food Agric.* 78:134-140 (1998)).

Between species, algae contain very different amounts of crude protein (6-71%), but show favorable amino acid profiles compared with other reference proteins (Becker, "Micro-algae as a Source of Protein," *Biotechnology Advances* 25:207-210 (2007); Becker, "18 Microalgae in Human and Animal Nutrition," *Handbook of Microalgal Culture: Biotechnology and Applied Phycology* 312 (2004)). Microalgae have long been valued as a food and feed supplement, or as a substitute for conventional protein sources. In 1957, Grau et al., "Sewage-grown Algae as a Feedstuff for Chicks," *Poultry Science* 36:1046-1051 (1957) used 20% sewage-grown *Chlorella* and *Scenedesmus* sp. in chick diets and reported no difference in the growth performance compared with chicks fed corn-soybean meal diets. *Spirulina platensis* was incorporated into broiler diets at different concentrations, and showed no effect on feed efficiency compared with corn-soybean diet fed chicks, but inclusion of more than 10% algae into diets lowered average daily weight gains of chicks (Ross et al., "The Nutritional Value of Dehydrated, Blue-green Algae (*Spirulina plantensis*) for Poultry," *Poultry Science* 69:794-800 (1990)).

Four or 8% of *Spirulina* sp. in broiler diets caused no difference in body weights, liver, abdominal fat, and kidney compared with unsupplemented control diets (Toyomizu et al., "Effects of Dietary *Spirulina* on Meat Colour in Muscle of Broiler Chickens," *British Poultry Science* 42:197-202 (2001)). 12% *Spirulina maxima* containing diets for sows caused no differences in growth performance of weaned pigs and growth and litter characteristics of piglets (Fevrier et al., in Incorporation of a Spiruline (*Spirulina maxima*) in Swine Food, Annales de la nutrition et de l'alimentation," p. 625 (1975)). Replacing 7.5% corn and soybean meal with defatted *Staurospira* Sp. in weanling pig diets did not affect growth performance and plasma biochemical indicators of health; however, 15% replacement caused lowered body weight due an inability to tolerate high crude protein content (Isaacs et al., "A Partial Replacement of Soybean Meal by Whole or Defatted Algal Meal in Diet for Weanling Pigs Does Not Affect Their Plasma Biochemical Indicators," *J. Anim. Sci.* 89:723 (2011); Lum et al., "Effects of Various Replacements of Corn and Soy by Defatted Microalgal Meal on Growth Performance and Biochemical Status of Weanling Pigs," *J. Anim. Sci.* 90:701 (2012)).

Dietary supplementation with defatted diatom, *Staurosira* sp., with additional, appropriate amino acids could replace 7.5% of soybean meal in broiler diets (Austic et al., "Potential and Limitation of a New Defatted Diatom Microalgal Biomass in Replacing Soybean Meal and Corn in Diets for Broiler Chickens," *Journal of Agricultural and Food Chemistry* 61:7341-7348 (2013)). Furthermore, with dietary protease, increased inclusion of defatted diatom could go up to 15% without affecting growth performance of weanling pigs and broiler chicks (Ekmay et al., "Nutritional and Metabolic Impacts of a Defatted Green Marine Microalgal (*Desmodesmus* sp.) Biomass in Diets for Weanling Pigs and Broiler Chickens," *Journal of Agricultural and Food Chemistry* 62:9783-9791 (2014)).

For defatted microalgae, after cultivation, microalgae are dehydrated, cells disrupted, particle size decreased, and dried to extract lipids (Doe, "National Algal Biofuels Technology Roadmap," *U.S. Dept. Energy, Office of Energy Efficiency and Renewable Energy, Biomass Program* (2010)). After this lipid extraction, microalgae residue contains a higher percentage of proteins than before. Also, Li et al., "A Comparative Study: The Impact of Different Lipid Extraction Methods on Current Microalgal Lipid Research," *Microbial Cell Factories* 13:14 (2014), examined different fatty acid extraction methods and revealed different extraction rates of saturated fatty acids, mono unsaturated fatty acids, and poly-unsaturated fatty acids. This indicated fatty acid profiles of defatted microalgae could be different from un-defatted microalgae depending on the extraction method.

Microalgae are the dominant producers of long chain PUFA in the biosphere (Behrens et al., "Microalgae as a Source of Fatty Acids," *Journal of Food Lipids* 3:259-272 (1996)). Fish products are a major source of n-3 fatty acids (Papadopoulos et al., "Effects of Dietary Supplements of Algae, Containing Polyunsaturated Fatty Acids, on Milk Yield and the Composition of Milk Products in Dairy Ewes," *Journal of Dairy Research* 69:357-365 (2002)); however, fish cannot synthesize n-3 fatty acids so they obtain these n-3 fatty acids by consuming microalgae or other algae-consuming fish (Stamey et al., "Use of Algae or Algal Oil Rich in n-3 Fatty Acids as a Feed Supplement for Dairy Cattle," *Journal of Dairy Science* 95:5269-5275 (2012)).

PUFAs, especially n-3 fatty acids, have beneficial effects on human health (Daviglus et al., "Fish Consumption and the 30-year Risk of Fatal Myocardial Infarction," *New England Journal of Medicine* 336:1046-1053 (1997); Albert et al., "Fish Consumption and Risk of Sudden Cardiac Death," *JAMA* 279:23-28 (1998)), and eggs fortified with n-3 fatty acids are a natural, healthy, inexpensive, and effective way to supplement n-3 fatty acids to humans (Oliveira et al., "Effects of Lipid Sources in the Diet of Laying Hens on the Fatty Acid Profiles of Egg Yolks," *Poultry Science* 89:2484-2490 (2010); Grobas et al., "Influence of Source and Percentage of Fat Added to Diet on Performance and Fatty Acid Composition of Egg Yolks of Two Strains of Laying Hens," *Poultry Science* 80:1171-1179 (2001)).

Among n-3 fatty acids (ALA, EPA, and DHA), EPA and DHA have more biological effects than ALA. Moreover, ALA is not efficiently converted into EPA and DHA in both chickens and humans (Carrillo et al., "Potential Use of Seaweeds in the Laying Hen Ration to Improve the Quality of n-3 Fatty Acid Enriched Eggs," In *Nineteenth International Seaweed Symposium*, Borowitzka, M.; Critchley, A.; Kraan, S.; Peters, A.; Sjøtun, K.; Notoya, M., Eds. Springer Netherlands: 2:271-278 (2009); Wang et al., "n-3 Fatty Acids From Fish or Fish-Oil Supplements, but not α-Linolenic Acid, Benefit Cardiovascular Disease Outcomes in Primary- and Secondary-Prevention Studies: A Systematic Review," *The American Journal of Clinical Nutrition* 84:5-17 (2006)).

Besides high protein and PUFA content, microalgae also contain other bioactive nutrients, vitamins, minerals, antioxidants, and carotenoids (Austic et al., "Potential and Limitation of a New Defatted Diatom Microalgal Biomass in Replacing Soybean Meal and Corn in Diets for Broiler Chickens," *Journal of Agricultural and Food Chemistry* 61:7341-7348 (2013)). Combs, "Algae (*Chlorella*) as a Source of Nutrients for the Chick," *Science* 116:453-454 (1952)) reported 10% *Chlorella* supplementation into riboflavin, vitamin B, and vitamin A deficient diets improved feed efficiency and growth performance of chicks. Also, microalgae supplementation increased carotenoid content of eggs from laying hens (Kotrbáček et al., "Retention of Carotenoids in Egg Yolks of Laying Hens Supplemented with Heterotrophic *Chlorella,*" *Czech J. Anim. Sci* 58:193-200 (2013); Guedes et al., "Microalgae as Sources of Carotenoids," *Marine Drugs* 9:625-644 (2011); Fredriksson et al., "Fatty Acid and Carotenoid Composition of Egg Yolk as an Effect of Microalgae Addition to Feed Formula for Laying Hens," *Food Chemistry* 99:530-537 (2006)). The nutritional properties of microalgae provide potential for novel diet formulations to increase concentrations of EPA and DHA.

The feasibility of incorporating various types of defatted diatom and green microalgal biomasses into broiler chicken (Austic et al., "Potential and Limitation of a New Defatted Diatom Microalgal Biomass in Replacing Soybean Meal and Corn in Diets for Broiler Chickens," *J. Agric. Food Chem.* 61(30):7341-7348 (2013); Ekmay et al., "Nutritional and Metabolic Impacts of a Defatted Green Marine Microalgal (*Desmodesmus* sp.) Biomass in Diets for Weanling Pigs and Broiler Chickens," *J. Agric. Food Chem.* 62(40):9783-9791 (2014)) and laying hen (Leng et al., "Effect of Dietary Defatted Diatom Biomass on Egg Production and Quality of Laying Hens," *Journal of Animal Science and Biotechnology* 5(1):3 (2014)) diets has been investigated. These data conclude that moderate levels (~7.5%) of supplementation do not negatively affect growth or production performance.

The biofuel research industry is constantly evolving to generate superior biofuel products and optimized residual byproducts. Currently, green microalgae are used for their promise for biofuel production and the superior nutrient content of their defatted biomass. So, the question arises if poultry could tolerate higher levels of the nutritionally superior biomass. The microalgal biomass contains relatively high concentrations of neutral detergent fiber ("NDF") and acid detergent fiber ("ADF") (Gatrell et al., "Nonruminant Nutrition Symposium: Potential of Defatted Microalgae from the Biofuel Industry as an Ingredient to Replace Corn and Soybean Meal in Swine and Poultry Diets," *J. Anim. Sci.* 92(4):1306-1314. (2014)). It remains unclear if exogenous, non-starch polysaccharide-degrading enzymes (NSPase) improve nutritional values of the biomass-containing diets (Ekmay et al., "Nutritional and Metabolic Impacts of a Defatted Green Marine Microalgal (*Desmodesmus* sp.) Biomass in Diets for Weanling Pigs and Broiler Chickens," *J. Agric. Food Chem.* 62(40):9783-9791 (2014)). More importantly, the current biomass contains relatively high levels of sodium, phosphorus, and ash (Gatrell et al., "Nonruminant Nutrition Symposium: Potential of Defatted Microalgae from the Biofuel Industry as an Ingredient to Replace Corn and Soybean Meal in Swine and Poultry Diets," *J. Anim. Sci.* 92(4):1306-1314 (2014)). Being a single cell protein supplement, the defatted microalgae biomass also contains high levels of nucleic acids as well (Becker, "Microalgae in Human and Animal Nutrition," in: *Handbook of Microalgal Culture: Biotechnology and Applied Phycology*, Richmond, A., ed. Blackwell Science Ltd, Oxford, p. 312 (2004)). However, indicators of metabolic fate or excretion level of these nutrients have not been assessed. In particular, potential impacts of feeding the biomass on phosphorus excretion and water intake of poultry may be a major environmental concern (Bourgeois, "A Discounted Threat: Environmental Impacts of the Livestock Industry," *Earth Common Journal* 2 (1) (2012)).

Consuming diets high in long chain omega-3 PUFAs has been linked to a decreased prevalence of cardiovascular disease, diabetes, arthritis, and cancer (Daviglus et al., "Fish Consumption and the 30-Year Risk of Fatal Myocardial Infarction," *N. Engl. J. Med.* 336:1046-1053 (1997); Albert et al., "Fish Consumption and Risk of Sudden Cardiac Death," *JAMA* 279:23-28 (1998); Ruggiero et al., "Omega-3 Polyunsaturated Fatty Acids and Immune-Mediated Diseases: Inflammatory Bowel Disease and Rheumatoid Arthritis," *Curr. Pharm. Des.* 15:4135-4148 (2009); Sala-Vila et al., "Update on the Relationship of Fish Intake with Prostate, Breast, and Colorectal Cancers," *Crit. Rev. Food Sci. Nutr.* 51:855-871 (2011); Delgado-Lista et al., "Long Chain Omega-3 Fatty Acids and Cardiovascular Disease: A Systematic Review," *Br. J. Nutr.* 107 (2): S201-13 (2012)). However, modern dietary habits tend to be high in saturated fats and contain an unbalanced ratio of the "pro-inflammatory" omega-6 (also referred to herein as n-6) and "anti-inflammatory" n-3 PUFAs. In typical Western diets, the average n-6:n-3 ratio ranges from 20-30:1, as opposed to traditional ranges of 1-2:1 (Simopoulos, "Essential Fatty Acids in Health and Chronic Disease," *Am. J. Clin. Nutr.* 70:560s-569s (1999)). Increasing public interest in nutrition and the health benefits of n-3 fatty acids has led to researchers attempting to alter the fatty acid profile of commonly consumed animal products. Since the average American consumes about 40 kg of broiler chicken annually (USDA Economic Research Service Poultry Yearbook, Young chicken: Per Capita Consumption, Retail Weight Basis (2006)), poultry meat is a promising candidate for n-3 enrichment.

For decades, it has been well established that the fatty acid profile of chicken breast, thigh, and skin is comparable to the fatty acids found in the diet (Marion et al., "The Fatty Acid Composition of Breast, Thigh, and Skin Tissues of Chicken Broilers as Influenced by Dietary Fats," *Poult. Sci.* 42:1202-1207 (1963)). Previously, n-3 fatty acid incorporation into poultry meat by dietary manipulation has focused on marine sources, mainly fish oil and fish meal (Edwards et al., "Studies with Menhaden Oil in Practical-Type Broiler Rations," *Poult. Sci.* 44:685-689 (1965); Hulan et al., "Omega-3 Fatty Acid Levels and Performance of Broiler Chickens Fed Redfish Meal or Redfish Oil," *Can. J. Anim. Sci.* 68:533-547 (1988); Lopez-Ferrer et al., "n-3 Enrichment of Chicken Meat. 1. Use of Very Long-Chain Fatty Acids in Chicken Diets and Their Influence on Meat Quality: Fish Oil," *Poult. Sci.* 80:741-752 (2001)). However, recent cost increases due to demand for fishmeal has led to the investigation of alternative n-3 fatty acid rich sources for a more sustainable industry.

It is well documented that consuming diets high in PUFAs ultimately enriches cell membranes in the fatty acids, subsequently altering signaling molecules involved in carbohydrate and lipid metabolism (Clarke et al., "Dietary Polyunsaturated Fatty Acid Regulation of Gene Transcription," *Annu. Rev. Nutr.* 14:83-98 (1994)). Enzymes involved in de novo fatty acid synthesis, such as malic enzyme (ME) and fatty acid synthase (FASN) are known to be affected by dietary manipulation and feeding status (Clarke et al., "Nutritional Control of Rat Liver Fatty Acid Synthase and S14 mRNA Abundance," *J. Nutr.* 120:218-224 (1990); Blake et al., "Suppression of Rat Hepatic Fatty Acid Synthase and S14 Gene Transcription by Dietary Polyunsaturated Fat," *J. Nutr.* 120:1727-1729 (1990); Katsurada et al., "Influence of Diet on the Transcriptional and Post-Transcriptional Regulation of Malic Enzyme Induction in the Rat Liver," *European Journal of Biochemistry* 168:487-491 (1987); Goodridge, "Dietary Regulation of Gene Expression: Enzymes Involved in Carbohydrate and Lipid Metabolism," *Annu. Rev. Nutr.* 7:157-185 (1987)). Additionally, desaturase enzymes, which introduce double bonds into fatty acids, including $\Delta$-6 and $\Delta$-9 desaturase, are also affected by nutritional status (Nakamura et al., "Structure, Function, and Dietary Regulation of $\Delta 6$, $\Delta 5$, and $\Delta 9$ Desaturases," *Nutrition* 24 (2004); Dridi et al., "The Regulation of Stearoyl-CoA Desaturase Gene Expression is Tissue Specific in Chickens," *J. Endocrinol.* 192:229-236 (2007)). However, the effect of defatted microalgal biomass, specifically on the expression of fatty acid metabolism genes, is unknown.

The present invention is directed to overcoming these and other deficiencies in the art.

SUMMARY OF THE INVENTION

One aspect of the present invention relates to a method of producing poultry eggs with elevated amounts of n-3 fatty acids. This method involves feeding poultry an amount of defatted microalgae under conditions effective for the poultry to produce an egg comprising about 300 to about 550 mg of n-3 fatty acids.

Another aspect of the present invention relates to an egg produced by the above method of the present invention.

A further aspect of the present invention relates to a treatment method. This method involves feeding a subject the egg of the present invention to increase the amount of n-3 fatty acids in the subject under conditions effective to treat the subject.

Another aspect of the present invention relates to a method of preventing weight loss in poultry fed a dietary supplement of flaxseed or flaxseed oil. This method involves identifying poultry being fed a dietary supplement of flaxseed or flaxseed oil and feeding the poultry an amount of defatted microalgae under conditions effective to prevent weight loss in the poultry as a result of the flaxseed or flaxseed oil.

A further aspect of the present invention relates to a method of producing poultry meat with elevated amounts of n-3 fatty acids. This method involves feeding poultry an amount of defatted microalgae under conditions effective to enrich a meat product of the poultry for n-3 fatty acids compared to that of poultry not fed the defatted microalgae.

Another aspect of the present invention relates to poultry meat produced by the above method of the present invention.

A further aspect of the present invention relates to a treatment method. This method involves feeding a subject the poultry meat of the present invention to increase the amount of n-3 fatty acids in the subject under conditions effective to treat the subject.

In the present invention, flaxseed oil and microalgae were combined into laying hen diets to produce n-3 fatty acid fortified eggs. Experiments set forth in the Examples infra examined the effect of inclusion of 0, 7.5, and 10% of defatted microalgae (Algae A) with 0, 3, and 5% of flaxseed oil on feed intake, body weight, egg production traits, and egg fatty acid composition. In addition, different species of defatted microalgae (Algae A, Algae B, and Algae C) were supplemented with 3.0% flaxseed oil into laying hen diets to determine the synergetic effects on feed intake, body weight, egg production traits, and egg fatty acid composition.

In addition, two broiler experiments were conducted to determine effects of a newly-acquired defatted green microalgal biomass in diets with or without NSPase on broiler growth performance, water intake, bone properties, and soluble inorganic phosphorus and DNA retentions and excretions.

BRIEF DESCRIPTION OF THE DRAWINGS

FIG. 3A=n-3, FIG. 3B=n-3:n-6, FIG. 3C=EPA; FIG. 3D=DHA. Data are expressed as mean±SEM (n=6/treatment). Values with different letters in each group differ significantly according to one-way ANOVA ($P<0.05$). Linear regression analyses were also deemed significant at $P<0.05$. DGA=defatted green microalgal biomass (*Nannochloropsis oceanica*, Cellana, Kailua-Kona, Hi.).

FIG. 4A=11-3, FIG. 4B=n-3:n-6, FIG. 4C=EPA, FIG. 4D=DHA. Data are expressed as mean±SEM (n=6/treatment). Values with different superscripts in each group differ significantly according to one-way ANOVA ($P<0.05$). Linear regression analyses were also deemed significant at $P<0.05$. DGA=defatted green microalgal biomass (*Nannochloropsis oceanica*, Cellana, Kailua-Kona, Hi.).

FIGS. 6C-E are graphs showing that supplemental defatted microalgae produces dose-dependent effects on expression of various genes in different tissues.

DETAILED DESCRIPTION OF THE INVENTION

Figure 1A:
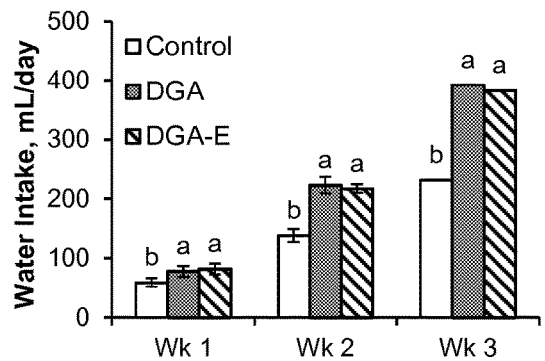
FIGS. 1A-B are graphs illustrating the effect of dietary microalgal biomass and NSPase inclusion on water intake and relative organ weights. Data are expressed as mean±SEM (n=5/treatment). Values with different letters in each group differ significantly according to one-way ANOVA ($P<0.05$). DGA=defatted green microalgal biomass (*Nannochloropsis oceanica*, Cellana, Kailua-Kona, Hi.). DGA-E=defatted green microalgal biomass plus NSPase. The NSPase was a 1:4:5 ratio of Ronozyme WX:Ronozyme A:Roxazyme G2, (DSM Nutritional Products Inc., Parsippany, N.J.).

The present invention relates to omega-3 fatty acid enrichment of poultry products using animal feed supplemented with defatted microalgae, and treatment methods involving such poultry products. As used herein, "poultry" is any domesticated fowl, such as chickens, turkeys, ducks, geese, quail, Japanese quail, or any other bird raised for meat or eggs. In specific embodiments of the present invention, the poultry is a laying hen (particularly as it pertains to methods of producing poultry eggs) or a broiler chicken (particularly as it pertains to producing poultry meat).

One aspect of the present invention relates to a method of producing poultry eggs with elevated amounts of n-3 fatty acids. This method involves feeding poultry an amount of defatted microalgae under conditions effective for the poultry to produce an egg comprising about 300 to about 550 mg of n-3 fatty acids.

As used herein, the terms "microalgae" and "algae" are used interchangeably and mean a eukaryotic microbial organism that contains a chloroplast, and which may or may not be capable of performing photosynthesis. Microalgae include obligate photoautotrophs which cannot metabolize a fixed carbon source as energy, as well as heterotrophs, which can live solely off of a fixed carbon source, including obligate heterotrophs, which cannot perform photosynthesis. Microalgae include unicellular organisms that separate from sister cells shortly after cell division, such as *Chlamydomonas*, as well as microbes such as, for example, *Volvox*, which is a simple multicellular photosynthetic microbe of two distinct cell types.

In one embodiment, the defatted microalgae used in this and other methods of the present invention, is selected from species of microalgae selected from *Nannochloropsis* or *Desmodesmus*. For example, suitable nonlimiting examples include *N. salina; N. avicula,* including *N. acceptata, N. biskanterae, N. pseudotenelloides, N. pelliculosa,* and *N. saprophila.* Other microalgae may include cells such as *Chlorella, Parachlorella,* and *Dunaliella. Chlorella* is a genus of single-celled green algae belonging to the phylum Chlorophyta. *Chlorella* cells are generally spherical in shape, about 2 to 10 μm in diameter, and lack flagella. Some species of *Chlorella* are naturally heterotrophic. Non-limiting examples of *Chlorella* species suitable for use in this and other methods of the present invention include *Chlorella protothecoides, Chlorella ellipsoidea, Chlorella minutissima, Chlorella zofinienesi, Chlorella luteoviridis, Chlorella kessleri, Chlorella sorokiniana, Chlorella fiusca* var. *vacuolata Chlorella* sp., *Chlorella* cf. *minutissima,* and *Chlorella emersonii. Chlorella protothecoides* is known to have a high composition of lipids.

Other species of *Chlorella* suitable for use in the methods of the present invention include, without limitation, the species *anitrata, antarctica, aureoviridis, Candida, capsulate, desiccate, ellipsoidea* (including strain CCAP 211/42), *glucotropha, infusionum* (including var. *actophila* and var. *auxenophila*), kessleri (including any of UTEX strains 397, 2229, 398), *lobophora* (including strain SAG 37.88), *luteoviridis* (including strain SAG 2203 and var. *aureoviridis* and *lutescens*), *miniata, mutabilis, nocturna, ovalis, parva, photophila, pringsheimii, protothecoides* (including any of UTEX strains 1806, 411, 264, 256, 255, 250, 249, 31, 29, 25 or CCAP 211/8D, or CCAP 211/17 and var. *acidicola*), *regularis* (including var. *minima,* and *umbricata*), *reisiglii* (including strain CCP 11/8), *saccharophila* (including strain CCAP 211/31, CCAP 211/32 and var. *ellipsoidea*), *salina, simplex, sorokiniana* (including strain SAG 211.40B), *sphaerica, stigmatophora, trebouxioides, vanniellii, vulgaris* (including strains CCAP 211/1 IK, CCAP 211/80 and f. *tertia* and var. *autotrophica, viridis, vulgaris, tertia, viridis*), *xanthella,* and *zofingiensis.*

Other genera of microalgae can also be used in the methods of the present invention and may include, for example, *Parachlorella kessleri, Parachlorella beijerinckii, Neochloris oleabundans, Bracteacoccus*, including *B. grandis, B. cinnabarinas*, and *B. aerius, Bracteocococcus* sp. and *Scenedesmus rebescens*.

Other nonlimiting examples of microalgae species include *Achnanthes orientalis; Agmenellum; Amphiprora hyaline; Amphora*, including *A. coffieiformis* including *A. c. linea, A. c. punctata, A. c. taylori, A. c. tenuis, A. c. delicatissima, A. c. delicatissima capitata; Anabaena; Ankistrodesmus*, including *A. falcatus; Boekelovia hooglandii; Borodinella; Botryococcus braunii*, including *B. sudeticus; Bracteoccocus*, including *B. aerius, B. grandis, B. cinnabarinas, B. minor*, and *B. medionucleatus; Carteria; Chaetoceros*, including *C. gracilis, C. muelleri*, and *C. muelleri subsalsum; Chlorococcum*, including *C. infusionum; Chlorogonium; Chroomonas; Chrysosphaera; Cricosphaera; Crypthecodinium cohnii; Cryptomonas; Cyclotella*, including *C. cryptica* and *C. meneghiniana; Dunaliella*, including *D. bardawil, D. bioculata, D. granulate, D. maritime, D. minuta, D. parva, D. peircei, D. primolecta, D. salina, D. terricola, D. tertiolecta*, and *D. viridis; Eremosphaera*, including *E. viridis; Ellipsoidon; Euglena; Franceia; Fragilaria*, including *F. crotonensis; Gleocapsa; Gloeothamnion; Hymenomonas; Isochrysis*, including *I. aff galbana* and *I. galbana; Lepocinclis; Micractinium* (including UTEX LB 2614); *Monoraphidium*, including *M. minutum; Monoraphidium; Nannochloris; Neochloris oleabundans; Nephrochloris; Nephroselmis; Nitschia communis; Nitzschia*, including *N. alexandrina, N. communis, N. dissipata, N. frustulum, N. hantzschiana, N. inconspicua, N. intermedia, N. microcephala, N. pusilla, N. pusilla elliptica, N. pusilla monoensis*, and *N. quadrangular; Ochromonas; Oocystis*, including *O. parva* and *O. pusilla; Oscillatoria*, including *O. limnetica* and *O. subbrevis; Parachlorella*, including *P. beijerinckii* (including strain SAG 2046) and *P. kessleri* (including any of SAG strains 11.80, 14.82, 21.11H9); *Pascheria*, including *P. acidophila; Pavlova; Phagus; Phormidium; Platymonas; Pleurochrysis*, including *P. carterae* and *P. dentate; Prototheca*, including *P. stagnora* (including UTEX 327), *P. portoricensis*, and *P. moriformis* (including UTEX strains 1441, 1435, 1436, 1437, 1439); *Pseudochlorella aquatica; Pyramimonas; Pyrobotrys; Rhodococcus opacus; Sarcinoid chrysophyte; Scenedesmus*, including *S. armatus* and *S. rubescens; Schizochytrium; Spirogyra; Spirulina platensis; Stichococcus; Synechococcus; Tetraedron; Tetraselmis*, including *T. suecica; Thalassiosira weissflogii*; and *Viridiella fridericiana*.

A suitable source of microalgae for the methods of the present invention is algal biomass. Algal biomass is material produced by growth and/or propagation of microalgal cells. Biomass may contain cells and/or intracellular contents as well as extracellular material. Extracellular material includes, but is not limited to, compounds secreted by a cell.

Typically, microalgae are cultured in liquid media to propagate biomass. For example, microalgal species may be grown in a medium containing a fixed carbon and/or fixed nitrogen source in the absence of light. Such growth is known as heterotrophic growth. For some species of microalgae, heterotrophic growth for extended periods of time such as 10 to 15 or more days under limited nitrogen conditions results in accumulation of high lipid content in the microalgal cells.

One particularly suitable source of microalgae for use in the present invention is microalgae cultivated for biofuel production. Microalgae cultivated for biofuel production includes algae before oils have been harvested from the algae (full-fat algae) and algae that has undergone oil extraction (defatted algae). Thus, as used herein, defatted algae have undergone an oil extraction process and so contains less oil relative to algae prior to oil extraction. Cells of defatted algae are predominantly lysed. Defatted algae include algal biomass that has been solvent (e.g., hexane) extracted.

Oils harvested from algae include any triacylglyceride (or triglyceride oil) produced by algae. Defatted algae contain less oil by dry weight or volume than the microalgae contained before extraction.

In one embodiment, defatted algae include algae having 50-99.9% of its oil extracted so that the defatted algae contains, for example about 0.1-50% of the oil content of biomass before extraction. However, the biomass still has a high nutrient value in content of protein and other constituents which makes it suitable for use in animal feed.

The process of preparing defatted (or delipidated) algae for use in the methods of the present invention can be carried out by standard methods known to those of ordinary skill in the art. For example, algal cells can be lysed, which can be achieved by any convenient means, including heat-induced lysis, adding a base, adding an acid, using enzymes such as proteases and polysaccharide degradation enzymes such as amylases, using ultrasound, mechanical pressure-based lysis, and lysis using osmotic shock. Each of these methods for lysing a microorganism can be used as a single method or in combination simultaneously or sequentially. The extent of cell disruption can be observed by microscopic analysis. Using one or more of the methods above, typically more than 70% cell breakage is observed.

Lipids and oils generated by the microalgae can be recovered by extraction. In some cases, extraction can be performed using an organic solvent or an oil, or can be performed using a solventless-extraction procedure.

For organic solvent extraction of the microalgal oil, a typical organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid components to form a solution with the organic solvent. In some cases, the solution can then be further refined to recover specific desired lipid components. The mixture can then be filtered and the hexane removed by, for example, rotoevaporation. Hexane extraction methods are well known in the art (see, e.g., Frenz et al., "Hydrocarbon Recovery by Extraction with a Biocompatible Solvent from Free and Immobilized Cultures of *Botryococcus-braunii*," *Enzyme Microb. Technol.* 11:717-724 (1989), which is hereby incorporated by reference in its entirety. Miao and Wu, "Biodiesel Production from Heterotrophic Microalgal Oil," *Biosource Technology* 97:841-846 (2006), which is hereby incorporated by reference in its entirety, describe a protocol of the recovery of microalgal lipid from a culture of *Chlorella protothecoides* in which the cells were harvested by centrifugation, washed with distilled water, and dried by freeze drying. The resulting cell powder was pulverized in a mortar and then extracted with n-hexane.

In some cases, microalgal oils can be extracted using liquefaction (see, e.g., Sawayama et al., "Possibility of Renewable Energy Production and C02 Mitigation by Thermochemical Liquefaction of Microalgae," *Biomass and Bioenergy* 17:33-39 (1999), which is hereby incorporated by reference in its entirety); oil liquefaction (see, e.g., Minowa et al, "Oil Production from Algal Cells of *Dunaliella tertiolecta* by Direct Thermochemical Liquefaction," Fuel 74(12): 1735-1738 (1995), which is hereby incorporated by reference in its entirety); or supercritical $CO_2$ extraction (see, e.g., Mendes et al., "Supercritical Carbon Dioxide Extraction of Compounds with Pharmaceutical Importance from Microalgae," *Inorganica Chimica Acta* 356:328-334 (2003), which is hereby incorporated by reference in its entirety). Algal oil extracted via supercritical $CO_2$ extraction contains all of the sterols and carotenoids from the algal biomass and naturally do not contain phospholipids as a function of the extraction process. The residual from the processes essentially comprises defatted (or delipidated) algal biomass devoid of oil, but still retains the protein and carbohydrates of the pre-extraction algal biomass. Thus, the residual defatted algal biomass is a suitable source of protein concentrate/isolate and dietary fiber.

Oil extraction also includes the addition of an oil directly to a lysate without prior separation of the lysate components. After addition of the oil, the lysate separates either of its own accord or as a result of centrifugation or the like into different layers. The layers can include in order of decreasing density: a pellet of heavy solids, an aqueous phase, an emulsion phase, and an oil phase. The emulsion phase is an emulsion of lipids and aqueous phase.

Depending on the percentage of oil added with respect to the lysate (w/w or v/v), the force of centrifugation, if any, volume of aqueous media, and other factors, either or both of the emulsion and oil phases can be present. Incubation or treatment of the cell lysate or the emulsion phase with the oil is performed for a time sufficient to allow the lipid produced by the microorganism to become solubilized in the oil to form a heterogeneous mixture.

Lipids can also be extracted from a lysate via a solventless extraction procedure without substantial or any use of organic solvents or oils by cooling the lysate. Sonication can also be used, particularly if the temperature is between room temperature and 65° C. Such a lysate on centrifugation or settling can be separated into layers, one of which is an aqueous/lipid layer. Other layers can include a solid pellet, an aqueous layer, and a lipid layer. Lipid can be extracted from the emulsion layer by freeze thawing or otherwise cooling the emulsion. In such methods, it is not necessary to add any organic solvent or oil. If any solvent or oil is added, it can be below 5% v/v or w/w of the lysate.

Algae used in the methods of the present invention is typically dried and/or ground into algal meal. Drying microalgal biomass, either predominantly intact or in homogenate form, is advantageous to facilitate further processing or for use of the biomass in the composition and feed supplement of the present invention. Drying refers to the removal of free or surface moisture/water from predominantly intact biomass or the removal of surface water from a slurry of homogenized (e.g., by micronization) biomass. In some cases, drying the biomass may facilitate a more efficient microalgal oil extraction process.

In one embodiment, concentrated microalgal biomass is drum dried to a flake form to produce algal flake. In another embodiment, the concentrated microalgal biomass is spray or flash dried (i.e., subjected to a pneumatic drying process) to form a powder containing predominantly intact cells to produce algal powder. In another embodiment, the concentrated microalgal biomass is micronized (homogenized) to form a homogenate of predominantly lysed cells that is then spray or flash dried to produce algal flour.

In one embodiment of this method of the present invention, poultry is fed defatted microalgae at an amount of about 1% to about 23%, or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, or about 23%, on a weight/weight basis of the poultry's total diet.

As used herein, "weight/weight" or "w/w" refers to proportions by weight, and means the ratio of the weight of one substance in a composition to the total weight of the composition, or the weight of one substance in the composition to the weight of another substance of the composition. For example, reference to a composition that comprises algae totaling 15% w/w of the composition means that 15% of the composition's weight is composed of algae (e.g., such a composition having a weight of 100 mg would contain 15 mg of algae) and the remainder of the weight of the composition (e.g., 85 mg in this example) is composed of other ingredients.

The defatted microalgae of the present invention may be fed to poultry by substituting a portion of the poultry's normal diet with defatted microalgae. According to one embodiment, the portion of the poultry's normal diet substituted with defatted microalgae is an animal feed component having similar nutrient (e.g., protein) qualities to algae. This may include, for example, substituting a portion of the poultry's maize or soy component of feed with defatted microalgae.

In one embodiment, the poultry are fed defatted microalgae, in addition to a non-algal protein source, in an amount totaling about 7.5% to about 15% weight/weight of the feed composition. Non-algal protein sources include those commonly part of poultry feed, including, without limitation, meat, fish protein, soy protein, whey protein, wheat protein, bean protein, rice protein, pea protein, milk protein, etc.

In this method of the present invention, poultry is fed an amount of defatted microalgae for the poultry to produce eggs comprising about 300 to about 550 mg of n-3 fatty acids. For example, the eggs may comprise about 300 mg, 310 mg, 320 mg, 330 mg, 340 mg, 350 mg, 375 mg, 400 mg, 425 mg, 450 mg, 475 mg, 500 mg, 525 mg, or 550 mg of n-3 fatty acids.

As used herein, n-3 fatty acids (also known as omega-3 fatty acids, co-3 fatty acids) and n-6 fatty acids (also known as omega-6 fatty acids, co-6 fatty acids) are taken to mean long-chain polyunsaturated fatty acids (PUFAs) having a carbon-carbon double bond at the third carbon atom from the end of the carbon chain, and a final carbon-carbon double bond at the sixth carbon atom from the end of the carbon chain, respectively. Exemplary n-3 fatty acids include α-Linolenic acid (ALA), stearidonic acid, eicosatetraenoic acid (ETA), eicosapentaenoic acid (EPA), docosapentaenoic acid (DPA), hexadecatrienoic acid (HTA), eicosatrienoic acid (ETE), heneicosapentaenoic acid (HPA), tetracosapentaenoic acid, tetracosahexaenoic acid, and docosahexanoic acid (DHA). Exemplary n-6 fatty acids include linoleic acid, gamma-linolenic acid, calendric acid, eicosadienoic acid, dihomo-gamma-linolenic acid, arachidonic acid, docosadienoic acid, adrenic acid, docosapentaenoic acid, tetracosatetraenoic acid, and tetracosapentaenoic acid. According to the USDA National Nutrient Database for Standard Reference, one whole, raw, fresh egg contains approximately 60 mg DHA and 0 mg EPA.

This method of the present invention is carried out to produce poultry eggs with elevated amounts of n-3 fatty acids, in particular, EPA and DHA. In one embodiment, the egg produced by the method of the present invention contains at least about 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, or more of a combination of docosahexanoic acid (DHA) and eicosapentaenoic acid (EPA).

This method of the present invention is also carried out to produce poultry eggs with improved n-6 to n-3 fatty acid ratios, and/or decreased n-9 fatty acids. In one embodiment, the egg has a ratio of n-3:n-6 fatty acids greater than that of eggs produced by laying hens not fed defatted microalgae under the conditions. In this or another embodiment, the egg has decreased n-9 fatty acids compared to that of eggs produced by poultry not fed defatted microalgae under the conditions.

According to another embodiment, the poultry is also fed a non-microalgae source of n-3 fatty acids. In one embodiment, the non-microalgae source of n-3 fatty acids is flaxseed or flaxseed oil. For example, the flaxseed may be fed to the poultry at an amount of about 0.5% to about 5% on a weight/weight basis, or at least about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%, on a weight/weight basis of the poultry's total diet. Alternatively, the non-microalgae source of n-3 fatty acids is fish oil or fish meal.

The present invention further encompasses the egg produced by this method.

Another aspect of the present invention relates to a treatment method. This method involves feeding a subject the n-3 fatty acid enriched egg of the present invention to increase the amount of n-3 fatty acids in the subject under conditions effective to treat the subject.

According to one embodiment of this aspect of the present invention, the subject is fed the enriched egg to increase the amount of n-3 fatty acids in various tissues, and to improve the n-6:n-3 fatty acid ratio and decrease the n-9 fatty acids in the subject.

In carrying out this method of the present invention, the egg can be fed to the subject as part of the subject's diet and/or as a food supplement, e.g., in drinks, soup, processed foods, nutritional and health supplements in original, crude, extracted, or purified forms.

In accordance with this aspect of the present invention, the subject may be a human, or any of various food-producing, companion/pet, recreational, zoo, wild-life, laboratory, or other relevant species, including, without limitation, a dog, cat, horse, cow, sheep, goat, pig, mouse, rat, guinea pig, or monkey. Preferably, the subject is a human.

Treatment in the subject may include, without limitation, decreasing blood and/or tissue triglycerides in a normal or overweight or obese individual. Such treatment may involve, for example and without limitation, preventing or treating fatty liver, obesity, and other triglyceride-related disorders. In one embodiment, the subject is treated for a n-3 fatty acid responsive disease or disorder including, but not limited to, heart-related conditions, diabetes, obesity, fatty liver, inflammation, cancer, high blood pressure, aging, neurodegeneration, loss of immune functions, declined fertility, muscle atrophy, digestive bowl diseases, etc. In one embodiment, the heart-related condition includes, but is not limited to, hypercholesterolemia, coronary artery disease, congestive heart failure, and myocardial infarction.

A further aspect of the present invention relates to a method of preventing weight loss in poultry fed a dietary supplement of flaxseed or flaxseed oil. This method involves identifying poultry being fed a dietary supplement of flaxseed or flaxseed oil and feeding the poultry an amount of defatted microalgae under conditions effective to prevent weight loss in the poultry as a result of the flaxseed or flaxseed oil.

In one embodiment, the dietary supplement of flaxseed or flaxseed oil is an amount of about 5% or more on a weight/weight basis of the poultry's total diet.

Defatted microalgae as well as methods of preparing and feeding defatted microalgae are described supra.

Another aspect of the present invention relates to a method of producing poultry meat with elevated amounts of n-3 fatty acids. This method involves feeding poultry an amount of defatted microalgae under conditions effective to enrich a meat product of the poultry for n-3 fatty acids compared to that of poultry not fed the defatted microalgae.

Defatted microalgae as well as methods of preparing and feeding defatted microalgae are described supra.

According to one embodiment of this aspect of the present invention, the poultry is fed defatted microalgae at an amount of about 2% to about 16%, or about 2%, 3%, 4%, 5%, 6%, 7%, 8%, 9%, 10%, 11%, 12%, 13%, 14%, 15%, or 16% or more on a weight/weight basis of the poultry's total diet.

This method of the present invention is carried out to produce poultry meat with elevated amounts of n-3 fatty acids, in particular, EPA and DHA. In one embodiment, the enriched meat product contains more of the n-3 fatty acids docosahexanoic acid (DHA) and eicosapentaenoic acid (EPA) compared to that of poultry not fed the defatted microalgae. According to the USDA National Nutrient Database for Standard Reference, poultry meat products contain less than about 20 g EPA and less than about 60 g DHA per 100 g. Thus, according to one embodiment, this aspect of the present invention involves enriching a meat product of poultry by elevating the n-3 fatty acids to a level greater than 20 g EPA and/or 60 g DHA per 100 g, or a combined level of EPA and DHA greater than about 80 g per 100 g.

This method of the present invention is also carried out to produce poultry meat with improved n-6 to n-3 fatty acid ratios, and/or decreased n-9 fatty acids. In one embodiment, the meat has a ratio of n-3:n-6 fatty acids greater than that of poultry not fed defatted microalgae under the conditions. In this or another embodiment, the poultry meat has decreased n-9 fatty acids compared to that of poultry meat produced by poultry not fed defatted microalgae under the conditions.

In one embodiment, the enriched meat product is selected from breast muscle, thigh muscle, and/or other organs such as liver and adipose tissue.

In another embodiment, the enriched meat product contains an at least about 3-fold to 15-fold increase in n-3 fatty acids compared to that of poultry not fed the defatted microalgae under the conditions, or about a 2-fold, 3-fold, 4-fold, 5-fold, 6-fold, 7-fold, 8-fold, 9-fold, 10-fold, 11-fold, 12-fold, 13-fold, 14-fold, or 15-fold or more increase in n-3 fatty acids compared to that of poultry not fed the defatted microalgae under the conditions.

In one embodiment, the enriched meat product contains a ratio of n-3:n-6 fatty acids greater than that of poultry not fed defatted microalgae under the conditions.

Yet a further aspect of the present invention relates to a treatment method that involves feeding a subject the poultry meat of the present invention to increase the amount of n-3 fatty acids in the subject under conditions effective to treat the subject.

Treatments pertaining to this aspect of the present invention include those described supra.

According to one embodiment of this aspect of the present invention, the subject is fed the enriched poultry meat to increase the amount of n-3 fatty acids in various tissues, and to improve the n-6:n-3 fatty acid ratio and decrease the n-9 fatty acids in the subject.

In carrying out this method of the present invention, the poultry meat can be fed to the subject as part of the subject's diet and/or as a food supplement, e.g., in drinks, soup, processed foods, nutritional and health supplements in original, crude, extracted, or purified forms.

In accordance with this aspect of the present invention, the subject may be a human, or any of various food-producing, companion/pet, recreational, zoo, wild-life, laboratory, or other relevant species, including, without limitation, a dog, cat, horse, cow, sheep, goat, pig, mouse, rat, guinea pig, or monkey. Preferably, the subject is a human.

Treatment in the subject may include, without limitation, decreasing blood and/or tissue triglycerides in a normal or overweight or obese individual. Such treatment may involve, for example and without limitation, preventing or treating fatty liver, obesity, and other triglyceride-related disorders. In one embodiment, the subject is treated for a n-3 fatty acid responsive disease or disorder including, but not limited to, heart-related conditions, diabetes, obesity, fatty liver, inflammation, cancer, high blood pressure, aging, neurodegeneration, loss of immune functions, declined fertility, muscle atrophy, digestive bowl diseases, etc. Heart-related conditions are discussed supra.

Treatment methods of the present invention may be carried out to stimulate endogenous n-3 fatty acid synthesis pathways, up-regulate or down-regulate key enzyme gene expression, and the invention described herein reveals the diet composition and the dose that may be administered to carry out such treatment methods.

Effective target genes include, without limitation, Δ-9 desaturase, Δ-6 desaturase, malic enzyme, fatty acid synthase, acetyl-CoA carboxylase, elongase 2, elongase 3, elongase 4, elongase 5, and acyl-CoA thioesterase 4. These genes may be altered by defatted microalgae or other dietary components, chemicals, drugs, or genetic manipulation for enriching n-3 fatty acids in the tissues of various species or treating and preventing diseases or disorders related to n-3 fatty acids.

EXAMPLES

The following examples are provided to illustrate embodiments of the present invention but are by no means intended to limit its scope.

Example 1—Comparative Effects of Microalgal Biomass and Flaxseed Oil on n-3 Fatty Acid Enrichment of Eggs Materials and Methods Animals Animal protocols were approved by the Cornell University Institutional Animal Care and Use Committee. The three types of microalgal biomass (Table 1) were obtained from Cellana (Kailua-Kona, Hi.). Type A was full-fatted *Staurosira* sp., type B was defatted *Desmodesmus* sp., and type C was defatted *Nannochloropsis oceanica*. The flaxseed oil was purchased from Dyets (Bethlehem, Pa., Catalog #402511).

TABLE 1

Proximate Analysis (%) and Fatty Acid Composition (%) of Flaxseed Oil and Algae Used in Experiments I and II

|  | Flaxseed oil | Algae A | Algae B | Algae C |
|---|---|---|---|---|
| Dry matter, % | — | 85.80 | 96.00 | 95.30 |
| Crude protein, % | — | 13.90 | 31.20 | 38.20 |
| Ether extract, % | 100.00 | 30.10 | 1.10 | 1.50 |
| Lysine, % | — | 0.57 | 1.61 | 2.27 |
| Methionine, % | — | 0.26 | 0.21 | 0.57 |
| Cysteine, % | — | 0.19 | 0.33 | 0.30 |
| Calcium, % | — | 3.81 | 0.33 | 0.28 |
| Phosphorus, % | — | 0.60 | 0.65 | 0.69 |
| Fatty acid, % | | | | |
| C14:0 | 0.04 | 8.31 | 1.21 | 7.44 |
| C14:1 | N.D. | 0.11 | N.D. | 0.12 |
| C16:0 | 4.59 | 51.84 | 35.61 | 29.21 |
| C16:1 | 0.05 | 35.68 | 1.59 | 25.24 |
| C18:0 | 2.74 | 0.84 | 2.24 | 0.54 |
| C18:1n9 | 14.12 | 0.71 | 19.27 | 12.14 |
| C18:2n6 | 14.94 | 1.04 | 10.82 | 2.13 |
| C18:3n3 | 62.72 | N.D. | 22.13 | 0.11 |
| C18:3n6 | N.D. | 0.24 | 1.64 | 0.42 |
| C20:2n6 | N.D. | 0.12 | 2.85 | 0.14 |
| C20:4n6 | N.D. | 0.41 | N.D. | 5.84 |
| C20:5n3 | N.D. | 0.49 | 0.41 | 16.41 |
| C24:0 | N.D. | 0.11 | 0.38 | N.D. |
| SFA | 7.42 | 61.09 | 40.21 | 37.21 |
| MUFA | 14.17 | 36.64 | 21.91 | 37.68 |
| PUFA | 77.66 | 2.27 | 37.88 | 25.14 |
| n-3 | 62.72 | 0.51 | 22.64 | 16.52 |
| n-6 | 14.94 | 1.78 | 15.28 | 8.56 |
| n-9 | 14.17 | 0.71 | 20.26 | 12.18 |

ND.; not detected,
SFA; saturated fatty acid,
MUFA; mono-unsaturated fatty acid,
PUFA; poly-unsaturated fatty acid,
n-3; omega-3 fatty acids,
n-6; omega-6 fatty acids,
n-9; omega-9 fatty acids.

Experiment I

A 3 by 3 factorial experiment with 3 levels of flaxseed oil inclusion (0, 3, and 5%) and 3 levels of microalgae A (0, 7.5, and 10%) (Table 2) was conducted for 4 weeks. Ninety Shaver Leghorn laying hens (20 weeks old) were housed in individual cages in triple deck batteries and allotted to the 9 treatment groups (n=10/treatment). The environment was controlled at 23° C., 20% relative humidity, and 8:16 hours of dark:light cycle during the 4 week experiment. Ten birds were randomly assigned to each treatment. The experimental diets were formulated based on the NRC requirement (NRC., "Nutrient Requirements of Poultry," in National Research Council, National Academy Press Washington, USA (1994), which is hereby incorporated by reference in its entirety). The birds had free access to feed and water through the experiment period.

TABLE 2

Composition (g/kg) of Diets for Experiment I

| | Flaxseed oil, % | | | | | | | | |
|---|---|---|---|---|---|---|---|---|---|
| | 0 | 3 | 5 | 0 | 0 | 3 | 3 | 5 | 5 |
| | | | | Algae A, % | | | | | |
| | 0 | 0 | 0 | 7.5 | 10 | 7.5 | 10 | 7.5 | 10 |
| Corn, grain | 652.2 | 547.5 | 477.8 | 582.0 | 555.6 | 581.5 | 555.0 | 477.5 | 505.0 |
| Soybean meal 48% | 216.9 | 200.0 | 210.0 | 205.2 | 202.5 | 205.9 | 203.0 | 187.9 | 192.0 |
| Flaxseed oil# | — | 30.0 | 50.0 | — | — | 30.0 | 30.0 | 50.0 | 50.0 |
| Algae | — | — | — | 75.0 | 100.0 | 75.0 | 100.0 | 75.0 | 100.0 |
| Wheat middling | — | 100.0 | 100.0 | — | — | — | — | 100.0 | 55.4 |
| Corn oil | 18.8 | — | — | 38.7 | 45.8 | 8.5 | 15.9 | — | — |
| Dicalcium Phosphate | 20.0 | 18.5 | 18.0 | 17.5 | 16.5 | 17.5 | 16.5 | 15.5 | 15.5 |
| Limestone | 85.0 | 85.5 | 86.0 | 78.5 | 76.5 | 78.5 | 76.5 | 80.0 | 77.0 |
| Lysine-HCl | — | — | 1.0 | — | — | — | — | — | 0.5 |
| Choline | 1.0 | 1.0 | 1.0 | 1.0 | 1.0 | 1.0 | 1.0 | 01.0 | 1.0 |
| DL-Methionine | 1.6 | 1.6 | 1.6 | 1.6 | 1.6 | 1.6 | 1.6 | 01.6 | 1.6 |
| Sodium Chloride | 4.0 | 4.0 | 4.0 | — | — | — | — | — | — |
| Vit/Min mixture* | 0.5 | 0.5 | 0.5 | 0.5 | 0.5 | 0.5 | 0.5 | 0.5 | 0.5 |
| Celite | — | 11.4 | 50.1 | — | — | — | — | 11.0 | 1.5 |
| Calculated value | | | | | | | | | |
| ME, MJ/kg | 12.02 | 11.60 | 11.44 | 12.08 | 12.09 | 12.08 | 12.09 | 11.68 | 11.89 |
| Crude protein, g/kg | 160.63 | 159.54 | 158.46 | 159.47 | 159.34 | 159.71 | 159.53 | 158.14 | 158.81 |
| Methionine, g/kg | 4.20 | 4.10 | 4.05 | 3.99 | 3.92 | 3.99 | 3.93 | 3.90 | 3.88 |
| Cysteine, g/kg | 2.74 | 2.75 | 2.69 | 2.53 | 2.46 | 2.53 | 2.46 | 2.53 | 2.47 |
| Lysine, g/kg | 8.12 | 8.03 | 8.93 | 7.59 | 7.44 | 7.61 | 7.45 | 7.49 | 7.77 |
| Phosphorus, g/kg | 6.88 | 7.05 | 6.83 | 6.60 | 6.47 | 6.60 | 6.47 | 6.68 | 6.55 |
| Calcium, g/kg | 36.57 | 36.47 | 36.56 | 36.42 | 36.63 | 36.42 | 36.40 | 36.59 | 36.40 |

Purchased from Dyets (Bethlehem, PA), Catalog # 40251
*Vitamin and mineral mixture provided the following nutrients per kilogram of diet: vitamin A, 11,000 IU; vitamin D, 5,000 IU; vitamin E, 75 IU; menadione bisulfite, 3 mg; riboflavin, 8 mg; D-Ca pantothenate, 15 mg; niacin, 60 mg; vitamin B-12, 0.016 mg; biotin, 4 mg; folic acid, 2 mg; thiamine-HCl, 3 mg; pyridoxine-HCl, 4 mg; $CuSO_4 \cdot 5H_2O$, 16 mg; KI, 1.25 mg; $MnSO_4 \cdot H_2O$, 120 mg; $Na_2SeO_3$, 0.3 mg; ZnO, 100 mg; $Na_2MoO_4 \cdot 2H_2O$, 0.001261 mg.

Experiment II

This experiment included 5 treatment groups (Table 3). Group 1 was fed a corn-soy control diet (NRC., "Nutrient Requirements of Poultry," in National Research Council, National Academy Press Washington, USA (1994), which is hereby incorporated by reference in its entirety) without microalgae or flaxseed oil, Group 2 and Group 3 were fed diets containing 7.5% microalgae A and B, respectively, and Groups 4 and 5 were fed diets containing 7.5 and 15% microalgae C, respectively. The experimental diets for Groups 2-5 contained 3% flaxseed oil. Fifty Shaver Leghorn laying hens (28 weeks old) were selected and housed in individual cages in triple deck batteries, and were randomly assigned to each treatment (n=10). The experiment lasted 4 weeks, and the birds had free access to feed and water.

TABLE 3

Composition (g/kg) of Diets for Experiment II

| | Flaxseed oil, % | | | | |
|---|---|---|---|---|---|
| | 0 | 3 | 3 | 3 | 3 |
| | | | Algae % | | |
| | 0 | Algae A 7.5 | Algae B 7.5 | Algae C 7.5 | Algae C 15.0 |
| Corn, grain | 652.2 | 581.5 | 605.0 | 607.0 | 605.0 |
| Algae A | — | 75.0 | — | — | — |
| Algae B | — | — | 75.0 | — | — |
| Algae C | — | — | — | 75.0 | 150.0 |
| Soybean meal 48% | 216.9 | 205.9 | 175.0 | 165.0 | 104.0 |
| Dicalcium Phosphate | 20.0 | 17.5 | 16.5 | 16.5 | 16.0 |
| Limestone | 85.0 | 78.5 | 87.0 | 78.6 | 87.0 |
| Flaxseed oil | — | 30.0 | 30.0 | 30.0 | 30.0 |
| Choline | 1.0 | 1.0 | 1.0 | 1.0 | 1.0 |
| dl-Methionine | 1.6 | 1.6 | 1.6 | 1.6 | 1.6 |
| Sodium Chloride | 4.0 | — | — | — | — |
| Vit. And Min. Mixture* | 0.5 | 0.5 | 0.5 | 0.5 | 0.5 |
| Celite | — | — | 8.4 | 16.8 | 4.9 |
| Corn oil | 18.8 | 8.5 | — | — | — |
| Isoleucine-HCl | — | — | — | — | 0.11 |
| Valine-HCl | — | 0.06 | — | — | — |

TABLE 3-continued

Composition (g/kg) of Diets for Experiment II

| | Flaxseed oil, % | | | | |
|---|---|---|---|---|---|
| | 0 | 3 | 3 | 3 | 3 |
| | | | Algae % | | |
| | 0 | Algae A 7.5 | Algae B 7.5 | Algae C 7.5 | Algae C 15.0 |
| Calculated value | | | | | |
| ME, MJ/kg | 12.02 | 12.08 | 12.16 | 12.08 | 12.27 |
| Crude protein, g/kg | 160.60 | 159.70 | 159.71 | 160.32 | 159.14 |
| Methionine, g/kg | 4.20 | 4.15 | 4.19 | 4.19 | 4.21 |
| Cysteine, g/kg | 2.74 | 2.64 | 2.60 | 2.51 | 2.29 |
| Lysine, g/kg | 8.12 | 8.14 | 7.96 | 8.16 | 8.06 |
| Phosphorus, g/kg | 6.88 | 6.60 | 6.33 | 6.30 | 6.34 |
| Calcium, g/kg | 36.57 | 36.42 | 36.66 | 36.45 | 36.53 |

*Vitamin and mineral mixture provided the following nutrients per kilogram of diet: vitamin A, 11,000 IU; vitamin D, 5,000 IU; vitamin E, 75 IU; menadione bisulfite, 3 mg; riboflavin, 8 mg; D-Ca pantothenate, 15 mg; niacin, 60 mg; vitamin B-12, 0.016 mg; biotin, 4 mg; folic acid, 2 mg; thiamine-HCl, 3 mg; pyridoxine-HCl, 4 mg; $CuSO_4 \cdot 5H_2O$, 16 mg; KI, 1.25 mg; $MnSO_4 \cdot H_2O$, 120 mg; $Na_2SeO_3$, 0.3 mg; ZnO, 100 mg; $Na_2MoO_4 \cdot 2H_2O$, 0.001261 mg Measurements Body weight and feed intake were recorded weekly, and eggs were collected daily. Five eggs from each treatment were randomly selected weekly and whole egg, egg shell, albumen, and yolk weight were measured. Blood was collected from wing veins at the end of each experiment, and plasma was obtained by centrifugation (3000×g, 15 min at 4° C.) and stored at −20° C. until analyses.

Plasma uric acid ("UA") concentration was determined using a uric acid kit (Infinity™ Uric Acid Liquid Stable Reagent, Thermo scientific, Middletown, Va.). Plasma inorganic phosphorus ("PIP") was measured after precipitation with 12.5% trichloroacetic acid using an Elon (p-methyl-aminophenol sulfate) solution (Gomori, "A Modification of the Colorimetric Phosphorus Determination for Use with the Photoelectric Colorimeter," *J. Lab. Clin. Med* 27:1941-42 (1942), which is hereby incorporated by reference in its entirety). Alkaline phosphatase ("AKP") was quantified by hydrolysis of p-nitrophenol phosphate to p-nitrophenol (Bowers et al., "A Continuous Spectrophotometric Method for Measuring the Activity of Serum Alkaline Phosphatase," *Clinical Chemistry* 12:70-89 (1966), which is hereby incorporated by reference in its entirety).

Fatty Acid Analysis

Fatty acids from eggs were methylated with methanolic-KOH according to Ichihara et al., "An Improved Method for Rapid Analysis of the Fatty Acids of Glycerolipids," *Lipids* 31:535-539 (1996), which is hereby incorporated by reference in its entirety. Methyl esters of fatty acids were analyzed using a gas chromatograph (Agilent 6890N, Agilent Technologies, Santa Clara, Calif.) fitted with a flame-ionization detector. A fused-silica capillary column coated with CP-SIL 88 for fatty acid methyl ester (100 m×0.25 mm i.d., 0.2 mm film thickness) (Varian Inc, Lake Forest, Calif.) was used. Oven temperature was programmed to be held for 4 min at 140° C., increased by 4° C. per min to 220° C., and then held for 5 min. Carrier gas was $N_2$ with constant flow rate of 2 ml/s and injector temperature was 230° C. and detector temperature was 280° C. Tritridecanoin (Sigma-Aldrich Co., St Louis, Mo.) was used as an internal standard, and each fatty acid was identified by its retention time against a fatty acid methyl ester standard (Sigma-Aldrich Co., St Louis, Mo.).

Statistical Analysis

Data were analyzed by ANOVA using the SAS system (SAS Institute, Cary, N.C.). Two-way (3×3 factorial arrangement) ANOVA was used for Experiment I, and main factors were flaxseed oil and microalgae, and Duncan's post hoc test was used for treatment mean comparisons. One-way ANOVA with Duncan's post hoc test was used for data analysis of Experiment II. Significance of difference was defined at $P<0.05$.

Experiment I Results

Inclusion of 5%, but not 3% flaxseed oil into the diets (Table 4), decreased ($P<0.05$) body weights compare with the control group at the end of study ($P<0.05$). The microalgae supplementations (7.5% and 10%) prevented the weight loss in the hens fed 5% flaxseed oil. Neither microalgae nor flaxseed oil inclusion affected average daily feed intake or plasma uric acid concentrations. Both plasma inorganic phosphorus concentrations and AKP activities were decreased ($P<0.05$) by the microalgae inclusions.

TABLE 4

Body Weight, Feed Intake, and Plasma Biomarkers of Hens in Experiment I

| | Flaxseed oil, % | | | | | | | | | | |
|---|---|---|---|---|---|---|---|---|---|---|---|
| | 0 | 3 | 5 | 0 | 0 | 3 | 3 | 5 | 5 | | |
| | | | | | Algae A, % | | | | | Pooled | |
| | 0 | 0 | 0 | 7.5 | 10 | 7.5 | 10 | 7.5 | 10 | SEM | Factor* |
| | | | | | Body weight, g | | | | | | |
| Week 0 | 1377 | 1351 | 1353 | 1439 | 1386 | 1362 | 1391 | 1414 | 1396 | 10 | |
| Week 4 | 1517[a] | 1494[a] | 1382[b] | 1575[a] | 1548[a] | 1477[a] | 1514[a] | 1544[a] | 1537[a] | 12 | A |

TABLE 4-continued

Body Weight, Feed Intake, and Plasma Biomarkers of Hens in Experiment I

| | Flaxseed oil, % | | | | | | | | | | |
|---|---|---|---|---|---|---|---|---|---|---|---|
| | 0 | 3 | 5 | 0 | 0 | 3 | 3 | 5 | 5 | | |
| | | | | | Algae A, % | | | | | Pooled | |
| | 0 | 0 | 0 | 7.5 | 10 | 7.5 | 10 | 7.5 | 10 | SEM | Factor* |
| Average Daily Feed Intake, g | | | | | | | | | | | |
| Week 0-4 | 111.6 | 114.5 | 113.0 | 114.9 | 110.6 | 109.1 | 110.9 | 108.9 | 113.8 | 1.1 | |
| Plasma Biomarkers | | | | | | | | | | | |
| UA#, mg/dL | 4.79 | 5.34 | 4.11 | 4.63 | 4.86 | 6.21 | 5.85 | 6.64 | 6.86 | 0.27 | |
| PIP, ppm | 5.79$^{ab}$ | 6.03$^{ab}$ | 7.37$^a$ | 5.60$^b$ | 4.47$^b$ | 4.32$^b$ | 5.45$^b$ | 4.93$^b$ | 5.08$^b$ | 0.21 | A |
| AKP, U/L | 418.94$^{ab}$ | 474.54$^a$ | 536.40$^a$ | 258.12$^c$ | 196.10$^c$ | 273.31$^{bc}$ | 198.00$^c$ | 235.60$^c$ | 190.72$^c$ | 25.15 | A |

$^{a-b}$Means in same row without a common letter differ (P < 0.05).
*Factor determined by two way ANOVA, A; microalgae (P < 0.05).
UA; uric acid, PIP; plasma inorganic phosphorus, AKP; alkaline phosphatase activity.

Number of eggs, egg weight, albumen weight (egg white), egg yolk weight, and egg shell weight were not affected by dietary supplementations of microalgae and(or) flaxseed oil (Table 5). At week 2 (Table 6 and Table 8), saturated fatty acid ("SFA") concentrations of egg yolk were decreased (P<0.05) with increases in flaxseed oil or microalgae supplementation. Mono-unsaturated fatty acid ("MUFA") contents were decreased (P<0.05) by 5% flaxseed oil and both 7.5% and 10% microalgae. Concentrations of PUFA and n-3 fatty acids were elevated (P<0.05) by flaxseed oil, but were not affected by microalgae supplementation. Concentrations of n-6 and n-9 fatty acids were decreased (P<0.05) by 5% flaxseed oil and (or) 10% microalgae. At week 4 (Table 7 and Table 9), concentrations of SFA in egg yolk were decreased (P<0.05) by flaxseed oil and microalgae, and so were concentrations of MUFA by microalgae. While concentrations of PUFA were enhanced (P<0.05) by both flaxseed oil and microalgae, concentrations of n-3 fatty acids were elevated (P<0.05) by flaxseed oil, with a greater (P<0.05) increment in the presence of 10% microalgae. Concentrations of n-9 fatty acids were decreased (P<0.05) by microalgae.

TABLE 5

Egg Production, Egg Component, and Fatty Acid Profiles of Egg in Experiment I

| | | Flaxseed oil, % | | | | | | | | | | |
|---|---|---|---|---|---|---|---|---|---|---|---|---|
| | | 0 | 3 | 5 | 0 | 0 | 3 | 3 | 5 | 5 | | |
| | | | | | | Algae A, % | | | | | Pooled | |
| | | 0 | 0 | 0 | 7.5 | 10 | 7.5 | 10 | 7.5 | 10 | SEM | Factor* |
| Egg production (28 days) | | | | | | | | | | | | |
| | Number | 27.11 | 27.20 | 26.90 | 27.20 | 27.20 | 27.90 | 26.80 | 27.20 | 27.60 | 0.22 | |
| Egg component weight, g | | | | | | | | | | | | |
| | Egg | 56.85 | 56.15 | 56.77 | 56.30 | 55.95 | 55.89 | 57.11 | 55.46 | 56.85 | 0.21 | |
| | Albumen | 33.93 | 32.91 | 34.51 | 34.20 | 33.40 | 33.34 | 34.70 | 33.55 | 34.24 | 0.17 | |
| | Yolk | 14.86 | 15.03 | 14.70 | 13.78 | 14.44 | 14.58 | 14.37 | 14.04 | 14.72 | 0.08 | |
| | Shell | 5.63 | 5.76 | 5.68 | 5.78 | 5.53 | 5.54 | 5.60 | 5.60 | 5.93 | 0.03 | |
| Fatty acids content, mg/egg | | | | | | | | | | | | |
| Week 2 | | | | | | | | | | | | |
| | SFA | 1623.1$^a$ | 1404.6$^b$ | 1275.6$^c$ | 1468.9$^c$ | 1584.7$^a$ | 1366.4$^b$ | 1374.0$^b$ | 1263.2$^c$ | 1305.1$^c$ | 19.3 | F, A, FA |
| | MUFA | 1923.6$^a$ | 1908.0$^a$ | 1728.2$^{bc}$ | 1735.2$^c$ | 1740.6$^c$ | 1768.5$^c$ | 1727.2$^{bc}$ | 1634.9$^c$ | 1693.1$^{bc}$ | 16.3 | F, A |
| | PUFA | 428.4$^d$ | 713.0$^b$ | 933.7$^a$ | 475.6$^{cd}$ | 527.8$^c$ | 759.4$^b$ | 738.9$^b$ | 855.8$^a$ | 949.2$^a$ | 29.2 | F |
| | n-3 | 61.3$^d$ | 485.1$^c$ | 697.7$^a$ | 76.4$^d$ | 69.5$^d$ | 478.9$^c$ | 423.5$^c$ | 624.5$^b$ | 633.9$^{ab}$ | 37.5 | F |
| | n-6 | 367.1$^{bc}$ | 227.9$^d$ | 236.0$^d$ | 399.2$^{ab}$ | 458.3$^a$ | 280.6$^{cd}$ | 315.4$^{bcd}$ | 231.3$^d$ | 315.2$^{bcd}$ | 14.1 | F, A |
| | n-9 | 1793.0$^a$ | 1774.1$^a$ | 1611.8$^b$ | 1594.2$^{bc}$ | 1578.1$^{bc}$ | 1604.5$^b$ | 1558.8$^{bc}$ | 1486.9$^c$ | 1521.1$^{bc}$ | 18.1 | F, A |
| Week 4 | | | | | | | | | | | | |
| | SFA | 1421.4$^a$ | 1320.4$^b$ | 1244.4$^{cd}$ | 1252.5$^{cd}$ | 1320.5$^b$ | 1266.3$^c$ | 1256.7$^{cd}$ | 1209.4$^d$ | 1233.7$^{cd}$ | 10.3 | F, A, FA |
| | MUFA | 1697.4$^{ab}$ | 1801.4$^a$ | 1665.1$^b$ | 1530.5$^{cd}$ | 1477.9$^d$ | 1606.1$^{bc}$ | 1528.8$^{cd}$ | 1545.0$^{cd}$ | 1535.5$^{cd}$ | 18.4 | F, A |
| | PUFA | 870.0$^e$ | 910.7$^{de}$ | 1030.3$^{bc}$ | 939.8$^{bcd}$ | 1073.4$^{ab}$ | 1032.5$^{bc}$ | 1063.0$^{ab}$ | 1004.6$^{bcd}$ | 1169.3$^a$ | 17.3 | F, A |
| | n-3 | 39.4$^e$ | 343.0$^c$ | 421.8$^b$ | 48.1$^e$ | 46.2$^e$ | 356.0$^c$ | 296.7$^d$ | 435.0$^b$ | 519.1$^a$ | 26.8 | F, FA |

TABLE 5-continued

Egg Production, Egg Component, and Fatty Acid Profiles of Egg in Experiment I

| | Flaxseed oil, % | | | | | | | | | |
|---|---|---|---|---|---|---|---|---|---|---|
| | 0 | 3 | 5 | 0 | 0 | 3 | 3 | 5 | 5 | |
| | | | | Algae A, % | | | | | | Pooled |
| | 0 | 0 | 0 | 7.5 | 10 | 7.5 | 10 | 7.5 | 10 | SEM | Factor* |
| n-6 | 830.7$^{bc}$ | 567.8$^e$ | 608.6$^{ed}$ | 891.7$^b$ | 1027.2$^a$ | 681.6$^d$ | 766.3$^c$ | 569.6$^e$ | 650.2$^{de}$ | 23.7 | F, A, FA |
| n-9 | 1603.5$^{ab}$ | 1699.7$^a$ | 1566.2$^{bc}$ | 1401.2$^d$ | 1373.4$^d$ | 1476.2$^{cd}$ | 1401.3$^d$ | 1424.5$^d$ | 1395.6$^d$ | 20.0 | A |

$^{a-e}$Means in same row without a common letter differ (P < 0.05).
*Factor determined by two way ANOVA, A; microalgae, F; flaxseed oil, FA; microalgae and flaxseed oil interaction (P < 0.05).
SFA, saturated fatty acid; MUFA, mono-unsaturated fatty acids; PUFA, polyunsaturated fatty acids; n-3, omega-3 fatty acids; n-6, omega-6 fatty acids; n-9;, omega-9 fatty acids.
Fatty acids composition of each week provided in supplemental tables.

TABLE 6

Fatty Acid Composition (%) of Egg Yolk from Experiment I (Week 2)

| | Flaxseed oil, % | | | | | | | | | |
|---|---|---|---|---|---|---|---|---|---|---|
| | 0 | 3 | 5 | 0 | 0 | 3 | 3 | 5 | 5 | |
| | | | | Algae A, % | | | | | | Pooled |
| | 0 | 0 | 0 | 7.5 | 10 | 7.5 | 10 | 7.5 | 10 | SEM | Factor* |
| C16:0 | 31.41$^a$ | 25.92$^b$ | 23.26$^c$ | 30.28$^a$ | 31.23$^a$ | 25.92$^c$ | 26.55$^c$ | 24.31$^c$ | 23.58$^c$ | 0.48 | F |
| C16:1n7 | 3.25$^{cd}$ | 3.30$^{bcd}$ | 2.93$^d$ | 3.79$^{abc}$ | 4.17$^a$ | 4.17$^a$ | 4.34$^a$ | 3.90$^{ab}$ | 4.08$^a$ | 0.09 | A |
| C18:0 | 9.05 | 8.69 | 8.88 | 9.21 | 9.42 | 8.79 | 8.86 | 9.02 | 9.26 | 0.08 | |
| C18:1n9 | 44.36$^a$ | 43.49$^a$ | 40.37$^{bc}$ | 42.50$^{ab}$ | 40.13$^{bc}$ | 40.51$^{bc}$ | 39.93$^{bc}$ | 39.01$^c$ | 38.07$^c$ | 0.40 | F, A |
| C18:2n6 | 6.67$^{bc}$ | 4.42$^e$ | 4.85$^{cd}$ | 8.04$^{ab}$ | 8.93$^a$ | 5.66$^{cd}$ | 6.47$^{bcd}$ | 4.96$^{de}$ | 6.70$^{bc}$ | 0.29 | F, A |
| C18:3n3 | 0.47$^c$ | 8.36$^b$ | 14.08$^a$ | 0.63$^c$ | 0.57$^c$ | 8.38$^b$ | 7.64$^b$ | 12.85$^a$ | 12.56$^a$ | 0.80 | F |
| C18:3n6 | 0.16$^a$ | 0.08$^c$ | 0.07$^c$ | 0.18$^a$ | 0.19$^a$ | 0.03$^e$ | 0.09$^b$ | 0.03$^c$ | 0.03$^c$ | 0.01 | F, FA |
| C20:1n9 | 0.33$^a$ | 0.23$^{bcd}$ | 0.24$^{bc}$ | 0.35$^a$ | 0.35$^a$ | 0.25$^b$ | 0.24$^b$ | 0.21$^{cd}$ | 0.20$^d$ | 0.01 | A |
| C20:2n6 | 0.26$^c$ | 0.12$^f$ | 0.14$^{ef}$ | 0.35$^b$ | 0.40$^a$ | 0.17$^{de}$ | 0.19$^d$ | 0.13$^e$ | 0.12$^f$ | 0.01 | F, A, FA |
| C20:3n6 | 0.32$^b$ | 0.25$^c$ | 0.26$^c$ | 0.39$^a$ | 0.42$^a$ | 0.33$^b$ | 0.32$^b$ | 0.27$^c$ | 0.26$^c$ | 0.01 | F, A, FA |
| C20:4n6 | 1.74$^a$ | 0.76$^d$ | 0.62$^e$ | 1.77$^a$ | 1.82$^a$ | 0.93$^c$ | 1.06$^b$ | 0.70$^{de}$ | 0.83$^{cd}$ | 0.07 | |
| C20:5n3 | N.D.$^e$ | 0.32$^b$ | 0.39$^a$ | N.D.$^e$ | N.D.$^e$ | 0.24$^c$ | 0.18$^d$ | 0.33$^b$ | 0.37$^{ab}$ | 0.02 | F, A, FA |
| C22:6n3 | 1.06$^d$ | 3.28$^{ab}$ | 3.10$^b$ | 1.43$^c$ | 1.22$^c$ | 3.55$^a$ | 3.09$^b$ | 3.30$^{ab}$ | 3.02$^b$ | 0.14 | F, A |
| SFA | 40.46$^{ab}$ | 34.61$^c$ | 32.14$^e$ | 39.49$^b$ | 40.65$^a$ | 34.71$^c$ | 35.41$^c$ | 33.33$^d$ | 32.84$^{de}$ | 0.48 | F |
| MUFA | 47.94$^a$ | 47.02$^{ab}$ | 43.54$^{de}$ | 46.64$^{abc}$ | 44.65$^a$ | 44.93$^{bcd}$ | 44.51$^{cde}$ | 43.12$^{ed}$ | 42.35$^e$ | 0.31 | F, A |
| PUFA | 10.68$^d$ | 17.62$^b$ | 23.57$^a$ | 12.79$^{cd}$ | 13.55$^c$ | 19.33$^b$ | 19.07$^b$ | 22.61$^a$ | 23.92$^a$ | 0.71 | F |
| n-3 | 1.53$^e$ | 11.95$^b$ | 17.57$^a$ | 2.06$^c$ | 1.79$^c$ | 12.17$^b$ | 10.91$^b$ | 16.48$^a$ | 15.95$^a$ | 0.93 | F |
| n-6 | 9.15$^{bc}$ | 5.66$^e$ | 6.00$^{de}$ | 10.73$^{ab}$ | 11.76$^a$ | 7.16$^{cde}$ | 8.16$^{cd}$ | 6.13$^{de}$ | 7.97$^{cd}$ | 0.36 | F, A |
| n-9 | 44.69$^a$ | 43.72$^a$ | 40.61$^{bc}$ | 42.85$^{ab}$ | 40.48$^{bc}$ | 40.76$^{bc}$ | 40.17$^{bc}$ | 39.22$^c$ | 38.27$^c$ | 0.39 | F, A |

$^{a-f}$Means in same row without a common letter differ by one-way ANOVA with Duncan's multiple range test (P < 0.05).
*Factor determined by two way ANOVA, A; algae, F; flaxseed oil, FA; algae and flaxseed oil interaction.
ND.; not detected;
SFA; saturated fatty acid, MUFA; mono-unsaturated fatty acid, PUFA; poly-unsaturated fatty acid, n-3; omega-3 fatty acids,n-6; omega-6 fatty acids, n-9; omega-9 fatty acids.

TABLE 7

Fatty Acid Composition (%) of Egg Yolk from Experiment I (Week 4)

| | Flaxseed oil, % | | | | | | | | | |
|---|---|---|---|---|---|---|---|---|---|---|
| | 0 | 3 | 5 | 0 | 0 | 3 | 3 | 5 | 5 | |
| | | | | Algae A, % | | | | | | Pooled |
| | 0 | 0 | 0 | 7.5 | 10 | 7.5 | 10 | 7.5 | 10 | SEM | Factor* |
| C16:0 | 25.82$^a$ | 23.2$^c$ | 22.49$^c$ | 24.71$^b$ | 24.53$^b$ | 23.21$^c$ | 23.36$^c$ | 22.33$^{cd}$ | 21.67$^d$ | 0.22 | F |
| C16:1n7 | 2.34$^b$ | 2.51$^b$ | 2.49$^b$ | 2.74$^b$ | 2.68$^b$ | 3.30$^a$ | 3.28$^a$ | 3.18$^a$ | 3.52$^a$ | 0.08 | F, A |
| C18:0 | 9.6 | 9.33 | 8.87 | 8.96 | 9.34 | 8.96 | 9.03 | 9.58 | 9.38 | 0.08 | |
| C18:1n9 | 39.76$^{ab}$ | 41.70$^b$ | 39.28$^{ab}$ | 37.39$^{bc}$ | 35.00$^c$ | 37.32$^{bc}$ | 35.94$^c$ | 37.42$^{bc}$ | 34.96$^c$ | 0.43 | A |
| C18:2n6 | 17.25$^{cd}$ | 12.45$^g$ | 13.81$^{efg}$ | 21.04$^b$ | 23.08$^a$ | 15.55$^c$ | 17.72$^c$ | 13.63$^{bc}$ | 14.83$^{ef}$ | 0.53 | F, A, FA |
| C18:3n3 | 0.27$^d$ | 5.68$^b$ | 7.50$^b$ | 0.34$^d$ | 0.35$^d$ | 5.95$^b$ | 5.01$^b$ | 8.57$^b$ | 10.12$^a$ | 0.54 | F, FA |
| C18:3n6 | 0.14$^a$ | 0.07$^c$ | 0.07$^c$ | 0.12$^{ab}$ | 0.14$^a$ | 0.08$^c$ | 0.09$^c$ | 0.06$^c$ | 0.07$^c$ | 0.01 | F |
| C20:1n9 | 0.20$^{bc}$ | 0.19$^c$ | 0.19$^{bc}$ | 0.27$^a$ | 0.22$^{ab}$ | 0.18$^{bc}$ | 0.18$^{bc}$ | 0.16$^{bc}$ | 0.15$^c$ | 0.01 | F |

TABLE 7-continued

Fatty Acid Composition (%) of Egg Yolk from Experiment I (Week 4)

| | Flaxseed oil, % | | | | | | | | | | |
|---|---|---|---|---|---|---|---|---|---|---|---|
| | 0 | 3 | 5 | 0 | 0 | 3 | 3 | 5 | 5 | Pooled | |
| | | | | Algae A, % | | | | | | | |
| | 0 | 0 | 0 | 7.5 | 10 | 7.5 | 10 | 7.5 | 10 | SEM | Factor* |
| C20:2n6 | 0.18[b] | 0.09[d] | 0.10[d] | 0.17[bc] | 0.25[a] | 0.12[cd] | 0.14[bcd] | 0.10[c] | 0.10[c] | 0.01 | F, A |
| C20:3n6 | 0.26[ab] | 0.2[c] | 0.22[bc] | 0.24[abc] | 0.29[a] | 0.24[bc] | 0.24[abc] | 0.21[c] | 0.21[c] | 0.01 | F |
| C20:4n6 | 2.88[a] | 1.18[ed] | 1.12[ed] | 2.4[c] | 2.59[c] | 1.32[d] | 1.55[c] | 1.03[e] | 1.14[de] | 0.11 | F, A, FA |
| C20:5n3 | N.D.[e] | 0.24[b] | 0.21[bc] | N.D.[e] | N.D.[e] | 0.18[c] | 0.13[d] | 0.28[e] | 0.30[a] | 0.02 | F, A |
| C22:6n3 | 0.71[e] | 2.53[c] | 2.92[a] | 0.95[d] | 0.83[de] | 2.79[ab] | 2.50[c] | 2.63[bc] | 2.65[bc] | 0.13 | F, FA |
| SFA | 35.42[a] | 32.53[d] | 31.36[d] | 33.67[bc] | 33.87[b] | 32.17[d] | 32.39[cd] | 31.91[d] | 31.05[d] | 0.21 | F |
| MUFA | 42.30[ab] | 44.40[a] | 41.96[ab] | 40.40[bc] | 37.90[c] | 40.80[bc] | 39.40[bc] | 40.76[bc] | 38.63[c] | 0.38 | A |
| PUFA | 21.69[d] | 22.44[cd] | 25.95[b] | 25.26[bc] | 27.53[ab] | 26.23[c] | 27.38[ab] | 26.51[ab] | 29.42[a] | 0.45 | F, A |
| n-3 | 0.98[e] | 8.45[cd] | 10.63[b] | 1.29[e] | 1.18[e] | 8.92[c] | 7.64[d] | 11.48[b] | 13.07[a] | 0.64 | F, FA |
| n-6 | 20.71[c] | 13.99[f] | 15.32[def] | 23.97[b] | 26.35[a] | 17.31[d] | 19.74[c] | 15.03[ef] | 16.35[ed] | 0.62 | F, A, FA |
| n-9 | 39.96[ab] | 41.89[a] | 39.47[ab] | 37.66[bc] | 35.22[c] | 37.50[bc] | 36.12[c] | 37.58[bc] | 35.11[c] | 0.43 | A |

[a-g]Means in same row without a common letter differ by one-way ANOVA with Duncan's multiple range test (P < 0.05).
*Factor determined by two way ANOVA, A; algae, F; flaxseed oil, FA; algae and flaxseed oil interaction.
ND.; not detected;
SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

TABLE 8

Fatty Acid Content (mg/egg Yolk) of Egg Yolk from Experiment I (Week 2)

| | Flaxseed oil, % | | | | | | | | | | |
|---|---|---|---|---|---|---|---|---|---|---|---|
| | 0 | 3 | 5 | 0 | 0 | 3 | 3 | 5 | 5 | Pooled | |
| | | | | Algae A, % | | | | | | | |
| | 0 | 0 | 0 | 7.5 | 10 | 7.5 | 10 | 7.5 | 10 | SEM | Factor* |
| C16:0 | 1260.1[a] | 1052.0[c] | 923.0[d] | 1126.4[c] | 1217.5[a] | 1020.2[c] | 1030.2[c] | 921.4[d] | 937.1[d] | 18.4 | F, A, FA |
| C16:1n7 | 130.6[cd] | 133.8[cd] | 116.4[d] | 141.0[bcd] | 162.5[ab] | 164.0[b] | 168.5[a] | 148.0[abc] | 162.0[ab] | 3.5 | A |
| C18:0 | 362.9 | 352.6 | 352.6 | 342.5 | 367.2 | 346.2 | 343.8 | 341.8 | 368.0 | 3.4 | |
| C18:1n9 | 1779.9[a] | 1764.9[a] | 1602.3[b] | 1581.2[bc] | 1564.5[bc] | 1594.8[b] | 1549.3[bc] | 1479.0[c] | 1513.2[bc] | 18.0 | F, A |
| C18:2n3 | 267.5[abc] | 179.3[d] | 192.6[cd] | 299.3[ab] | 348.3[a] | 222.9[bcd] | 251.0[bcd] | 188.0[cd] | 266.2[abc] | 11.3 | F, A |
| C18:3n3 | 18.8[a] | 339.4[c] | 558.9[a] | 23.4[c] | 22.0[c] | 329.7[c] | 296.5[c] | 487.1[b] | 499.0[a] | 31.6 | F |
| C18:3n6 | 6.2[a] | 3.1[c] | 2.7[c] | 6.6[a] | 7.3[a] | 1.3[c] | 3.5[b] | 1.3[c] | 1.1[c] | 0.4 | F, A, FA |
| C20:1n9 | 13.2[a] | 9.3[b] | 9.4[b] | 13.0[a] | 13.5[a] | 9.7[b] | 9.5[b] | 7.9[c] | 7.9[c] | 0.3 | F |
| C20:2n6 | 10.6[c] | 4.8[f] | 5.5[ef] | 13.1[b] | 15.6[a] | 6.7[ed] | 7.4[d] | 4.9[f] | 4.9[f] | 0.6 | F, A, FA |
| C20:3n6 | 13.0[bc] | 10.1[d] | 10.5[d] | 14.4[b] | 16.4[a] | 13.1[bc] | 12.5[c] | 10.3[d] | 10.2[d] | 0.3 | F, A, FA |
| C20:4n6 | 69.7[a] | 30.7[e] | 24.8[f] | 65.9[a] | 70.8[a] | 36.6[bc] | 41.0[b] | 26.7[ef] | 32.8[cd] | 2.8 | F, A, FA |
| C20:5n3 | N.D.[f] | 12.8[ab] | 15.6[a] | N.D.[f] | N.D.[f] | 9.4[c] | 7.1[e] | 12.4[c] | 14.8[ab] | 1.0 | F, A, FA |
| C22:6n3 | 42.6[d] | 132.9[ab] | 123.2[bc] | 53.1[d] | 47.5[d] | 139.8[a] | 120.0[c] | 125.0[c] | 120.1[c] | 5.8 | F, A |
| SFA | 1623.1[a] | 1404.6[c] | 1275.6[d] | 1468.9[d] | 1584.7[a] | 1366.4[c] | 1374.0[c] | 1263.2[d] | 1305.1[d] | 19.3 | F, A, FA |
| MUFA | 1923.6[a] | 1908.0[a] | 1728.2[bc] | 1735.2[c] | 1740.6[c] | 1768.5[c] | 1727.2[bc] | 1634.9[c] | 1693.1[bc] | 16.3 | F, A |
| PUFA | 428.4[d] | 713.0[b] | 933.7[a] | 475.6[cd] | 527.8[c] | 759.4[b] | 738.9[b] | 855.8[a] | 949.2[a] | 29.2 | F |
| n-3 | 61.3[d] | 485.1[d] | 697.7[a] | 76.4[d] | 69.5[d] | 478.9[c] | 423.5[c] | 624.5[b] | 633.9[ab] | 37.5 | F |
| n-6 | 367.1[bc] | 227.9[d] | 236.0[d] | 399.2[ab] | 458.3[a] | 280.6[cd] | 315.4[bcd] | 231.3[d] | 315.2[bcd] | 14.1 | F, A |
| n-9 | 1793.0[a] | 1774.2[a] | 1611.8[b] | 1594.2[bc] | 1578.1[bc] | 1604.5[b] | 1558.8[bc] | 1486.9[c] | 1521.1[bc] | 18.1 | F, A |

[a-f]Means in same row without a common letter differ by one-way ANOVA with Duncan's multiple range test (P < 0.05).
*Factor determined by two way ANOVA, A; algae, F; flaxseed oil, FA; algae and flaxseed oil interaction.
ND.; not detected;
SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

TABLE 9

Fatty Acid Content (mg/egg Yolk) of Egg Yolk from Experiment I (Week 4)

| | Flaxseed oil, % | | | | | | | | | Pooled | |
|---|---|---|---|---|---|---|---|---|---|---|---|
| | 0 | 3 | 5 | 0 | 0 | 3 | 3 | 5 | 5 | | |
| | | | | Algae A, % | | | | | | | |
| | 0 | 0 | 0 | 7.5 | 10 | 7.5 | 10 | 7.5 | 10 | SEM | Factor* |
| C16:0 | 1036.1$^a$ | 941.7$^{bc}$ | 892.5$^{ed}$ | 919.3$^{bcd}$ | 956.4$^b$ | 913.7$^{bcd}$ | 906.4$^{cd}$ | 846.4$^f$ | 861.1$^{ef}$ | 9.0 | F, A, FA |
| C16:1n7 | 93.9$^d$ | 101.7$^d$ | 98.9$^d$ | 101.9$^d$ | 104.5$^{cd}$ | 129.8$^{ab}$ | 127.4$^{ab}$ | 120.5$^{bc}$ | 140.0$^a$ | 2.9 | F, A |
| C18:0 | 385.3 | 378.8 | 352.0 | 333.2 | 364.0 | 352.7 | 350.3 | 363.0 | 372.6 | 3.5 | |
| C18:1n9 | 1595.4$^{ab}$ | 1692.1$^a$ | 1558.9$^{bc}$ | 1391.2$^d$ | 1364.7$^d$ | 1469.2$^{cd}$ | 1394.4$^d$ | 1418.6$^d$ | 1389.5$^d$ | 19.9 | A |
| C18:2n6 | 692.0$^c$ | 505.4$^e$ | 548.3$^{ed}$ | 782.6$^b$ | 899.9$^a$ | 612.3$^d$ | 687.5$^c$ | 516.8$^e$ | 589.5$^d$ | 20.0 | F, A, FA |
| C18:3n6 | 5.8$^a$ | 2.8$^c$ | 2.9$^c$ | 4.3$^b$ | 5.6$^a$ | 3.2$^{bc}$ | 3.5$^{bc}$ | 2.3$^c$ | 2.9$^c$ | 0.2 | F |
| C18:3n3 | 10.8$^d$ | 230.6$^c$ | 297.7$^b$ | 12.5$^d$ | 13.8$^d$ | 234.1$^c$ | 194.5$^c$ | 324.7$^b$ | 402.2$^a$ | 21.4 | F, FA |
| C20:1n9 | 8.1$^{abc}$ | 7.6$^{abc}$ | 7.4$^{bc}$ | 10.0$^a$ | 8.6$^{ab}$ | 7.1$^c$ | 7.0$^{bc}$ | 5.9$^c$ | 6.1$^c$ | 0.3 | F |
| C20:2n6 | 7.1$^b$ | 3.6$^d$ | 4.1$^d$ | 6.5$^{bc}$ | 9.7$^a$ | 4.9$^{cd}$ | 5.5$^{bcd}$ | 3.6$^d$ | 4.1$^d$ | 0.3 | F, A |
| C20:3n6 | 10.5$^{ab}$ | 8.2$^c$ | 8.8$^{bc}$ | 9.1$^{bc}$ | 11.2$^a$ | 9.4$^{bc}$ | 9.5$^{abc}$ | 7.9$^c$ | 8.3$^c$ | 0.2 | F |
| C20:4n6 | 115.4$^a$ | 47.8$^b$ | 44.5$^{ef}$ | 89.2$^c$ | 100.9$^d$ | 51.8$^e$ | 60.3$^d$ | 39.1$^f$ | 45.5$^{ef}$ | 4.1 | F, A, FA |
| C20:5n3 | N.D.$^f$ | 9.7$^b$ | 8.3$^c$ | N.D.$^f$ | N.D.$^f$ | 6.9$^d$ | 5.1$^e$ | 10.5$^{ab}$ | 11.8$^a$ | 0.7 | F, FA |
| C22:6n3 | 28.6$^e$ | 102.7$^{bcd}$ | 115.8$^a$ | 35.5$^e$ | 32.4$^e$ | 109.9$^{ab}$ | 97.1$^d$ | 99.7$^{cd}$ | 105.2$^{bc}$ | 5.3 | F, FA |
| SFA | 1421.4$^a$ | 1320.4$^b$ | 1244.6$^{cd}$ | 1252.5$^{cd}$ | 1320.5$^b$ | 1266.3$^c$ | 1256.7$^{cd}$ | 1209.4$^d$ | 1233.7$^{cd}$ | 10.3 | F, A, FA |
| MUFA | 1697.4$^{ab}$ | 1801.4$^a$ | 1665.1$^b$ | 1530.5$^{cd}$ | 1477.9$^d$ | 1606.1$^{bc}$ | 1528.8$^{cd}$ | 1545.0$^{cd}$ | 1535.5$^{cd}$ | 18.4 | F, A |
| PUFA | 870.0$^a$ | 910.7$^{ed}$ | 1030.3$^{bc}$ | 939.7$^{bcd}$ | 1073.4$^{ab}$ | 1032.5$^{bc}$ | 1063.0$^{ab}$ | 1004.6$^{bcd}$ | 1169.3$^a$ | 17.3 | F |
| n-3 | 39.4$^e$ | 343.0$^c$ | 421.8$^b$ | 48.1$^e$ | 46.2$^e$ | 356.0$^c$ | 296.7$^d$ | 435.0$^b$ | 519.1$^a$ | 26.8 | F, FA |
| n-6 | 830.7$^{bc}$ | 567.8$^e$ | 608.6$^{ed}$ | 891.7$^b$ | 1027.5$^a$ | 681.6$^d$ | 766.3$^c$ | 569.6$^e$ | 650.2$^{de}$ | 23.7 | F, A, FA |
| n-9 | 1603.5$^{ab}$ | 1699.7$^a$ | 1566.2$^{bc}$ | 1401.2$^d$ | 1373.4$^d$ | 1476.2$^{cd}$ | 1401.3$^d$ | 1424.5$^d$ | 1395.6$^d$ | 20.0 | A |

$^{a-f}$Means in same row without a common letter differ by one-way ANOVA with Duncan's multiple range test (P < 0.05).
*Factor determined by two way ANOVA, A; algae, F; flaxseed oil, FA; algae and flaxseed oil interaction.
N.D.; not detected; SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

Experiment II Results

Dietary treatments exerted no effects on body weight, feed intake, or plasma uric acid and inorganic phosphorus concentrations or AKP activity (Table 10). Likewise, egg production or egg and egg component weights were not affected by dietary treatments (Table 11).

TABLE 10

Body Weight, Feed Intake, and Plasma Biomarkers of Hens in Exp. II

| | Flaxseed oil, % | | | | | |
|---|---|---|---|---|---|---|
| | 0 | 3 | 3 | 3 | 3 | |
| | | | Algae % | | | |
| | 0 | Algae A 7.5% | Algae B 7.5% | Algae C 7.5% | Algae C 15% | Pooled SEM |
| | | | Body Weight, g | | | |
| Week 0 | 1756 | 1690 | 1632 | 1729 | 1766 | 29 |
| Week 4 | 1675 | 1706 | 1634 | 1710 | 1561 | 23 |
| | | | Average Daily Feed Intake, g | | | |
| Week 0 to 4 | 113.04 | 112.01 | 119.73 | 111.90 | 100.60 | 2.28 |
| | | | Plasma Biomarkers | | | |
| UA#, mg/dL | 9.65 | 10.56 | 9.61 | 9.03 | 10.26 | 0.56 |
| AKP, U/L | 189.53 | 222.32 | 179.21 | 185.46 | 239.65 | 19.78 |
| PIP, ppm | 7.48 | 7.52 | 7.91 | 5.56 | 5.03 | 0.52 |

UA; uric acid, PIP; plasma inorganic phosphorus, AKP; alkaline phosphatase activity.

TABLE 11

Egg Production, Egg Component, Egg Fatty Acid Profile in Exp. II

| | Flaxseed oil, % | | | | | |
|---|---|---|---|---|---|---|
| | 0% | 3% | 3% | 3% | 3% | |
| | | | Algae % | | | |
| | 0% | Algae A 7.5% | Algae B 7.5% | Algae C 7.5% | Algae C 15% | Pooled SEM |
| | | | Egg production | | | |
| Number | 26.50 | 24.90 | 25.20 | 25.70 | 25.90 | 0.27 |
| | | | Egg component weight, g | | | |
| Egg | 62.35 | 60.39 | 59.75 | 60.31 | 59.84 | 0.36 |
| Albumen | 36.18 | 33.74 | 34.45 | 34.65 | 35.69 | 0.26 |
| Yolk | 16.99 | 17.49 | 16.80 | 16.81 | 16.12 | 0.15 |
| Shell | 6.11 | 5.75 | 5.86 | 5.67 | 5.64 | 0.06 |
| | | | Fatty acid content, mg/egg | | | |
| Week 2 | | | | | | |
| SFA | 1631.4$^a$ | 1582.3$^{ab}$ | 1516.1$^c$ | 1539.8$^{bc}$ | 1413.5$^d$ | 16.3 |
| MUFA | 1943.1$^a$ | 2009.6$^a$ | 1925.8$^a$ | 1928.5$^a$ | 1727.9$^b$ | 25.0 |
| PUFA | 988.8 | 1105.5 | 1069.5 | 1045.4 | 1174.3 | 26.6 |
| n-3 | 53.4$^b$ | 350.5$^a$ | 373.6$^a$ | 359.0$^a$ | 388.6$^a$ | 27.2 |
| n-6 | 935.5$^a$ | 755.0$^b$ | 695.8$^b$ | 686.4$^b$ | 785.7$^b$ | 26.0 |
| n-9 | 1834.8$^a$ | 1858.7$^a$ | 1807.0$^a$ | 1812.0$^a$ | 1587.6$^a$ | 24.0 |
| Week 4 | | | | | | |
| SFA | 1619.2$^a$ | 1545.4$^b$ | 1495.3$^c$ | 1528.0$^{bc}$ | 1442.5$^d$ | 14.5 |
| MUFA | 1942.4$^a$ | 1967.3$^a$ | 1905.1$^a$ | 1927.2$^a$ | 1723.9$^b$ | 24.2 |
| PUFA | 991.5$^b$ | 1167.9$^a$ | 1097.0$^a$ | 1055.8$^{ab}$ | 1142.5$^a$ | 22.3 |
| n-3 | 47.2$^b$ | 354.4$^a$ | 401.4$^a$ | 374.3$^b$ | 398.8$^a$ | 28.2 |
| n-6 | 944.2$^a$ | 813.5$^b$ | 695.6$^c$ | 681.5$^c$ | 743.7$^{bc}$ | 24.4 |
| n-9 | 1830.6$^a$ | 1819.5$^a$ | 1789.3$^a$ | 1979.9$^a$ | 1593.3$^b$ | 26.4 |

$^{a-d}$Means in same row without a common letter differ (P < 0.05).
SFA, saturated fatty acid; MUFA, mono-unsaturated fatty acid; PUFA, poly-unsaturated fatty acid; n-3, omega-3 fatty acids; n-6, omega-6 fatty acids; n-9, omega-9 fatty acids.

At week 2 (Table 12 and Table 13), concentrations of SFA in egg yolk were decreased (P<0.05) by 7.5% Algae B or Algae C (all with 3% flaxseed oils). When the inclusion rate of Algae C was increased to 15%, the decrease was greater (P<0.05). Concentrations of MUFA were (P<0.05) decreased by 15% microalgae C compared with the control. While PUFA concentrations remained unchanged across different treatment groups, concentrations of n-3 and n-6 fatty acids were increased (P<0.05) and decreased (P<0.05), respectively, when diets were supplemented with microalgae (and 3% flaxseed oil) compared with the control. Concentrations of n-9 fatty acids were deceased (P<0.05) by 15% microalgae C compared with other treatments (P<0.05).

TABLE 12

Fatty Acid Composition (%) of Egg from Experiment II (Week 2)

| | Flaxseed oil, % | | | | | |
|---|---|---|---|---|---|---|
| | 0 | 3 | 3 | 3 | 3 | |
| | | | Algae % | | | |
| | 0 | Algae A 7.5 | Algae B 7.5 | Algae C 7.5 | Algae C 15.0 | Pooled SEM |
| C16:0 | 25.73$^a$ | 23.95$^b$ | 23.50$^b$ | 23.95$^b$ | 23.43$^b$ | 0.48 |
| C16:1n7 | 2.33$^c$ | 3.16$^{ab}$ | 2.59$^{bc}$ | 2.73$^{abc}$ | 3.28$^a$ | 0.09 |
| C18:0 | 9.41 | 9.19 | 9.62 | 9.08 | 8.88 | 0.08 |
| C18:1n9 | 39.27$^a$ | 38.74$^a$ | 39.29$^a$ | 38.52$^a$ | 35.46$^b$ | 0.40 |
| C18:2n6 | 17.80 | 14.53 | 14.05 | 14.23 | 16.19 | 0.29 |
| C18:3n3 | 0.33$^c$ | 4.52$^b$ | 5.40$^{ab}$ | 5.43$^{ab}$ | 6.16$^a$ | 0.80 |
| C18:3n6 | 0.14$^a$ | 0.08$^b$ | 0.08$^b$ | 0.09$^b$ | 0.09$^b$ | 0.01 |
| C20:1n9 | 0.25$^a$ | 0.19$^b$ | 0.18$^b$ | 0.18$^b$ | 0.18$^b$ | 0.01 |
| C20:2n6 | 0.18$^a$ | 0.12$^b$ | 0.11$^b$ | 0.11$^b$ | 0.13$^b$ | 0.02 |
| C20:3n6 | 0.26$^a$ | 0.22$^b$ | 0.22$^b$ | 0.20$^b$ | 0.21$^b$ | 0.01 |
| C20:3n3 | N.D.$^c$ | 0.09$^b$ | 0.11$^{ab}$ | 0.10$^b$ | 0.12$^a$ | 0.01 |
| C20:4n6 | 2.68$^c$ | 1.59$^b$ | 1.36$^b$ | 1.60$^b$ | 1.74$^b$ | 0.07 |
| C20:5n3 | N.D.$^d$ | 0.18$^c$ | 0.21$^c$ | 0.29$^b$ | 0.38$^a$ | 0.02 |
| C22:6n3 | 0.82$^b$ | 2.64$^a$ | 2.55$^a$ | 2.67$^a$ | 2.79$^a$ | 0.20 |
| SFA | 35.14$^a$ | 33.14$^b$ | 33.12$^b$ | 33.03$^b$ | 32.31$^b$ | 2.09 |
| MUFA | 41.85$^a$ | 42.09$^a$ | 42.06$^a$ | 41.43$^a$ | 38.92$^b$ | 0.61 |
| PUFA | 22.21$^b$ | 23.88$^b$ | 23.98$^b$ | 24.62$^{ab}$ | 27.69$^a$ | 1.78 |
| n-3 | 1.15$^d$ | 7.34$^c$ | 8.16$^b$ | 8.39$^b$ | 9.33$^a$ | 0.54 |
| n-6 | 21.06$^a$ | 16.54$^b$ | 15.82$^b$ | 16.23$^b$ | 18.36$^{ab}$ | 2.05 |
| n-9 | 39.52 | 38.93 | 39.47 | 38.70 | 35.64 | 2.06 |

$^{a-d}$Means in same row without a common letter differ by one-way ANOVA with Duncan's multiple range test (P < 0.05).
N.D.; not detected; SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

TABLE 13

Fatty Acid Content (mg/egg Yolk) of Egg from Experiment II (Week 2)

| | Flaxseed oil, % | | | | | |
|---|---|---|---|---|---|---|
| | 0 | 3 | 3 | 3 | 3 | |
| | | | Algae % | | | |
| | 0 | Algae A 7.5 | Algae B 7.5 | Algae C 7.5 | Algae C 15.0 | Pooled SEM |
| C16:0 | 1194.6$^a$ | 1143.6$^a$ | 1075.8$^b$ | 1081.4$^b$ | 1026.9$^b$ | 14.7 |
| C16:1n7 | 108.2$^b$ | 150.9$^a$ | 118.8$^b$ | 116.5$^b$ | 140.3$^{ab}$ | 5.2 |
| C18:0 | 436.8 | 438.7 | 440.4 | 458.4 | 386.6 | 11.8 |
| C18:1n9 | 1823.2$^a$ | 1849.8$^a$ | 1798.8$^a$ | 1803.0$^a$ | 1580.2$^b$ | 27.0 |
| C18:2n6 | 825.9$^a$ | 693.7$^b$ | 643.4$^b$ | 628.4$^b$ | 710.5$^{ab}$ | 22.2 |
| C18:3n3 | 15.4$^b$ | 215.6$^a$ | 247.4$^a$ | 229.9$^a$ | 252.5$^a$ | 20.3 |
| C18:3n6 | 8.3$^a$ | 2.4$^b$ | 1.9$^b$ | 2.9$^b$ | 3.9$^b$ | 0.6 |
| C20:1n9 | 11.7$^a$ | 8.9$^b$ | 8.2$^b$ | 9.1$^b$ | 7.4$^b$ | 0.4 |
| C20:2n6 | 10.5$^a$ | 7.7$^b$ | 6.8$^b$ | 7.3$^b$ | 6.3$^b$ | 0.4 |
| C20:3n6 | 12.0$^a$ | 10.4$^b$ | 10.1$^{bc}$ | 9.5$^{bc}$ | 9.1$^c$ | 0.3 |
| C20:4n6 | 78.8$^a$ | 40.8$^b$ | 33.6$^b$ | 38.2$^b$ | 56.0$^b$ | 4.6 |
| C20:5n3 | N.D.$^d$ | 8.8$^c$ | 9.4$^{bc}$ | 12.6$^{ab}$ | 15.4$^a$ | 1.2 |
| C22:6n3 | 38.0$^b$ | 126.1$^a$ | 116.8$^a$ | 116.6$^a$ | 120.7$^a$ | 7.2 |
| SFA | 1631.4$^a$ | 1582.3$^{ab}$ | 1516.1$^c$ | 1539.6$^{bc}$ | 1413.5$^d$ | 16.3 |
| MUFA | 1943.1$^a$ | 2009.6$^a$ | 1925.8$^a$ | 1928.5$^a$ | 1727.9$^b$ | 25.0 |
| PUFA | 988.8 | 1105.5 | 1069.5 | 1045.4 | 1174.3 | 26.6 |
| n-3 | 53.4$^b$ | 350.5$^a$ | 373.6$^a$ | 359.1$^a$ | 388.6$^a$ | 27.2 |
| n-6 | 935.5$^b$ | 755.0$^b$ | 695.8$^b$ | 686.4$^b$ | 785.7$^b$ | 26.0 |
| n-9 | 1834.8$^a$ | 1858.7$^a$ | 1807.0$^a$ | 1812.0$^a$ | 1587.6$^b$ | 24.0 |

$^{a-d}$Means in same row without a common letter differ by one-way ANOVA with Duncan's multiple range test (P < 0.05).
N.D.; not detected; SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

At week 4 (Table 14 and Table 15), eggs from the control treatment contained higher (P<0.05) SFA than those from the other four groups (Table 11, supra). Concentrations of MUFA were decreased (P<0.05) by 15% microalgae C (3% flaxseed oil) compared with the control. Hens fed 7.5% microalgae A and B and 15% microalgae C (3% flaxseed oil) produced eggs containing greater amounts of (P<0.05) PUFA in yolk than control hens. Hens fed microalgae with 3% flaxseed oil produced eggs containing greater amounts of (P<0.05) n-3 fatty acids than the control hens. Concentrations of n-6 fatty acids in egg yolk were lowest in the group fed 7.5% microalgae C, followed by 7.5% microalgae B, 15% microalgae C, and 7.5% microalgae A. Concentrations of n-9 fatty acids were decreased (P<0.05) by 15% microalgae C compared with other treatments.

TABLE 14

Fatty Acid Composition (%) of Egg from Experiment II (Week 4)

| | Flaxseed oil, % | | | | |
| --- | --- | --- | --- | --- | --- |
| | 0 | 3 | 3 | 3 | 3 |
| | | | Algae % | | |
| | 0 | Algae A 7.5 | Algae B 7.5 | Algae C 7.5 | Algae C 15.0 | Pooled SEM |
| C16:0 | 26.20$^a$ | 23.37$^b$ | 23.73$^b$ | 23.62 | 23.33$^b$ | 0.21 |
| C16:1n7 | 2.42 | 3.13 | 2.55 | 2.82 | 3.00 | 0.07 |
| C18:0 | 9.10 | 9.36 | 9.23 | 9.78 | 9.82 | 0.08 |
| C18:1n9 | 39.68 | 38.35 | 39.29 | 39.11 | 36.40 | 0.43 |
| C18:2n6 | 17.40 | 15.26$^{ab}$ | 13.61$^b$ | 13.52$^b$ | 15.04$^{ab}$ | 0.54 |
| C18:3n3 | 0.28$^b$ | 4.76$^a$ | 5.82$^a$ | 5.30$^a$ | 6.03$^a$ | 0.54 |
| C18:3n6 | 0.14$^a$ | 0.08$^b$ | 0.09$^b$ | 0.07$^b$ | 0.08$^b$ | 0.01 |
| C20:1n9 | 0.22$^a$ | 0.18$^{ab}$ | 0.16$^b$ | 0.19$^{ab}$ | 0.21$^a$ | 0.01 |
| C20:2n6 | 0.17$^a$ | 0.12$^{bc}$ | 0.10$^d$ | 0.11$^{cd}$ | 0.14$^b$ | 0.01 |
| C20:3n6 | 0.26 | 0.23 | 0.22 | 0.22 | 0.22 | 0.01 |
| C20:4n6 | 2.61$^a$ | 1.53$^b$ | 1.31$^c$ | 1.52$^b$ | 1.60$^b$ | 0.10 |
| C20:5n3 | N.D.$^d$ | 0.18$^c$ | 0.23$^{bc}$ | 0.31$^{ab}$ | 0.36$^a$ | 0.01 |
| C22:6n3 | 0.75$^b$ | 2.57$^a$ | 2.80$^a$ | 2.57$^a$ | 2.77$^a$ | 0.04 |
| SFA | 35.30$^a$ | 32.73$^b$ | 32.96$^b$ | 33.40$^b$ | 33.15$^b$ | 2.54 |
| MUFA | 42.32 | 41.66 | 42.00 | 42.12 | 39.00 | 1.70 |
| PUFA | 21.61$^b$ | 24.73$^{ab}$ | 24.18$^{ab}$ | 23.62$^b$ | 26.24$^a$ | 0.79 |
| n-3 | 1.03$^c$ | 7.51$^b$ | 8.85$^{ab}$ | 8.18$^{ab}$ | 9.16$^a$ | 0.59 |
| n-6 | 20.58$^a$ | 17.22$^b$ | 15.33$^b$ | 15.44$^b$ | 17.08$^b$ | 1.28 |
| n-9 | 39.90 | 38.53 | 39.45 | 39.30 | 36.61 | 2.21 |

$^{a-d}$Means in same row without a common letter differ by one-way ANOVA with Duncan's multiple range test (P < 0.05).
N.D.; not detected; SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

TABLE 15

Fatty Acid Content (mg/egg) of Egg from Experiment II (Week 4)

| | Flaxseedoil, % | | | | |
| --- | --- | --- | --- | --- | --- |
| | 0 | 3 | 3 | 3 | 3 |
| | | | Algae % | | |
| | 0 | Algae A 7.5 | Algae B 7.5 | Algae C 7.5 | Algae C 15.0 | Pooled SEM |
| C16:0 | 1201.9$^a$ | 1103.5$^b$ | 1076.5$^b$ | 1080.6$^b$ | 1015.2$^c$ | 13.9 |
| C16:1n7 | 110.8 | 147.9 | 115.8 | 129.2 | 130.6 | 4.6 |
| C18:0 | 417.3 | 442.0 | 418.8 | 447.4 | 427.3 | 9.3 |
| C18:1n9 | 1820.3$^a$ | 1810.8$^a$ | 1782.0$^a$ | 1789.4$^a$ | 1584.1$^b$ | 28.2 |
| C18:2n6 | 798.4$^a$ | 720.5$^{ab}$ | 617.3$^c$ | 618.8$^c$ | 654.5$^c$ | 20.3 |
| C18:3n6 | 6.5 | 4.0 | 4.2 | 3.0 | 3.4 | 0.4 |
| C18:3n3 | 12.8$^b$ | 224.6$^a$ | 263.9$^a$ | 242.5$^a$ | 262.5$^a$ | 20.3 |
| C20:1n9 | 10.3$^a$ | 8.7$^{ab}$ | 7.3$^b$ | 8.5$^{ab}$ | 9.1$^a$ | 0.3 |
| C20:2n6 | 8.0$^a$ | 5.8$^b$ | 4.4$^c$ | 6.1$^b$ | 6.3$^b$ | 0.3 |
| C20:3n6 | 11.8 | 10.9 | 10.1 | 10.1 | 9.8 | 0.2 |
| C20:4n6 | 119.5$^a$ | 72.3$^b$ | 59.5$^c$ | 43.6$^d$ | 69.8$^b$ | 5.2 |
| C20:5n3 | N.D.$^d$ | 8.5$^c$ | 10.5$^{bc}$ | 14.1$^{ab}$ | 15.7$^a$ | 1.2 |
| C22:6n3 | 34.4$^b$ | 121.3$^a$ | 127.0$^a$ | 117.8$^a$ | 120.7$^a$ | 7.0 |
| SFA | 1619.2$^a$ | 1545.4$^b$ | 1495.3$^c$ | 1528.0$^{bc}$ | 1442.5$^d$ | 14.5 |
| MUFA | 1942.4$^a$ | 1967.3$^a$ | 1905.1$^a$ | 1927.2$^a$ | 1723.9$^b$ | 24.2 |
| PUFA | 991.5$^b$ | 1167.9$^a$ | 1097.0$^a$ | 1055.79$^{ab}$ | 1142.5$^a$ | 22.3 |
| n-3 | 47.2$^a$ | 354.4$^b$ | 401.4$^b$ | 374.3$^b$ | 398.8$^b$ | 28.2 |
| n-6 | 944.2$^a$ | 813.5$^b$ | 695.6$^b$ | 681.5$^c$ | 743.7$^{bc}$ | 24.4 |
| n-9 | 1830.6$^a$ | 1819.5$^a$ | 1789.3$^a$ | 1980.0$^a$ | 1593.3$^b$ | 26.4 |

$^{a-d}$Means in same row without a common letter differ by one-way ANOVA with Duncan's multiple range test (P < 0.05).
N.D.; not detected; SFA; saturated fatty acid, MUFA; mono-unsaturated fatty acid, PUFA; poly-unsaturated fatty acid, n-3; omega-3 fatty acids, n-6; omega-6 fatty acids, n-9; omega-9 fatty acids.

Discussion

Flaxseed meal and oil are known feed ingredients for producing n-3 fatty acids-enriched eggs. With high content of ALA (Gonzalez-Esquerra et al., "Studies on the Metabolizable Energy Content of Ground Full-Fat Flaxseed Fed in Mash, Pellet, and Crumbled Diets Assayed with Birds of Different Ages," Poultry Science 79:1603-1607 (2000); Jia et al., "The Effect of Enzyme Supplementation on Egg Production Parameters and Omega-3 Fatty Acid Deposition in Laying Hens Fed Flaxseed and Canola Seed," Poultry Science 87:2005-2014 (2008); Jiang et al., "Effects of Feeding Flax and Two Types of Sunflower Seeds on Fatty Acid Compositions of Yolk Lipid Classes," Poultry Science 70:2467-2475 (1991), which are hereby incorporated by reference in their entirety), flaxseed meal supplementation (10%) indeed enriches egg yolk with ALA, docosapentaenoic acid ("DPA"), and DHA compared with corn-soybean meal based diets (Scheideler et al., "The Combined Influence of Dietary Flaxseed Variety, Level, Form, and Storage Conditions on Egg Production and Composition Among Vitamin E-Supplemented Hens," Poultry Science 75:1221-1226 (1996), which is hereby incorporated by reference in its entirety). As flaxseed contains about 45% oil (NRC., "Nutrient Requirements of Poultry," in National Research Council, National Academy Press, Washington, USA (1994), which is hereby incorporated by reference in its entirety), supplementing 5% flaxseed oil in this study is similar to that of 12% flaxseed. However, including more than 10% flaxseed has shown a negative effect on egg production (Leeson et al., "Response of Layers to Dietary Flaxseed According to Body Weight Classification at Maturitym," The Journal of Applied Poultry Research 9:297-302 (2000); Bean et al., "Long-term Effects of Feeding Flaxseed on Performance and Egg Fatty Acid Composition of Brown and White Hens," Poultry Science 82:388-394 (2003), which are hereby incorporated by reference in their entirety). Schumann et al., "Effect of Dietary Flaxseed, Flax Oil and n-3 Fatty Acid Supplement on Hepatic and Plasma Characteristics Relevant to Fatty Liver Haemorrhagic Syndrome in Laying Hens," British Poultry Science 41:465-472 (2000), which is hereby incorporated by reference in its entirety, demonstrated that 5% flaxseed oil supplementation had a negative effect on body and liver weights of hens, probably by decreasing lipid synthesis. In fact, 5% flaxseed oil supplementation caused a decrease in body weight of hens in Experiment I. This negative effect of 5% flaxseed oil on body weights was prevented by 7.5 or 10% microalgae A.

Similar to results of Lipstein et al., "The Nutritional Value of Algae for Poultry. Dried *Chlorella* in Layer Diets," *British Poultry Science* 21:23-27 (1980), which is hereby incorporated by reference in its entirety, the microalgae supplementations did not exert negative effects on egg production, feed intake, egg component traits, or plasma biomarkers of phosphorus and nitrogen metabolism (Ravindran et al., "Phytates: Occurrence, Bioavailability and Implications in Poultry Nutrition," *Poultry and Avian Biology Reviews* (*United Kingdom*) (1995); Sauveur et al., "Plasma Inorganic Phosphorus Concentration During Eggshell Formation. II.— Inverse Relationships with Intestinal Calcium Content and Eggshell Weight," *Reproduction Nutrition Développement* 23:755-764 (1983); Hester et al., "Plasma Inorganic Phosphate, Calcium, and Magnesium Levels of Hens Which Laid Soft-Shelled or Shell-Less Eggs," *Poultry Science* 59:2336-2341 (1980); Hurwitz et al., "The Response of Plasma Alkaline Phosphatase, Parathyroids and Blood and Bone Minerals to Calcium Intake in the Fowl," *The Journal of Nutrition* 73:177-185 (1961), which are hereby incorporated by reference in their entirety).

In Experiment 1, flaxseed oil produced a dose-dependent enrichment of n-3 fatty acids in egg yolk, whereas microalgae A showed no effect alone or in combination with flaxseed oil. This is somewhat different from findings of previous studies (Stamey et al., "Use of Algae or Algal Oil Rich in n-3 Fatty Acids as a Feed Supplement for Dairy Cattle," *Journal of Dairy Science* 95:5269-5275 (2012); Fredriksson et al., "Fatty Acid and Carotenoid Composition of Egg Yolk as an Effect of Microalgae Addition to Feed Formula for Laying Hens," *Food Chemistry* 99:530-537 (2006), which are hereby incorporated by reference in their entirety). One of the reasons could be the lipid concentration and fatty acid profile differences of microalgae between the previous study and the study described here. The microalgae used in one of the previous studies (*N. oculata*) (Fredriksson et al., "Fatty Acid and Carotenoid Composition of Egg Yolk as an Effect of Microalgae Addition to Feed Formula for Laying Hens," *Food Chemistry* 99:530-537 (2006), which is hereby incorporated by reference in its entirety) contained 44.1% of n-3 fatty acids, in comparison with only 1.6% in microalgae A. Compared with week 2, enrichment of n-3 fatty acids in egg yolk by the same levels of flax seed oil seemed to be attenuated at week 4. This was probably due to the high n-3 PUFA, especially ALA, concentration in diets. PUFA (n-3) decreases hepatic lipid biosynthesis and secretion, while promoting proximal β-oxidation of fat (Harris, "Fish Oils and Plasma Lipid and Lipoprotein Metabolism in Humans: A Critical Review," *Journal of Lipid Research* 30:785-807 (1989), which is hereby incorporated by reference in its entirety). Conversion of C18:3n3 (ALA) to C16:0, C16:1n7, C18:0, and C18:1n9 recycles the carbons for longer chain fatty acid (DHA and EPA) synthesis (Burdge et al., "Conversion of α-Linolenic Acid to Palmitic, Palmitoleic, Stearic and Oleic Acids in Men and Women," *Prostaglandins, Leukotrienes and Essential Fatty Acids* 69:283-290 (2003), which is hereby incorporated by reference in its entirety). The major fatty acids in microalgae A are C16:0 and C16:1, and 10% microalgae A with 5% flaxseed oil increased n-3 fatty acids in eggs, especially in C18:3113 (ALA) (Table 9, supra) at the expense of C18:1n9. These results indicate microalgae A might lower recycling of ALA to other non-essential fatty acids and maintain it for producing longer chain fatty acids (DHA and EPA) by supplying other fatty acid sources (C16:0 or C16:1) for recycling carbon sources.

In Experiment II, all three types of microalgae, in the diets containing 3% flaxseed oil, caused very similar enrichments of n-3 fatty acids in egg yolk. Fatty acid profiles of microalgae B and C are different from that of microalgae A. If the sustained production of n-3 fatty acid-fortified eggs were just due to fatty acid profiles (such as C16:0 and C16:1), a diminished n-3 fatty acid content of egg yolk would have been expected from hens fed microalgae B or C. In contrast, these two types of defatted biomass sustained n-3 fortified egg production. This could be due to direct biofortification of n-3 fatty acids from microalgae B and C. Also, all microalgae supplementations decreased n-6 fatty acids in egg yolk. The n-6 fatty acids are important precursors of the eicosanoids for the paracrine system (e.g., prostaglandins, leukotrienes, prostacyclins, thromxanes, and hydroxyacids) (Brenna et al., "International Society for the Study of Fatty Acids and Lipids, ISSFAL. Alpha-Linolenic Acid Supplementation and Conversion to n-3 Long-Chain Polyunsaturated Fatty Acids in Humans," *Prostaglandins Leukot Essent Fatty Acids* 80:85-91 (2009), which is hereby incorporated by reference in its entirety). But in the Western diets, total fat, saturated fat and n-6 fatty acids contents are high, with undesirable ratios of n-6 to n-3 fatty acids (~15) (Fredriksson et al., "Fatty Acid and Carotenoid Composition of Egg Yolk as an Effect of Microalgae Addition to Feed Formula for Laying Hens," *Food Chemistry* 99:530-537 (2006); Simopoulos, "New Products from the Agri-Food Industry: The Return of n-3 Fatty Acids into the Food Supply," *Lipids* 34: S297-S301 (1999), which are hereby incorporated by reference in their entirety). The enzymes delta 6 and delta 5 desaturases are the limiting factors in the balance between n-6 and n-3 fatty acids that compete for the same enzymes. Thus, diets rich in n-6 fatty acids tend to inhibit the formation of EPA and DHA from ALA (Sargent et al., "Requirement Criteria for Essential Fatty Acids," *Journal of Applied Ichthyology* 11:183-198 (1995), which is hereby incorporated by reference in its entirety). The shorter chain ALA needs to be converted into long chain EPA and DHA to have biological activity (Riediger et al., "A Systemic Review of the Roles of n-3 Fatty Acids in Health and Disease," *Journal of the American Dietetic Association* 109:668-679 (2009), which is hereby incorporated by reference in its entirety). These long chain n-3 fatty acids (EPA and DHA) are more rapidly incorporated into plasma and membrane lipids and produce more rapid effects than does ALA (Simopoulos, "Human Requirement for N-3 Polyunsaturated Fatty Acids," *Poultry Science* 79:961-970 (2000), which is hereby incorporated by reference in its entirety). However, humans have less than 5% of conversion of ALA to EPA or DHA (Gerster, H., "Can Adults Adequately Convert Alpha-Linolenic Acid (18: 3n-3) to Eicosapentaenoic Acid (20: 5n-3) and Docosahexaenoic Acid (22: 6n-3)?" *International Journal for Vitamin and Nutrition Research. Internationale Zeitschrift fur Vitamin-und Ernahrungsforschung. Journal international de vitaminologie et de nutrition* 68:159-173 (1997); Brenna, "Efficiency of Conversion of α-Linolenic Acid to Long Chain n-3 Fatty Acids in Man, "*Current Opinion in Clinical Nutrition & Metabolic Care* 5:127-132 (2002), which are hereby incorporated by reference in their entirety). Dietary consumption of ALA-fortified eggs will have limited health promoting effects. Although ALA and DHA content in egg yolk was not changed by supplementation of microalgae with flaxseed oil, EPA content was slightly improved by microalgae supplementation (Table 15, supra). If EPA content in algae is the sole factor that affects EPA content in eggs, eggs from Algae B groups should show less EPA content than that from Algae A groups. The EPA enrichment in egg yolk from the microalgae B group was comparable with that from the microalgae A group, suggesting that EPA in the microalgae was not the sole source of the enrichment and other compounds from microalgae might modulate EPA production.

Fishy smell or off-flavor is a major complaint of consumers of n-3 fatty acid fortified eggs. This is due to a carry-over effect of feed ingredients (fish oil or fish meal) to eggs and/or oxidation of PUFA. For lessening this fishy smell or off flavor of n-3 fatty acid fortified eggs, the level of dietary supplementation of fish oil or fish meal applied to laying hen diets can be limited (Gonzalez-Esquerra et al., "Effect of Feeding Hens Regular or Deodorized Menhaden Oil on Production Parameters, Yolk Fatty Acid Profile, and Sensory Quality of Eggs," *Poultry Science* 79:1597-1602 (2000); Baucells et al., "Incorporation of Different Polyunsaturated Fatty Acids into Eggs," *Poultry Science* 79:51-59 (2000), which are hereby incorporated by reference in their entirety) or high dosage of synthetic anti-oxidants have been supplied into laying hen diets (Meluzzi et al., "Effects of Dietary Vitamin E on the Quality of Table Eggs Enriched with n-3 Long-Chain Fatty Acids," *Poultry Science* 79:539-545 (2000); Parpinello et al., "Sensory Evaluation of Egg Products and Eggs Laid from Hens Fed Diets with Different Fatty Acid Composition and Supplemented with Antioxidants," *Food Research International* 39:47-52 (2006), which are hereby incorporated by reference in their entirety). Besides n-3 fatty acids, microalgae contain high amounts of bioactive nutrients, vitamins, minerals, antioxidants, and carotenoids (Austic et al., "Potential and Limitation of a New Defatted Diatom Microalgal Biomass in Replacing Soybean Meal and Corn in Diets for Broiler Chickens," *Journal of Agricultural and Food Chemistry* 61:7341-7348 (2013), which is hereby incorporated by reference in its entirety). Carotenoids found in plants and photosynthetic organisms have high antioxidant activity (Paiva et al., "13-Carotene and Other Carotenoids as Antioxidants," *Journal of the American College of Nutrition* 18:426-433 (1999), which is hereby incorporated by reference in its entirety). Supplementation of microalgae in laying hen diets darkened egg yolk color by enhancing carotenoid deposition (Fredriksson et al., "Fatty Acid and Carotenoid Composition of Egg Yolk as an Effect of Microalgae Addition to Feed Formula for Laying Hens," *Food Chemistry* 99:530-537 (2006); Lorenz et al., "Commercial Potential for *Haematococcus* Microalgae as a Natural Source of Astaxanthin," *Trends in Biotechnology* 18:160-167 (2000); Herber-McNeill et al., "Dietary Marine Algae Maintains Egg Consumer Acceptability While Enhancing Yolk Color," *Poultry Science* 77:493-496 (1998), which are hereby incorporated by reference in their entirety), which would decrease fatty acid oxidation and prevent off-flavor.

These experiments demonstrate that microalgae is useful as a protein and fatty acid source with flaxseed oil to produce n-3 fatty acid-enriched eggs, without adverse effects on hen body weight, feed intake, and egg production traits. The inclusion level of microalgae could reach 7.5 to 15% to replace corn and soybean meal in diets for laying hens. Microalgae also could alleviate negative effects of flaxseed oil on body weight. The supplementation also decreases n-6 fatty acids, and increases EPA and DNA concentrations in egg yolk, resulting in production of eggs more beneficial for human health. The major problem of n-3 fatty acid fortified eggs—fishy smell and/or off-flavor—is moderated by supplementation of microalgae into hen diets. The microalgae treatments used in these studies helped produce n-3 fatty acid fortified eggs that were acceptable to consumers, principally due to decreases in off flavor. Such diets have application in the production of "consumer friendly" health foods.

Example 2—Supplemental Defatted Green Microalgal Biomass Exerts Dose-Dependent Effects on Growth Performance, Water Intake, Phosphorus and DNA Retention, and Bone Properties of Broilers Materials and Methods
Experimental Diets and Animal Care All animal protocols were approved by the Institutional Animal Care and Use Committee of Cornell University. Both experiments were conducted at the Cornell University Poultry Research Farm. Male hatchling Ross broiler chicks (1 day old) were obtained from a commercial hatchery and housed in temperature-controlled cage batteries. During the starter (0 to 3 weeks) and grower (3 to 6 weeks) periods, chicks were housed in groups of 6 and 4 per cage, respectively. All birds had free access to feed and water and received a lighting schedule of 22 hours of light and 2 hours of darkness daily. Body weights ("BW") were recorded at the beginning of each experiment, and BW and feed consumption were recorded weekly thereafter. Water intakes were recorded daily in Experiment 1 and for weeks 0-3 in Experiment 2, in which water was provided in 500 mL chick waterers for week 1, and then in 3 L water pans for weeks 2 and 3. Water was provided by water lines in the grower period of Experiment 2, and water intake was not assessed. Nutrient composition of the DGA biomass (*Nannochloropsis oceanica*, Cellana, Kailua-Kona, Hi.) is shown in Table 16. The corn-soybean meal basal diet (BD) and all other experimental diets were isonitrogenous and isoenergetic and met all of the nutrient requirements for each stage of growth (NRC, "Nutrient Requirements of Poultry," $9^{th}$ rev. ed. Natl. Acad. Press, Washington, D.C. (1994), which is hereby incorporated by reference in its entirety). Feed was withheld for 6 h prior to recording weekly animal BW and(or) taking blood and tissue samples.

TABLE 16

Nutrient Composition of Defatted Green Microalgal Biomass[1]

| Nutrient (%, 'as is') | | Amino Acid (% 'as is') | |
|---|---|---|---|
| DM | 95.3 | Pro | 4.00 |
| CP | 38.2 | Glu | 3.34 |
| Crude Fat | 3.60 | Leu | 2.90 |
| ADF | 7.40 | Asp | 2.80 |
| NDF | 24.2 | Lys | 2.27 |
| Ash | 19.6 | Ala | 2.22 |
| Ca | 0.28 | Val | 2.13 |
| P | 0.69 | Arg | 1.99 |
| Na | 4.73 | Gly | 1.92 |
| K | 1.20 | Phe | 1.57 |
| Mg | 0.63 | Thr | 1.54 |
| Fe, mg/kg | 2560 | Ile | 1.50 |
| Cu, mg/kg | 10.0 | Ser | 1.21 |
| Mn, mg/kg | 207 | Tyr | 1.20 |
| Zn, mg/kg | 39.0 | His | 0.64 |
| Mo, mg/kg | 1.50 | Met | 0.57 |
| Se, mg/kg | 0.01 | Trp | 0.49 |
| | | Cys | 0.30 |

[1]Proximate analysis was carried out by Dairy One Inc. (Ithaca, NY), and amino acids were determined by the Agricultural Experiment Station Chemical Laboratories at the University of Missouri (Columbia, MO).

In Experiment 1, day-old chicks (total=90) were divided into 3 treatment groups (n=5 cages/treatment), and fed a corn-soybean meal based diet ("BD"), BD+20% DGA (DGA) or BD+20% DGA+NSPase (DGA-E, a 1:4:5 ratio of Ronozyme WX:Ronozyme A:Roxazyme G2, (DSM Nutritional Products Inc., Parsippany, N.J.) (Table 17) for 3 weeks.

TABLE 17

Formula and Nutrient Composition of Diets Used in Exp. 1 (Wk 0-3)

| Item | Diet | | |
|---|---|---|---|
| | BD | DGA | DGA-E |
| Ingredient, % | | | |
| Corn (yellow) | 54.8 | 49.0 | 49.0 |
| Soybean meal (48.5% CP) | 36.8 | 21.5 | 21.5 |
| Green Microalgae | — | 20.0 | 20.0 |
| Corn oil | 3.80 | 6.00 | 6.00 |
| Dicalcium phosphate | 1.95 | 1.95 | 1.95 |
| Limestone | 1.30 | 1.30 | 1.30 |
| Sodium chloride | 0.40 | — | — |
| DL-methionine | 0.35 | 0.35 | 0.35 |
| L-lysine HCl | 0.05 | 0.05 | 0.05 |
| L-threonine | 0.08 | 0.08 | 0.08 |
| Vitamin mix[1] | 0.10 | 0.10 | 0.10 |
| Mineral mix[2] | 0.10 | 0.10 | 0.10 |
| Nutritional composition | | | |
| ME, kcal/kg | 3470 | 3430 | 3530 |
| [3]CP, % | 22.6 | 21.1 | 22.8 |
| [3]Crude fat, % | 7.04 | 9.28 | 9.28 |
| [3]NDF, % | 10.0 | 10.8 | 6.9 |
| [3]Ca, % | 0.81 | 0.78 | 0.80 |
| [3]P, % | 0.77 | 0.74 | 0.86 |
| [3]Na, % | 0.13 | 0.93 | 1.10 |
| [3]Fe, mg/kg | 276 | 627 | 778 |

[1]Provided (in mg/kg of diet): Copper sulfate, 31.42; potassium iodide, 0.046; iron sulfate, 224.0; manganese sulfate, 61.54; sodium selenite, 0.13; zinc oxide, 43.56; and sodium molybdate, 1.26.
[2]Provided (in IU/kg of diet): vitamin A, 6500; vitamin D3, 3500; vitamin E, 25 and (in mg/kg of diet): riboflavin, 25; d-calcium pantothenate, 25; nicotinic acid, 150; cyanocobalamin, 0.011; choline chloride, 1250; biotin, 1.0; folic acid, 2.5; thiamine hydrochloride, 7.0; pyridoxine hydrochloride, 25.0; and menadione sodium bisulfite, 5.0.
[3]Analyzed values.

In Experiment 2, day-old chicks (total=180) were divided into 5 treatment groups (n=6 cages/treatment) and fed the BD containing 0, 2, 4, 8, or 16% of DGA "as is" for 6 weeks. Starter diets were fed from week 0 to 3 (Table 18) and grower diets were fed from week 3 to 6 (Table 19).

TABLE 18

Composition of Diets Used in the Starter Period of Experiment 2

| Item | Diet DGA (%) | | | | |
|---|---|---|---|---|---|
| | 0 | 2 | 4 | 8 | 16 |
| Ingredient, % | | | | | |
| Corn (yellow, fine ground) | 54.1 | 53.9 | 53.9 | 52.9 | 51.4 |
| Soybean meal (48.5% CP) | 36.8 | 35.3 | 33.7 | 30.6 | 24.5 |
| Green Algae | — | 2.00 | 4.00 | 8.00 | 16.0 |
| Corn oil | 4.60 | 4.45 | 4.25 | 4.30 | 4.00 |
| Dicalcium phosphate | 1.95 | 1.95 | 1.95 | 1.95 | 1.9 |
| Limestone | 1.30 | 1.30 | 1.30 | 1.30 | 1.30 |
| Sodium chloride | 0.40 | 0.20 | — | — | — |
| DL-methionine | 0.35 | 0.35 | 0.35 | 0.35 | 0.35 |
| L-threonine | 0.08 | 0.08 | 0.08 | 0.08 | 0.08 |
| L-lysine HCl | 0.05 | 0.05 | 0.05 | 0.05 | 0.05 |
| Vitamin mix[1] | 0.10 | 0.10 | 0.10 | 0.10 | 0.10 |
| Mineral mix[2] | 0.10 | 0.10 | 0.10 | 0.10 | 0.10 |
| Nutritional composition | | | | | |
| ME, kcal/kg | 3110 | 3110 | 3110 | 3120 | 3110 |
| [3]CP, % | 22.0 | 22.4 | 22.3 | 22.2 | 21.8 |
| [3]Crude fat, % | 6.80 | 6.80 | 6.70 | 6.90 | 7.60 |
| [3]Ash, % | 5.43 | 5.63 | 5.61 | 6.13 | 7.65 |
| [3]Ca, % | 0.77 | 0.77 | 0.78 | 0.80 | 0.89 |
| [3]P, % | 0.72 | 0.73 | 0.72 | 0.76 | 0.79 |
| [3]Na, % | 0.17 | 0.23 | 0.20 | 0.41 | 0.84 |
| [3]Fe, PPM | 305 | 388 | 367 | 458 | 643 |

[1]Provided (in mg/kg of diet): Copper sulfate, 31.42; potassium iodide, 0.046; iron sulfate, 224.0; manganese sulfate, 61.54; sodium selenite, 0.13; zinc oxide, 43.56; and sodium molybdate, 1.26.
[2]Provided (in IU/kg of diet): vitamin A, 6500; vitamin D3, 3500; vitamin E, 25 and (in mg/kg of diet): riboflavin, 25; d-calcium pantothenate, 25; nicotinic acid, 150; cyanocobalamin, 0.011; choline chloride, 1250; biotin, 1.0; folic acid, 2.5; thiamine hydrochloride, 7.0; pyridoxine hydrochloride, 25.0; and menadione sodium bisulfite, 5.0.
[3]Analyzed values.

TABLE 19

Composition of Diets Used in the Grower Period of Experiment 2

| Item | Diet DGA (%) | | | | |
|---|---|---|---|---|---|
| | 0 | 2 | 4 | 8 | 16 |
| Ingredient, % | | | | | |
| Corn (yellow) | 61.6 | 61.3 | 61.3 | 60.5 | 58.8 |
| Soybean meal (48.5% CP) | 30.0 | 28.5 | 26.9 | 23.8 | 17.6 |
| Green Algae | — | 2.00 | 4.00 | 8.00 | 16.0 |
| Corn oil | 4.60 | 4.55 | 4.35 | 4.25 | 4.10 |
| Dicalcium phosphate | 1.60 | 1.60 | 1.60 | 1.60 | 1.60 |
| Limestone | 1.20 | 1.20 | 1.20 | 1.20 | 1.20 |
| Sodium chloride | 0.30 | 0.20 | — | — | — |
| DL-methionine | 0.20 | 0.20 | 0.20 | 0.20 | 0.20 |
| L-threonine | 0.08 | 0.08 | 0.08 | 0.08 | 0.08 |
| L-lysine HCl | 0.05 | 0.05 | 0.05 | 0.05 | 0.05 |
| Vitamin mix[1] | 0.10 | 0.10 | 0.10 | 0.10 | 0.10 |
| Mineral mix[2] | 0.10 | 0.10 | 0.10 | 0.10 | 0.10 |
| Nutritional composition | | | | | |
| ME, kcal/kg | 3200 | 3200 | 3200 | 3200 | 3200 |
| [3]CP, % | 19.7 | 20.4 | 20.0 | 19.5 | 19.5 |
| [3]Crude fat, % | 7.00 | 7.00 | 7.00 | 7.90 | 7.70 |
| [3]Ash, % | 4.61 | 4.83 | 5.20 | 6.04 | 7.79 |
| [3]Ca, % | 0.62 | 0.70 | 0.75 | 0.74 | 0.87 |
| [3]P, % | 0.61 | 0.69 | 0.70 | 0.67 | 0.77 |
| [3]Na, % | 0.12 | 0.15 | 0.17 | 0.39 | 0.93 |
| [3]Fe, PPM | 234 | 308 | 353 | 412 | 709 |

[1]Provided (in mg/kg of diet): Copper sulfate, 31.42; potassium iodide, 0.046; iron sulfate, 224.0; manganese sulfate, 61.54; sodium selenite, 0.13; zinc oxide, 43.56; and sodium molybdate, 1.26.
[2]Provided (in IU/kg of diet): vitamin A, 6500; vitamin D3, 3500; vitamin E, 25 and (in mg/kg of diet): riboflavin, 25; d-calcium pantothenate, 25; nicotinic acid, 150; cyanocobalamin, 0.011; choline chloride, 1250; biotin, 1.0; folic acid, 2.5; thiamine hydrochloride, 7.0; pyridoxine hydrochloride, 25.0; and menadione sodium bisulfite, 5.0.
[3]Analyzed values.

Blood Collection, Tissue Extraction, and Biochemical Analyses

Blood was collected from 2 chicks/cage at week 3 in both Experiment 1 and Experiment 2, and additionally at week 6 in Experiment 2. Blood was drawn from heart puncture, after the animal was anesthetized with $CO_2$, using heparinized needles. Blood was chilled on ice, centrifuged at 3000 g for 15 minutes and the resulting plasma was stored at −20° C. until analysis. Pectoralis major, liver, and heart were removed and weighed in Experiment 1 (week 3) and in Experiment 2 (weeks 3 and 6). At weeks 3 and 6 of Experiment 2, total gastrointestinal tract including gizzard and proventriculus was removed and washed with PBS for 3 times to measure weights and(or) lengths of various segments.

Plasma alanine aminotransferase ("ALT") and alkaline phosphatase ("AKP") activities and plasma inorganic phosphorus concentrations were determined as previously described (Austic et al., "Potential and Limitation of a New Defatted Diatom Microalgal Biomass in Replacing Soybean Meal and Corn in Diets for Broiler Chickens," *J. Agric. Food Chem.* 61(30):7341-7348 (2013), which is hereby incorporated by reference in its entirety). Plasma glucose concentration was determined using a commercial kit (GAGO20, Sigma-Aldrich, St. Louis, Mo.). Plasma DNA was isolated using phenol:chloroform:isoamyl alcohol (25: 24:1, Invitrogen, Grand Island, N.Y.) and resulting DNA quality and quantity was detected spectrophotometrically (A260/280).

Tibia Characteristics

Tibias were obtained from one chick per cage at week 6 of Experiment 2. After removing the fibula and the surrounding connective tissue and muscle, the cleaned tibias were stored in closed plastic bags at 4° C. until analysis. The length and weight of the bones were recorded and the mechanical properties were determined using a 3-point bending test using the Instron Universal Testing Instrument 5965 (Norwood, Mass.). Maximum extension, maximum slope, maximum load, and the extension at maximum load were collected.

Nutrient Digestion and Retention

At week 6 of Experiment 2, two birds were selected from each cage for total excreta collection and indirect estimates of phosphorus and DNA digestibility and retention using both chromium oxide was an indigestible marker (0.3% inclusion). After a 4-day acclimation period of feeding the chromium oxide-containing diets and 8 hours fasting, fresh feed was weighed and fed to the birds to collect total excreta from each cage twice daily for 3 days. The collected excreta was stored at −20° C. until drying. At the end of the 3-day collection period, all animals were fasted for 6 hours and humanely euthanized via $CO_2$ to collect digesta samples from the ileum. Excreta and digesta were weighed and then dried at 80° C. in a forced-air oven (Ravindran et al., "A Comparison of Ileal Digesta and Excreta Analysis for the Determination of Amino Acid Digestibility in Food Ingredients for Poultry," *Br. Poult. Sci.* 40(2):266-274 (1999), which is hereby incorporated by reference in its entirety). Excreta were pooled within cage and any feathers or debris were removed before the drying process. Resulting samples were then weighed, ground to a fine powder and stored at −20° C. for analysis. Chromium oxide in the ileal digesta and feed sample were determined by the method of Bolin and colleagues (Bolin et al., "A Simplified Method for the Determination of Chromic Oxide ($Cr_2O_3$) When Used as an Index Substance," *Science* 116(3023):634-635 (1952), which is hereby incorporated by reference in its entirety). Soluble inorganic phosphorus and DNA were analyzed in both the ileal digesta and excreta for the estimates of digestibility and retention, respectively. The same procedures as described above for the analysis of plasma inorganic phosphorus and DNA were applied to determine their concentrations in the dried ileal digesta and excreta.

Statistical Analyses

Data for both Experiments 1 and 2 were analyzed using the GLM procedure of PC-SAS 8.1 (SAS Inst. Inc., Cary, N.C.). The overall main effects of dietary treatment were determined using one-way ANOVA. Mean comparisons were conducted using the Duncan's multiple range test. Data of Experiment 2 were also analyzed using the linear and quadratic regression models of SAS. Data are expressed as mean, and P<0.05 was considered statistically significant, and P<0.10 was considered a trend.

Experiment I Results

Growth performance data for Experiment 1 is shown in Table 20. Average chick weight was not different across dietary groups at the start of the experiment. The chicks consuming all of the DGA-containing diets demonstrated increased body weight at weeks 1 and 2 (P<0.05); however, DGA inclusion did not affect weight at week 3. Chicks fed the DGA diets had greater (P<0.05) ADG than those fed BD at week 1, but not at weeks 2 or 3. Chicks fed the NSPase diet had increased ADFI (P<0.05) than those fed the BD+DGA diet at week 1. Chicks fed the DGA diets had greater feed use efficiency at week 1 and over the entire 3 week period (P=0.05). Additionally, DGA nor NSPase had any effect on plasma activities of AKP and ALT or concentrations of glucose and inorganic phosphorus.

TABLE 20

Effects of Supplemental Defatted Microalgae and NSPase on Growth Performance and Plasma Biochemical Profile of Broiler Chicks in Experiment 1

| Item | Diet | | | SEM | P-Value |
|---|---|---|---|---|---|
| | Control | DGA[1] | DGA-E[2] | | |
| BW, g | | | | | |
| Wk 0 | 32.2 | 32.2 | 32.2 | 0.09 | NS |
| Wk 1 | 131[b] | 162[a] | 163[b] | 5.30 | 0.008 |
| Wk 2 | 375[b] | 433[a] | 429[a] | 11.3 | 0.05 |
| Wk 3 | 691 | 738 | 732 | 12.4 | NS |
| ADG, g | | | | | |
| Wk 1 | 14.1[b] | 17.4[a] | 18.8[a] | 0.68 | 0.005 |
| Wk 2 | 34.8 | 37.0 | 37.4 | 1.20 | NS |
| Wk 3 | 52.7 | 49.2 | 50.8 | 0.92 | NS |
| Overall | 33.9 | 34.5 | 35.7 | 0.61 | NS |
| ADFI, g | | | | | |
| Wk 1 | 17.6[ab] | 16.1[b] | 18.3[a] | 0.42 | 0.07 |
| Wk 2 | 40.7 | 45.5 | 43.7 | 1.21 | NS |
| Wk 3 | 71.4 | 70.7 | 71.6 | 0.88 | NS |
| Overall | 37.0 | 36.9 | 37.6 | 0.56 | NS |
| G:F | | | | | |
| Wk 1 | 0.80[b] | 1.09[a] | 1.09[a] | 0.05 | 0.008 |
| Wk 2 | 0.85 | 0.82 | 0.87 | 0.01 | NS |
| Wk 3 | 0.74 | 0.72 | 0.71 | 0.01 | NS |
| Overall | 0.79[b] | 0.87[a] | 0.89[a] | 0.02 | 0.05 |
| Plasma Biochemical Profile[3] | | | | | |
| AKP, units/mL | 186 | 176 | 170 | 17.8 | NS |
| ALT, units/mL | 2.18 | 1.83 | 2.53 | 0.28 | NS |
| Glucose, mg/dl | 276 | 318 | 330 | 11.7 | NS |
| Inorganic P, mg/dl | 0.67 | 0.71 | 0.77 | 0.03 | NS |

Data are expressed as mean (n = 5/treatment).
[1]DGA = defatted green microalgal biomass (Nannochloropsis oceanica, Cellana, Kailua-Kona, HI).
[2]A 1:4:5 ratio of Ronozyme WX: Ronozyme A: Roxazyme G2, (DSM Nutritional Products Inc., Parsippany, NJ).
[3]AKP =alkaline phosphatase, ALT = alanine aminotransferase.
[a-b]Values with different superscripts in each row differ according to one-way ANOVA (P < 0.05)
NS: not significant.

Figure 1B:
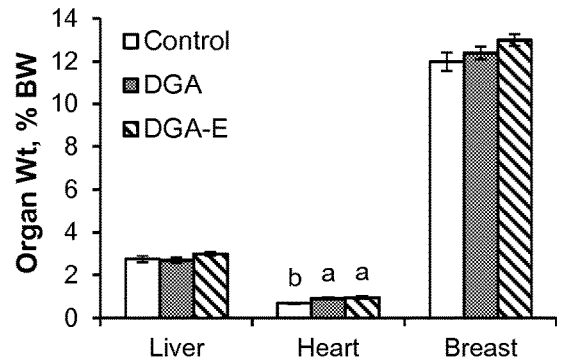
Figure 2A:
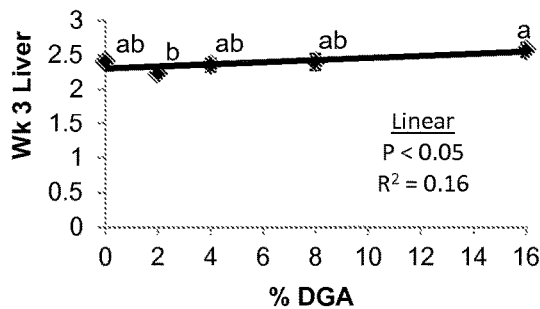
FIGS. 2A-F are graphs showing the effect of increasing levels of dietary microalgal biomass on week 3 and week 6 relative organ weights in broiler chicks. Data are expressed as mean±SEM (n=6/treatment). Values with different letters in each group differ significantly according to one-way ANOVA ($P<0.05$). Linear and quadratic regression analyses were also deemed significant at $P<0.05$. DGA=defatted green microalgal biomass (*Nannochloropsis oceanica*, Cellana, Kailua-Kona, Hi.).
Figure 2B:
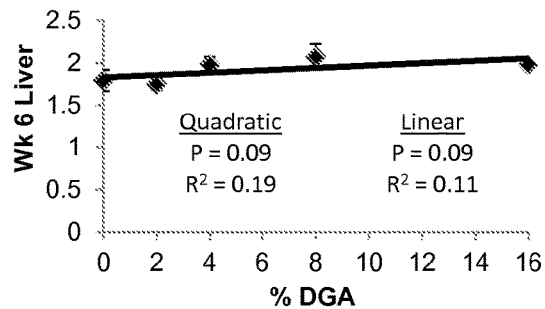
Figure 2C:
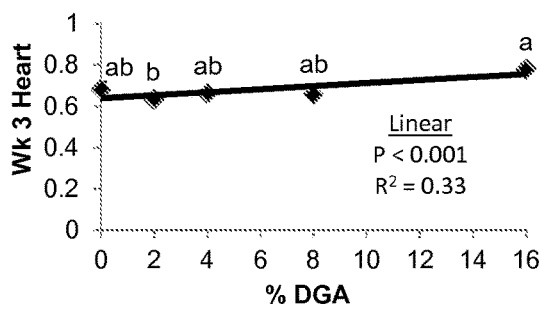
Figure 2D:
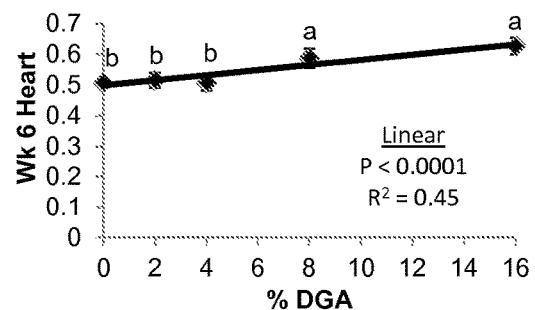
Figure 2E:
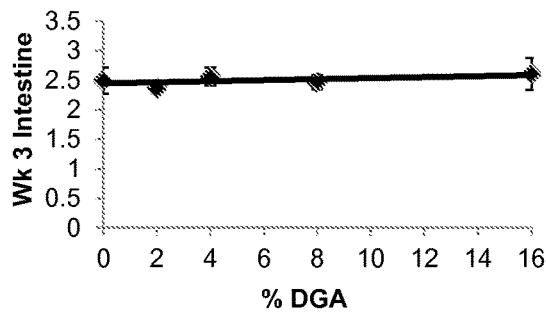
Figure 2F:
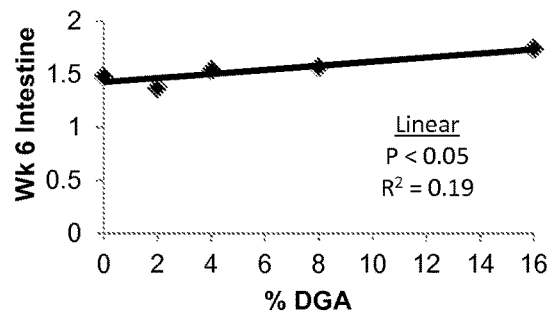

Daily water intakes (FIG. 1A) were elevated (P<0.0001) by feeding the DGA-containing diets compared with the control at all time-points, increasing 54% during the 3 week experiment. Whereas dietary treatments showed no effect on the relative weights of liver or breast at week 3, feeding the DGA diets elevated those of heart by 35 to 41% over the controls (FIG. 1B).

Experiment II Results

Body weight was decreased at week 3 and week 6 with increasing DGA. At week 3 and week 6, there were linear (P<0.05, $R^2$=0.15 and P<0.01, $R^2$=0.37, respectively) and quadratic (P<0.01, $R^2$=0.37 and P<0.05, $R^2$=0.40, respectively) effects of DGA consumption. However, only the 16% DGA-fed birds' weight displayed a reduction in body weight compared with the control-fed birds. There were linear (P=0.05, $R^2$=0.13) and quadratic (P<0.01, $R^2$=0.38) effects of increasing dietary DGA concentrations on ADG during weeks 0-3, but not weeks 3-6 or weeks 0-6 (Table 21). At each time point, ADG of chicks fed the 16% DGA diet was lower (P<0.05) than that of all other treatment groups. Whereas ADFI was not affected by any level of DGA inclusion, there was a linear reduction in feed use efficiency during the grower (P<0.01) and the entire period (P<0.01) with the increased DGA inclusions. Chicks fed the 16% DGA had lower (P<0.05) feed use efficiency than that of the control and(or) the other treatment groups. Water intakes were increased in a linear fashion in response to the increased DGA inclusions at wk 1 (P<0.01, $R^2$=0.29), 2 (P<0.0001, $R^2$=0.82) and 3 (P<0.0001, $R^2$=0.91, data not shown). During the 3 week starter period, water intake increased linearly (P<0.0001, $R^2$=0.76); Chicks fed the 8 and 16% DGA diets over weeks 0 to 3 consumed 16 to 39% (P<0.05) more water, compared with the control.

FIGS. 2A-F show linear increases in relative weights of liver at weeks 3 (FIG. 2A, P<0.05, $R^2$=0.16) and 6 (FIG. 2B, P<0.10, $R^2$=0.19), of heart at weeks 3 (FIG. 2C, P=0.001, $R^2$=0.33) and 6 (FIG. 2D, P<0.0001, $R^2$=0.45), and intestine at weeks 6 (FIG. 2F, P<0.05, $R^2$=0.19) with inclusion of DGA. However, there was no such effect on week 6 relative weights of breast (13.5±0.48%), gizzard (1.24±0.15%), proventriculus (0.24±0.04%), or intestinal weight per length (0.25±0.02 g/cm).

Although there were linear reductions in tibial weight (P=0.01, $R^2$=0.27) and length (P<0.05, $R^2$=0.21) with increasing DGA inclusions, only tibia weight, but not length, of chicks fed the 16% DGA diet was lower (P<0.05) than that of chicks fed the BD (Table 22). There were no linear or quadratic effects of DGA inclusion on max slope or energy to and extension at maximum load. However, chicks fed the 8% DGA diet had lower (P=0.10) max slope than that fed the 4 or 16% DGA diet and lower (P<0.10) extension at maximum load than that of chicks fed the control diet. Plasma inorganic phosphorus concentrations at week 6 were not affected by the DGA inclusion. There was a linear (P<0.01, $R^2$=0.26) decrease in ileal soluble inorganic phosphorus digestibility, but linear (P<0.001, $R^2$=0.39) increase in soluble inorganic phosphorus retention with the increased DGA inclusions. The daily excretion of soluble inorganic phosphorus showed a decline trend (P=0.10) with the increased DGA inclusions. Neither plasma nor excreta concentrations of DNA were affected by DGA inclusion (Table 23). However, there were linear increases in ileal DNA concentration (P<0.0001, $R^2$=0.50) and DNA retention (P<0.001, $R^2$=0.46) in response to different levels of DGA supplementation.

TABLE 21

Effects of Increasing Levels of Supplemental Defatted Microalgae on Growth Performance and Water Intake of Broiler Chicks in Exp. 2

| | Diet DGA[1] (%) | | | | | | P-Value[2] | |
| --- | --- | --- | --- | --- | --- | --- | --- | --- |
| Item | 0 | 2 | 4 | 8 | 16 | SEM | Linear | Quad |
| BW | | | | | | | | |
| Wk 0, g | 39.5 | 39.7 | 39.5 | 39.5 | 39.5 | 0.06 | NS[3] | NS |
| Wk 3, kg | 0.96[ab] | 1.00[a] | 0.99[a] | 1.02[a] | 0.92[b] | 0.01 | 0.03 | 0.004 |
| Wk 6, kg | 2.82[a] | 2.84[a] | 2.75[a] | 2.87[a] | 2.53[b] | 0.03 | 0.002 | 0.04 |
| ADG, g | | | | | | | | |
| Wk 0-3 | 44.1[ab] | 46.0[a] | 45.1[a] | 46.9[a] | 41.7[b] | 0.51 | 0.05 | 0.003 |
| Wk 3-6 | 96.1[a] | 95.1[a] | 90.8[a] | 95.7[a] | 82.4[b] | 1.47 | NS[2] | NS |
| Wk 0-6 | 71.2[a] | 71.8[a] | 69.5[a] | 72.6[a] | 63.8[b] | 0.85 | NS | NS |
| ADFI, g | | | | | | | | |
| Wk 0-3 | 57.0 | 58.5 | 59.5 | 59.4 | 56.1 | 0.78 | NS | NS |
| Wk 3-6 | 184 | 178 | 183 | 188 | 176 | 1.75 | NS | NS |
| Wk 0-6 | 120 | 118 | 121 | 124 | 116 | 1.04 | NS | NS |
| G:F | | | | | | | | |
| Wk 0-3 | 0.77[ab] | 0.79[ab] | 0.76[ab] | 0.80[a] | 0.74[b] | 0.007 | NS | NS |
| Wk 3-6 | 0.52[a] | 0.53[a] | 0.50[ab] | 0.51[ab] | 0.47[b] | 0.008 | 0.01 | NS |
| Wk 0-6 | 0.65[a] | 0.66[a] | 0.63[ab] | 0.65[a] | 0.61[b] | 0.006 | 0.007 | NS |
| Daily water intake, mL/day | | | | | | | | |
| Wk 1 | 97.2[b] | 95.3[b] | 99.6[b] | 102[b] | 112[a] | 1.83 | 0.001 | NS |
| Wk 2 | 155[c] | 161[c] | 166[c] | 195[b] | 225[a] | 5.37 | <0.0001 | NS |
| Wk 3 | 235[c] | 247[c] | 250[c] | 285[b] | 375[a] | 10.3 | <0.0001 | 0.11 |
| Wk 0-3 | 162[c] | 168[c] | 172[c] | 197[b] | 237[a] | 5.61 | <0.0001 | NS |

Data are expressed as mean (n = 6/treatment).
[1]DGA = defatted green microalgal biomass (*Nannochloropsis oceanica*, Cellana, Kailua-Kona, HI)
[2]Data were analyzed using linear and quadratic regression models of SAS.
[a-c]Values with different superscripts in each row differ according to one-way ANOVA (P < 0.05).
[3]NS = not significant.

TABLE 22

Effects of Increasing Levels of Defatted Microalgae on Tibia Characteristics and Soluble Inorganic Phosphorus Digestion and Retention in Experiment 2

| Item | Diet DGA[1] (%) | | | | | SEM | P-Value[2] | |
|---|---|---|---|---|---|---|---|---|
| | 0 | 2 | 4 | 8 | 16 | | Linear | Quad |
| Tibia Characteristics | | | | | | | | |
| Weight, g | 113$^a$ | 112$^{ab}$ | 116$^a$ | 113$^a$ | 105$^b$ | 1.08 | 0.01 | NS[3] |
| Length, cm | 23.8$^{ab}$ | 26.3$^a$ | 25.7$^{ab}$ | 23.7$^{ab}$ | 19.4$^b$ | 0.76 | 0.03 | NS |
| Max Slope, N/mm | 152$^{ab}$ | 161$^{ab}$ | 132$^b$ | 181$^a$ | 126$^b$ | 6.95 | NS | NS |
| Extension at Max Load, mm | 3.27$^a$ | 3.25$^a$ | 3.02$^{ab}$ | 2.53$^b$ | 3.48$^a$ | 0.11 | NS | 0.01 |
| Energy to Max Load, J | 0.51 | 0.62 | 0.42 | 0.44 | 0.42 | 0.03 | NS | NS |
| Soluble Inorganic Phosphorus | | | | | | | | |
| Plasma, mg/dL | 1.50 | 1.48 | 1.47 | 1.50 | 1.55 | 0.03 | NS | NS |
| Digestibility[4], % | 95.8$^a$ | 96.1$^a$ | 94.9$^{ab}$ | 92.0$^{ab}$ | 91.1$^b$ | 0.70 | 0.004 | NS |
| Retention[5], % | 84.1$^c$ | 90.3$^b$ | 92.9$^a$ | 91.9$^{ab}$ | 93.2$^a$ | 0.72 | 0.0004 | <0.0001 |
| Excretion[5], mg/chick*day | 76.8 | 74.1 | 66.9 | 76.2 | 58.3 | 3.70 | 0.10 | NS |

Data are expressed as mean (n = 6/treatment).
[1]DGA = defatted green microalgal biomass (*Nannochloropsis oceanica*, Cellana, Kailua-Kona, HI)
[2]Data were analyzed using linear and quadratic regression models of SAS.
$^{a-c}$Values with different superscripts in each row differ according to one-way ANOVA (P < 0.05).
[3]NS = not significant.
[4]Estimated at week 6 using the indirect method of chromium oxide as an indigestible marker.
[5]Estimated at week 6 using the total collection data.

TABLE 23

Effects of Increasing Levels of Supplemental Defatted Microalgae on Phosphorus and DNA Concentrations in Plasma, Ileal Digesta and Excreta of Chicks at Wk 6 of Exp. 2

| Item | Diet DGA[1] (%) | | | | | SEM | P-Value[2] | |
|---|---|---|---|---|---|---|---|---|
| DNA | 0 | 2 | 4 | 8 | 16 | | Linear | Quad |
| Diet, mg/kg | 181 | 184 | 226 | 292 | 486 | | | |
| Plasma, mg/dL | 304 | 490 | 479 | 608 | 776 | 111 | NS[3] | NS |
| Ileum, mg/kg | 297$^b$ | 388$^b$ | 300$^b$ | 626$^a$ | 639$^a$ | 35.7 | <0.0001 | NS |
| Excreta, mg/kg | 716 | 727 | 778 | 846 | 841 | 33.1 | NS | NS |
| Retention[4], % | 38.5$^b$ | 35.7$^b$ | 42.6$^b$ | 45.8$^b$ | 66.1$^a$ | 3.31 | 0.0003 | NS |

Data are expressed as mean (n = 5/treatment).
[1]DGA = defatted green microalgal biomass (*Nannochloropsis oceanica*, Cellana, Kailua-Kona, HI)
[2]Data were analyzed using linear and quadratic regression models of SAS.
$^{a-c}$Values with different superscripts in each row differ according to the one-way ANOVA (P < 0.05).
[3]NS = not significant.
[4]Estimated at wk 6 based on data from the total excreta collection study.

Discussion

The most significant finding from both Experiments 1 and 2 was the substantial increases in daily water intakes by chicks fed diets containing 8% or higher levels of DGA, compared with the controls. When high salt concentrations of the defatted marine microalgal biomass did lead us to previous observations of bulky excreta by the experimental chicks (Austic et al., "Potential and Limitation of a New Defatted Diatom Microalgal Biomass in Replacing Soybean Meal and Corn in Diets for Broiler Chickens," *J. Agric. Food Chem.* 61(30):7341-7348 (2013); Leng et al., "Effect of Dietary Defatted Diatom Biomass on Egg Production and Quality of Laying Hens," *Journal of Animal Science and Biotechnology* 5(1):3 (2014), which are hereby incorporated by reference in their entirety), the present study represents the first direct measurement of the actual water intake increase by feeding the biomass. Although the increased water intake is associated with the 20% DGA diets in Experiment 1 and with the 8% DGA diet in Experiment 2 did not depress growth performance, the extra water usage will lead to not only higher demand for the agricultural water needs but also larger amount of litter. The latter is a major concern in modern poultry production (Francesch et al., "Nutritional Factors Affecting Excreta/Litter Moisture and Quality," *Worlds Poult. Sci. J.* 60(01):64-75. (2004), which is hereby incorporated by reference in its entirety). Chicks consuming the 20% DGA diets in Experiment 1 and the 16% DGA diet in Experiment 2 also displayed incidences of water regurgitation when feeding after a bout of drinking. That was probably due to pressure exerted on the crop and could lead to feed loss. Concurrently, the increased consumption of the DGA diets, mainly due to the high salt intake, produced heavier heart and(or) liver weights. Mirsalimi et al., "Blood Volume Increase in Salt-Induced Pul monary Hypertension, Heart Failure and Ascites in Broiler and White Leghorn Chickens," *Can. J. Vet. Res.* 57(2):110-113 (1993), which is hereby incorporated by reference in its entirety, reported increased relative weights of right and total ventricle and total blood volume in broiler chicks consuming 0.5% salt water compared with untreated controls. Metabolically, high sodium intake leads to increases in blood volume and flow, ultimately causing right ventricular hypertrophy and pulmonary hypertension (Julian et al., "The Effect of Dietary Sodium on Right Ventricular Failure-Induced Ascites, Gain and Fat Deposition in Meat-Type Chickens," *Can. J. Vet. Res.* 56(3):214-219 (1992), which is hereby incorporated by reference in its entirety). Apparently, additional processing steps must be taken to remove the extra salt present in the DGA biomass for the full potential of its high protein and other nutrients in animal feeding.

Another novel finding from the present study is the linear increases in retention and linear decreases in excretion of total soluble inorganic phosphorus in chicks fed the grade levels of DGA in Experiment 2. Remarkably, chicks fed the 16% DGA diet decreased their total soluble phosphorus excretion by 24% compared with the controls. This decrease is an unanticipated benefit of feeding this new type of DGA biomass because minimizing environmental pollution of manure phosphorus excretion is currently a major interest of animal agriculture (Bourgeois, "A Discounted Threat: Environmental Impacts of the Livestock Industry," *Earth Common Journal* 2 (1) (2012), which is hereby incorporated by reference in its entirety). Apparently, more extensive research is needed to follow up this finding for fully understanding the mechanism and environmental impact of this decreased phosphorus excretion associated with the DGA feeding. Interestingly, ileal total soluble phosphorus digestibility displayed a linear decrease with increases in dietary DGA inclusion. Opposite responses between digestion and retention of nutrients to microalgal feeding were previously reported. Weanling pigs fed the microalgae *Spirulina maxima* displayed reduced apparent nutrient digestibility with a simultaneous increase in the metabolic utilization of the absorbed nutrient, compensating for the low digestibility (Fevrier et al., "Incorporation of a Spiruline (*Spirulina maxima*) in Swine Food," *Ann. Nutr. Aliment.* 29(6):625-650 (1975), which is hereby incorporated by reference in its entirety). In the present study, ileal phosphorus digestibility was fairly high irrespective of DGA inclusion levels. Plasma inorganic phosphorus concentrations were not affected by the DGA levels either. Although the DGA inclusions caused dose-dependent linear decreases in tibial weights and lengths, the treatments did not affect tibial bone strength or other functional indices. In fact, the decreased tibial weight or length in chicks fed the 16% DGA diet can potentially be explained by the corresponding decrease in body size.

Altogether, phosphorus from the DGA biomass was as bioavailable as, if not more than, that from the ingredients of the BD for maintaining body phosphorus status and bone function. This feature of DGA is a requisite for its application in broiler feeding, because selections for rapid growth in broilers may render them prone to skeletal deformities or bone breakage (Julian, "Rapid Growth Problems: Ascites and Skeletal Deformities in Broilers," *Poult. Sci.* 77(12): 1773-1780 (1998), which is hereby incorporated by reference in its entirety). These problems lead to mortality, low productivity and carcass condemnations and are associated with a loss of several hundred million dollars annually (Rath et al., "Factors Regulating Bone Maturity and Strength in Poultry," *Poult. Sci.* 79(7):1024-1032. (2000), which is hereby incorporated by reference in its entirety).

The present study signifies the first effort to determine fate and retention of DNA in the DGA. One noted concern for the use of single-cell protein sources such as microalgae is the high content of nucleic acids (Schulz et al., "Composition and Nutritive Value of Single-Cell Protein (SCP)," *Anim. Feed Sci. Technol.* 1(1):9-24 (1976); Giesecke et al., "Availability and Metabolism of Purines of Single-Cell Proteins in Monogastric Animals," *Proc. Nutr. Soc.* 41(03):319-327 (1982), which are hereby incorporated by reference in their entirety). Nucleic acids and other non-protein nitrogen contribute 10% of the total nitrogen found in microalgae (Becker, "Micro-algae as a Source of Protein," *Biotechnol. Adv.* 25(2):207-210 (2007), which is hereby incorporated by reference in its entirety). Excess nucleic acid consumption results in high production of uric acid that may cause gout and kidney stone formation in animals lacking the uricase enzyme (Ravindra, "Value-added Food: Single Cell Protein," *Biotechnol. Adv.* 18(6):459-479 (2000), which is hereby incorporated by reference in its entirety). Because uric acid is the end product of protein metabolism in chicks, they may be evolved for consuming feeds high in nucleic acid content (Shannon et al., "The Effect of Different Dietary Levels of an-Paraffin-Grown Yeast on the Growth and Food Intake of Broiler Chicks," *Br. Poult. Sci.* 13(3):267-272 (1972), which is hereby incorporated by reference in its entirety). However, the metabolic fate and excretion of the nucleic acids in DGA have not been examined. The preliminary findings from the present study demonstrated that an increased consumption of DGA did not alter plasma DNA concentrations. When ileal DNA concentrations were increased linearly with DGA inclusion in the 6-week old chicks, their excreta DNA remained similar among treatment groups, potentially due to gut microbe contribution. Notably, DNA retention was increased with DGA supplementation. Retained nucleotides may be used for nucleic acid synthesis, resulting in increased DNA and RNA contents in organs and muscles (Schulz et al., "Composition and Nutritive Value of Single-Cell Protein (SCP)," *Anim. Feed Sci. Technol.* 1(1):9-24 (1976), which is hereby incorporated by reference in its entirety).

Supplementing NSPase in the 20% DGA diet showed no additional growth-promoting or water intake-sparing benefit to broilers during the starter period. Although this lack of impact is better than the detrimental effects on growth performance seen in a previous broiler experiment (Ekmay et al., "Nutritional and Metabolic Impacts of a Defatted Green Marine Microalgal (*Desmodesmus* sp) Biomass in Diets for Weanling Pigs and Broiler Chickens," *J. of Agric. Food Chem.* 62(40):9783-9791 (2014), which is hereby incorporated by reference in its entirety), it is hard to explain in the context of high levels of fiber and NSPs, including cellulose (Northcote et al., "The Chemical Composition and Structure of the Cell Wall of *Hydrodictyon africanum* Yaman," *Biochem. J.* 70(3):391 (1958); Fu et al., "Hydrolysis of Microalgae Cell Walls for Production of Reducing Sugar and Lipid Extraction," *Bioresour. Technol.* 101(22): 8750-8754. (2010), which are hereby incorporated by reference in their entirety) and xylose (Takeda, H., "Classification of *Chlorella* Strains by Means of the Sugar Components of the Cell Wall," *Biochem. Syst. Ecol.* 16(4): 367-371 (1988), which is hereby incorporated by reference in its entirety) in microalgae. Elevated NSP consumption may have detrimental effect on nutrient digestion, and diets high in NSPs may cause high gut viscosity, ultimately reducing the efficiency of nutrient absorption through the intestinal wall (Johnson et al., "Effect of Gel-Forming Gums on the Intestinal Unstirred Layer and Sugar Transport In Vitro," *Gut* 22(5):398-403 (1981), which is hereby incorporated by reference in its entirety). Therefore, NSPase enzymes have been commonly incorporated to increase the nutritive value of broiler diets (Edney et al., "The Effect of β-glucanase Supplementation on Nutrient Digestibility and Growth in Broilers Given Diets Containing Barley, Oat Groats or Wheat," *Anim. Feed Sci. Technol.* 25(1):193-200. (1989); Viveros et al., "Effect of Enzyme Supplementation of a Diet Based on Barley, and Autoclave Treatment, on Apparent Digestibility, Growth Performance and Gut Morphology of Broilers," *Anim. Feed Sci. Technol.* 48(3):237-251 (1994); Vranjes et al., "The Influence of Extruded vs. Untreated Barley in the Feed, with and Without Dietary Enzyme Supplement on Broiler Performance," *Anim. Feed Sci. Technol.* 54(1):21-32 (1995); Steenfeldt et al., "Enzyme Supplementation of Wheat-Based Diets for Broilers: 1. Effect on Growth Performance and Intestinal Viscosity," *Anim. Feed Sci. Technol.* 75(1):7-43 (1998); Wang et al., "Effects of Enzyme Supplementation on Performance, Nutrient Digestibility, Gastrointestinal Morphology, and Volatile Fatty Acid Profiles in the Hindgut of Broilers Fed Wheat-Based Diets," *Poult. Sci.* 84(6):875-881 (2005), which are hereby incorporated by reference in their entirety). Subsequently, these enzymes are supposed to improve digestion and utilization of nutrients in the DGA containing relatively high levels of fiber. When there was no benefit of the supplemental NSPase in Experiment 1 shown, a linear increase in relative intestinal weights with increasing dietary DGA inclusion in Experiment 2 was observed. It has been documented that high dietary fiber intake increases relative small intestine weight (Abdelsamie et al., "The Influence of Fibre Content and Physical Texture of the Diet on the Performance of Broilers in the Tropics," *Br. Poult. Sci.* 24(3):383-390 (1983); JøRgensen et al., "The Influence of Dietary Fibre Source and Level on the Development of the Gastrointestinal Tract, Digestibility and Energy Metabolism in Broiler Chickens," *Br. J. Nutr.* 75(03):379-395 (1996), which are hereby incorporated by reference in their entirety).

Overall, results from Experiment 1 indicate that supplementing 20% DGA in the starter diets for broilers did not affect their growth performance, but increased their water intake by over 50%. Adding the NSPase enzymes to the diet demonstrated no consistent benefit to growth or water intake. Multiple measures in Experiment 2 show that broiler chicks tolerated well the 4% inclusion of DGA throughout the starter and grower periods. Despite no adverse effect on growth performance or various biochemical and metabolic measures (Austic et al., "Potential and Limitation of a New Defatted Diatom Microalgal Biomass in Replacing Soybean Meal and Corn in Diets for Broiler Chickens," *J. Agric. Food Chem.* 61(30):7341-7348 (2013), which is hereby incorporated by reference in its entirety), the 8% DGA diet resulted in elevated water consumption and relative weights of vital organs. Meanwhile, the 16% DGA diet caused many, if not all, responses inferior to the control. With 38% CP, excellent profile of amino acids, and non-recognized concerns over palatability (feed intake), phosphorus, or nucleic acids (DNA), the most limiting factor of the tested DGA biomass is likely its high salt concentration. The direct adverse effects included elevated water intake and hypertrophy of heart and(or) other organs. The lack of effect on growth performance by the 20% DGA diet in Experiment 1 might be confounded with BW increase from the "feed-driven" water consumption. Clearly, the extra salt in the DGA must be removed using additional processing steps for exploring its full nutritional, metabolic, and environmental potentials.

Example 3—Creating Omega-3 Enriched Broiler Chicken Using De-Fatted Green Microalgal Biomass Materials and Methods Animals, Diets, and Management All protocols of this experiment were approved by the Institutional Animal Care and Use Committee of Cornell University. Male hatchling Ross broiler chicks were obtained from a commercial hatchery and housed in a temperature-controlled room in an animal research building at the Cornell University Poultry Research Farm. The broiler chicks were housed in thermostatically-controlled cage batteries for the first 3 weeks, with 6 chicks per cage; 4 chicks were then transferred to grower cages at room temperature from weeks 3 to 6. Chicks had free access to feed and water and received a lighting schedule of 22 hours of light and 2 hours of darkness. Birds were fed one of five dietary treatments (n=6), containing 0% (Control), 2%, 4%, 8%, or 16% DGA, on an "as is" basis, replacing a mixture of corn and soybean meal. Starter (0 to 3 weeks) and grower (3-6 weeks) diets were formulated to be isoenergetic and to meet the requirements for all essential nutrients for each phase of growth (NRC *Nutrient Requirements of Poultry: Ninth Revised Edition*, The National Academies Press: Washington, D.C. (1994), which is hereby incorporated by reference in its entirety). The fatty acid profiles of each starter and grower diet are given in Table 24. At weeks 3 and 6, two birds were euthanized via asphyxiation with $CO_2$, after which blood was drawn from heart puncture using heparinized needles from 2 chicks per cage. Blood was stored on ice, centrifuged at 3000 g for 15 minutes, and plasma was stored at −20° C. until analysis. Liver, breast muscle, and legs were removed and a portion of each was snap frozen in liquid nitrogen and stored at −80° C. for future analysis. Whole skinless breast and legs were sealed in plastic bags and frozen for fatty acid analysis.

TABLE 24

Fatty Acid Composition of DGA and Experiment Starter and Grower Diets

| Item | DGA | Starter Diet (Wk 0-3) DGA (%) | | | | | Grower Diet (Wk 4-6) DGA (%) | | | | |
| --- | --- | --- | --- | --- | --- | --- | --- | --- | --- | --- | --- |
| | | 0 | 2 | 4 | 8 | 16 | 0 | 2 | 4 | 8 | 16 |
| $C_{14:0}$ | 6.89 | 0.0 | 0.1 | 0.3 | 0.5 | 1.0 | 0.1 | 0.2 | 0.2 | 0.5 | 0.9 |
| $C_{16:0}$ | 27.1 | 12.2 | 12.1 | 12.5 | 13.0 | 14.2 | 12.0 | 12.6 | 12.5 | 13.2 | 13.9 |
| $C_{16:1}$ | 27.3 | 0.1 | 0.5 | 0.9 | 1.8 | 3.8 | 0.1 | 0.6 | 0.9 | 1.9 | 3.5 |
| $C_{18:0}$ | 0.56 | 2.2 | 2.1 | 2.1 | 2.0 | 1.9 | 2.1 | 2.1 | 2.2 | 2.0 | 1.9 |
| $C_{18:1n-9}$ | 13.4 | 26.2 | 26.4 | 25.9 | 25.2 | 25.0 | 25.9 | 25.4 | 26.5 | 25.8 | 24.8 |
| $C_{18:2n-6}$ | 2.09 | 56.4 | 55.8 | 55.2 | 53.8 | 49.3 | 57.2 | 56.4 | 54.6 | 52.9 | 50.5 |

TABLE 24-continued

Fatty Acid Composition of DGA and Experiment Starter and Grower Diets

| Item | DGA | Starter Diet (Wk 0-3) DGA (%) | | | | | Grower Diet (Wk 4-6) DGA (%) | | | | |
|---|---|---|---|---|---|---|---|---|---|---|---|
| | | 0 | 2 | 4 | 8 | 16 | 0 | 2 | 4 | 8 | 16 |
| $C_{18:3n-3}$ | 0.00 | 1.7 | 1.5 | 1.5 | 1.4 | 1.4 | 1.6 | 1.6 | 1.5 | 1.4 | 1.3 |
| $C_{18:3n-6}$ | 0.89 | 0.1 | 0.1 | 0.1 | 0.1 | 0.0 | 0.0 | 0.0 | 0.0 | 0.0 | 0.0 |
| $C_{20:0}$ | 0.00 | 0.4 | 0.4 | 0.4 | 0.4 | 0.3 | 0.4 | 0.4 | 0.4 | 0.4 | 0.3 |
| $C_{20:1n-9}$ | 0.00 | 0.3 | 0.3 | 0.3 | 0.3 | 0.2 | 0.3 | 0.3 | 0.3 | 0.2 | 0.2 |
| $C_{20:4n-6}$ | 4.50 | 0.0 | 0.1 | 0.2 | 0.4 | 0.8 | 0.0 | 0.1 | 0.2 | 0.4 | 0.7 |
| $C_{20:5n-3}$ | 16.5 | 0.0 | 0.2 | 0.4 | 0.8 | 1.7 | 0.0 | 0.2 | 0.3 | 0.9 | 1.6 |
| $C_{22:0}$ | 0.00 | 0.2 | 0.2 | 0.1 | 0.1 | 0.1 | 0.2 | 0.2 | 0.2 | 0.2 | 0.1 |
| $C_{22:6n-3}$ | 0.00 | 0.0 | 0.0 | 0.0 | 0.0 | 0.0 | 0.0 | 0.0 | 0.0 | 0.0 | 0.0 |
| $C_{24:0}$ | 0.00 | 0.2 | 0.2 | 0.2 | 0.2 | 0.2 | 0.2 | 0.2 | 0.2 | 0.2 | 0.2 |
| Total | 100.0 | 100.0 | 100.0 | 100.0 | 100.0 | 100.0 | 100.0 | 100.0 | 100.0 | 100.0 | 100.0 |
| SFA | 35.4 | 15.2 | 15.1 | 15.6 | 16.3 | 17.7 | 15.0 | 15.5 | 15.6 | 16.4 | 17.3 |
| MUFA | 40.7 | 26.6 | 27.1 | 27.1 | 27.3 | 29.1 | 26.2 | 26.2 | 27.6 | 28.0 | 28.5 |
| PUFA | 24.0 | 58.2 | 57.8 | 57.4 | 56.4 | 53.1 | 58.8 | 58.3 | 56.8 | 55.5 | 54.1 |
| n-3 | 16.5 | 1.7 | 1.7 | 1.9 | 2.2 | 3.1 | 1.6 | 1.8 | 1.9 | 2.2 | 2.9 |
| n-6 | 7.47 | 56.4 | 56.0 | 55.4 | 54.2 | 50.1 | 57.2 | 56.5 | 54.9 | 53.3 | 51.3 |
| n-6:n-3 | 0.45 | 33.2 | 32.9 | 29.2 | 24.6 | 16.2 | 35.8 | 31.4 | 28.9 | 24.2 | 17.7 |

Fatty Acid Extraction

For fatty acid extraction, all diets were ground to a fine powder. Tissue samples were taken from the liver, the core of the whole breast (pectoralis major), and thigh (bicep femoris). Fatty acids from diets, plasma, and tissue were methylated with methanolic-KOH according to Ichihara et al., "An Improved Method for Rapid Analysis of the Fatty Acids of Glycerolipids," Lipids 31:535-539 (1996), which is hereby incorporated by reference in its entirety, using tridecanoic acid (Sigma-Aldrich Co., St Louis, Mo.) as an internal standard. Each fatty acid was identified by its retention with a fatty acid methyl ester standard (Sigma-Aldrich Co., St Louis, Mo.). Methyl esters of fatty acids were analyzed using a gas chromatography instrument (Agilent 6890N, Agilent Technologies, Santa Clara, Calif.) fitted with a flame-ionization detector and used a fused-silica capillary column coated with CP-SIL 88 (100 m×0.25 mm i.d., 0.2 mm film thickness; Varian Inc, Lake Forest, Calif.). Oven temperature was programmed to be held for 4 min at 140° C., increased by 4° C. per min to 220° C., and then held for 5 min. Carrier gas was $N^2$ with a constant flow rate of 2 ml/s and injector temperature was 230° C. and detector temperature was 280° C.

Gene Expression

Real time RT-PCR was performed on the snap frozen liver samples to estimate the abundance of mRNA using β-actin as a reference gene. Target genes included ME, FASN, Δ-6 desaturase and Δ-9 desaturase. The RNA was isolated, its quality verified by agarose gel and spectrometry (A260/A280), and transcribed using a commercially available kit (Applied Biosystems, Grand Island, N.Y.). The resulting cDNA (0.3 μg) was added to a 10 μL total reaction which included Power SYBR Green PCR mater mix (Applied Biosystems) and 0.625 μM forward and reverse primers (Table 25). Real-time PCR analysis was performed using a 7900HT Fast Real-Time PCR System (Applied Biosystems). The PCR included an initial 2 minute 50° C. step and a "hot start" step at 95° C. for 10 minutes, followed by 40 cycles of a 95° C. denaturing step for 15 s and a 60° C. annealing step for 60 s. A melt curve was analyzed for all primers to assess the quality of the amplification product. Each sample was analyzed in duplicate for both the target gene and genes of interest. Relative mRNA abundance was determined using the Δ cycle threshold (ΔCt) method. For each sample the Ct difference between the target and reference gene was calculated ($\Delta Ct = Ct^{target} - ct^{reference}$). The ΔCt values were then converted to fold differences by raising 2 to the power −ΔCt ($2^{-\Delta Ct}$).

TABLE 25

Primer Design

| Gene | Primer Design | PCR product (bp) |
|---|---|---|
| ME | 5'-GGATAGGGCTGCTTTCAACA (SEQ ID NO: 1) 3'-CTCCAGGGAACACGTAGGAA (SEQ ID NO: 2) | 206 |
| FASN | 5'-GCAGGGAAAATTCTGTGGAA (SEQ ID NO: 3) 3'-CAGCGGTCAACAACAACATC (SEQ ID NO: 4) | 200 |
| Δ-9 desaturase | 5'-CCACCATACATTCCCCTACG (SEQ ID NO: 5) 3'-CGCTCTTGTGACTCCCATCT (SEQ ID NO: 6) | 176 |
| Δ-6 desaturase | 5'-CGCATTCAGCAGATGAGTCT (SEQ ID NO: 7) 3'-GCCGTAGGTGTCCTCATTGT (SEQ ID NO: 8) | 204 |
| B-actin | 5'-CACAATGTACCCTGGCATTG (SEQ ID NO: 9) 3'-TCCGGATTCATCGTACTCCT (SEQ ID NO: 10) | 190 |

Statistical Analyses

Data were pooled within cage for an experimental unit of 6. Data were analyzed by ANOVA and linear regression models using PC-SAS 9.2. Differences between dietary groups were determined by ANOVA and separated using Duncan's multiple range test. For the gene expression data, only selected treatment effects were directly compared with the control group using the t-test. Data are expressed as mean±SEM, and data were deemed significant at P<0.05, and a trend at P<0.10.

Results and Discussion

Moderate levels (8%) of DGA were tolerated for 6 weeks without affecting growth performance. However, the metabolic fate of the residual n-3 fatty acids in the biomass was not previously known. This experiment demonstrated that dietary defatted-microalgal biomass consumption was able to alter the fatty acid profile of plasma, liver, and breast and thigh muscle of broiler chicken.

The fatty acid composition of the defatted microalgal biomass and experimental diet is shown in Table 24, supra. The total lipid content of the DGA was 3.6%, with its total EPA content 16.5% of total fatty acids. The fatty acid profile (as percentage of total fatty acids) of week 6 plasma is shown in Table 26, and week 3 is shown on Table 27.

TABLE 26

Effects of Increasing Levels of Supplemental Defatted Microalgae on Week 6 Plasma Fatty Acid Profile, as a Percentage of Total Fatty Acids, in Broiler Chicks

| Fatty Acid | DGA[1] (%) | | | | | SEM | P-Value | | $R^2$ |
| --- | --- | --- | --- | --- | --- | --- | --- | --- | --- |
| | 0 | 2 | 4 | 8 | 16 | | ANOVA | Linear[2] | |
| $C_{16:0}$ | $21.1^{ab}$ | $20.3^b$ | $19.9^b$ | $22.4^a$ | $21.0^{ab}$ | 0.29 | 0.06 | NS[3] | |
| $C_{16:1}$ | $0.73^c$ | $0.71^c$ | $1.15^{bc}$ | $1.49^a$ | $1.40^{ab}$ | 0.08 | 0.0004 | 0.005 | 0.30 |
| $C_{18:0}$ | $22.6^{ab}$ | $22.4^{ab}$ | $23.9^a$ | $21.5^b$ | $21.2^b$ | 0.29 | 0.01 | 0.08 | 0.12 |
| $C_{18:1\,n-9}$ | $13.4^{ab}$ | $12.2^{ab}$ | $14.1^{ab}$ | $14.0^a$ | $11.8^b$ | 0.30 | 0.09 | NS | |
| $C_{18:2\,n-6}$ | $33.6^{ab}$ | $34.7^a$ | $30.8^{bc}$ | $27.8^c$ | $31.0^{abc}$ | 0.69 | 0.006 | 0.10 | 0.11 |
| $C_{20:2\,n-6}$ | 0.31 | 0.28 | 0.25 | 0.28 | 0.17 | 0.03 | NS | NS | |
| $C_{20:3\,n-6}$ | $2.26^{ab}$ | $1.89^b$ | $2.65^a$ | $1.81^b$ | $1.18^c$ | 0.12 | 0.0004 | 0.002 | 0.34 |
| $C_{20:4\,n-6}$ | 4.89 | 5.27 | 4.99 | 5.57 | 5.34 | 0.18 | NS | NS | |
| $C_{20:5\,n-3}$ | $0.03^c$ | $0.44^c$ | $0.33^c$ | $1.69^b$ | $3.09^a$ | 0.22 | <0.0001 | <0.0001 | 0.87 |
| $C_{22:6\,n-3}$ | $0.37^c$ | $1.55^b$ | $1.77^b$ | $3.30^a$ | $3.48^a$ | 0.25 | <0.0001 | <0.0001 | 0.50 |
| TOTAL | | | | | | | | | |
| SFA | 44.1 | 42.7 | 43.9 | 44.0 | 42.2 | 0.35 | NS | NS | |
| MUFA | $14.7^{ab}$ | $13.0^b$ | $15.3^{ab}$ | $15.5^a$ | $13.3^b$ | 0.33 | 0.08 | NS | |
| PUFA | $41.7^{ab}$ | $44.3^{ab}$ | $40.8^{ab}$ | $40.6^b$ | $44.5^a$ | 0.59 | 0.08 | NS | |
| n-3 | $0.45^d$ | $2.10^c$ | $2.30^c$ | $5.04^b$ | $6.61^a$ | 0.45 | <0.0001 | <0.0001 | 0.75 |
| n-6 | $41.3^a$ | $42.2^a$ | $38.7^{abc}$ | $35.5^c$ | $37.9^{bc}$ | 0.68 | 0.005 | 0.02 | 0.22 |
| n-6:n-3 | $32.6^a$ | $20.1^b$ | $14.2^c$ | $6.83^d$ | $5.80^d$ | 1.71 | <0.0001 | <0.0001 | 0.53 |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
a-dValues with different superscripts in each row differ according to one-way ANOVA (P < 0.05).
[3]NS = not significant.

TABLE 27

Effects of Increasing Levels of Supplemental Defatted Microalgae on Week 3 Plasma Fatty Acid Profile, as a Percentage of Total Fatty Acids, in Broiler Chicks

| Fatty Acid | DGA[1] (%) | | | | | SEM | P-Value | | $R^2$ |
| --- | --- | --- | --- | --- | --- | --- | --- | --- | --- |
| | 0 | 2 | 4 | 8 | 16 | | ANOVA | Linear[2] | |
| $C_{14:0}$ | $0.18^b$ | $0.22^{ab}$ | $0.25^a$ | $0.28^a$ | $0.25^a$ | 0.01 | 0.02 | 0.02 | 0.19 |
| $C_{14:1}$ | 0.61 | 0.95 | 1.31 | 1.64 | 0.82 | 0.22 | NS[3] | NS | |
| $C_{16:0}$ | 18.5 | 18.0 | 17.7 | 18.4 | 19.0 | 0.20 | NS | NS | |
| $C_{16:1}$ | $0.58^c$ | $0.72^{bc}$ | $0.67^{bc}$ | $0.85^{ab}$ | $1.00^a$ | 0.04 | 0.002 | <0.0001 | 0.50 |
| $C_{18:0}$ | $19.3^a$ | $17.7^{ab}$ | $18.4^{ab}$ | $17.2^b$ | $16.7^b$ | 0.31 | 0.04 | 0.006 | 0.27 |
| $C_{18:1\,n-9}$ | $10.2^b$ | $9.69^{ab}$ | $9.17^{ab}$ | $9.37^{ab}$ | $8.36^b$ | 0.21 | 0.05 | 0.003 | 0.31 |
| $C_{18:2\,n-6}$ | 27.9 | 28.3 | 27.8 | 27.2 | 26.6 | 0.41 | NS | NS | |
| $C_{18:3\,n-6}$ | $0.50^a$ | $0.55^a$ | $0.49^a$ | $0.44^b$ | $0.31^b$ | 0.03 | 0.03 | 0.001 | 0.35 |
| $C_{18:3\,n-3}$ | 0.26 | 0.31 | 0.27 | 0.29 | 0.24 | 0.01 | NS | NS | |
| $C_{20:2\,n-6}$ | 0.49 | 0.53 | 0.57 | 0.58 | 0.47 | 0.03 | NS | NS | |
| $C_{20:3\,n-6}$ | $2.12^a$ | $1.78^{ab}$ | $1.59^b$ | $1.73^{ab}$ | $1.10^c$ | 0.09 | 0.0001 | <0.0001 | 0.55 |
| $C_{20:4\,n-6}$ | 17.0 | 16.7 | 16.7 | 15.0 | 17.0 | 0.43 | NS | NS | |
| $C_{20:5\,n-3}$ | $0.21^d$ | $0.66^d$ | $1.15^c$ | $1.95^b$ | $3.62^a$ | 0.26 | <0.0001 | <0.0001 | 0.93 |
| $C_{22:6\,n-3}$ | $1.10^d$ | $1.66^c$ | $2.00^c$ | $2.56^b$ | $3.67^a$ | 0.19 | <0.0001 | <0.0001 | 0.86 |
| TOTAL | | | | | | | | | |
| SFA | 38.8 | 37.8 | 38.0 | 38.1 | 37.6 | 0.43 | NS | NS | |
| MUFA | 11.6 | 11.7 | 11.4 | 12.1 | 10.4 | 0.30 | NS | NS | |
| PUFA | 49.6 | 50.5 | 50.6 | 49.8 | 52.0 | 0.60 | NS | NS | |

TABLE 27-continued

Effects of Increasing Levels of Supplemental Defatted Microalgae on Week 3 Plasma Fatty Acid Profile, as a Percentage of Total Fatty Acids, in Broiler Chicks

| Fatty Acid | DGA[1] (%) | | | | | SEM | P-Value | | |
|---|---|---|---|---|---|---|---|---|---|
| | 0 | 2 | 4 | 8 | 16 | | ANOVA | Linear[2] | $R^2$ |
| n-3 | $1.58^d$ | $2.67^c$ | $3.46^c$ | $4.82^b$ | $7.57^a$ | 0.44 | <0.0001 | <0.0001 | 0.93 |
| n-6 | 48.0 | 47.8 | 47.2 | 45.0 | 44.5 | 0.60 | NS | 0.01 | 0.22 |
| n-6:n-3 | $28.3^a$ | $18.1^b$ | $13.7^c$ | $9.94^d$ | $5.99^e$ | 1.60 | <0.0001 | <0.0001 | 0.75 |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
[a-d]Values with different superscripts in each row differ according to one-way ANOVA (P < 0.05).
[3]NS = not significant.

The main fatty acid found in all dietary treatments at both time points was linoleic acid (C18:2 n6), followed by palmitic acid (C16:0) and stearic acid (C18:0). There was no effect of DGA inclusion on saturated fatty acids ("SFA"), monounsaturated fatty acids ("MUFA"), or PUFAs, regardless of age. However, there was a linear increase in n-3 fatty acids (P<0.0001), which increased 5- and 15-fold when chicks consumed the 16% DGA-diet compared with the control at weeks 3 (P<0.0001, $R^2$=0.93) and 6 (P<0.0001, $R^2$=0.75), respectively. The increase in n-3 fatty acids is due to an increase in both EPA (C20:5 n3) and DHA (C22:6 n3). At week 6, there was a linear reduction in n-6 fatty acids (P<0.05), resulting in a corresponding decrease in the ratio of n-6 to n-3 fatty acids (P<0.0001).

The fatty acid profile (as percentage of total fatty acids) of week 6 (Table 28) and week 3 (Table 29) liver was also affected by dietary DGA inclusion. At week 6, the main 4 fatty acids, regardless of dietary treatment were palmitic acid, stearic acid, elaidic acid (C18:1 n9) and linoleic acid. Also, percentage of total SFA, MUFA, and PUFAs were not affected by DGA inclusion. Total n-3 fatty acids did linearly increase (P<0.001, $R^2$=0.38), increasing 3.1-fold with the 16% DGA diet compared with the control. Similar to the plasma, the increase in n-3 fatty acids is evident by an increase in both EPA (P<0.0001, $R^2$=0.47) and DHA (P=0.002, $R^2$=0.31). There was a trend (P=0.09, $R^2$=0.10) for a linear decrease in n-6 fatty acids, leading to a corresponding linear decrease in the n-6 to n-3 ratio (P=0.0002, $R^2$=0.40). Similar results were shown at week 3.

TABLE 28

Effects of Increasing Levels of Supplemental Defatted Microalgae on Week 6 Liver Fatty Acid Profile, as a Percentage of Total Fatty Acids, in Broiler Chicks

| Fatty Acid | DGA[1] (%) | | | | | SEM | P-Value | | |
|---|---|---|---|---|---|---|---|---|---|
| | 0 | 2 | 4 | 8 | 16 | | ANOVA | Linear[2] | $R^2$ |
| $C_{16:0}$ | $22.0^{ab}$ | $20.3^b$ | $20.8^b$ | $22.8^a$ | $20.9^b$ | 0.30 | 0.05 | 0.08 | 0.11 |
| $C_{16:1}$ | 1.35 | 1.15 | 1.36 | 1.74 | 1.44 | 0.07 | NS[3] | NS | |
| $C_{18:0}$ | 22.8 | 23.2 | 22.8 | 20.2 | 23.0 | 0.47 | NS | NS | |
| $C_{18:1\ n-9}$ | 21.3 | 17.2 | 19.9 | 22.7 | 18.5 | 0.72 | NS | NS | |
| $C_{18:2\ n-6}$ | 24.0 | 27.4 | 24.8 | 22.8 | 24.4 | 0.58 | NS | NS | |
| $C_{18:3\ n-6}$ | 0.46 | 0.59 | 0.53 | 0.47 | 0.40 | 0.04 | NS | 0.08 | 0.11 |
| $C_{18:3\ n-3}$ | 0.42 | 0.53 | 0.41 | 0.47 | 0.38 | 0.04 | NS | NS | |
| $C_{20:0}$ | 0.22 | 0.16 | 0.22 | 0.12 | 0.30 | 0.03 | NS | NS | |
| $C_{20:2\ n-6}$ | 0.40 | 0.43 | 0.43 | 0.30 | 0.40 | 0.02 | NS | NS | |
| $C_{20:3\ n-6}$ | $1.65^a$ | $1.44^{ab}$ | $1.67^a$ | $1.23^b$ | $1.31^b$ | 0.05 | 0.02 | 0.03 | 0.16 |
| $C_{20:4\ n-6}$ | 3.62 | 4.26 | 3.80 | 3.03 | 3.69 | 0.14 | NS | NS | |
| $C_{20:5\ n-3}$ | $0.06^c$ | $0.50^{bc}$ | $0.39^{bc}$ | $0.83^{ab}$ | $1.29^a$ | 0.10 | 0.0008 | <0.0001 | 0.47 |
| $C_{22:6\ n-3}$ | $1.04^b$ | $2.33^a$ | $2.14^a$ | $2.58^a$ | $3.23^a$ | 0.20 | 0.005 | 0.002 | 0.31 |
| TOTAL | | | | | | | | | |
| SFA | 45.3 | 43.9 | 44.2 | 43.6 | 44.6 | 0.51 | NS | NS | |
| MUFA | 22.9 | 18.6 | 21.6 | 24.7 | 20.3 | 0.78 | NS | NS | |
| PUFA | 31.7 | 37.5 | 34.2 | 31.7 | 35.1 | 0.83 | NS | NS | |
| n-3 | $1.57^c$ | $3.36^b$ | $2.94^{bc}$ | $3.89^{ab}$ | $4.90^a$ | 0.29 | 0.002 | 0.0004 | 0.38 |
| n-6 | $30.1^{ab}$ | $34.2^a$ | $31.2^{ab}$ | $27.8^b$ | $30.2^{ab}$ | 0.69 | 0.05 | 0.09 | 0.10 |
| n-6:n-3 | $21.6^a$ | $11.2^b$ | $11.4^b$ | $8.06^b$ | $7.20^b$ | 1.12 | P < 0.0001 | 0.0002 | 0.40 |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
[a-d]Values with different superscripts in each row differ according to one-way ANOVA (P < 0.05).
[3]NS = not significant.

TABLE 29

Effects of Increasing Levels of Supplemental Defatted Microalgae on Week 3 Liver Fatty Acid Profile, as a Percentage of Total Fatty Acids, in Broiler Chicks

| Fatty Acid | DGA[1] (%) | | | | | SEM | P-Value | | $R^2$ |
| --- | --- | --- | --- | --- | --- | --- | --- | --- | --- |
| | 0 | 2 | 4 | 8 | 16 | | ANOVA | Linear[2] | |
| $C_{16:0}$ | 21.3 | 20.8 | 19.6 | 21.3 | 21.3 | 0.25 | NS[3] | NS | |
| $C_{16:1}$ | $0.82^b$ | $0.78^b$ | $0.86^b$ | $1.14^a$ | $1.06^{ab}$ | 0.05 | 0.04 | 0.01 | 0.20 |
| $C_{18:0}$ | $27.4^{ab}$ | $27.9^a$ | $27.3^{ab}$ | $26.0^{ab}$ | $25.3^b$ | 0.33 | 0.06 | 0.004 | 0.26 |
| $C_{18:1\ n-9}$ | 14.0 | 12.3 | 14.2 | 14.2 | 12.3 | 0.39 | NS | NS | |
| $C_{18:2\ n-6}$ | 25.8 | 26.1 | 25.6 | 24.4 | 25.8 | 0.37 | NS | NS | |
| $C_{18:3\ n-6}$ | 0.56 | 0.58 | 0.55 | 0.28 | 0.40 | 0.05 | NS | 0.10 | 0.10 |
| $C_{18:3\ n-3}$ | 0.00 | 0.09 | 0.16 | 0.19 | 0.20 | 0.03 | NS | 0.09 | 0.10 |
| $C_{20:2\ n-6}$ | 0.52 | 0.54 | 0.54 | 0.51 | 0.57 | 0.01 | NS | NS | |
| $C_{20:3\ n-6}$ | $2.16^a$ | $1.88^{ab}$ | $1.77^b$ | $1.79^{ab}$ | $1.34^c$ | 0.07 | 0.002 | <0.0001 | 0.43 |
| $C_{20:4\ n-6}$ | $5.58^a$ | $5.87^a$ | $5.37^{ab}$ | $4.87^b$ | $4.87^b$ | 0.11 | 0.006 | 0.002 | 0.29 |
| $C_{20:5\ n-3}$ | $0.00^d$ | $0.09^d$ | $0.47^c$ | $0.99^b$ | $1.48^a$ | 0.11 | <0.0001 | <0.0001 | 0.85 |
| $C_{22:6\ n-3}$ | $1.92^d$ | $2.90^c$ | $3.32^{bc}$ | $4.07^b$ | $5.22^a$ | 0.23 | <0.0001 | 0.0001 | 0.74 |
| TOTAL | | | | | | | | | |
| SFA | 48.6 | 48.8 | 47.1 | 47.5 | 46.7 | 0.44 | NS | NS | |
| MUFA | 15.9 | 13.2 | 15.2 | 15.4 | 13.4 | 0.42 | NS | NS | |
| PUFA | 36.5 | 38.0 | 37.7 | 37.1 | 39.9 | 0.51 | NS | 0.07 | 0.12 |
| n-3 | $1.92^d$ | $3.08^c$ | $3.95^c$ | $5.24^b$ | $6.89^a$ | 0.35 | <0.0001 | <0.0001 | 0.80 |
| n-6 | 34.6 | 34.9 | 33.8 | 33.0 | 31.9 | 0.41 | NS | 0.07 | 0.11 |
| n-6:n-3 | $18.4^a$ | $11.5^b$ | $8.70^c$ | $6.42^d$ | $5.15^d$ | 0.91 | <0.0001 | <0.0001 | 0.62 |

Data are expressed as mean (n = 6/treatment).
[1]DGA = defatted green microalgal biomass (Cellana, Kailua-Kona, HI).
[2]Data were analyzed using the linear regression model of SAS.
[a-d]Values with different superscripts in each row differ according to one-way ANOVA ($P < 0.05$).
[3]NS = not significant.

Figure 3A:
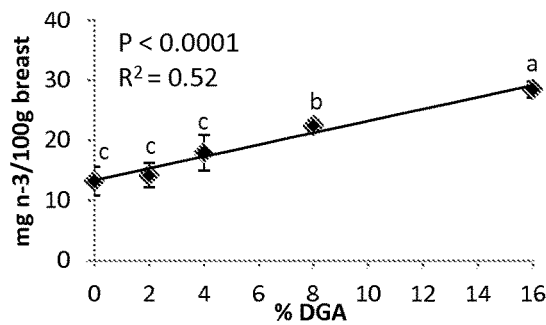
FIGS. 3A-D are graphs showing the effect of increasing levels of dietary microalgal biomass on week 6 n-3 fatty acid profile of broiler chicken breast.
Figure 3B:
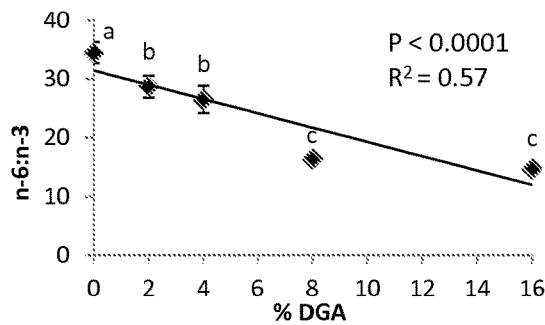
Figure 3C:
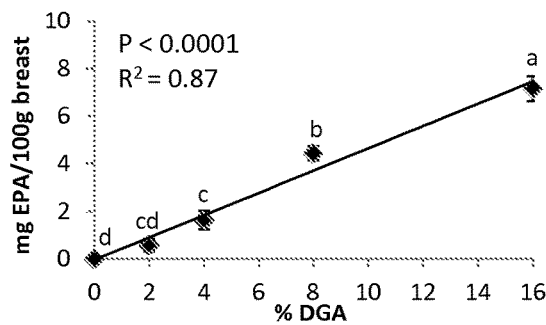
Figure 3D:
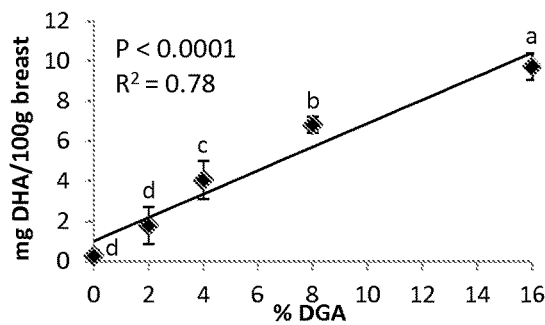

Table 30 shows the fatty acid profile (as percentage of total fatty acids and mg/g of muscle) of week 6 breast. The predominant fatty acids in this tissue were not affected by DGA inclusion and were elaidic acid and linoleic acid, followed by palmitic acid. Similar to the results shown in the plasma and liver, there was no effect of DGA on total SFA, MUFA, or PUFA; however, there was a linear increase in n-3 fatty acids ($P<0.0001$, $R^2=0.76$). Similar results were shown for week 3 (Table 31). Total fatty acids, expressed as mg per 100 grams of muscle sample were also assessed. Dietary DGA inclusion had no effect of total fat, nor total SFA, MUFA, or PUFA. However, DGA inclusion linearly increased n-3 (FIG. 3A, $P<0.0001$, $R^2=0.52$), EPA (FIG. 3C, $P<0.0001$, $R^2=0.87$), and DHA (FIG. 3D, $P<0.0001$, $R^2=0.78$), and decreased the n-6:n-3 ratio (FIG. 3B, $P<0.0001$, $R^2=0.57$). Total combined EPA and DHA in 100 grams of breast muscle tissue reached 16.9 mg with the consumption of the 16% DFA diet, which was over a 60-fold increase compared with the chicks consuming the control diet. Although not extensively studied, similar experiments have supported the notion of n-3 supplementation with microalgal products. Broiler chicks fed full-fat golden marine algae (Mooney et al., "Lipid and Flavour Quality of Stored Breast Meat from Broilers Fed Marine Algae," *J. Sci. Food Agric.* 78:134-140 (1998), which is hereby incorporated by reference in its entirety) and DHA-rich microalgae (Kalogeropoulos et al., "Nutritional Evaluation and Bioactive Micoconstituents (Carotenoids, Tocopherols, Sterols and Squalene) of Raw and Roasted Chicken Fed on DHA-Rich Microalgae," *Food Res. Int.* 43:2006-2013 (2010); Abril et al., "Production of Docosahexaenoic Acid-Enriched Poultry Eggs and Meat Using an Algae-Based Feed Ingredient," *The Return of W3 Fatty Acids Into the Food Supply: Land-Based Animal Food Products and Their Health Effects* 1:77-88 (1998), which are hereby incorporated by reference in their entirety) displayed an increase in breast muscle total n-3 content and decrease in n-6:n-3 ratios compared with those consuming a control ration.

TABLE 30

Effects of Increasing Levels of Supplemental Defatted Microalgae on Week 6 Breast Fatty Acid Profile, as a Percentage of Total Fatty Acids and mg/100 g Sample, in Broiler Chicks

| Fatty Acid | DGA[1] (%) | | | | | SEM | P-Value | | $R^2$ |
| --- | --- | --- | --- | --- | --- | --- | --- | --- | --- |
| | 0 | 2 | 4 | 8 | 16 | | ANOVA | Linear[2] | |
| $C_{14:0}$ | $0.59^b$ | $0.53^b$ | $0.50^b$ | $0.62^{ab}$ | $0.82^a$ | 0.02 | 0.03 | 0.02 | 0.19 |
| $C_{16:0}$ | 23.0 | 22.6 | 23.4 | 23.4 | 22.4 | 0.17 | NS[3] | NS | |
| $C_{16:1}$ | $3.13^{cd}$ | $2.99^d$ | $3.36^{bc}$ | $4.22^{ab}$ | $4.68^a$ | 0.16 | <0.0001 | <0.0001 | 0.55 |
| $C_{18:0}$ | 8.73 | 8.36 | 8.65 | 8.11 | 7.82 | 0.20 | NS | NS | |
| $C_{18:1\ n-9}$ | 30.9 | 31.4 | 30.8 | 31.3 | 29.9 | 0.40 | NS | NS | |
| $C_{18:2\ n-6}$ | 29.1 | 29.7 | 28.9 | 27.6 | 29.1 | 0.29 | NS | NS | |
| $C_{18:3\ n-6}$ | 0.25 | 0.27 | 0.24 | 0.24 | 0.20 | 0.03 | NS | NS | |
| $C_{18:3\ n-3}$ | $0.94^a$ | $1.00^a$ | $0.68^b$ | $0.89^{ab}$ | $0.85^{ab}$ | 0.03 | 0.04 | NS | |
| $C_{20:2\ n-6}$ | 0.42 | 0.39 | 0.36 | 0.53 | 0.36 | 0.06 | NS | NS | |
| $C_{20:3\ n-6}$ | 1.03 | 0.86 | 0.80 | 0.76 | 0.72 | 0.04 | NS | 0.10 | 0.11 |

TABLE 30-continued

Effects of Increasing Levels of Supplemental Defatted Microalgae on Week 6 Breast Fatty Acid Profile, as a Percentage of Total Fatty Acids and mg/100 g Sample, in Broiler Chicks

| Fatty Acid | DGA[1] (%) | | | | | SEM | P-Value | | $R^2$ |
| --- | --- | --- | --- | --- | --- | --- | --- | --- | --- |
| | 0 | 2 | 4 | 8 | 16 | | ANOVA | Linear[2] | |
| $C_{20:4\ n-6}$ | 1.44 | 1.21 | 1.27 | 1.19 | 1.31 | 0.16 | NS | NS | |
| $C_{20:5\ n-3}$ | 0.00[d] | 0.06[cd] | 0.08[c] | 0.39[b] | 0.54[a] | 0.06 | <0.0001 | <0.0001 | 0.86 |
| $C_{22:6\ n-3}$ | 0.01[c] | 0.18[bc] | 0.34[b] | 0.62[a] | 0.79[a] | 0.06 | <0.0001 | <0.0001 | 0.78 |
| Total, % | | | | | | | | | |
| SFA | 32.5 | 31.6 | 32.6 | 32.2 | 31.1 | 0.32 | NS | NS | |
| MUFA | 34.4 | 34.7 | 34.7 | 35.8 | 34.9 | 0.50 | NS | NS | |
| PUFA | 33.2 | 33.7 | 32.7 | 32.0 | 34.0 | 0.37 | NS | NS | |
| n-3 | 0.96[d] | 1.23[c] | 1.24[c] | 1.89[b] | 2.18[a] | 0.13 | <0.0001 | <0.0001 | 0.76 |
| n-6 | 32.2 | 32.4 | 31.6 | 30.1 | 31.8 | 0.37 | NS | NS | |
| mg/100 g | | | | | | | | | |
| Total | 1319 | 1256 | 1329 | 1222 | 1343 | 37.1 | NS | NS | |
| SFA | 418 | 394 | 429 | 390 | 413 | 10.4 | NS | NS | |
| MUFA | 461 | 439 | 466 | 442 | 479 | 15.5 | NS | NS | |
| PUFA | 439 | 423 | 434 | 390 | 451 | 12.2 | NS | NS | |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
[a-d]Values with different superscripts in each row differ according to one-way ANOVA (P < 0.05).
[3]NS = not significant.

TABLE 31

Effects of Increasing Levels of Supplemental Defatted Microalgae on Week 3 Breast Fatty Acid Profile, as a Percentage of Total Fatty Acids and mg/100 g Sample, in Broiler Chicks

| Fatty Acid | DGA[1] (%) | | | | | SEM | P-Value | | $R^2$ |
| --- | --- | --- | --- | --- | --- | --- | --- | --- | --- |
| | 0 | 2 | 4 | 8 | 16 | | ANOVA | Linear[2] | |
| $C_{14:0}$ | 0.37[c] | 0.49[b] | 0.52[b] | 0.55[b] | 0.70[a] | 0.02 | <0.0001 | <0.0001 | 0.68 |
| $C_{16:0}$ | 22.7 | 23.9 | 23.0 | 23.1 | 23.4 | 0.20 | NS[3] | NS | |
| $C_{16:1}$ | 2.32[b] | 2.47[b] | 2.45[b] | 3.11[a] | 3.46[a] | 0.12 | 0.001 | <0.0001 | 0.47 |
| $C_{18:0}$ | 11.9 | 10.8 | 11.3 | 10.7 | 11.6 | 0.20 | NS | NS | |
| $C_{18:1\ n-9}$ | 27.4[a] | 27.4[a] | 26.6[a] | 26.7[a] | 24.5[b] | 0.32 | 0.009 | 0.0003 | 0.38 |
| $C_{18:2\ n-6}$ | 28.3 | 28.2 | 28.5 | 28.5 | 27.9 | 0.18 | NS | NS | |
| $C_{18:3\ n-6}$ | 0.51 | 0.45 | 0.39 | 0.41 | 0.33 | 0.02 | NS | 0.02 | 0.19 |
| $C_{18:3\ n-3}$ | 0.85 | 0.87 | 0.84 | 0.85 | 0.73 | 0.02 | NS | 0.03 | 0.16 |
| $C_{20:0}$ | 0.47 | 0.36 | 0.42 | 0.43 | 0.53 | 0.02 | NS | 0.07 | 0.12 |
| $C_{20:1\ n-9}$ | 0.46[a] | 0.43[ab] | 0.45[ab] | 0.38[b] | 0.38[b] | 0.01 | 0.08 | 0.01 | 0.21 |
| $C_{20:2\ n-6}$ | 0.64 | 0.61 | 0.76 | 0.63 | 0.67 | 0.02 | NS | NS | |
| $C_{20:3\ n-6}$ | 1.64 | 1.42 | 1.47 | 1.27 | 1.33 | 0.05 | NS | 0.08 | 0.11 |
| $C_{20:4\ n-6}$ | 1.95 | 1.81 | 1.97 | 1.71 | 1.97 | 0.05 | NS | NS | |
| $C_{20:5\ n-3}$ | 0.00[e] | 0.22[d] | 0.39[c] | 0.63[b] | 0.97[a] | 0.07 | <0.0001 | <0.0001 | 0.84 |
| $C_{22:6\ n-3}$ | 0.09[d] | 0.35[c] | 0.55[b] | 0.68[b] | 1.07[a] | 0.07 | <0.0001 | <0.0001 | 0.82 |
| Total, % | | | | | | | | | |
| SFA | 35.7 | 35.8 | 35.5 | 35.1 | 36.6 | 0.32 | NS | NS | |
| MUFA | 30.4 | 30.3 | 29.6 | 30.2 | 28.4 | 0.34 | NS | 0.06 | 0.12 |
| PUFA | 34.0 | 33.9 | 34.9 | 34.7 | 34.9 | 0.20 | NS | 0.10 | 0.10 |
| n-3 | 0.94[e] | 1.44[d] | 1.78[c] | 2.17[b] | 2.77[a] | 0.12 | <0.0001 | <0.0001 | 0.89 |
| n-6 | 33.0 | 32.5 | 33.1 | 32.5 | 32.2 | 0.19 | NS | NS | |
| n-6:n-3 | 36.0[a] | 23.1[b] | 19.0[c] | 15.1[d] | 11.7[e] | 1.60 | <0.0001 | <0.0001 | 0.67 |
| mg/100 g | | | | | | | | | |
| Total | 715 | 748 | 712 | 725 | 683 | 23.1 | NS | NS | |
| SFA | 251 | 267 | 248 | 251 | 245 | 6.78 | NS | NS | |
| MUFA | 222 | 230 | 216 | 223 | 198 | 8.93 | NS | NS | |
| PUFA | 242 | 252 | 248 | 251 | 240 | 8.00 | NS | NS | |

TABLE 31-continued

Effects of Increasing Levels of Supplemental Defatted Microalgae on Week 3 Breast Fatty Acid Profile, as a Percentage of Total Fatty Acids and mg/100 g Sample, in Broiler Chicks

| Fatty Acid | DGA[1] (%) | | | | | SEM | P-Value | | |
|---|---|---|---|---|---|---|---|---|---|
| | 0 | 2 | 4 | 8 | 16 | | ANOVA | Linear[2] | $R^2$ |
| n-3 | 6.74[d] | 10.6[c] | 12.3[c] | 15.5[b] | 18.6[a] | 0.87 | <0.0001 | <0.0001 | 0.69 |
| EPA | 0.00[e] | 1.61[d] | 2.61[c] | 4.51[b] | 6.21[a] | 0.42 | <0.0001 | <0.0001 | 0.87 |
| DHA | 0.49[d] | 2.33[c] | 3.50[c] | 4.70[b] | 7.10[a] | 0.45 | <0.0001 | <0.0001 | 0.81 |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
[a-d]Values with different superscripts in each row differ according to one-way ANOVA (P < 0.05).
[3]NS = not significant.

Figure 4A:
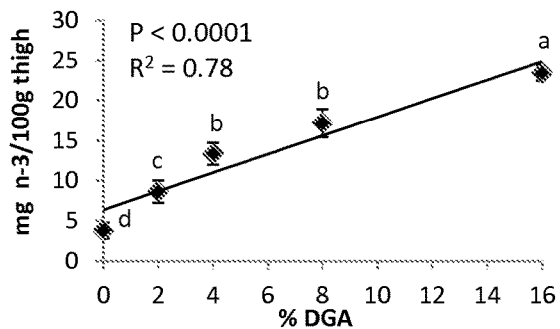
FIGS. 4A-D are graphs showing the effect of increasing levels of dietary microalgal biomass on week 6 n-3 fatty acid profile of broiler chicken thigh.
Figure 4B:
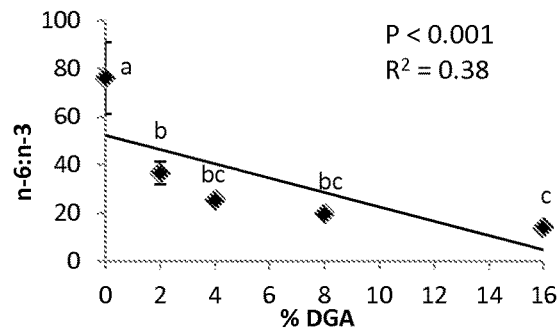
Figure 4C:
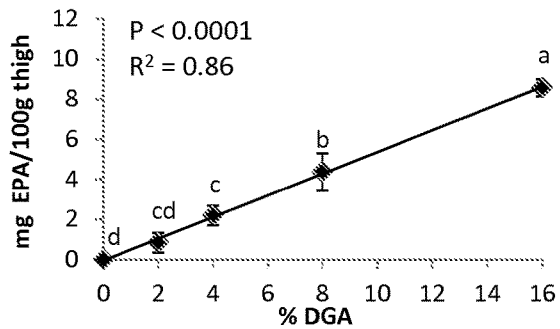
Figure 4D:
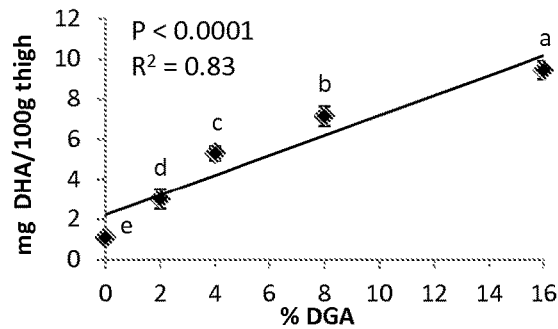

The predominant fatty acids (as a percentage of total fatty acids and mg/g of muscle) in the thigh were similar to those found in the breast tissue (Table 32). Interestingly, at weeks 3 and 6 there was a trend (P=0.09) and a significant linear reduction (P=0.01, $R^2$=0.20), in percentage of SFA, respectively, however, no effect on MUFA or PUFA. Additionally, at week 6, there was a linear increase in percentage of n-3 fatty acids (P<0.0001, $R^2$=0.80). Similar results were shown at week 3 (Table 33). When expressed as mg/100 grams of tissue, there was a significant increase in week 6 thigh muscle PUFA (P=0.05) and a trend for an increase in total fat (P=0.08) and SFA (P=0.10, $R^2$=0.10) with increasing DGA inclusion; presumably due to an increase in dietary SFA. Increasing DGA consumption also reduced the ratio of n-6:n-3 fatty acids (FIG. 4B, P<0.001, $R^2$=0.38), which decreased 5.5-fold with the highest level of DGA inclusion. Furthermore, there was a linear increase in n-3 (FIG. 4A, P<0.0001, $R^2$=0.78), EPA (FIG. 4C, P<0.0001, $R^2$=0.86) and DHA (FIG. 4D, P<0.0001, $R^2$=0.83). Total combined EPA and DHA in 100 grams of thigh muscle was 18 mg at the highest level of DGA inclusion, which is a 16.5-fold increase from the control.

TABLE 32

Effects of Increasing Levels of Supplemental Defatted Microalgae on Week 6 Thigh Fatty Acid Profile, as a Percentage of Total Fatty Acids and mg/100 g Sample, in Broiler Chicks

| Fatty Acid | DGA[1] (%) | | | | | SEM | P-Value | | |
|---|---|---|---|---|---|---|---|---|---|
| | 0 | 2 | 4 | 8 | 16 | | ANOVA | Linear[2] | $R^2$ |
| $C_{14:0}$ | 0.39[b] | 0.43[b] | 0.52[a] | 0.56[a] | 0.59[a] | 0.02 | 0.0002 | <0.0001 | 0.45 |
| $C_{16:0}$ | 22.9 | 23.3 | 22.4 | 22.6 | 22.0 | 0.17 | NS[3] | 0.03 | 0.16 |
| $C_{16:1}$ | 2.33[c] | 2.43[c] | 3.19[b] | 3.80[ab] | 4.08[a] | 0.16 | <0.0001 | <0.0001 | 0.58 |
| $C_{18:0}$ | 11.0[a] | 10.7[ab] | 10.2[ab] | 9.55[b] | 9.66[b] | 0.20 | 0.06 | 0.01 | 0.21 |
| $C_{18:1\,n-9}$ | 26.5 | 25.4 | 27.3 | 27.3 | 26.3 | 0.40 | NS | NS | |
| $C_{18:2\,n-6}$ | 27.8 | 28.6 | 27.5 | 27.4 | 27.0 | 0.29 | NS | NS | |
| $C_{18:3\,n-6}$ | 0.23 | 0.20 | 0.31 | 0.32 | 0.39 | 0.03 | NS | 0.07 | 0.12 |
| $C_{18:3\,n-3}$ | 0.35[b] | 0.57[a] | 0.57[a] | 0.56[a] | 0.53[ab] | 0.03 | 0.04 | NS | |
| $C_{20:1\,n-9}$ | 0.77[a] | 0.62[ab] | 0.50[ab] | 0.46[b] | 0.33[b] | 0.05 | 0.03 | 0.003 | 0.28 |
| $C_{20:2\,n-6}$ | 0.68 | 0.52 | 0.60 | 0.52 | 0.56 | 0.06 | NS | NS | |
| $C_{20:3\,n-6}$ | 1.19[a] | 1.12[ab] | 0.93[bc] | 0.88[c] | 0.83[c] | 0.04 | 0.008 | 0.001 | 0.31 |
| $C_{20:4\,n-6}$ | 5.03 | 5.00 | 4.57 | 4.31 | 4.93 | 0.16 | NS | NS | |
| $C_{20:5\,n-3}$ | 0.00[d] | 0.12[cd] | 0.23[c] | 0.44[b] | 0.88[a] | 0.06 | <0.0001 | <0.0001 | 0.84 |
| $C_{22:6\,n-3}$ | 0.12[d] | 0.42[c] | 0.56[c] | 0.76[b] | 1.04[a] | 0.06 | <0.0001 | <0.0001 | 0.74 |
| Total, % | | | | | | | | | |
| SFA | 34.9 | 34.9 | 33.7 | 33.2 | 32.8 | 0.32 | NS | 0.01 | 0.20 |
| MUFA | 29.7 | 28.5 | 31.1 | 31.6 | 31.0 | 0.50 | NS | NS | |
| PUFA | 35.4 | 36.6 | 35.2 | 35.2 | 36.2 | 0.37 | NS | NS | |
| n-3 | 0.46[d] | 1.11[c] | 1.36[c] | 1.76[b] | 2.45[a] | 0.13 | <0.0001 | <0.0001 | 0.80 |
| n-6 | 35.0 | 35.5 | 33.9 | 33.4 | 33.7 | 0.37 | NS | NS | |
| mg/100 g | | | | | | | | | |
| Total | 758 | 795 | 976 | 986 | 956 | 37.1 | NS | 0.08 | 0.11 |
| SFA | 261 | 270 | 323 | 324 | 313 | 10.4 | NS | 0.10 | 0.10 |
| MUFA | 228 | 237 | 308 | 323 | 300 | 15.5 | NS | NS | |
| PUFA | 270 | 290 | 346 | 343 | 346 | 12.2 | NS | 0.05 | 0.13 |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
[a-d]Values with different superscripts in each row differ according to one-way ANOVA (P < 0.05).
[3]NS = not significant.

TABLE 33

Effects of Increasing Levels of Supplemental Defatted Microalgae on Week 3 Thigh Fatty Acid Profile, as a Percentage of Total Fatty Acids and mg/100 g Sample, in Broiler Chicks

| Fatty Acid | DGA[1] (%) 0 | 2 | 4 | 8 | 16 | SEM | P-Value ANOVA | Linear[2] | $R^2$ |
|---|---|---|---|---|---|---|---|---|---|
| $C_{14:0}$ | $0.20^c$ | $0.36^b$ | $0.37^b$ | $0.43^b$ | $0.55^a$ | 0.03 | 0.0001 | <0.0001 | 0.52 |
| $C_{16:0}$ | 20.5 | 20.7 | 21.3 | 20.9 | 20.8 | 0.14 | NS[3] | NS | |
| $C_{16:1}$ | $2.61^{bc}$ | $2.28^c$ | $2.29^c$ | $2.95^{ab}$ | $3.39^a$ | 0.11 | 0.0003 | <0.0001 | 0.50 |
| $C_{18:0}$ | 10.6 | 12.0 | 11.7 | 10.6 | 11.3 | 0.23 | NS | NS | |
| $C_{18:1\ n-9}$ | $26.1^a$ | $24.1^{ab}$ | $23.2^b$ | $23.8^{ab}$ | $22.1^b$ | 0.41 | 0.03 | 0.01 | 0.22 |
| $C_{18:2\ n-6}$ | 31.2 | 30.7 | 30.7 | 30.8 | 30.1 | 0.16 | NS | 0.08 | 0.11 |
| $C_{18:3\ n-3}$ | 0.61 | 0.58 | 0.51 | 0.50 | 0.48 | 0.02 | NS | NS | |
| $C_{20:0}$ | $0.22^b$ | $0.38^a$ | $0.39^a$ | $0.22^b$ | $0.33^{ab}$ | 0.03 | 0.03 | NS | |
| $C_{20:1\ n-9}$ | 0.31 | 0.43 | 0.40 | 0.33 | 0.29 | 0.02 | NS | NS | |
| $C_{20:2\ n-6}$ | $0.75^b$ | $0.85^{ab}$ | $1.00^a$ | $0.81^{ab}$ | $0.77^b$ | 0.03 | 0.10 | NS | |
| $C_{20:3\ n-6}$ | $0.91^{ab}$ | $1.06^a$ | $1.12^a$ | $0.94^{ab}$ | $0.79^b$ | 0.04 | 0.07 | 0.01 | 0.22 |
| $C_{20:4\ n-6}$ | 5.06 | 5.59 | 5.72 | 5.50 | 6.09 | 0.20 | NS | NS | |
| $C_{20:5\ n-3}$ | $0.00^c$ | $0.00^c$ | $0.07^c$ | $0.64^b$ | $1.09^a$ | 0.09 | <0.0001 | <0.0001 | 0.83 |
| $C_{22:6\ n-3}$ | $0.17^c$ | $0.29^c$ | $0.38^c$ | $0.75^b$ | $1.21^a$ | 0.04 | <0.0001 | <0.0001 | 0.74 |
| Total, % | | | | | | | | | |
| SFA | $31.6^b$ | $33.6^a$ | $33.9^a$ | $32.3^{ab}$ | $33.2^{ab}$ | 0.30 | 0.09 | NS | |
| MUFA | 29.5 | 27.2 | 26.6 | 27.6 | 26.2 | 0.43 | NS | NS | |
| PUFA | 38.8 | 39.2 | 39.5 | 40.1 | 40.6 | 0.26 | NS | 0.04 | 0.15 |
| n-3 | $0.83^c$ | $0.86^c$ | $0.96^c$ | $1.97^b$ | $2.78^a$ | 0.15 | <0.0001 | <0.0001 | 0.82 |
| n-6 | 38.0 | 38.3 | 38.5 | 38.1 | 37.8 | 0.23 | NS | NS | |
| n-6:n-3 | $45.2^a$ | $48.2^a$ | $39.2^a$ | $21.2^b$ | $13.7^b$ | 3.00 | <0.0001 | <0.0001 | 0.63 |
| mg/100 g | | | | | | | | | |
| Total | 994 | 866 | 724 | 962 | 982 | 40.5 | NS | NS | |
| SFA | 317 | 286 | 244 | 306 | 319 | 11.0 | NS | NS | |
| MUFA | 289 | 240 | 194 | 275 | 266 | 14.2 | NS | NS | |
| PUFA | 389 | 341 | 287 | 382 | 399 | 15.9 | NS | NS | |
| n-3 | $8.49^c$ | $7.87^c$ | $7.14^c$ | $17.9^b$ | $26.7^a$ | 1.54 | <0.0001 | <0.0001 | 0.79 |
| EPA | $0.00^c$ | $0.00^c$ | $0.62^c$ | $5.66^b$ | $10.5^a$ | 0.82 | <0.0001 | <0.0001 | 0.87 |
| DHA | $2.01^c$ | $2.59^c$ | $2.93^c$ | $6.29^b$ | $11.0^a$ | 0.70 | <0.0001 | <0.0001 | 0.79 |

Data are expressed as mean (n = 6/treatment).
[1]DGA = defatted green microalgal biomass (*Nannochloropsis oceanica*, Cellana, Kailua-Kona, HI).
[2]Data were analyzed using the linear regression model of SAS.
[a-d]Values with different superscripts in each row differ according to one-way ANOVA (P < 0.05).
[3]NS = not significant.

Increasing DGA inclusion elevated total dietary n-3 fatty acids by its contribution of EPA, while being completely devoid of DHA. However, deposition of both EPA and DHA increased in all tissues analyzed with DGA consumption. Interestingly, the deposition of DHA was 1.12 to 2.50-fold higher than EPA in tissues of chicks consuming the 16% DGA diet, indicating an efficient in vivo conversion of EPA to DHA. Also, the defatted DGA elevated EPA, DHA, and total n-3 fatty acids and decreased the n-6:n-3 ratio in all tissues measured. While high levels of DGA produced the most dramatic results, as little as 2% inclusion of the microalgal product was able to significantly increase n-3 content and decrease the n-6 to n-3 ratio in plasma, liver, breast and thigh tissues. These data highlight the feasibility of DGA creating a healthier, value-added meat product.

Genes involved in hepatic lipogenesis, such as FAS and ME, are known to be nutritionally controlled (Clarke et al., "Nutritional Control of Rat Liver Fatty Acid Synthase and S14 mRNA Abundance," *J. Nutr.* 120:218-224 (1990); Blake et al., "Suppression of Rat Hepatic Fatty Acid Synthase and S14 Gene Transcription by Dietary Polyunsaturated Fat," *J. Nutr.* 120:1727-1729 (1990); Hillgartner et al., "Glucose Stimulates Transcription of Fatty Acid Synthase and Malic Enzyme in Avian Hepatocytes," *Am. J. Physiol.* 274: E493-501 (1998), which are hereby incorporated by reference in their entirety). Understanding this control is important, as altered regulation of fatty acid synthesis is associated with several diseases (Hillgartner et al., "Glucose Stimulates Transcription of Fatty Acid Synthase and Malic Enzyme in Avian Hepatocytes," *Am. J. Physiol.* 274: E493-501 (1998), which is hereby incorporated by reference in its entirety). While there was no effect of DGA inclusion on malic enzyme (Table 34), there was an increase in fatty acid synthase (P<0.10) in chicks consuming the 8% DGA diet compared with the control. These data are in disagreement with others, who have found that increasing consumption of PUFA leads to a subsequent decrease in FAS expression (Blake et al., "Suppression of Rat Hepatic Fatty Acid Synthase and S14 Gene Transcription by Dietary Polyunsaturated Fat," *J. Nutr.* 120:1727-1729 (1990); Clarke et al., "Dietary Polyunsaturated Fats Uniquely Suppress Rat Liver Fatty Acid Synthase and S14 mRNA Content," *J. Nutr.* 120:225-231 (1990), which are hereby incorporated by reference in their entirety); however, these experiments utilized diets containing 20% menhaden oil. It is possible that the diets tested here did not contain high enough levels of PUFA to elicit a similar response.

TABLE 34

Effects of Increasing Levels of Supplemental Defatted Microalgae on Week 6 Liver Gene Expression

| Gene | DGA[1] (%) | | | | | |
|---|---|---|---|---|---|---|
| | 0 | 2 | 4 | 8 | 16 | SEM |
| ME[2] | 1.00 | 1.25 | 1.76 | 1.19 | 1.43 | 0.17 |
| FASN | 1.00 | 1.15 | 1.22 | 1.35‡ | 1.04 | 0.09 |
| Δ-9 desaturase | 1.00 | 1.39 | 1.49 | 1.88† | 1.34 | 0.13 |
| Δ-6 desaturase | 1.00 | 1.42 | 1.96† | 1.75‡ | 1.35 | 0.15 |

Data are expressed as mean (n = 6/treatment).
[1]DGA = defatted green microalgal biomass (*Nannochloropsis oceanica*, Cellana, Kailua-Kona, HI).
[2]ME—malic enzyme, FASN—fatty acid synthase.
Values are expressed as a ratio to β-actin and normalized to the control.
Data were separated using a t-test and †P < 0.05 compared with the control, and ‡P < 0.1 compared with the control.

Desaturase enzymes, which introduce double bonds into long-chain fatty acids, produce unsaturated fatty acids that are essential for cellular functions. It is well know that PUFAs are a main dietary regulator of these enzymes (Nakamura et al., "Structure, Function, and Dietary Regulation of Δ6, Δ5, and Δ9 Desaturases," *Nutrition* 24 (2004); Cho et al., "Cloning, Expression, and Nutritional Regulation of the Mammalian Delta-6 Desaturase," *J. Biol. Chem.* 274:471-477 (1999), which are hereby incorporated by reference in their entirety). Specifically, expression of Δ-9 and Δ-6 desaturases, the enzymes responsible for the catalysis of the synthesis of MUFA and PUFA, respectively, is typically blunted in the presence of PUFA supplementation (Cho et al., "Cloning, Expression, and Nutritional Regulation of the Mammalian Delta-6 Desaturase," *J. Biol. Chem.* 274:471-477 (1999); Ntambi et al., "A Model Cell Line to Study Regulation of Stearoyl-CoA Desaturase Gene 1 Expression by Insulin and Polyunsaturated Fatty Acids," *Biochem. Biophys. Res. Commun.* 220:990-995 (1996); Mauvoisin et al., "Hormonal and Nutritional Regulation of SCD1 Gene Expression," *Biochimie* 93:78-86 (2011), which are hereby incorporated by reference in their entirety). In this experiment, there was no evidence of linear or quadratic regression in gene expression. However, chicks consuming the 8% DGA diet displayed elevated Δ-9 desaturase expression (P<0.05) compared with those consuming the control. Chicks consuming both the 4 (P<0.05) and 8% (P<0.10) DGA diets also showed an increase in Δ-6 desaturase expression compared with those consuming the control diet. There was also a trend for correlation between week 6 body weight and Δ-9 desaturase (P=0.09, $R^2$=0.34); also, the expression of the lipogenic FAS was positively correlated with both Δ-9 (P=0.10, $R^2$=0.35) and Δ-6 desaturase (P=0.007, $R^2$=0.54) expression.

In summary, the results of the present experiment indicate that the defatted microalgal biomass *Nannochloropsis oceanica* significantly improves the fatty acid profile of broiler chicken products. While high levels of inclusion yielded the highest rate of muscle EPA and DHA deposition, DHA inclusion of as low as 2% was enough to significantly increase breast and thigh muscle n-3 fatty acid content and decrease the n-6:n-3 ratio.

Example 4—Dose-Dependent Responses to Dietary Defatted Microalgae Inclusion in Laying Hen Performance, Composition, and Gene Expression Materials and Methods
Animal Husbandry and Experimental Design
Protocols were approved by the Institutional Animal Care and Use Committee of Cornell University (Ithaca, N.Y.). Shaver-White laying hens (Midwest Hatcheries LLC; Blackstone, Va., USA) (n=50, 47 weeks old), with an initial average body weight of 1.70±0.27 kg, were randomly assigned to 5 dietary treatments. There were 10 birds per treatment. Each hen was individually caged in a 0.44 m high×0.30 meter wide×0.45 m deep pen that was equipped with a nipple drinker and trough feeder. Hens had free access to feed and water and were provided 16 hours of light per day. Birds were maintained on dietary treatments for 6 weeks.

Defatted green microalgae, *Nannochloropsis oceanica* (Cellana, Kailua-Kona, Hi.), were included in 5 experimental diets at 0, 2.86, 5.75, 11.5, and 23% in partial substitution for soybean meal and ground corn. Crystalline amino acids, minerals, and vitamins were added to satisfy nutrient requirements (1.5 times the levels recommended by NRC, 1994). All diets were designed to be isocaloric and isonitrogenous. Proximate and mineral analyses were completed by Dairy One, Inc. (Ithaca, N.Y., USA). Diet formulations are shown in Table 35 and fatty acid compositions are reported in Table 36.

TABLE 35

Laying Hen Diet Formulation[1]

| Algae | 0% | 2.85% | 5.75% | 11.5% | 23% | DFA[2] |
|---|---|---|---|---|---|---|
| Proximate composition, % | | | | | | |
| Arg | 10.8 | 9.6 | 9.3 | 8.7 | 7.5 | 1.5 |
| Ca, % | 3.05 | 3.31 | 3.28 | 3.29 | 3.52 | 0.56 |
| Moisture | 11.0 | 9.0 | 9.3 | 9.4 | 8.8 | 4.0 |
| Crude fat | 5.0 | 4.9 | 5.1 | 5.1 | 4.9 | 5.2 |
| CP | 15.9 | 15.0 | 14.5 | 14.3 | 13.5 | 43.9 |
| Ash | 12.1 | 12.3 | 12.3 | 13.2 | 14.8 | 20.6 |
| ADF | 3.2 | 4.6 | 3.0 | 1.7 | 1.5 | 3.1 |
| NDF | 8.0 | 8.7 | 7.3 | 7.4 | 8.3 | 19.1 |
| Mineral | | | | | | |
| Ca, % | 3.05 | 3.31 | 3.28 | 3.29 | 3.52 | 0.56 |
| P, % | 0.66 | 0.65 | 0.67 | 0.63 | 0.69 | 0.74 |
| Mg, % | 0.16 | 0.16 | 0.18 | 0.19 | 0.25 | 0.66 |
| K, % | 0.69 | 0.63 | 0.63 | 0.60 | 0.53 | 1.66 |
| Na, % | 0.15 | 0.20 | 0.27 | 0.49 | 0.94 | 3.87 |
| Fe, ppm | 415 | 469 | 531 | 636 | 904 | 2620 |
| Zn, ppm | 66 | 64 | 63 | 69 | 74 | 45 |
| Cu, ppm | 17 | 15 | 15 | 13 | 17 | 11 |
| Mn, ppm | 19 | 24 | 27 | 35 | 55 | 216 |
| Mo, ppm | 1.4 | 1.0 | 1.1 | 1.1 | 1.1 | 2.2 |
| Amino acids, % | | | | | | |
| Arg | 10.8 | 9.6 | 9.3 | 8.7 | 7.5 | 1.5 |
| Cys | 3.0 | 2.7 | 2.7 | 2.5 | 2.2 | 0.3 |
| His | 4.6 | 4.1 | 4.0 | 3.7 | 3.2 | 0.5 |
| Ile | 7.0 | 6.4 | 6.3 | 6.2 | 6.0 | 1.1 |
| Leu | 15.3 | 14.3 | 14.3 | 14.3 | 14.4 | 2.3 |
| Lys | 8.9 | 8.2 | 8.2 | 8.2 | 8.2 | 1.6 |
| Met | 6.6 | 6.5 | 6.5 | 6.5 | 6.5 | 0.5 |
| Thr | 6.3 | 5.9 | 6.0 | 6.1 | 6.4 | 1.3 |
| Trp | 2.0 | 1.8 | 1.8 | 1.7 | 1.6 | 0.4 |
| Tyr | 6.0 | 5.5 | 5.4 | 5.3 | 5.1 | 1.0 |
| Val | 8.0 | 7.5 | 7.5 | 7.6 | 7.9 | 1.6 |

[1]Proximate and mineral analyses were carried out by Dairy One Coop Inc. (Ithaca, NY).
[2]DFA = Defatted Microalgae, *Cellana*,, Kailua-Kona, HI.

TABLE 36

Laying Hen Diet Fatty Acid Composition, mg/g Sample

| Algae | 0% | 2.85% | 5.75% | 11.5% | 23% | DFA |
|---|---|---|---|---|---|---|
| 14:0 | 0 | 0.08 | 0.17 | 0.37 | 0.67 | 2.86 |
| 14:1 | 0 | 0 | 0 | 0 | 0.03 | 0.08 |
| 16:0 | 3.21 | 2.81 | 3.76 | 5.09 | 5.71 | 11.63 |
| 16:1 | 0 | 0.28 | 0.60 | 1.27 | 2.30 | 10.97 |
| 18:0 | 0.52 | 0.40 | 0.50 | 0.59 | 0.50 | 0.22 |
| 18:1n-9c | 0 | 0.16 | 0 | 8.45 | 7.31 | 5.71 |
| 18:2n-6c | 6.36 | 5.20 | 6.81 | 0 | 0.11 | 0.12 |
| 18:3n-6 | 13.03 | 10.55 | 13.08 | 15.92 | 13.11 | 0.88 |
| 18:3n-3 | 0.52 | 0.34 | 0.38 | 0.41 | 0.28 | 0 |
| 20:3n-6 | 0 | 0 | 0 | 0 | 0 | 0 |
| 20:4n-6 | 0 | 0 | 0 | 0 | 0 | 0 |
| 20:5n-3 | 0 | 0.22 | 0.46 | 1.10 | 2.12 | 4.95 |
| 22:6n-3 | 0 | 0 | 0 | 0 | 0 | 0 |
| SFA | 3.73 | 3.29 | 4.57 | 6.33 | 7.59 | 17.76 |
| MUFA | 0 | 0.44 | 0.69 | 9.85 | 9.79 | 17.02 |
| PUFA | 19.99 | 16.38 | 20.81 | 17.51 | 15.68 | 6.02 |
| w3 | 0.52 | 0.57 | 0.85 | 1.51 | 2.40 | 4.95 |
| w6 | 19.47 | 15.81 | 19.97 | 16.00 | 13.28 | 1.07 |
| w6:w3 | 37.50 | 27.81 | 23.58 | 10.60 | 5.54 | 0.22 |
| DHA + EPA | 0 | 0.22 | 0.46 | 1.10 | 2.12 | 4.95 |

[1]DFA = Defatted Microalgae, Cellana, Kailua-Kona, HI.

Birds were weighed and blood was drawn from wing veins at 0, 2, 4, and 6 weeks following a 6 hour fast. After blood sampling, 5 birds per diet were euthanized by carbon dioxide asphyxiation at 6 weeks. Organs and gastrointestinal tracts were removed and weighed. Subsamples of breast muscle, thigh muscle, and liver were immediately frozen in liquid nitrogen and stored at −80° C. for gene expression analyses. Frozen breast, thigh, liver, and adipose tissue samples stored at −20° C. were used for compositional analyses.

Egg Quality

Eggs were collected daily and egg production was reported as percent production; the number of days each hen laid an egg shown as a percent. Whole egg weights were measured weekly. Egg components, including albumen, yolk, and shell, were weighed separately at 0, 2, 4, and 6 weeks. Yolk color, measured as L*-, a*-, and b*-values, was determined with a Macbeth Color Eye (Macbeth Division of Kollmorgen Instruments Corp. Newburgh, N.Y.). The L* value represents lightness (negative towards black, positive towards white), the a* value represents red-greenness (negative towards green, positive towards red), and the b* value represents the blue-yellow color scale (negative towards blue, positive towards yellow).

Tibia Strength

Tissue was removed manually prior to bone measurements and breaking. The length, width, and depth was measured at the center of the shaft for both tibias and averaged for each bird. Bone strength was measured on the right tibia using an Instron 5965 (Instron Corp., Norwood, Mass.) equipped with a 5 kN load cell and a cross head speed of 20 mm/min. Bluehill 3 Testing Software (Instron Corp., Norwood, Mass., USA) was used to perform a flexure test with a 38 mm supported length. Maximum slope, maximum load, and energy to maximum load were recorded for each tibia.

Plasma Assays

Blood was drawn from wing veins at 0, 2, 4, and 6 weeks after a 6 hour fast. Blood was held on ice during collection, centrifuged at 2,000 g for 20 min at 4° C., and stored at −80° C. until analyses. Plasma glucose levels were determined spectrophotometrically with glucose assay kit GAG020 (Sigma-Aldrich, Sigma Chemical Co., St. Louis, Mo.). Plasma uric acid was analyzed with Infinity Uric Acid Liquid Stable Reagent (Thermo-Fisher Scientific, Inc., MA). Plasma non-esterified fatty acids (NEFA), triglyceride (TAG), and total cholesterol (CHOL) were analyzed using commercial enzymatic kits following manufacturer's protocols (Wako Pure Chemical Industries, Ltd., Richmond, Va.). All samples were analyzed in duplicate.

Fatty Acid Extraction and Methylation

Raw muscle from breast and thigh was frozen in liquid nitrogen, powdered using a Waring commercial grade blender (Model 51BL31; Waring Commercial; Torrington, Conn.), and stored at −80° C. until analysis. Yolk, liver, and fat pad samples were minced at the time of analysis. A 0.5 g sample of yolk, liver, and powdered muscle, a 0.05 g sample of adipose tissue, and a 1 g sample of feed was used for fatty acid analysis with 200 μL of 13:0 at 400 mg/100 ml as an internal standard. Total lipids were extracted according to Bligh et al., "A Rapid Method of Total Lipid Extraction and Purification," *Canadian Journal of Biochemistry and Physiology* 37:911-917 (1959), which is hereby incorporated by reference in its entirety, using a chloroform-methanol mixture (2:1 v/v). Fatty acids were then methylated using methods described by Fritshe et al., "Effect of Dietary-Linolenic Acid on Growth, Metastasis, Fatty Acid Profile and Prostaglandin Production of Two Murine Mammary Adenocarcinomas," *Journal of Nutrition* 120:1601-1609 (1990), which is hereby incorporated by reference in its entirety. Fatty acid methyl esters ("FAMEs") were quantified using gas chromatography (Hewllet-Packard 6890; Palo-Alto Calif.) with a flame ionization detector. A wall-coated, open-tubular (WCOT) fused silica capillary column (100-m length, 0.25-mm inside diameter; Varian Inc., Walnut Creek, Calif.), with a stationary phase of CP-Sil 88, and nitrogen as the carrier gas separated the FAMEs. The oven temperature was held at 125° C. for 1 min, ramped 4° C./min to 220° C. (held for 5 min), then ramped 4° C./min to 235° C. (held for 20 min). The total separation time per sample was 57.5 minutes. FAMEs were identified based on comparison to retention times of standard FAMEs (Supelco™ quantitative standard FAME 37; Sigma-Aldrich, St. Louis, Mo.). Peak area counts were computed by an integrator using the ChemStation Plus software (Agilent Technologies, Santa Clara, Calif.).

Gene Expression

To isolate RNA, 20-50 mg of tissue was homogenized in 1 mL of TRIzol (Invitrogen; Carlsbad, Calif.) using a Polytron PT3100 (Kinematica AG; Littau-Luzern, Switzerland). Total RNA was isolated per manufacturer's protocol. The RNA pellet was washed with 75% ethanol and resuspended in nuclease-free water. The RNA concentration and quality were determined on a Bio-tek spectrophotometer at an optical density of 260 nm and on an Agilent Bioanalyzer 2100 (Agilent Technologies, Santa Clara, Calif.). Reverse Transcription was performed with random primer/oligo primer mixture following the manufacturer's instructions (Life Technologies, Carlsbad, Calif.). Relative gene expression was determined by RT-qPCR using SYBR Green on an ABI 7700 (Life Technologies, Carlsbad, Calif.). Primers were designed using Primer3 Software (Steve Rozen and Helen J. Skaletsky (1998), Primer3). Whitehead Institute for Biomedical Research Cambridge, Mass., USA) and are reported in Table 37.

TABLE 37

Real-Time PCR Primers[1]

| Gene | Name | Accession Number | Forward Primer | Reverse Primer |
|---|---|---|---|---|
| actb | b-actin | NM_205518 | CACAATGTACCCTGGCATTG (SEQ ID NO: 11) | TCCGGATTCATCGTACTCCT (SEQ ID NO: 12) |
| acc | Acetyl-Co Carboxylase | NM_205505 | GTTCCAGGAGGACCAAACAA (SEQ ID NO: 13) | TCTCCTAAAGCCCACATTGC (SEQ ID NO: 14) |
| fasn | Fatty Acid Synthase | NM_205155 | GCAGGGAAAATTCTGTGGAA (SEQ ID NO: 15) | CAGCGGTCAACAACAACATC (SEQ ID NO: 16) |
| fads5 | Δ5-Desaturase | XM_421052 | AGCTTTGAACCCAGCAAGAA (SEQ ID NO: 17) | AGCAACGCAGAGAAGAGGAA (SEQ ID NO: 18) |
| fads6 | Δ6-Desaturase | NM_001160428 | CGCATTCAGCAGATGAGTCT (SEQ ID NO: 19) | GCCGTAGGTGTCCTCATTGT (SEQ ID NO: 20) |
| fads9 | Δ9-Desaturase | NM_204890 | CCACCATACATTCCCCTACG (SEQ ID NO: 21) | CGCTCTTGTGACTCCCATCT (SEQ ID NO: 22) |
| elovl2 | Elongase 2 | NM_001197308 | CTTGGGATTACGCTGCTCTC (SEQ ID NO: 23) | TCTGGCTGCTTTCTTCCTC (SEQ ID NO: 24) |
| elovl3 | Elongase 3 | XM_001234270 | GGATGAGGTCTGCCTTTTCA (SEQ ID NO: 25) | AAAAGTTCCCCTTTCCCTCA (SEQ ID NO: 26) |
| elovl4 | Elongase 4 | NM_001197309 | TTCACTTTGTGGTGGATTGG (SEQ ID NO: 27) | TGGCCAATAGTCACATGGAA (SEQ ID NO: 28) |
| elovl5 | Elongase 5 | NM_001199197 | CCAAAGTACATGCGGAACAA (SEQ ID NO: 29) | CCACCAGAGGACACGTATGA (SEQ ID NO: 30) |
| acot4 | Acyl-CoA Thioesterase 4 | XM_004941668 | GCCATCATCTGGTGAGAGGT (SEQ ID NO: 31) | GATTTCGGTTTTGCTGCCTA (SEQ ID NO: 32) |
| me | Mahe Enzyme | NM_204303 | GGATAGGGCTGCTTTCAACA (SEQ ID NO: 33) | CTCCAGGGAACACGTAGGAA (SEQ ID NO: 34) |

[1]Primers were designed using Primer3 Software (Steve Rozen and Helen J. Skaletsky (1998), Primer3. Whitehead Institute for Biomedical Research Cambridge, MA, USA)

Each sample was run in duplicate. Relative gene expression for each sample was adjusted with the expression of control gene, actb (NM_205518.1), using the ΔΔCt equation (Livak et al., "Analysis of Relative Gene Expression Data Using Real-Time Quantitative PCR and the 2[-delta delta C(T)] Method," *Methods* 25:402-408 (2001), which is hereby incorporated by reference in its entirety) and normalized to the control hens.

Statistical Analysis

All data were analyzed using analysis of variance to test for main effects of diet with or without time-repeated measurements using PC-SAS (Version 9.1, SAS Institute, Inc., Cary, N.C.) general linear models procedure. The significance level for differences was $P<0.05$. The correlation procedure was used in SAS for correlation analyses. The p-value was adjusted using a Bonferroni Correction procedure for multiple regression analyses setting the significance level at $P \leq 0.002$.

Results

Figure 5A:
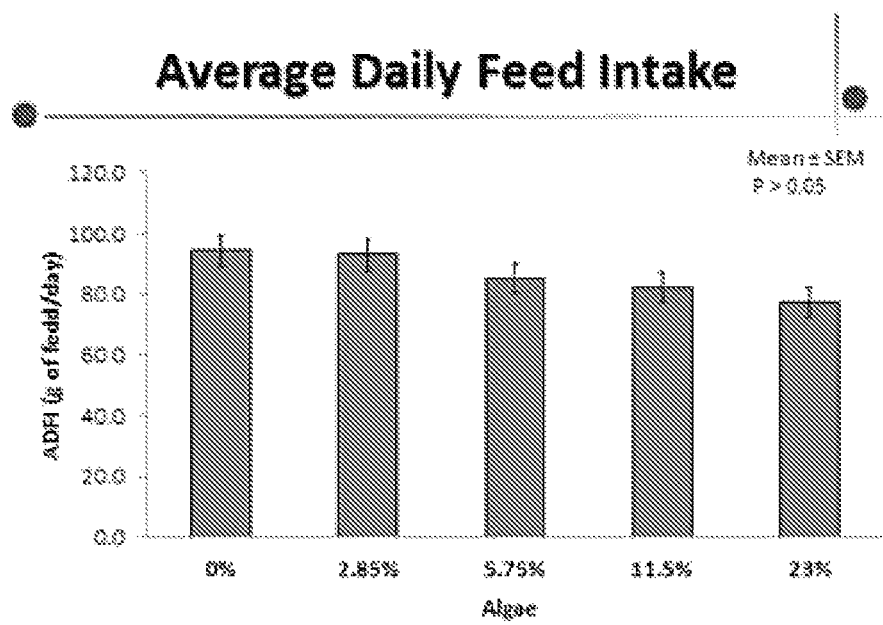
FIGS. 5A-B are graphs showing that supplemental defatted microalgae has no effect on body weight or feed intake of hens. Values with different letters in each group differ significantly according to one-way ANOVA ($P<0.05$).
Figure 5B:
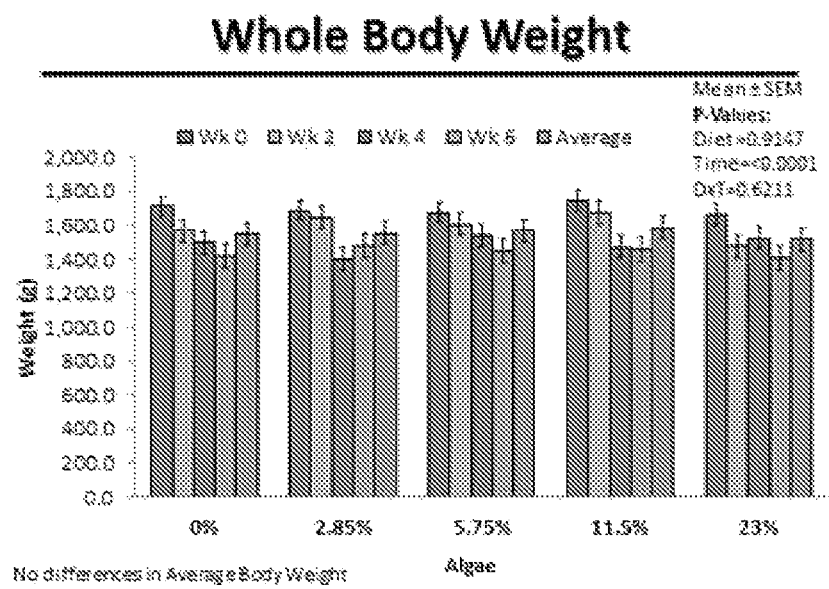

There were no effects of diet on WBW, ADFI, or organ weights; except hens fed 0% algae did have larger ceca (Table 38 and FIGS. 5A and 5B).

TABLE 38

Growth and Feed Intake[1,2]

| | Diets | | | | | | P-Values | | |
|---|---|---|---|---|---|---|---|---|---|
| Algae | 0% | 2.85% | 5.75% | 11.5% | 23% | SEM | Diet | Time | Time × Diet |
| WBW, g | | | | | | | 0.9147 | <0.0001 | 0.6211 |
| Initial | 1711.8 | 1689.8 | 1676.1 | 1747.1 | 1665.1 | 58.8 | | | |
| Final | 1418.3 | 1479.9 | 1451.1 | 1456.8 | 1409.5 | 70.7 | | | |
| Feed Intake, g | | | | | | | 0.1890 | <0.0001 | <0.0001 |
| Initial | 768.9[bc] | 816.6[c] | 732.7[bc] | 668.4[b] | 359.7[a] | 49.0 | | | |
| Final | 742.0[b] | 630.1[ab] | 609.5[a] | 574.9[a] | 669.3[ab] | 42.5 | | | |
| ADFI, g/day | 94.4 | 93.1 | 85.4 | 82.3 | 77.5 | 5.1 | 0.1891 | | |
| Tissue Weights at 6 Weeks, % WBW | | | | | | | | | |
| Breast | 2.1 | 2.1 | 2.2 | 2.4 | 2.2 | 0.10 | 0.3471 | | |
| Thigh | 2.5 | 2.3 | 2.4 | 2.7 | 2.5 | 0.13 | 0.2599 | | |
| Liver | 2.6 | 2.2 | 2.4 | 2.3 | 2.5 | 0.17 | 0.5000 | | |

TABLE 38-continued

Growth and Feed Intake[1,2]

| Algae | Diets | | | | | | P-Values | | |
|---|---|---|---|---|---|---|---|---|---|
| | 0% | 2.85% | 5.75% | 11.5% | 23% | SEM | Diet | Time | Time × Diet |
| Heart | 0.57 | 0.53 | 0.57 | 0.61 | 0.57 | 0.05 | 0.8285 | | |
| Fat Pad | 2.9 | 3.1 | 2.4 | 2.6 | 2.3 | 0.47 | 0.6845 | | |
| Viscera | 5.6 | 4.8 | 5.7 | 4.5 | 5.7 | 0.91 | 0.8135 | | |
| Ovary | 2.6 | 2.9 | 2.9 | 3.4 | 2.5 | 0.21 | 0.0593 | | |
| Ceca | $0.76^c$ | $0.57^a$ | $0.58^{ab}$ | $0.68^{bc}$ | $0.66^c$ | 0.04 | 0.0071 | | |
| Gizzard | 2.7 | 2.7 | 2.4 | 2.8 | 2.9 | 0.11 | 0.5542 | | |
| Tibias at 6 Weeks | | | | | | | | | |
| Weight, g | 6.5 | 5.9 | 6.1 | 6.1 | 7.2 | 0.34 | 0.1046 | | |
| Length, mm | 53.8 | 54.4 | 53.8 | 54.1 | 53.2 | 1.24 | 0.9741 | | |
| Width, mm | 6.9 | 6.9 | 7.0 | 6.8 | 6.9 | 0.08 | 0.3085 | | |
| Depth, mm | 7.1 | 7.1 | 7.5 | 7.0 | 7.7 | 0.17 | 0.5530 | | |
| Max Slope[3], N/mm | 233.5 | 184.3 | 211.6 | 264.1 | 293.9 | 32.2 | 0.1798 | | |
| Energy[3], J | $0.07^a$ | $0.09^{ab}$ | $0.06^a$ | $0.06^a$ | $0.11^b$ | 0.01 | 0.0117 | | |

[1]Data are reported as LSMeans (n = 5 hens/diet). Means that do not have similar superscripts are considered significantly different (P ≤ 0.05).
[2]Initial data were recorded at day 0 of study and final data were recorded at week 6 of study.
[3]Bone strength was measured on the right tibia using an Instron 5965 (Instron Corp., Norwood, MA, USA) equipped with a 5 kN load cell and a cross head speed of 20 mm/min. Bluehill 3 Testing Software (Instron Corp., Norwood, MA, USA) was used to perform a flexure test with a 38 mm supported length.

Figure 6A:
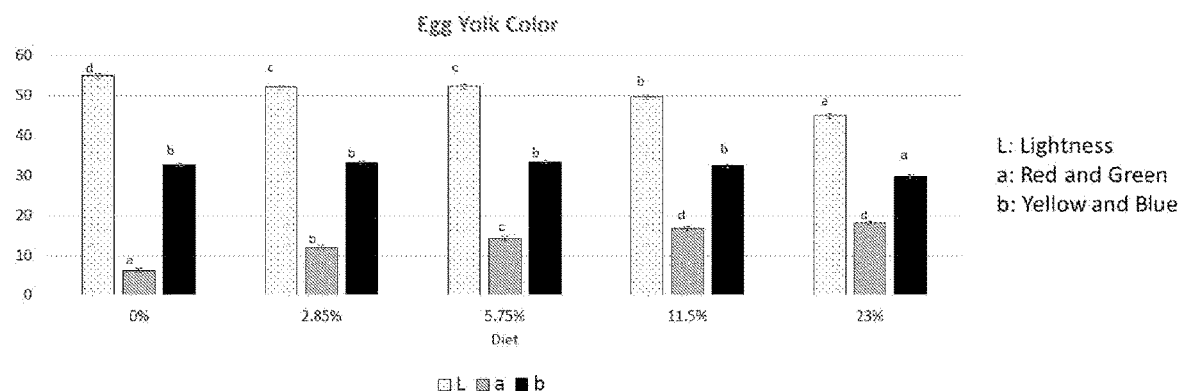
FIGS. 6A-E show that supplemental defatted microalgae produces dose-dependent linear increases in egg yolk redness (FIG. 6A) and linear decreases in egg yolk lightness and egg yolk yellowness (FIG. 6B).
Figure 6B:
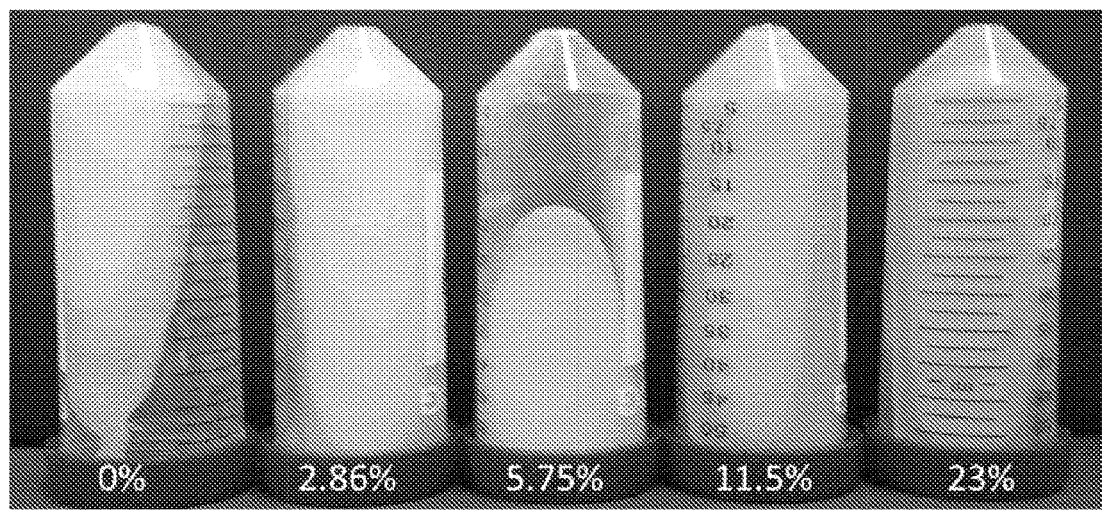

There were also no differences between diets in tibia morphology measurements. However, tibias from hens fed 23% algae required greater energy to break (Table 38, supra). Increased dietary algae inclusion did not affect egg production, weight, or yolk, albumen, and shell contents (Table 39). Eggs from hens fed the 23% algae diet did have the lowest L*- and b*-values and had a 3-fold increase in a*-values when compared to eggs from the control group (Table 39 and FIGS. 6A-B). Additionally, plasma parameters, glucose, NEFA, TAG, CHOL and uric acid, did not differ with diet (Table 40).

TABLE 39

Egg Quality at 6 Weeks[1,]

| Algae | Diets | | | | | | P-Value |
|---|---|---|---|---|---|---|---|
| | 0% | 2.85% | 5.75% | 11.5% | 23% | SEM | |
| Production[2], % | 84.8 | 89.9 | 82.8 | 86.5 | 78.6 | 3.56 | 0.3431 |
| Egg Weight, g | 62.7 | 62.2 | 61.2 | 63.9 | 61.4 | 1.5 | 0.4326 |
| Yolk, % | 26.8 | 26.8 | 27.7 | 27.2 | 26.9 | 0.91 | 0.9335 |
| Albumen, % | 60.8 | 60.2 | 58.7 | 59.5 | 59.5 | 0.86 | 0.4437 |
| Shell, % | 12.3 | 12.9 | 13.6 | 13.3 | 13.7 | 0.38 | 0.1455 |
| L*[3] | $54.9^d$ | $52.1^c$ | $52.3^c$ | $49.6^b$ | $44.9^a$ | 0.59 | <0.0001 |
| a*[3] | $6.1^a$ | $12.0^b$ | $14.4^c$ | $16.7^d$ | $18.1^d$ | 0.50 | <0.0001 |
| b*[3] | $32.7^b$ | $33.3^b$ | $33.4^b$ | $32.5^b$ | $29.8^a$ | 0.41 | <0.0001 |

[1]Data are reported as LSMeans (n = 5 hens/diet). Means that do not have similar superscripts are considered significantly different (P ≤ 0.05).
[2]Eggs were collected daily and egg production was reported as percent production; the number of days each hen laid an egg shown as a percent.
[3]Yolk color, measured as L*-, a*-, and b*-values, was determined with a Macbeth Color Eye (Macbeth Division of Kollmorgen Instruments Corp. Newburgh, NY, USA). The L* value represents lightness (negative towards black, positive towards white), the a* value represents red-greenness (negative towards green, positive towards red), and the b* value represents the blue-yellow color scale (negative towards blue, positive towards yellow).

TABLE 40

Plasma Assays[1, 2]

| Algae | Diets | | | | | | P-Values | | |
|---|---|---|---|---|---|---|---|---|---|
| | 0% | 2.85% | 5.75% | 11.5% | 23% | SEM | Diet | Time | Time × Diet |
| Glucose[3], mg/dL | | | | | | | 0.0524 | 0.1723 | 0.3852 |
| Initial | 2.09 | 2.17 | 2.05 | 2.36 | 2.04 | 1.43 | | | |
| Final | 2.19 | 1.87 | 1.81 | 2.06 | 1.82 | 0.16 | | | |
| NEFA[4], µg/mL | | | | | | | 0.2073 | <0.0001 | 0.6393 |
| Initial | 608.1 | 545.9 | 560.1 | 534.4 | 540.9 | 43.9 | | | |
| Final | 566.9 | 517.5 | 429.0 | 612.5 | 498.3 | 55.8 | | | |
| Triglyceride[4], mg/dL | | | | | | | 0.4773 | <0.0001 | 0.9394 |
| Initial | 120.7 | 131.8 | 122.0 | 126.1 | 134.6 | 8.2 | | | |
| Final | 1211.6 | 1307.7 | 1523.8 | 1276.5 | 1049.9 | 337.9 | | | |
| Total Cholesterol[4], mg/dL | | | | | | | 0.4500 | <0.0001 | 0.1997 |
| Initial | 116.3 | 98.9 | 102.8 | 116.6 | 82.7 | 12.3 | | | |
| Final | 60.7 | 50.4 | 48.0 | 54.9 | 56.3 | 3.7 | | | |

TABLE 40-continued

Plasma Assays[1, 2]

| Algae | Diets | | | | | SEM | P-Values | | |
|---|---|---|---|---|---|---|---|---|---|
| | 0% | 2.85% | 5.75% | 11.5% | 23% | | Diet | Time | Time × Diet |
| Uric Acid[5], mg/dL | | | | | | | 0.8351 | <0.0001 | 0.1071 |
| Initial | 49.1 | 54.3 | 46.6 | 50.4 | 55.5 | 3.16 | | | |
| Final | 63.2 | 50.9 | 51.7 | 52.4 | 71.4 | 4.3 | | | |

[1]Data are reported as LSMeans (n = 5 hens/diet). Means that do not have similar superscripts are considered significantly different ($P \leq 0.05$). All analyses were run in duplicate.
[2]Initial data were recorded at day 0 of study and final data were recorded at week 6 of study.
[3]Plasma glucose levels were determined spectrophotometrically with glucose assay kit GAG020 (Simgma-Aldrich, Sigma Chemical Co., St. Louis, MO, USA).
[4]Plasma non-esterified fatty acids (NEFA), triglyceride (TAG), and total cholesterol (CHOL) were analyzed using commercial enzymatic kits following manufacturer's protocols (Wako Pure Chemical Industries, Ltd., Richmond, VA, USA).
[5]Plasma uric acid was analyzed with Infinity Uric Acid Liquid Stable Reagent (Thermo-Fisher Scientific, Inc., MA, USA).

There was no effect of diet or diet×week interaction on yolk 16:0, 18:0, 18:1n-9, 18:2n-6, 18:3n-6, 18:3n-3, SFA, MUFA, PUFA, or ω6. However, these fatty acids did have significant effects of week. In general, 16:0 and 16:1 increased from week 0 to 6 in eggs from hens fed 23% algae. Eggs from all diets increased in 18:2n-6, 18:3n-6, PUFA, and ω6 from week 0 to 6 (Table 41).

TABLE 41

Yolk Fatty Acid Composition[1, 2], mg/g of Sample

| | 16:0 | 16:1 | 18:0 | 18:1n-9 | 18:2n-6 | 18:3n-6 | 18:3n-3 | 20:3n-6 | 20:4n-6 |
|---|---|---|---|---|---|---|---|---|---|
| 0% Algae | | | | | | | | | |
| Initial | 34.9$^{abcd}$ | 2.9$^{cde}$ | 13.8$^{abc}$ | 50.9$^{cd}$ | 16.5$^{ab}$ | 0$^a$ | 0.34$^{abcd}$ | 0.26$^{bcd}$ | 0$^a$ |
| Final | 38.2$^{cd}$ | 2.3$^{abcde}$ | 16.1$^c$ | 49.4$^{cd}$ | 26.7$^e$ | 0.21$^b$ | 0.38$^{bcd}$ | 0.30$^{cd}$ | 0$^a$ |
| 2.85% Algae | | | | | | | | | |
| Initial | 35.8$^{abcd}$ | 3.2$^c$ | 14.3$^{abc}$ | 52.8$^d$ | 16.8$^{ab}$ | 0$^a$ | 0.32$^{abcd}$ | 0.26$^{bcd}$ | 0$^a$ |
| Final | 40.2$^{de}$ | 2.9$^{cde}$ | 15.4$^{abc}$ | 51.5$^{cd}$ | 26.1$^c$ | 0.19$^b$ | 0.46$^d$ | 0.32$^{cd}$ | 0$^a$ |
| 5.75% Algae | | | | | | | | | |
| Initial | 37.6$^{bcd}$ | 3.2$^f$ | 15.4$^{abc}$ | 52.5$^d$ | 17.7$^{abc}$ | 0$^a$ | 0.34$^{abcd}$ | 0.27$^{bcd}$ | 0$^a$ |
| Final | 36.2$^{abcd}$ | 2.6$^{bcdef}$ | 14.7$^{abc}$ | 45.4$^{abcd}$ | 22.4$^{abcde}$ | 0.15$^b$ | 0.42$^{cd}$ | 0.35$^d$ | 0$^a$ |
| 11.5% Algae | | | | | | | | | |
| Initial | 38.2$^{cd}$ | 3.2$^c$ | 15.9$^b$ | 53.4$^d$ | 17.6$^{abc}$ | 0$^a$ | 0.35$^{abcd}$ | 0.22$^{abcd}$ | 0$^a$ |
| Final | 38.7$^{cd}$ | 3.0$^{de}$ | 11.9$^{abc}$ | 48.9$^{bcd}$ | 24.8$^{de}$ | 0.16$^b$ | 0.44$^{cd}$ | 0.34$^d$ | 0.17$^a$ |
| 23% Algae | | | | | | | | | |
| Initial | 36.1$^{abcd}$ | 3.3$^f$ | 14.2$^{abc}$ | 49.8$^{cd}$ | 16.1$^a$ | 0$^a$ | 0.33$^{abcd}$ | 0.13$^{abc}$ | 0$^a$ |
| Final | 42.1$^e$ | 4.2$^g$ | 11.0$^a$ | 48.9$^{bcd}$ | 23.6$^{cde}$ | 0.12$^b$ | 0.47$^d$ | 0.06$^b$ | 0.41$^a$ |
| SEM | 3.6 | 0.3 | 1.7 | 5.5 | 2.5 | 0.02 | 0.09 | 0.07 | 0.04 |
| P-Values | | | | | | | | | |
| Diet | 0.7060 | 0.0004 | 0.3010 | 0.8616 | 0.9292 | 0.6768 | 0.8626 | 0.0104 | <0.0001 |
| Week | <0.0001 | <0.0001 | 0.0484 | 0.0003 | <0.0001 | <0.0001 | <0.0001 | 0.3236 | 0.0005 |
| D × Wk | 0.9804 | 0.4235 | 0.7996 | 0.9547 | 0.9834 | 0.8421 | 0.9621 | 0.8047 | 0.0024 |

| | 20:5n-3 | 22:6n-3 | SFA | MUFA | PUFA | ω3 | ω6 | ω3:ω6 | EPA + DHA |
|---|---|---|---|---|---|---|---|---|---|
| 0% Algae | | | | | | | | | |
| Initial | 0$^a$ | 1.76$^{abc}$ | 49.2$^{abc}$ | 53.8$^{cd}$ | 18.8$^{ab}$ | 2.1$^{ab}$ | 16.7$^{ab}$ | 8.0$^{abc}$ | 1.8$^{abc}$ |
| Final | 0$^a$ | 1.65$^{ab}$ | 54.7$^c$ | 51.7$^{cd}$ | 29.3$^{de}$ | 2.0$^{ab}$ | 27.2$^d$ | 14.9$^i$ | 1.7$^{ab}$ |

TABLE 41-continued

| Yolk Fatty Acid Composition[1,2], mg/g of Sample |
|---|

| | | | | | | | | | |
|---|---|---|---|---|---|---|---|---|---|
| 2.85% Algae | | | | | | | | | |
| Initial | $0^a$ | $1.73^{abc}$ | $50.6^{abc}$ | $56.2^d$ | $19.1^{ab}$ | $2.1^{ab}$ | $17.1^{ab}$ | $8.3^{def}$ | $1.7^{abc}$ |
| Final | $0.04^{ab}$ | $2.66^{cde}$ | $56.1^c$ | $54.4^{cd}$ | $29.7^e$ | $3.2^{cdef}$ | $26.6^d$ | $9.1^{efg}$ | $2.7^{cdef}$ |
| 5.75% Algae | | | | | | | | | |
| Initial | $0^a$ | $2.05^{abc}$ | $53.5^{bc}$ | $55.8^d$ | $20.4^{abcd}$ | $2.4^{abcd}$ | $17.9^{ab}$ | $7.5^{bcde}$ | $2.1^{abc}$ |
| Final | $0.07^b$ | $2.53^{bcde}$ | $51.3^{abc}$ | $48.1^{abcd}$ | $25.9^{bcde}$ | $3.0^{bcde}$ | $22.9^{abcd}$ | $7.7^{bcde}$ | $2.6^{bcde}$ |
| 11.5% Algae | | | | | | | | | |
| Initial | $0^a$ | $1.83^{abc}$ | $54.5^c$ | $56.6^d$ | $19.9^{ab}$ | $2.2^{abc}$ | $17.8^{ab}$ | $8.1^{cdef}$ | $1.8^{abc}$ |
| Final | $0.28^c$ | $4.03^{fg}$ | $51.1^{abc}$ | $51.9^{cd}$ | $30.0^e$ | $4.8^{gh}$ | $25.3^{cd}$ | $5.5^{abc}$ | $4.3^{hi}$ |
| 23% Algae | | | | | | | | | |
| Initial | $0^a$ | $1.79^{abc}$ | $50.7^{abc}$ | $53.1^{cd}$ | $18.4^a$ | $2.1^{ab}$ | $16.3^a$ | $7.9^{bcde}$ | $1.8^{abc}$ |
| Final | $0.62^d$ | $4.84^h$ | $53.7^{bc}$ | $53.3^{cd}$ | $29.7^e$ | $5.9^k$ | $23.8^{bcd}$ | $4.8^a$ | $5.5^j$ |
| SEM | 0.02 | 035 | 5.02 | 5.82 | 2.69 | 0.38 | 2.49 | 0.94 | 0.35 |
| P-Values | | | | | | | | | |
| Diet | <0.0001 | <0.0001 | 0.8573 | 0.8645 | 0.9030 | <0.0001 | 0.9230 | <0.0001 | <0.0001 |
| Week | <0.0001 | <0.0001 | 0.0005 | 0.0002 | <0.0001 | <0.0001 | <0.0001 | 0.8328 | <0.0001 |
| D × Wk | <0.0001 | <0.0001 | 0.9800 | 0.9546 | 0.9713 | <0.0001 | 0.9827 | <0.0001 | <0.0001 |

[1]Data are reported as LSMeans (n = 5 hens/diet). Means that do not have similar superscripts are considered significantly different (P ≤ 0.05).
[2]Initial data were recorded at day 0 of study and final data were recorded at week 6 of study.

Eggs from hens fed 23% algae had the greatest amounts of 16:1, 20:4n-6, 20:5n-3, 22:6n-3, ω3, and DHA+EPA and lowest ω6:ω3 at 6 weeks when compared to the other diets (Table 41). The level of algae inclusion in the diets was positively correlated (P<0.002) with 14:1, 16:1, 20:5n-3, 22:6n-3, ω3, and EPA+DHA ($R^2$=0.9776, 0.8993, 0.9843, 0.9143, 0.9394, 0.9418, and 0.7145, respectively). Conversely, algae inclusion in the diets was negatively correlated (P<0.002) with ω6:ω3, L*-, and b*-values ($R^2$=0.6535, 0.9729, and 0.7963, respectively).

Figure 6C:
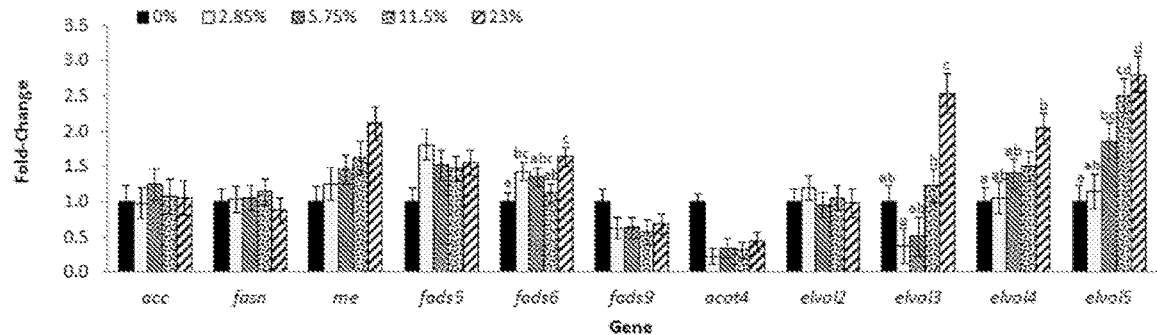
Figure 6D:
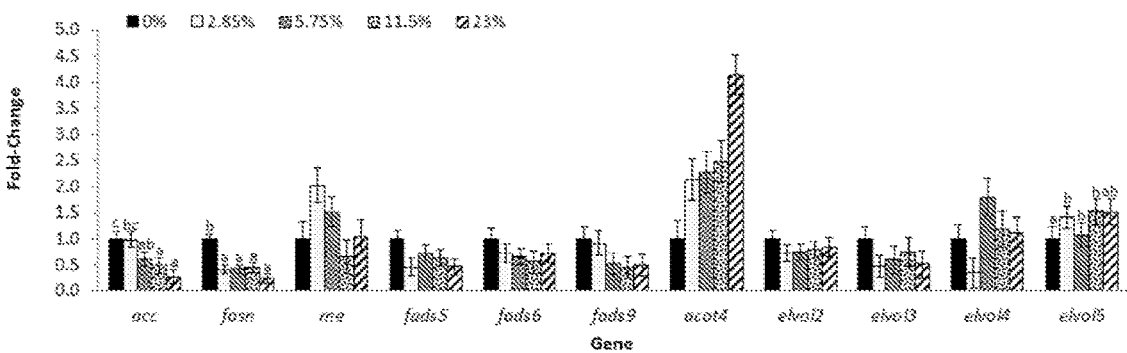
Figure 6E:
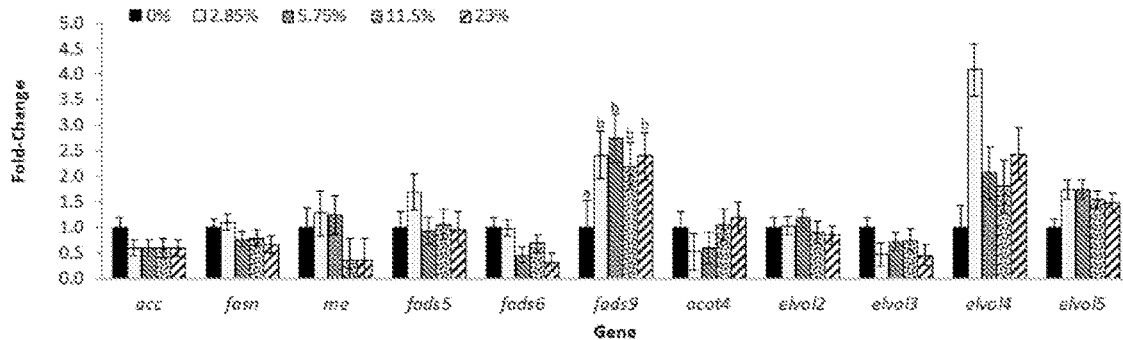

Dietary inclusion of algae increased expression of fads6 and decreased expression of acot4 in hen livers when compared to birds fed 0% algae (FIG. 6C). Liver me, elvol3, elcol4, and elvol5 had dose-dependent increases in expression that were significantly correlated (P<0.002) with dietary levels of algae ($R^2$=0.9724, 0.7837, 0.9667, and 0.8588, respectively). Breast fasn expression was decreased at all levels of algae inclusion when compared to birds fed 0% algae. Breast acc expression decreased ($R^2$=0.8677) and acot4 expression increased ($R^2$=0.9145) as algae inclusion increased (FIG. 6D). Thigh fads6 and elvol5 expression increased at all levels of algae inclusion when compared to hens on the control diet. Thigh elvol4 expression had over a 4-fold increase in birds fed the 2.85% algae diet (FIG. 6E).

Laying hen liver and fat pad fatty acid composition, mg/g of sample, is shown in Table 42.

Laying hen breast and thigh fatty acid composition, mg/g of sample, is shown in Table 43.

TABLE 42

Laying Hen Liver and Fat Pad Fatty Acid Composition, mg/g of sample[1,2]

| | Liver Fatty Acid Composition, mg/g | | | | | | | Fat Pad Fatty Acid Composition, mg/g | | | | | | |
|---|---|---|---|---|---|---|---|---|---|---|---|---|---|---|
| Algae (%) | 0 | 2.86 | 5.75 | 11.5 | 23 | SEM | P-Values | 0 | 2.86 | 5.75 | 11.5 | 23 | SEM | P-Values |
| 14:0 | 0.18 | 0.2 | 0.14 | 0.15 | 0.16 | 0.003 | 0.9184 | 4.2 | 3.1 | 3.60 | 3.6 | 3.9 | 0.7 | 0.8103 |
| 14:1 | — | — | — | — | — | — | — | 0.5 | 0.4 | 0.3 | 0.4 | 0.6 | 0.2 | 0.8400 |
| 15:0 | — | — | — | — | — | — | — | 0.6 | 0.3 | 0.5 | 0.5 | 0.5 | 0.2 | 0.8567 |
| 16:0 | 12.2 | 14.9 | 10.8 | 10.1 | 9.6 | 1.8 | 0.2772 | 100.6 | 73.9 | 78.2 | 76.2 | 81.9 | 15.2 | 0.7356 |
| 16:1 | 0.7 | 0.9 | 0.6 | 0.7 | 0.7 | 0.2 | 0.7851 | 12.7 | 15.3 | 13.4 | 12.5 | 18.4 | 3.3 | 0.6819 |
| 17:0 | 0.13 | 0.17 | 0.12 | 0.12 | 0.12 | 0.01 | 0.1575 | 1.2 | 0.8 | 0.9 | 0.8 | 0.9 | 0.3 | 0.8787 |
| 17:1 | — | — | — | — | — | — | — | 0.8 | 0.7 | 0.7 | 0.6 | 0.7 | 0.2 | 0.9493 |
| 18:0 | 6.1 | 7.4 | 5.2 | 4.9 | 4.5 | 0.7 | 0.0767 | 30.7 | 18.8 | 23.3 | 24.9 | 23.2 | 4.5 | 0.4778 |
| 18:1n-9c | 18.9 | 24.9 | 15.9 | 14.5 | 13.5 | 4.1 | 0.3170 | 221.9 | 175.7 | 173.4 | 169.9 | 195.6 | 33.8 | 0.7958 |
| 18:2n-6c | 6.9 | 8.2 | 5.9 | 6.8 | 6.1 | 0.9 | 0.4809 | 115.5 | 82.90 | 94.80 | 96.3 | 100.50 | 18.2 | 0.7939 |
| 20:1 | 0.06 | 0.09 | 0.04 | 0.05 | 0.05 | 0.03 | 0.7606 | 1.6 | 0.8 | 2.0 | 1.0 | 0.9 | 0.5 | 0.4028 |
| 18:3n-6 | 0.03 | 0.06 | 0.04 | 0.05 | 0.05 | 0.03 | 0.9595 | 2.6 | 2.0 | 2.5 | 2.6 | 2.5 | 0.6 | 0.9563 |
| 20:0 | — | — | — | — | — | — | — | 1.2 | 1.0 | 1.2 | 1.1 | 1.5 | 0.4 | 0.8999 |
| 18:3n-3 | 0.06 | 0.124 | 0.05 | 0.07 | 0.08 | 0.02 | 0.3079 | — | — | — | — | — | — | — |
| 21:0 | 0.03 | 0.01 | 0.00 | 0.04 | 0.03 | 0.02 | 0.3612 | — | — | — | — | — | — | — |
| 22:0 | 0.11 | 0.13 | 0.11 | 0.11 | 0.1 | 0.01 | 0.4041 | — | — | — | — | — | — | — |
| 20:2 | $1.9^b$ | $2.2^b$ | $1.8^b$ | $1.8^b$ | $1.2^a$ | 0.2 | 0.0103 | — | — | — | — | — | — | — |
| 20:5n-3 | $0.13^b$ | $0.12^b$ | $0.1^b$ | $0.10^b$ | $0.05^a$ | 0.01 | 0.0016 | — | — | — | — | — | — | — |
| 22:6n-3 | $0.42^a$ | $0.66^b$ | $0.65^b$ | $0.89^c$ | $1.18^d$ | 0.07 | <0.0001 | — | — | — | — | — | — | — |
| SFA | 18.8 | 22.8 | 16.4 | 15.4 | 14.5 | 2.6 | 0.1936 | 138.5 | 97.8 | 107.8 | 107.3 | 112.1 | 20.9 | 0.7085 |

TABLE 42-continued

Laying Hen Liver and Fat Pad Fatty Acid Composition, mg/g of sample[1,2]

| | Liver Fatty Acid Composition, mg/g | | | | | | | Fat Pad Fatty Acid Composition, mg/g | | | | | | |
|---|---|---|---|---|---|---|---|---|---|---|---|---|---|---|
| Algae (%) | 0 | 2.86 | 5.75 | 11.5 | 23 | SEM | P-Values | 0 | 2.86 | 5.75 | 11.5 | 23 | SEM | P-Values |
| MUFA | 16.7 | 25.9 | 16.6 | 15.2 | 14.2 | 4.3 | 0.3333 | 237.5 | 192.9 | 189.8 | 184.4 | 216.2 | 37.4 | 0.8389 |
| PUFA | 9.6 | 11.3 | 8.7 | 9.8 | 8.6 | 0.9 | 0.2695 | 118.1 | 84.9 | 97.3 | 98.9 | 103.0 | 18.7 | 0.8019 |
| ω3 | $0.6^a$ | $0.9^{bc}$ | $0.8^{ab}$ | $1.1^c$ | $1.3^d$ | 0.1 | <0.0001 | — | — | — | — | — | — | — |
| ω6 | 7.0 | 8.3 | 6.0 | 6.9 | 6.2 | 1.0 | 0.5028 | 118.1 | 84.9 | 97.3 | 98.9 | 103 | 18.7 | 0.8019 |
| ω6:ω3 | $12.0^c$ | $9.5^{bc}$ | $7.5^{ab}$ | $6.5^{ab}$ | $5.1^a$ | 1.3 | 0.0154 | — | — | — | — | — | — | — |
| DHA + EPA | $0.6^a$ | $0.8^{bc}$ | $0.8^{ab}$ | $1.0^c$ | $1.2^d$ | 0.1 | <0.0001 | — | — | — | — | — | — | — |

[1]Data are reported as LSMeans (n = 5 hens/diet). Means that do not have similar superscripts are considered significantly different (P ≤ 0.05).
[2]Data were recorded at week 6 of study.

TABLE 43

Laying Hen Breast and Thigh Fatty Acid Composition, mg/g of Sample[1,2]

| | Breast Fatty Acid Composition, mg/g | | | | | | | Thigh Fatty Acid Composition, mg/g | | | | | | |
|---|---|---|---|---|---|---|---|---|---|---|---|---|---|---|
| Algae (%) | 0 | 2.86 | 5.75 | 11.5 | 23 | SEM | P-Values | 0 | 2.86 | 5.75 | 11.5 | 23 | SEM | P-Values |
| 14:0 | 0.07 | 0.09 | 0.10 | 0.07 | 0.07 | 0.02 | 0.6829 | 0.26 | 0.32 | 0.21 | 0.24 | 0.25 | 0.04 | 0.3184 |
| 16:0 | 2.5 | 2.7 | 3.0 | 2.4 | 2.2 | 0.3 | 0.5049 | 5.8 | 7.4 | 4.7 | 5.2 | 5.5 | 0.8 | 0.1842 |
| 16:1 | 0.2 | 0.3 | 0.3 | 0.3 | 0.2 | 0.1 | 0.2506 | 1.0 | 1.4 | 0.8 | 1.0 | 1.0 | 0.2 | 0.2790 |
| 17:0 | — | — | — | — | — | — | — | 0.04 | 0.08 | 0.04 | 0.05 | 0 | 1.9 | 0.1336 |
| 18:0 | 0.5 | 0.4 | 0.5 | 0.4 | 0.6 | 0.2 | 0.8640 | 1.9 | 2.2 | 1.7 | 1.8 | 1.9 | 0.2 | 0.4646 |
| 18:1n-9c | 2.4 | 1.9 | 2.9 | 2.2 | 2.6 | 0.8 | 0.9228 | 11.3 | 14.3 | 8.6 | 10.3 | 10.4 | 1.6 | 0.1732 |
| 18:2n-6c | 2.5 | 3.4 | 3.5 | 3.0 | 2.0 | 0.6 | 0.4817 | 6.3 | 7.7 | 5.0 | 6.2 | 6.0 | 0.8 | 0.2829 |
| 20:1 | — | — | — | — | — | — | — | — | — | — | — | — | — | — |
| 18:3n-6 | 0.9 | 1.3 | 1.2 | 1.2 | 0.4 | 0.6 | 0.7568 | 0.17 | 0.24 | 0.14 | 0.17 | 0.16 | 0.03 | 0.2839 |
| 18:3n-3 | — | — | — | — | — | — | — | 0.02 | 0.00 | 0.00 | 0.02 | 0.00 | 0.01 | 0.5686 |
| 21:0 | — | — | — | — | — | — | — | — | — | — | — | — | — | — |
| 22:0 | — | — | — | — | — | — | — | — | — | — | — | — | — | — |
| 20:2 | — | — | — | — | — | — | — | — | — | — | — | — | — | — |
| 20:3n-6 | 0.6 | 0.6 | 0.6 | 0.5 | 0.6 | 0.03 | 0.7995 | 0.53 | 0.58 | 0.57 | 0.56 | 0.55 | 0.03 | 0.6944 |
| 20:4n-6 | — | — | — | — | — | — | — | — | — | — | — | — | — | — |
| 20:5n-3 | — | — | — | — | — | — | — | — | — | — | — | — | — | — |
| 22:6n-3 | $0.02^a$ | $0.03^a$ | $0.05^a$ | $0.13^b$ | $0.19^b$ | 0.02 | <0.0001 | $0.0^a$ | $0.02^a$ | $0.02^a$ | $0.14^b$ | $0.16^b$ | 0.03 | <0.0001 |
| SFA | 3.1 | 3.2 | 3.7 | 2.9 | 2.9 | 0.4 | 0.6728 | 8.0 | 9.9 | 6.6 | 7.4 | 7.6 | 1.0 | 0.2219 |
| MUFA | 2.7 | 2.2 | 3.2 | 2.4 | 2.8 | 0.8 | 0.9172 | 12.4 | 15.7 | 9.4 | 11.3 | 11.4 | 1.8 | 0.1754 |
| PUFA | 4.0 | 5.3 | 5.3 | 4.9 | 3.2 | 1.2 | 0.6342 | 7.0 | 8.5 | 5.7 | 7.0 | 6.9 | 0.8 | 0.2933 |
| ω3 | $0.02^a$ | $0.03^a$ | $0.05^a$ | $0.13^b$ | $0.19^b$ | 0.02 | <0.0001 | $0.02^a$ | $0.02^a$ | $0.02^a$ | $0.16^b$ | $0.16^b$ | 0.03 | 0.0008 |
| ω6 | 3.9 | 5.3 | 5.2 | 4.7 | 2.9 | 1.2 | 0.5980 | 7.0 | 8.5 | 5.7 | 6.9 | 6.8 | 0.9 | 0.2934 |
| ω6:ω3 | 22.7 | 17.2 | 19.2 | 35.7 | 15.8 | 10.2 | 0.3252 | 69.5 | 72.6 | 31.5 | 45.9 | 32.7 | 7.5 | 0.0793 |
| DHA + EPA | $0.02^a$ | $0.03^a$ | $0.05^a$ | $0.13^b$ | $0.19^b$ | 0.02 | <0.0001 | $0.0^a$ | $0.02^a$ | $0.02^a$ | $0.14^b$ | $0.16^b$ | 0.02 | <0.0001 |

[1]Data are reported as LSMeans (n = 5 hens/diet). Means that do not have similar superscripts are considered significantly different (P ≤ 0.05).
[2]Data were recorded at week 6 of study.

Discussion

Objectives of the current study were to investigate the use of defatted microalgae as a source of dietary ω3 fatty acids to enrich chicken eggs. This study examined growth, egg production, egg quality, body composition, and expression of fatty acid synthesis genes in liver, white muscle, and red muscle of hens fed varying levels of microalgae inclusion ranging from 0 to 23% of the diet. Gene expression analyses allowed for identification of differentially-regulated genes responsible for physiological mechanisms that increase DHA synthesis in chickens. Although there were no differences in growth among dietary treatments, there were differences in quality and compositional attributes investigated in this study. Additionally, these findings were associated with differential gene expression in liver and white muscle. These findings suggest that laying hens may have differing fatty acid metabolisms which may contribute to differences in egg quality and composition observed with algae supplementation.

In general, the crude protein and crude lipid contents of microalgae is widely variable and depends on species (Gatrell et al., "Potential of Defatted Microalgae from the Biofuel Industry as an Ingredient to Replace Corn and Soybean Meal in Swine and Poultry Diets," *Journal of Animal Science* 92(4):1306-14 (2014), which is hereby incorporated by reference in its entirety). The Renew defatted green microalgae biomass, *Nannochloropsis oceanica*, has a crude protein content of 43.9%, which is approximately 90% of that in soybean meal (49.0%). The crude lipid content of these defatted microalgae is 5.2%, compared to 1.1 and 3.0% of soybean meal and corn, respectively. In general, marine microalgae contain greater amounts of ω3 fatty acids, including EPA and DHA, then conventional animal protein sources (Fredriksson et al., "Fatty Acid and Carotenoid Composition of Egg Yolks as an Effect of Microalgae Addition to Feed Formula for Laying Hens," *Food Chemistry* 99:530-537 (2006); Kalogeropoulos et al., "Nutritional Evaluation and Bioactive Microconstituents (Carotenoids, Tocopherols, Sterols, And Squalene) of Raw and Roasted Chicken Fed on DHA-rich Microalgae," *Food Research International* 43:2006-2013 (2010), which are hereby incorporated by reference in their entirety). Microalgae are also a source of carotenoids, lipid soluble pigments; astaxanthin is the main carotenoid in most microalgae (Dominguez-Bocanegra et al., "Influence of Environmental and Nutritional Factors in the Production of Astaxanthin from *Haematococcus pluvialis*," *Bioresource Technology* 92:209-214 (2004), which is hereby incorporated by reference in its entirety). These pigments are known to alter color of animal products when included in diets. Although, there were no effects of microalgae supplementation on egg production or component size, there were differences in yolk color. Yolks from hens fed algae were darker in color having lower L*- and b*-values and higher a*-value; indicating the yolks were blacker, bluer, and redder than yolks from hens fed the control diet.

Previous studies from our lab have shown soybean meal replacement up to 7.5% with defatted microalgae (*Staurosira* sp) maintained performance characteristics comparable to control diets in broiler chicks when essential amino acids (Met, Lys, Ile, Thr, Trp, and Val) were supplemented. Additionally, plasma responses, liver biomarkers, and gross examination of the digestive tracts showed no toxicity (Austic et al., "Potential and Limitation of a New Defatted Diatom Microalgal Biomass in Replacing Soybean Meal and Corn in Diets for Broiler Chickens," *Journal of Agricultural and Food Chemistry* 61:7341-7348 (2013), which is hereby incorporated by reference in its entirety). At 16% defatted algae inclusion, broiler breast meat had a 60-fold increase in the total amount of EPA and DHA, 16.9 mg compared to 0.28 mg EPA+DHA/100 g in broilers fed the control diet (Gatrell et al., "Potential of Defatted Microalgae from the Biofuel Industry as an Ingredient to Replace Corn and Soybean Meal in Swine and Poultry Diets," *Journal of Animal Science* 92(4):1306-14 (2014), which is hereby incorporated by reference in its entirety). The current study showed that yolks from hens fed 23% algae had a 3-fold increase of DHA after 6 weeks of supplementation, 4.8±0.35 mg compared to 1.7±0.35 mg of DHA/g of yolk. Interestingly, Renew defatted green microalgae biomass contains no DHA or ARA, but contain 4.9 mg of EPA/g and have 5.0 and 1.1 mg/g of ω3 and ω6, respectively.

Synthesis of ω3 fatty acids requires a series of elongation and desaturation steps. Both ω6 and ω3 PUFAs synthesis pathways are distinct with no cross reactions, but they do undergo the same alternating reactions employing the same enzymes to desaturate and elongate (Ratnayake et al., "Fat and Fatty Acid Terminology, Methods of Analysis and Fat Digestion, and Metabolism: A Background Review Paper," *Annals of Nutrition and Metabolism* 55 (1-3):8-43 (2009), which is hereby incorporated by reference in its entirety). The first step employs FADS6 followed by elongation by ELVOL5 and subsequent desaturation with FADS5 to form 20:4n-6 and 20:5n-3. FADS6 is the rate limiting step in mammals, and it has a higher affinity for 18:3n-3 compared to 18:2n-6 (Ratnayake et al., "Fat and Fatty Acid Terminology, Methods of Analysis and Fat Digestion, and Metabolism: A Background Review Paper," *Annals of Nutrition and Metabolism* 55 (1-3):8-43 (2009), which is hereby incorporated by reference in its entirety). The next step involves two successive elongation steps carried out by ELOVL2 and desaturation by FADS6 to form 24:6n-3. The fatty acids then undergo one round of β-oxidation to yield 22:6n-3 (Ratnayake et al., "Fat and Fatty Acid Terminology, Methods of Analysis and Fat Digestion, and Metabolism: A Background Review Paper," *Annals of Nutrition and Metabolism* 55 (1-3):8-43 (2009), which is hereby incorporated by reference in its entirety). Mammals have low levels of ω3 fatty acid synthesis because they have low expression levels and enzymatic activities of ELOVL2 and ELOVL5. Additionally, only ELOVL2 can synthesize DHA (Gregory et al., "Functional Characterization of the Chicken Fatty Acid Elongases 1, 2," *Journal of Nutrition* 143:12-16 (2013), which is hereby incorporated by reference in its entirety).

In general, expression of genes involved in PUFA synthesis was higher in livers of hens fed 23% algae when compared to control birds. The strong positively-correlated, dose-dependent responses of elvol3, elvol4, and elvol5 to increased levels of dietary algae inclusion not only suggest that expression of these genes is dependent on algae supplementation, it also suggests there may be increased flux through the PUFA synthesis pathways. The increased levels of ω3 fatty acids further support this assertion. Interestingly, there is evidence that chickens have increased ability to synthesize PUFAs, specifically DHA (Gregory et al., "Functional Characterization of the Chicken Fatty Acid Elongases 1, 2," *Journal of Nutrition* 143:12-16 (2013), which is hereby incorporated by reference in its entirety). Chicken liver ELOVL5 elongates DPA along with ELOVL2 and chickens have higher expression levels of elvol5 when compared to rat liver; only ELVOL2 has this capability in mammals (Gregory et al., "Functional Characterization of the Chicken Fatty Acid Elongases 1, 2," *Journal of Nutrition* 143:12-16 (2013), which is hereby incorporated by reference in its entirety). Gregory et al., "Functional Characterization of the Chicken Fatty Acid Elongases 1, 2," *Journal of Nutrition* 143:12-16 (2013), which is hereby incorporated by reference in its entirety, determined that elongases are an important difference, allowing chickens to have greater DHA synthesis when compared to mammals. These authors also showed expression levels of liver elvol2 and elvol5 were not altered when dietary tallow was replaced with canola oil, but there were subsequent increases in DHA with ALA supplementation through the added canola oil (Gregory et al., "Functional Characterization of the Chicken Fatty Acid Elongases 1, 2," *Journal of Nutrition* 143:12-16 (2013), which is hereby incorporated by reference in its entirety). However, this study showed that liver elvol5, as well as elvol3 and elvol4, expressions were increased when microalgae, a source of EPA, was added to the diet. Nevertheless, there is evidence that chickens have the ability to synthesize DHA and deposit it in tissues.

Expression profiles of the breast and thigh are different than those observed in the liver; although, this is not surprising since liver is the primary sight for fatty acid synthesis. Breasts from hens fed algae had decreased acc and fasn expression. Breast acc decreased in a dose-dependent manner associated with increasing levels of dietary microalgae inclusion, suggesting the decreased expression was dependent on algae supplementation. De novo fatty acid synthesis is considered to be highly conserved among species and involves two main enzymes, ACC and FASN. ACC is the rate determining step and catalyzes the cytosolic reaction that converts acetyl-CoA to malonyl-CoA. FAS is the second enzyme involved in fatty acid synthesis and is a multifunctional enzyme that catalyzes seven enzymatic reactions. FAS catalyzes the formation of 16:0 from seven acetyl-CoA molecules and malonyl-CoA (Chow, C. K., *Fatty Acids in Foods and their Health Implications*. Boca Raton, Fla.: Taylor and Francis Group, LLC (2008); Ratnayake et al., "Fat and Fatty Acid Terminology, Methods of Analysis and Fat Digestion, and Metabolism: A Background Review Paper," *Annals of Nutrition and Metabolism* 55 (1-3):8-43 (2009), which are hereby incorporated by reference in their entirety). Down-regulation of these genes suggests algae supplementation may have decreased synthesis of shorter-chained fatty acids. Breasts from chickens fed algae also showed a dose-dependent increase in acot4. ACOT4 is involved in PUFA β-oxidation which is the last step in DHA synthesis. Additionally, there was a 2-fold increase in thigh elvol5 expression. The only other genes affected by algae supplementation in the thigh were fads9 and elvol5; both genes had increased expression when algae were added to the diet. These findings suggest that the effects of algae supplementation may not only alter liver fatty acid metabolism, it may also impact fatty acid metabolism in muscle.

Data from this study indicate that algae supplementation may affect fatty acid metabolism in laying hens. Although there were no differences in growth or egg production, there were distinct differences in egg color and composition. Eggs from hens fed 23% algae had the greatest amounts of 20:5n-3, 22:6n-3, and total ω3 fatty acids at 6 weeks when compared to the other diets. Gene expression data suggest increased PUFA synthesis in hens fed algae. Liver me, elvol3, elcol4, and elvol5 had dose-dependent increases in expression. Breast acc and fasn expressions were decreased at all levels of algae inclusion when compared to birds fed 0% algae. Thigh elvol4 expression had over a 4-fold increase in birds fed the 2.85% algae diet. These results support Gregory et al., "Functional Characterization of the Chicken Fatty Acid Elongases 1, 2," *Journal of Nutrition* 143:12-16 (2013), which is hereby incorporated by reference in its entirety, findings; there is evidence that chickens have an increased ability to synthesize long-chain PUFAS, primarily DHA. Furthermore, these findings suggest that algae supplementation may not only alter liver fatty acid metabolism, it may also impact fatty acid metabolism in muscle. Overall, feeding defatted microalgae at moderate dietary inclusion levels to chickens does increase the ω3 fatty acid content of eggs. Therefore, microalgae are not only a source of protein; they are a source of essential fatty acids for animal feeds. Increasing ω3 fatty acid contents would be beneficial, not only to the health of consumers, but also to producers who can profit from producing value-added products.

Example 5—Low Concentrations of Supplemental Defatted Microalgae Affect Egg and Tissue Fatty Acid Composition Differently in Layers Fed Diets Containing Corn and Flaxseed Oils Materials and Methods Algae All algae were obtained from Cellana (Kailua-Kona, Hi., USA). Algae was *Nannochloropsis oceanica* after bio-fuel extraction.

Animals and Diet

Sixty shaver leghorn layer hens (about 20 weeks old) were housed in individual cages. The environment was controlled at 23° C., 20% relative humidity, with a 16 hour light and 8 hour dark cycle during a 6 week experiment. Ten birds were randomly assigned for each treatment, and each hen was considered as a replication. Six diets were formulated as a full factorial expansion (flaxseed oil×Algae A). The levels of flaxseed oil included were 0 and 1.5 of the total diet along with 0, 3, and 5% Algae (Table 44) based on NRC., "Nutrient Requirements of Poultry," in National Research Council, National Academy Press Washington, USA (1994), which is hereby incorporated by reference in its entirety. The birds had free access to feed and water through experiment period.

TABLE 44

| | 0% Algae | | 3% Algae | | 5% Algae | |
|---|---|---|---|---|---|---|
| | 1.5% Corn Oil | 1.5% Flaxseed Oil | 1.5% Corn Oil | 1.5% Flaxseed Oil | 1.5% Corn Oil | 1.5% Flaxseed Oil |
| SBM | 187.0 | 187.0 | 163.5 | 163.5 | 145.0 | 145.0 |
| Corn | 687.0 | 687.0 | 685.0 | 685.0 | 687.0 | 687.0 |
| Algae | — | — | 30.0 | 30.0 | 50.0 | 50.0 |
| Corn oil | 15.0 | — | 15.0 | — | 15.0 | — |
| Flaxseed oil | — | 15.0 | — | 15.0 | — | 15.0 |
| DCP | 19.0 | 19.0 | 18.0 | 18.0 | 18.0 | 18. |
| Limestone | 79.0 | 79.0 | 79.0 | 79.0 | 78.5 | 78.5 |
| NaCl | 5.5 | 5.5 | 0.2 | 0.2 | | |
| Methionine | 4.5 | 4.5 | 4.5 | 4.5 | 4.5 | 4.5 |
| Vit/min mix[1] | 3.0 | 3.0 | 3.0 | 3.0 | 3.0 | 3.0 |
| $ME_n$, Kcal/kg | 2905 | 2905 | 2901 | 2901 | 2901 | 2901 |
| Crude Pretein, % | 15.2 | 15.2 | 15.2 | 15.2 | 15.0 | 15.0 |
| Lysine, g/kg | 7.3 | 7.3 | 7.3 | 7.3 | 7.2 | 7.2 |
| Met + Cys, g/kg | 9.5 | 9.5 | 9.4 | 9.4 | 9.3 | 9.3 |
| Phosphate, g/kg | 7.07 | 7.07 | 6.92 | 6.92 | 6.94 | 6.94 |
| Calcium, g/kg | 33.6 | 33.6 | 33.5 | 33.5 | 33.0 | 33.0 |
| Sodium, g/kg | 2.4 | 2.4 | 2.4 | 2.4 | 2.6 | 2.6 |

Feed Composition (g/kg)

Body weight and feed intake were measured weekly, and eggs were collected every day to determine egg production. Every 7 days, all eggs were collected and whole egg, egg shell, albumen, and yolk weight were taken. Blood was collected from wing veins every second week. After keeping in ice during collection, plasma was obtained by centrifugation (3000×g, 15 min at 4° C.) and stored at −20° C. until analyses. Liver and adipose tissue were collected at the end of the experiment.

Plasma uric acid concentration was measured with a uric acid kit (Infinity™ Uric Acid Liquid Stable Reagent from Thermo Scientific (Middletown, Va.). Plasma triacylglycerol and cholesterol were measured using kits from Wako Chemical (Richmond, Va.).

Lipids were extracted from egg yolk, plasma, liver, and adipose tissue according to Folch et al., "A Simple Method for the Isolation and Purification of Total Lipids from Animal Tissues," *J. Biol. Chem.* 226:497-509 (1957), which is hereby incorporated by reference in its entirety. Fatty acids were methylated with methanolic sulfuric acid (1%) (Christie, "Preparation of Ester Derivatives of Fatty Acids for Chromatographic Analysis," in *Advances in Lipid Methodology—Two*, pp. 69-111, ed. W. W. Christie, Oily Press, Dundee (1993), which is hereby incorporated by reference in its entirety). Tritridecanoin (Sigma-Aldrich Co., St Louis, Mo.) was used as an internal standard, and each fatty acid was identified by its retention with fatty acid methyl ester standard (Sigma-Aldrich Co., St Louis, Mo.). Methyl esters of fatty acids were analyzed using a gas chromatography instrument (Agilent 6890N, Agilent Technologies, Santa Clara, Calif.) fitted with a flame-ionization detector. A fused-silica capillary column coated with CP-SIL 88 for fame (100 m×0.25 mm i.d., 0.2 mm film thickness) was used (Varian Inc, Lake Forest, Calif.). Oven temperature was programmed to be held for 4 min at 140° C., increased by 4° C. per min to 220° C., and then held for 5 min. Carrier gas was $N_2$ with constant flow rate of 2 ml/s and injector temperature was 230° C. and detector temperature was 280° C.

Statistical Analysis

Data were analyzed by GLM procedure using the SAS system (SAS Institute, Cary, N.C.) with Duncan's post hoc test. Significance of differences was defined at the P<0.05 level.

Results

Body weights and feed intakes during experiment were summarized in Table 45. Body weights were not affected by dietary treatments through experiment, and feed intake also was not affected. There was no difference in liver weight and percentage of liver weight to body weight at the end of experiment.

TABLE 45

Body Weight, Liver Weight, and Feed Intake

| | Corn | | | Flax | | |
|---|---|---|---|---|---|---|
| | 0 | 3 | 5 | 0 | 3 | 5 |
| Body weight, g | | | | | | |
| Day 0 | 1424 ± 64 | 1501 ± 88 | 1465 ± 71 | 1462 ± 88 | 1462 ± 96 | 1441 ± 99 |
| Day 7 | 1437 ± 73 | 1484 ± 82 | 1468 ± 56 | 1451 ± 97 | 1444 ± 100 | 1443 ± 73 |
| Day 14 | 1424 ± 69 | 1474 ± 92 | 1469 ± 81 | 1454 ± 110 | 1439 ± 98 | 1445 ± 84 |
| Day 21 | 1419 ± 72 | 1467 ± 92 | 1455 ± 102 | 1445 ± 114 | 1434 ± 102 | 1441 ± 94 |
| Day 28 | 1420 ± 69 | 1480 ± 98 | 1457 ± 103 | 1448 ± 104 | 1455 ± 94 | 1447 ± 91 |
| Day 35 | 1437 ± 60 | 1483 ± 98 | 1461 ± 95 | 1457 ± 104 | 1440 ± 110 | 1458 ± 98 |
| Day 42 | 1426 ± 107 | 1490 ± 93 | 1480 ± 109 | 1484 ± 87 | 1452 ± 115 | 1468 ± 94 |
| Liver wt, g | 40.56 ± 7.95 | 43.37 ± 8.80 | 40.08 ± 6.14 | 40.69 ± 5.75 | 41.36 ± 7.91 | 40.11 ± 5.24 |
| Liver % of BW | 2.83 ± 0.44 | 2.90 ± 0.50 | 2.70 ± 0.35 | 2.79 ± 0.32 | 2.83 ± 0.45 | 2.72 ± 0.25 |
| Feed Intake, g/d | | | | | | |
| Day 0-7 | 93.26 ± 8.80 | 89.62 ± 6.45 | 91.01 ± 9.20 | 89.39 ± 7.45 | 89.39 ± 7.45 | 89.61 ± 7.22 |
| Day 8-14 | 92.31 ± 5.39 | 92.02 ± 5.76 | 95.65 ± 11.21 | 91.60 ± 6.61 | 91.60 ± 6.61 | 96.04 ± 7.84 |
| Day 15-21 | 85.41 ± 8.45 | 85.90 ± 5.97 | 88.54 ± 12.28 | 87.38 ± 8.38 | 87.38 ± 8.38 | 92.00 ± 6.20 |
| Day 22-28 | 94.44 ± 3.67 | 95.26 ± 5.60 | 97.35 ± 7.45 | 94.88 ± 7.73 | 94.88 ± 7.73 | 96.67 ± 8.06 |
| Day 29-35 | 94.63 ± 4.96 | 97.25 ± 5.47 | 94.81 ± 5.94 | 92.82 ± 7.54 | 92.82 ± 7.54 | 96.72 ± 7.47 |
| Day 36-42 | 92.44 ± 13.02 | 99.35 ± 6.03 | 100.07 ± 6.14 | 98.55 ± 6.36 | 98.55 ± 6.36 | 102.11 ± 8.81 |
| Day 0-42 | 92.08 ± 4.59 | 93.23 ± 3.11 | 94.57 ± 7.15 | 92.44 ± 5.67 | 92.44 ± 5.67 | 95.52 ± 6.50 |

All hens showed more than 95% of egg production, and there was no dietary effect on egg production (Table 46). Egg component weight (whole egg, egg yolk, albumen, and egg shell) were not affected by flaxseed oil and algae supplementation. Egg yolk color was affected by algae supplementation but oil source did not have any effect on yolk color. As algae concentration was increased, yolk color was increased, and 5% algae supplementation showed about 14 point Roche color pan.

Plasma TG, cholesterol, and uric acid were present in Table 47. Plasma TG concentration was high and showed huge deviations. Plasma TG did not difference among treatment. Plasma cholesterol and uric acid were not affected by dietary treatments.

TABLE 46

Egg Production and Egg Component (Whole Egg Weight, Albumen, Egg Yolk, Egg Color, and Egg Shell) from Experiment

| | Corn | | | Flax | | |
|---|---|---|---|---|---|---|
| | 0 | 3 | 5 | 0 | 3 | 5 |
| Egg production, % | | | | | | |
| Day 0-7 | 100.00 ± 0.00 | 100.00 ± 0.00 | 100.00 ± 0.00 | 100.00 ± 0.00 | 100.00 ± 0.00 | 100.00 ± 0.00 |
| Day 8-14 | 100.00 ± 0.00 | 100.00 ± 0.00 | 100.00 ± 0.00 | 100.00 ± 0.00 | 98.41 ± 4.76 | 100.00 ± 0.00 |
| Day 15-21 | 98.41 ± 4.76 | 97.14 ± 9.03 | 100.00 ± 0.00 | 100.00 ± 0.00 | 98.41 ± 4.76 | 100.00 ± 0.00 |

TABLE 46-continued

Egg Production and Egg Component (Whole Egg Weight, Albumen, Egg Yolk, Egg Color, and Egg Shell) from Experiment

|  | Corn | | | Flax | | |
| --- | --- | --- | --- | --- | --- | --- |
|  | 0 | 3 | 5 | 0 | 3 | 5 |
| Day 22-28 | 98.41 ± 4.76 | 97.14 ± 6.02 | 98.57 ± 4.51 | 98.57 ± 4.51 | 98.41 ± 4.76 | 98.57 ± 4.51 |
| Day 29-35 | 100.00 ± 0.00 | 98.57 ± 4.51 | 100.00 ± 0.00 | 100.00 ± 0.00 | 100.00 ± 0.00 | 100.00 ± 0.00 |
| Day 36-42 | 96.82 ± 6.29 | 100.00 ± 0.00 | 98.57 ± 4.51 | 97.14 ± 6.02 | 100.00 ± 0.00 | 100.00 ± 0.00 |
| Day 0-42 | 98.94 ± 1.72 | 98.80 ± 3.02 | 99.76 ± 1.35 | 99.28 ± 4.60 | 99.20 ± 1.68 | 98.33 ± 4.49 |
| Egg component | | | | | | |
| Week 0 | | | | | | |
| Whole egg | 54.3 ± 3.7 | 55.4 ± 2.6 | 54.1 ± 3.1 | 55.5 ± 4.2 | 55.3 ± 2.7 | 56.3 ± 3.2 |
| Albumen | 32.7 ± 2.6 | 33.1 ± 2.1 | 32.6 ± 2.1 | 33.8 ± 3.3 | 33.6 ± 2.4 | 34 ± 3.2 |
| Yolk | 13.8 ± 1.2 | 14.3 ± 1.0 | 13.6 ± 0.9 | 13.9 ± 1.1 | 13.9 ± 1 | 14.2 ± 1.1 |
| Color | 9.9 ± 0.7 | 9.4 ± 1.0 | 10.1 ± 0.7 | 9.7 ± 1.3 | 10 ± 0.8 | 10.1 ± 0.6 |
| Egg shell | 5.4 ± 0.3 | 5.5 ± 0.4 | 5.5 ± 0.4 | 5.4 ± 0.3 | 5.4 ± 0.4 | 5.7 ± 0.3 |
| Week 1 | | | | | | |
| Whole egg | 54.8 ± 2.9 | 55.6 ± 3.7 | 54.4 ± 3.5 | 57.1 ± 4.4 | 55.2 ± 3.6 | 54.8 ± 2.6 |
| Albumen | 33.1 ± 2.4 | 33.7 ± 3.3 | 33.2 ± 2.4 | 34.9 ± 3.1 | 34.2 ± 2.9 | 33.4 ± 2.2 |
| Yolk | 13.4 ± 0.9 | 14.0 ± 0.9 | 13 ± 1.4 | 13.6 ± 0.9 | 13.1 ± 1.2 | 13.5 ± 0.9 |
| Color | 8.8 ± 0.8$^d$ | 11.4 ± 0.7$^c$ | 13.9 ± 0.7$^a$ | 8.9 ± 0.9d | 13.1 ± 0.9$^b$ | 14.6 ± 0.5$^a$ |
| Egg shell | 5.4 ± 0.3 | 5.4 ± 0.4 | 5.4 ± 0.5 | 5.3 ± 0.4 | 5.3 ± 0.6 | 5.4 ± 0.3 |
| Week 2 | | | | | | |
| Whole egg | 55.9 ± 3.3 | 56.3 ± 3.9 | 55.5 ± 3.4 | 57.4 ± 3.3 | 56.6 ± 3.4 | 55.6 ± 2.5 |
| Albumen | 33.3 ± 2.8 | 33.6 ± 3.4 | 33.3 ± 2.6 | 34.4 ± 3.1 | 34.3 ± 2.7 | 33.5 ± 2.3 |
| Yolk | 14.3 ± 0.7 | 14.8 ± 1.0 | 13.2 ± 3.6 | 14.7 ± 0.8 | 14.4 ± 0.7 | 14 ± 1 |
| Color | 7.6 ± 0.8 | 11.6 ± 1.0 | 13.4 ± 0.7 | 8.2 ± 0.6 | 12.4 ± 0.8 | 14.2 ± 0.6 |
| Egg shell | 5.5 ± 0.4 | 5.4 ± 0.5 | 5.4 ± 0.6 | 5.4 ± 0.4 | 5.4 ± 0.5 | 5.6 ± 0.4 |
| Week 3 | | | | | | |
| Whole egg | 55.4 ± 2.9 | 54.9 ± 3.2 | 55.6 ± 3.2 | 57.2 ± 3.7 | 56.5 ± 5.1 | 55.7 ± 2.8 |
| Albumen | 32.8 ± 2.4 | 33.2 ± 2.5 | 34 ± 3.2 | 34.5 ± 2.5 | 34.6 ± 3.8 | 33.8 ± 2.6 |
| Yolk | 14.3 ± 1.0 | 14.0 ± 1.2 | 14.4 ± 0.8 | 14.6 ± 1.1 | 14.1 ± 1.2 | 14.2 ± 1.1 |
| Color | 6.6 ± 0.5$^e$ | 10.4 ± 0.8$^d$ | 13.3 ± 0.8$^b$ | 7.2 ± 0.6$^e$ | 12.2 ± 0.8$^c$ | 14 ± 0.7$^a$ |
| Egg shell | 5.5 ± 0.4 | 5.3 ± 0.3 | 5.3 ± 0.6 | 5.4 ± 0.4 | 5.4 ± 0.6 | 5.5 ± 0.3 |
| Week 4 | | | | | | |
| Whole egg | 53.4 ± 2.9 | 53.4 ± 3.3 | 53.8 ± 2.5 | 55.5 ± 4.9 | 54.5 ± 2.8 | 52 ± 2 |
| Albumen | 30.3 ± 2.4 | 30.22 ± 2.8 | 30.6 ± 2.2 | 32.3 ± 3.6 | 31.9 ± 2.5 | 30.5 ± 3 |
| Yolk | 15.2 ± 1.0 | 15.4 ± 0.7 | 15.9 ± 0.9 | 15.3 ± 1.1 | 15.3 ± 1.5 | 14.9 ± 0.6 |
| Color | 6.9 ± 0.5$^e$ | 11.0 ± 0.8$^d$ | 12.8 ± 0.8$^b$ | 7.3 ± 0.5$^e$ | 11.9 ± 0.9$^c$ | 13.9 ± 0.3$^a$ |
| Egg shell | 5.5 ± 0.4 | 5.6 ± 0.3 | 5.3 ± 0.4 | 5.4 ± 0.5 | 5.4 ± 0.4 | 5.5 ± 0.3 |
| Week 5 | | | | | | |
| Whole egg | 56.4 ± 2.4 | 57.4 ± 3.6 | 56.7 ± 4.8 | 57.8 ± 4.8 | 57.9 ± 4.2 | 57.4 ± 3.1 |
| Albumen | 33.8 ± 2.4 | 33.6 ± 2.5 | 34.4 ± 3.6 | 35.9 ± 3.5 | 35.7 ± 3.1 | 34.6 ± 2.1 |
| Yolk | 14.3 ± 0.9 | 15.1 ± 0.6 | 14.5 ± 1.3 | 15.1 ± 1.1 | 14.6 ± 1.1 | 14.7 ± 1.6 |
| Color | 7.8 ± 1.0$^c$ | 11.7 ± 0.7$^b$ | 14.1 ± 0.6$^a$ | 8.2 ± 0.9$^c$ | 12.1 ± 0.7$^b$ | 14.4 ± 0.5$^a$ |
| Egg shell | 5.4 ± 0.3 | 5.6 ± 0.3 | 5.5 ± 0.6 | 5.5 ± 0.5 | 5.5 ± 0.7 | 5.6 ± 0.5 |
| Week 6 | | | | | | |
| Whole egg | 54.3 ± 2.8 | 54.5 ± 3.3 | 55.1 ± 3 | 56.1 ± 5.3 | 54.1 ± 4.5 | 54.2 ± 2.4 |
| Albumen | 30.3 ± 2.8 | 30.0 ± 2.8 | 31.3 ± 2.8 | 31.7 ± 4.7 | 31.7 ± 3 | 30.5 ± 2.5 |
| Yolk | 15.8 ± 1.4 | 16.3 ± 0.9 | 16.2 ± 1.6 | 16.3 ± 0.9 | 16 ± 1.6 | 16.4 ± 1.5 |
| Color | 7.3 ± 0.6$^d$ | 10.8 ± 0.8$^b$ | 13.1 ± 0.3$^a$ | 7.9 ± 0.6$^c$ | 10.8 ± 0.7$^b$ | 12.8 ± 0.4$^a$ |
| Egg shell | 5.5 ± 0.5 | 5.6 ± 0.3 | 5.6 ± 0.4 | 5.7 ± 0.4 | 5.5 ± 0.6 | 5.6 ± 0.5 |

$^{a-d}$Values with different superscripts in each row differ according to one-way ANOVA (P < 0.05).

TABLE 47

| | Plasma Triacylglycerol | | | | | |
| --- | --- | --- | --- | --- | --- | --- |
| | Corn | | | Flax | | |
| | 0 | 3 | 5 | 0 | 3 | 5 |
| | TG, mg/dL | | | | | |
| Day 14 | 1571 ± 831 | 1979 ± 727 | 1564 ± 779 | 1287 ± 353 | 1333 ± 695 | 1402 ± 442 |
| Day 28 | 1632 ± 1339 | 1628 ± 802 | 1162 ± 724 | 1026 ± 584 | 1054 ± 555 | 1268 ± 620 |
| Day 42 | 1028 ± 373 | 1009 ± 370 | 954 ± 189 | 1054 ± 411 | 915 ± 463 | 1047 ± 494 |

TABLE 47-continued

| | Plasma Triacylglycerol | | | | | |
|---|---|---|---|---|---|---|
| | Corn | | | Flax | | |
| | 0 | 3 | 5 | 0 | 3 | 5 |
| Cholesterol, mg/dL | | | | | | |
| Day 14 | 131 ± 47 | 148 ± 43 | 130 ± 49 | 110 ± 29 | 111 ± 32 | 128 ± 17 |
| Day 28 | 139 ± 57 | 129 ± 38 | 118 ± 48 | 100 ± 23 | 109 ± 30 | 125 ± 35 |
| Day 42 | 127 ± 29 | 137 ± 48 | 154 ± 49 | 117 ± 25 | 116 ± 25 | 139 ± 44 |
| Uric acid, mg/dl | | | | | | |
| Day 14 | 2.90 ± 0.85 | 2.31 ± 0.37 | 3.75 ± 1.91 | 2.36 ± 0.48 | 3.29 ± 1.01 | 2.85 ± 0.62 |
| Day 28 | 2.23 ± 0.51 | 2.13 ± 0.50 | 2.18 ± 0.52 | 2.24 ± 0.96 | 2.67 ± 1.46 | 2.22 ± 0.56 |
| Day 42 | 2.67 ± 1.28 | 2.75 ± 1.18 | 3.11 ± 1.31 | 3.21 ± 1.13 | 2.82 ± 0.95 | 2.56 ± 0.96 |

Adipose tissue fatty acid compositions are summarized in Table 48. C16:0 concentration was higher in corn oil fed treatments than flaxseed oil fed groups. Polyunsaturated fatty acid is known to decrease fatty acid synthesis, and high PUFA content in flaxseed oil containing diets might reduce fatty acid synthesis and result in decreased C16:0 fatty acid content. However, C18:0 was not affected by dietary treatment, and C18:1n9 also was not affected. In flaxseed oil fed groups, C18:2n6 was decreased, and C18:3n3 was increased. There was no long-chain PUFA (EPA and DHA) in adipose tissue. Polyunsaturated fatty acid was increased and saturated fatty acid was decreased by flaxseed oil supplementation. Flaxseed oil fed groups showed a higher percentage of n-3 fatty acid, and the 5% algae fed group showed higher n-3 than the 0% or 3% algae fed groups. But in corn oil fed groups, algae supplementation did not affect n-3 fatty acid composition. Corn oil fed groups showed higher n-6 fatty acid than flaxseed oil fed groups, and resulted in higher n-6 to n-3 fatty acid ratios.

unsaturated fatty acid and saturated fatty acids were not affected by dietary treatment, but PUFA was increased and resulted in decreased n-6 to n-3 ratio.

At the start of the experiment, there were no differences in the fatty acid profile of plasma (Table 50). Major fatty acids in plasma were C18:1n9 and C18:2n6 and monounsaturated fatty acids were about 50% of total fatty acids.

At week 2, plasma C16:0 was decreased by flaxseed oil supplementation, and C18:1n9 was increased (Table 51). Plasma EPA and DHA was increased by algae supplementation and flaxseed oil supplementation. MUFA, PUFA, and SAT were not changed by dietary treatment. Algae and flaxseed oil supplementation increased n-3 fatty acids but n-6 fatty acids were affected by only flaxseed oil supplementation. Plasma from the $4^{th}$ and $6^{th}$ weeks (Table 52 and Table 53) showed the same trend as the $2^{nd}$ week, but algae did not show any additional effect of EPA and DHA concentration of the flaxseed oil fed groups.

TABLE 48

| | Adipose Tissue Fatty Acid Composition (at Week 6) | | | | | |
|---|---|---|---|---|---|---|
| | Oil Source | | | | | |
| | Corn | | | Flax | | |
| Algae, % | 0 | 3 | 5 | 0 | 3 | 5 |
| c14:0 | 0.00 ± 0.01 | 0.00 ± 0.00 | 0.00 ± 0.00 | 0.00 ± 0.00 | 0.00 ± 0.00 | 0.00 ± 0.00 |
| C14:1 | 0.22 ± 0.22 | 0.25 ± 0.10 | 0.15 ± 0.01 | 0.15 ± 0.02 | 0.16 ± 0.1. | 0.15 ± 0.03 |
| C16:0 | 19.36 ± 0.78$^a$ | 19.15 ± 0.64$^a$ | 19.36 ± 1.17$^a$ | 18.33 ± 0.56$^{bc}$ | 18.99 ± 1.02$^{ab}$ | 17.93 ± 0.99$^c$ |
| c16:1 | 2.52 ± 0.14 | 2.86 ± 0.42 | 2.64 ± 0.33 | 2.41 ± 0.29 | 2.55 ± 0.40 | 2.83 ± 0.37 |
| C18:0 | 8.22 ± 0.54 | 7.94 ± 0.60 | 8.38 ± 0.74 | 8.00 ± 0.63 | 8.41 ± 0.70 | 7.90 ± 0.54 |
| c18:1n9 | 46.48 ± 1.74 | 46.09 ± 1.23 | 45.05 ± 1.41 | 45.52 ± 1.21 | 44.74 ± 1.16 | 45.42 ± 1.46 |
| C18:2n6 | 21.47 ± 1.77$^a$ | 21.82 ± 0.91$^a$ | 22.63 ± 1.37$^a$ | 20.19 ± 0.32$^b$ | 19.81 ± 1.12$^b$ | 19.57 ± 0.97$^b$ |
| C20:0 | 0.08 ± 0.05 | 0.09 ± 0.04 | 0.08 ± 0.04 | 0.08 ± 0.03 | 0.05 ± 0.05 | 0.10 ± 0.01 |
| C18:3n6 | 0.10 ± 0.06 | 0.18 ± 0.03 | 0.12 ± 0.06 | 0.08 ± 0.09 | 0.10 ± 0.07 | 0.11 ± 0.06 |
| C20:1c11 | 0.24 ± 0.10 | 0.27 ± 0.03 | 0.27 ± 0.05 | 0.33 ± 0.06 | 0.28 ± 0.12 | 0.34 ± 0.05 |
| C18:3n3 | 1.06 ± 0.12$^c$ | 1.12 ± 0.11$^c$ | 1.16 ± 0.12$^c$ | 4.73 ± 0.42$^b$ | 4.74 ± 0.59$^b$ | 5.47 ± 1.39$^a$ |
| MUFA | 49.51 ± 1.87 | 49.51 ± 1.14 | 48.12 ± 1.50 | 48.41 ± 1.33 | 47.75 ± 1.09 | 48.75 ± 1.46 |
| PUFA | 22.65 ± 1.89$^b$ | 23.12 ± 0.91$^b$ | 23.92 ± 1.36$^{ab}$ | 25.00 ± 0.73$^a$ | 24.65 ± 1.47$^a$ | 25.16 ± 1.73$^a$ |
| SAT | 27.84 ± 1.12$^a$ | 27.36 ± 1.02$^{ab}$ | 27.96 ± 1.69$^a$ | 26.59 ± 0.86$^{ab}$ | 27.60 ± 1.49$^a$ | 26.09 ± 1.26$^b$ |
| n3 | 1.06 ± 0.12$^c$ | 1.12 ± 0.11$^c$ | 1.16 ± 0.12$^c$ | 4.73 ± 0.42$^b$ | 4.74 ± 0.59$^b$ | 5.47 ± 1.39$^a$ |
| n6 | 21.59 ± 1.81$^a$ | 22.01 ± 0.90$^a$ | 22.76 ± 1.38$^a$ | 20.28 ± 0.38$^b$ | 19.92 ± 1.12$^b$ | 19.69 ± 0.95$^b$ |
| n6ton3 | 20.40 ± 1.82$^a$ | 19.88 ± 2.31$^a$ | 19.86 ± 2.83$^a$ | 4.32 ± 0.33$^b$ | 4.25 ± 0.48$^b$ | 3.83 ± 1.05$^b$ |

$^{a-d}$Values with different superscripts in each row differ according to one-way ANOVA (P < 0.05).

In Table 49, liver fatty acid profile is presented. C16:0 fatty acid was decreased by supplementation of flaxseed oil, but algae supplementation had no effects on C16:0 fatty acid in liver. C18:3n3 was increased in flaxseed oil fed groups, and EPA and DHA percentage was also increased. Mono- Egg fatty acid profile at week 0 showed that the major fatty acids were C18:1n9 and C18:2n6, and DHA content was about 1.3% of egg fatty acids (Table 54). After 1 week of experimental diets feeding (Table 55), C18:1n9 fatty acids were not affected by flaxseed oil supplementation, but algae supplementation tended to decrease C18:1n9. C18:2n6 was decreased by flaxseed oil supplementation. C18:3n3 was increased in flaxseed oil supplemented groups, and EPA and DHA concentrations were also increased by algae and flaxseed oil supplementation. n-3 and n-6 fatty acid was affected by flaxseed oil supplementation. Algae had no effects on n-3 and n-6 fatty acid composition, but the ratio of n-6 to n-3 was decreased by algae supplementation.

At week 2 (Table 56), C18:1n9 and C18:2n6 were decreased in flaxseed oil fed groups, and C18:3n3 was increased. EPA and DHA concentration was higher in flaxseed oil fed groups, and algae had some additional effects. Flaxseed oil decreased egg yolk n-6 fatty acid, and increased n-3 fatty acids. Algae also increased n-3 concentration as their inclusion rate increased. Data for egg fatty acid profiles of weeks 3-6 is provided in Tables 57-60, respectively.

TABLE 49

Liver Tissue Fatty Acid Composition (at Week 6)

| | Corn | | | Flax | | |
|---|---|---|---|---|---|---|
| | 0 | 3 | 5 | 0 | 3 | 5 |
| c14:0 | 0.41 ± 0.08 | 0.34 ± 0.17 | 0.40 ± 0.08 | 0.36 ± 0.06 | 0.40 ± 0.06 | 0.38 ± 0.06 |
| C14:1 | 0.04 ± 0.06 | 0.02 ± 0.05 | 0.03 ± 0.04 | 0.04 ± 0.07 | 0.04 ± 0.06 | 0.03 ± 0.05 |
| C16:0 | 22.12 ± 0.90$^a$ | 22.11 ± 0.7$^a$ | 21.86 ± 0.66$^{ab}$ | 20.63 ± 0.79$^c$ | 20.91 ± 1.12$^{bc}$ | 20.27 ± 1.22$^c$ |
| c16:1 | 2.13 ± 0.78 | 2.20 ± 0.34 | 1.89 ± 0.52 | 2.11 ± 0.43 | 2.32 ± 0.43 | 2.15 ± 0.52 |
| C18:0 | 10.11 ± 1.81 | 10.04 ± 0.69 | 10.81 ± 2.41 | 9.97 ± 1.37 | 9.56 ± 1.47 | 10.09 ± 1.11 |
| c18:1n9 | 49.79 ± 3.20 | 50.21 ± 2.41 | 49.10 ± 3.88 | 49.69 ± 1.58 | 49.74 ± 2.63 | 47.32 ± 3.45 |
| C18:2n6 | 12.85 ± 2.46 | 12.43 ± 0.78 | 12.93 ± 2.29 | 11.24 ± 2.05 | 11.54 ± 3.14 | 12.91 ± 3.17 |
| C20:0 | 0.05 ± 0.02 | 0.06 ± 0.01 | 0.06 ± 0.01 | 0.05 ± 0.02 | 0.05 ± 0.02 | 0.06 ± 0.01 |
| C18:3n6 | 0.10 ± 0.03 | 0.10 ± 0.03 | 0.10 ± 0.02 | 0.06 ± 0.03 | 0.08 ± 0.03 | 0.11 ± 0.03 |
| C20:1c11 | 0.17 ± 0.05 | 0.16 ± 0.03 | 0.18 ± 0.03 | 0.20 ± 0.04 | 0.18 ± 0.05 | 0.18 ± 0.04 |
| C18:3n3 | 0.20 ± 0.16$^b$ | 0.18 ± 0.11$^b$ | 0.26 ± 0.2$^b$ | 2.16 ± 0.58$^a$ | 2.13 ± 0.98$^a$ | 2.06 ± 0.59$^a$ |
| C20:2n6 | 0.06 ± 0.03 | 0.05 ± 0.01 | 0.05 ± 0.02 | 0.04 ± 0.01 | 0.03 ± 0.01 | 0.04 ± 0.02 |
| C22:0 | 0.06 ± 0.03 | 0.05 ± 0.03 | 0.05 ± 0.02 | 0.05 ± 0.01 | 0.04 ± 0.01 | 0.06 ± 0.01 |
| C20:3n6 | 0.24 ± 0.11 | 0.21 ± 0.08 | 0.21 ± 0.09 | 0.29 ± 0.10 | 0.21 ± 0.07 | 0.32 ± 0.16 |
| C20:4n6 | 0.82 ± 0.34 | 0.75 ± 0.31 | 0.74 ± 0.31 | 0.53 ± 0.16 | 0.48 ± 0.21 | 0.70 ± 0.31 |
| C20:5EPA | 0.00 ± 0.00$^c$ | 0.00 ± 0.00$^c$ | 0.00 ± 0.00$^c$ | 0.11 ± 0.03$^b$ | 0.10 ± 0.03$^b$ | 0.15 ± 0.08$^a$ |
| C24:1n9 | 0.00 ± 0.00 | 0.03 ± 0.03 | 0.02 ± 0.03 | 0.01 ± 0.02 | 0.01 ± 0.02 | 0.02 ± 0.04 |
| C22:6DHA | 0.84 ± 0.38$^c$ | 1.05 ± 0.41$^c$ | 1.24 ± 0.51$^{bc}$ | 2.45 ± 0.83$^{ab}$ | 2.15 ± 0.78$^a$ | 3.05 ± 1.44$^a$ |
| MUFA | 52.13 ± 3.81 | 52.62 ± 2.60 | 51.22 ± 4.09 | 52.04 ± 1.6 | 52.30 ± 2.75 | 49.71 ± 3.84 |
| PUFA | 15.10 ± 3.18 | 14.77 ± 1.45 | 15.54 ± 2.6 | 16.86 ± 2.43 | 16.71 ± 4.06 | 19.34 ± 4.03 |
| SAT | 32.77 ± 1.34 | 32.61 ± 1.33 | 33.24 ± 2.44 | 31.09 ± 1.55 | 31.00 ± 2.34 | 30.95 ± 1.72 |
| n3 | 1.04 ± 0.48$^b$ | 1.23 ± 0.46$^b$ | 1.50 ± 0.46$^b$ | 4.71 ± 0.57$^a$ | 4.37 ± 0.95$^a$ | 5.26 ± 1.31$^a$ |
| n6 | 14.06 ± 2.88 | 13.54 ± 1.05 | 14.03 ± 2.34 | 12.15 ± 2.12 | 12.34 ± 3.16 | 14.08 ± 3.29 |
| n6Ton3 | 15.31 ± 4.69$^a$ | 12.01 ± 3.43$^b$ | 9.77 ± 2.36$^b$ | 2.59 ± 0.44$^c$ | 2.81 ± 0.22$^c$ | 2.73 ± 0.61$^c$ |

$^{a-d}$Values with different superscripts in each row differ according to one-way ANOVA (P < 0.05).

TABLE 50

Plasma Fatty Acid Profiles at Week 0

| | Corn | | | Flax | | |
|---|---|---|---|---|---|---|
| | 0 | 3 | 5 | 0 | 3 | 5 |
| c14:0 | 0.01 ± 0.02 | 0.01 ± 0.01 | 0.01 ± 0.01 | 0.00 ± 0.01 | 0.01 ± 0.01 | 0.00 ± 0.01 |
| C14:1 | 0.08 ± 0.02 | 0.09 ± 0.09 | 0.09 ± 0.06 | 0.05 ± 0.03 | 0.08 ± 0.04 | 0.07 ± 0.03 |
| C16:0 | 20.25 ± 0.58 | 20.49 ± 0.85 | 20.71 ± 0.54 | 20.17 ± 0.54 | 20.37 ± 0.90 | 20.25 ± 0.45 |
| c16:1 | 1.63 ± 0.18 | 1.62 ± 0.22 | 1.53 ± 0.27 | 1.45 ± 0.19 | 1.48 ± 0.29 | 1.46 ± 0.24 |
| C18:0 | 8.28 ± 0.75 | 8.06 ± 0.46 | 8.63 ± 1.34 | 8.28 ± 0.63 | 8.71 ± 0.74 | 8.45 ± 0.42 |
| c18:1n9 | 47.61 ± 2.85 | 48.64 ± 1.22 | 47.50 ± 2.10 | 48.97 ± 1.44 | 48.04 ± 2.27 | 47.98 ± 1.44 |
| C18:2n6 | 15.48 ± 1.07 | 15.56 ± 1.10 | 15.95 ± 1.67 | 15.46 ± 1.33 | 14.62 ± 1.04 | 15.81 ± 1.00 |
| C18:3n6 | 0.11 ± 0.02 | 0.12 ± 0.02 | 0.11 ± 0.02 | 0.11 ± 0.03 | 0.13 ± 0.02 | 0.12 ± 0.02 |
| C20:1c11 | 0.27 ± 0.05 | 0.23 ± 0.02 | 0.26 ± 0.02 | 0.26 ± 0.04 | 0.23 ± 0.02 | 0.24 ± 0.03 |
| C18:3n3 | 0.14 ± 0.13 | 0.24 ± 0.09 | 0.20 ± 0.13 | 0.16 ± 0.09 | 0.12 ± 0.10 | 0.17 ± 0.14 |
| C20:2n6 | 0.07 ± 0.01 | 0.06 ± 0.01 | 0.07 ± 0.01 | 0.07 ± 0.01 | 0.06 ± 0.01 | 0.07 ± 0.01 |
| C22:0 | 0.04 ± 0.01 | 0.04 ± 0.01 | 0.04 ± 0.01 | 0.04 ± 0.01 | 0.05 ± 0.01 | 0.04 ± 0.01 |
| C20:3n6 | 0.24 ± 0.05 | 0.19 ± 0.02 | 0.21 ± 0.02 | 0.22 ± 0.03 | 0.21 ± 0.04 | 0.22 ± 0.04 |
| C20:4n6 | 0.87 ± 0.10 | 0.79 ± 0.05 | 0.81 ± 0.04 | 0.81 ± 0.07 | 0.89 ± 0.09 | 0.86 ± 0.1 |
| C22:6DHA | 1.66 ± 0.21 | 1.57 ± 0.19 | 1.58 ± 0.10 | 1.57 ± 0.13 | 1.67 ± 0.26 | 1.66 ± 0.18 |
| MUFA | 49.74 ± 2.94 | 50.72 ± 1.26 | 49.53 ± 2.27 | 50.87 ± 1.43 | 49.98 ± 2.43 | 49.90 ± 1.63 |
| PUFA | 18.56 ± 1.34 | 18.54 ± 1.28 | 18.91 ± 1.85 | 18.40 ± 1.43 | 17.70 ± 1.21 | 18.91 ± 1.09 |
| SAT | 31.70 ± 2.20 | 30.74 ± 0.84 | 31.56 ± 2.08 | 30.73 ± 1.14 | 32.32 ± 1.87 | 31.19 ± 0.94 |
| n3 | 1.80 ± 0.31 | 1.81 ± 0.26 | 1.77 ± 0.17 | 1.73 ± 0.18 | 1.79 ± 0.26 | 1.83 ± 0.13 |
| n6 | 16.76 ± 1.14 | 16.73 ± 1.13 | 17.14 ± 1.72 | 16.67 ± 1.35 | 15.90 ± 1.09 | 17.08 ± 1.04 |
| n6TOn3 | 9.46 ± 1.18 | 9.38 ± 1.19 | 9.68 ± 0.67 | 9.71 ± 0.93 | 9.00 ± 1.23 | 9.35 ± 0.70 |

$^{a-d}$Values with different superscripts in each row differ according to one-way ANOVA (P < 0.05).

TABLE 51

Plasma Fatty Acid Profiles at Week 2

| | Corn | | | Flax | | |
|---|---|---|---|---|---|---|
| | 0 | 3 | 5 | 0 | 3 | 5 |
| c14:0 | 0.01 ± 0.01 | 0.01 ± 0.01 | 0.00 ± 0.01 | 0.01 ± 0.01 | 0.00 ± 0.00 | 0.01 ± 0.01 |
| C14:1 | 0.05 ± 0.02 | 0.05 ± 0.02 | 0.10 ± 0.06 | 0.05 ± 0.02 | 0.05 ± 0.02 | 0.04 ± 0.02 |
| C16:0 | 21.16 ± 0.72$^a$ | 21.33 ± 0.56$^a$ | 21.18 ± 0.7$^a$ | 19.59 ± 0.42$^b$ | 20.1 ± 0.64$^b$ | 19.82 ± 0.59$^b$ |
| c16:1 | 1.68 ± 0.44 | 1.71 ± 0.41 | 1.70 ± 0.43 | 1.65 ± 0.24 | 1.86 ± 0.34 | 1.77 ± 0.42 |
| C18:0 | 7.74 ± 0.40 | 7.87 ± 0.55 | 8.11 ± 1.66 | 7.94 ± 0.56 | 7.76 ± 0.50 | 8.12 ± 0.74 |
| c18:1n9 | 46.07 ± 1.55$^a$ | 45.81 ± 0.82$^{ab}$ | 43.92 ± 2.16$^b$ | 47.61 ± 2.23$^a$ | 47.35 ± 1.40$^a$ | 47.84 ± 2.07$^a$ |
| C18:2n6 | 17.44 ± 0.33$^a$ | 17.42 ± 0.91$^a$ | 17.73 ± 1.5$^a$ | 13.4 ± 1.51$^b$ | 13.22 ± 1.45$^b$ | 12.45 ± 1.96$^b$ |
| C18:3n6 | 0.16 ± 0.06 | 0.16 ± 0.03 | 0.15 ± 0.06 | 0.10 ± 0.03 | 0.10 ± 0.02 | 0.10 ± 0.03 |
| C20:1c11 | 0.23 ± 0.04 | 0.20 ± 0.03 | 0.22 ± 0.03 | 0.21 ± 0.04 | 0.18 ± 0.03 | 0.18 ± 0.02 |
| C18:3n3 | 0.36 ± 0.04$^b$ | 0.38 ± 0.05$^b$ | 0.33 ± 0.17$^b$ | 2.67 ± 0.89$^a$ | 2.31 ± 0.69$^a$ | 2.31 ± 0.43$^a$ |
| C20:2n6 | 0.08 ± 0.01 | 0.07 ± 0.01 | 0.08 ± 0.02 | 0.05 ± 0.01 | 0.04 ± 0.01 | 0.04 ± 0.01 |
| C22:0 | 0.03 ± 0.01 | 0.03 ± 0.01 | 0.04 ± 0.01 | 0.02 ± 0.00 | 0.03 ± 0.01 | 0.02 ± 0.01 |
| C20:3n6 | 0.24 ± 0.02 | 0.22 ± 0.04 | 0.27 ± 0.05 | 0.20 ± 0.03 | 0.20 ± 0.04 | 0.19 ± 0.03 |
| C20:4n6 | 0.86 ± 0.13$^a$ | 0.83 ± 0.07$^a$ | 0.76 ± 0.38$^a$ | 0.52 ± 0.03$^b$ | 0.57 ± 0.07$^b$ | 0.56 ± 0.04$^b$ |
| C20:5EPA | 0.00 ± 0.01$^d$ | 0.03 ± 0.01$^c$ | 0.05 ± 0.01$^c$ | 0.11 ± 0.02$^b$ | 0.13 ± 0.02$^b$ | 0.15 ± 0.02$^a$ |
| C22:6DHA | 1.22 ± 0.17$^e$ | 1.67 ± 0.13$^d$ | 2.18 ± 0.11$^c$ | 3.56 ± 0.2b | 3.74 ± 0.32$^{ab}$ | 3.98 ± 0.61$^a$ |
| MUFA | 48.13 ± 1.52$^a$ | 47.88 ± 0.90$^{ab}$ | 46.05 ± 2.39$^b$ | 49.61 ± 2.12$^a$ | 49.54 ± 1.49$^a$ | 49.93 ± 1.96$^a$ |
| PUFA | 20.35 ± 0.57 | 20.79 ± 0.92 | 21.56 ± 1.72 | 20.64 ± 1.96 | 20.34 ± 1.92 | 19.79 ± 2.06 |
| SAT | 31.51 ± 1.16$^a$ | 31.31 ± 0.82$^{ab}$ | 32.39 ± 1.91$^a$ | 29.74 ± 0.29$^c$ | 30.11 ± 0.89$^c$ | 30.27 ± 0.68$^{bc}$ |
| n3 | 1.58 ± 0.17$^c$ | 2.09 ± 0.17$^{bc}$ | 2.56 ± 0.22$^b$ | 6.36 ± 1.07$^a$ | 6.19 ± 0.87$^a$ | 6.45 ± 0.60$^a$ |
| n6 | 18.77 ± 0.43$^a$ | 18.71 ± 0.89$^a$ | 19.00 ± 1.51$^a$ | 14.28 ± 1.54$^b$ | 14.15 ± 1.53$^b$ | 13.34 ± 2.02$^b$ |
| n6TOn3 | 11.98 ± 1.08$^a$ | 9.01 ± 0.79$^b$ | 7.42 ± 0.21$^c$ | 2.30 ± 0.44$^d$ | 2.32 ± 0.36$^d$ | 2.08 ± 0.4$^d$ |
| c14:0 | 0.01 ± 0.01 | 0.01 ± 0.01 | 0.00 ± 0.01 | 0.01 ± 0.01 | 0.00 ± 0.00 | 0.01 ± 0.01 |
| C14:1 | 0.05 ± 0.02 | 0.05 ± 0.02 | 0.10 ± 0.06 | 0.05 ± 0.02 | 0.05 ± 0.02 | 0.04 ± 0.02 |
| C16:0 | 21.16 ± 0.72$^a$ | 21.33 ± 0.56$^a$ | 21.18 ± 0.7$^a$ | 19.59 ± 0.42$^b$ | 20.1 ± 0.64$^b$ | 19.82 ± 0.59$^b$ |
| c16:1 | 1.68 ± 0.44 | 1.71 ± 0.41 | 1.70 ± 0.43 | 1.65 ± 0.24 | 1.86 ± 0.34 | 1.77 ± 0.42 |
| C18:0 | 7.74 ± 0.40 | 7.87 ± 0.55 | 8.11 ± 1.66 | 7.94 ± 0.56 | 7.76 ± 0.50 | 8.12 ± 0.74 |
| c18:1n9 | 46.07 ± 1.55$^a$ | 45.81 ± 0.82$^{ab}$ | 43.92 ± 2.16$^b$ | 47.61 ± 2.23$^b$ | 47.35 ± 1.40$^a$ | 47.84 ± 2.07$^a$ |
| C18:2n6 | 17.44 ± 0.33$^a$ | 17.42 ± 0.91$^a$ | 17.73 ± 1.5$^a$ | 13.4 ± 1.51$^b$ | 13.22 ± 1.45$^b$ | 12.45 ± 1.96$^b$ |
| C18:3n6 | 0.16 ± 0.06 | 0.16 ± 0.03 | 0.15 ± 0.06 | 0.10 ± 0.03 | 0.10 ± 0.02 | 0.10 ± 0.03 |
| C20:1c11 | 0.23 ± 0.04 | 0.20 ± 0.03 | 0.22 ± 0.03 | 0.21 ± 0.04 | 0.18 ± 0.03 | 0.18 ± 0.02 |
| C18:3n3 | 0.36 ± 0.04$^b$ | 0.38 ± 0.05$^b$ | 0.33 ± 0.17$^b$ | 2.67 ± 0.89$^a$ | 2.31 ± 0.69$^a$ | 2.31 ± 0.43$^a$ |
| C20:2n6 | 0.08 ± 0.01 | 0.07 ± 0.01 | 0.08 ± 0.02 | 0.05 ± 0.01 | 0.04 ± 0.01 | 0.04 ± 0.01 |
| C22:0 | 0.03 ± 0.01 | 0.03 ± 0.01 | 0.04 ± 0.01 | 0.02 ± 0.00 | 0.03 ± 0.01 | 0.02 ± 0.01 |
| C20:3n6 | 0.24 ± 0.02 | 0.22 ± 0.04 | 0.27 ± 0.05 | 0.20 ± 0.03 | 0.20 ± 0.04 | 0.19 ± 0.03 |
| C20:4n6 | 0.86 ± 0.13$^a$ | 0.83 ± 0.07$^a$ | 0.76 ± 0.38$^a$ | 0.52 ± 0.03$^b$ | 0.57 ± 0.07$^b$ | 0.56 ± 0.04$^b$ |
| C20:5EPA | 0.00 ± 0.01$^d$ | 0.03 ± 0.01$^c$ | 0.05 ± 0.01$^c$ | 0.11 ± 0.02$^b$ | 0.13 ± 0.02$^b$ | 0.15 ± 0.02$^a$ |
| C22:6DHA | 1.22 ± 0.17$^e$ | 1.67 ± 0.13$^d$ | 2.18 ± 0.11$^c$ | 3.56 ± 0.2b | 3.74 ± 0.32$^{ab}$ | 3.98 ± 0.61$^a$ |
| MUFA | 48.13 ± 1.52$^a$ | 47.88 ± 0.90$^{ab}$ | 46.05 ± 2.39$^b$ | 49.61 ± 2.12$^a$ | 49.54 ± 1.49$^a$ | 49.93 ± 1.96$^a$ |
| PUFA | 20.35 ± 0.57 | 20.79 ± 0.92 | 21.56 ± 1.72 | 20.64 ± 1.96 | 20.34 ± 1.92 | 19.79 ± 2.06 |
| SAT | 31.51 ± 1.16$^a$ | 31.31 ± 0.82$^{ab}$ | 32.39 ± 1.91$^a$ | 29.74 ± 0.29$^c$ | 30.11 ± 0.89$^c$ | 30.27 ± 0.68$^{bc}$ |
| n3 | 1.58 ± 0.17$^c$ | 2.09 ± 0.17$^{bc}$ | 2.56 ± 0.22$^b$ | 6.36 ± 1.07$^a$ | 6.19 ± 0.87$^a$ | 6.45 ± 0.60$^a$ |
| n6 | 18.77 ± 0.43$^a$ | 18.71 ± 0.89$^a$ | 19.00 ± 1.51$^a$ | 14.28 ± 1.54$^b$ | 14.15 ± 1.53$^b$ | 13.34 ± 2.02$^b$ |
| n6TOn3 | 11.98 ± 1.08$^a$ | 9.01 ± 0.79$^b$ | 7.42 ± 0.21$^c$ | 2.30 ± 0.44$^d$ | 2.32 ± 0.36$^d$ | 2.08 ± 0.4$^d$ |

$^{a-d}$Values with different superscripts in each row differ according to one-way ANOVA (P < 0.05).

TABLE 52

Plasma Fatty Acid Profiles at Week 4

| | Corn | | | Flax | | |
|---|---|---|---|---|---|---|
| | 0 | 3 | 5 | 0 | 3 | 5 |
| c14:0 | 0.01 ± 0.01 | 0.00 ± 0.00 | 0.01 ± 0.01 | 0.00 ± 0.01 | 0.00 ± 0.01 | 0.00 ± 0.01 |
| C14:1 | 0.05 ± 0.02 | 0.05 ± 0.01 | 0.06 ± 0.02 | 0.04 ± 0.02 | 0.06 ± 0.06 | 0.04 ± 0.01 |
| C16:0 | 21.18 ± 0.79 | 21.02 ± 0.54 | 18.70 ± 7.57 | 19.47 ± 0.74 | 20.35 ± 1.15 | 19.98 ± 0.21 |
| c16:1 | 1.77 ± 0.32 | 1.82 ± 0.26 | 1.78 ± 0.37 | 1.61 ± 0.33 | 1.75 ± 0.29 | 1.77 ± 0.20 |
| C18:0 | 8.49 ± 0.63 | 8.32 ± 0.39 | 8.39 ± 0.81 | 8.11 ± 1.11 | 7.98 ± 0.46 | 8.20 ± 0.47 |
| c18:1n9 | 46.52 ± 2.10 | 47.73 ± 1.36 | 47.61 ± 6.69 | 47.68 ± 1.71 | 45.61 ± 1.84 | 47.23 ± 2.10 |
| C18:2n6 | 16.37 ± 1.79$^a$ | 15.75 ± 0.91$^a$ | 16.75 ± 1.30$^a$ | 13.05 ± 1.3b | 13.63 ± 1.24$^b$ | 12.70 ± 1.85$^b$ |
| C18:3n6 | 0.14 ± 0.04$^a$ | 0.12 ± 0.02$^{ab}$ | 0.14 ± 0.05$^a$ | 0.09 ± 0.02$^c$ | 0.10 ± 0.02$^{bc}$ | 0.09 ± 0.01$^{bc}$ |
| C20:1c11 | 0.26 ± 0.05 | 0.23 ± 0.02 | 0.25 ± 0.07 | 0.22 ± 0.04 | 0.19 ± 0.03 | 0.19 ± 0.03 |
| C18:3n3 | 0.33 ± 0.06$^b$ | 0.37 ± 0.06$^b$ | 0.37 ± 0.09$^b$ | 2.29 ± 0.68$^a$ | 2.41 ± 0.74$^a$ | 2.49 ± 0.53$^a$ |
| C20:2n6 | 0.09 ± 0.03 | 0.07 ± 0.01 | 0.08 ± 0.02 | 0.06 ± 0.01 | 0.06 ± 0.02 | 0.05 ± 0.02 |
| C22:0 | 0.05 ± 0.01 | 0.04 ± 0.00 | 0.05 ± 0.02 | 0.03 ± 0.01 | 0.03 ± 0.01 | 0.03 ± 0.01 |
| C20:3n6 | 0.28 ± 0.07 | 0.21 ± 0.04 | 0.25 ± 0.03 | 0.22 ± 0.04 | 0.22 ± 0.07 | 0.21 ± 0.03 |
| C20:4n6 | 0.67 ± 0.41 | 0.61 ± 0.37 | 0.66 ± 0.40 | 0.52 ± 0.06 | 0.45 ± 0.26 | 0.53 ± 0.04 |
| C20:5EPA | 0.02 ± 0.02$^d$ | 0.04 ± 0.01$^{cd}$ | 0.05 ± 0.01$^c$ | 0.12 ± 0.02$^b$ | 0.13 ± 0.03$^b$ | 0.17 ± 0.03$^a$ |
| C22:6DHA | 1.27 ± 0.19$^c$ | 1.81 ± 0.16$^b$ | 2.06 ± 0.22$^b$ | 3.86 ± 0.33$^a$ | 3.94 ± 0.53$^a$ | 3.94 ± 0.41$^a$ |

TABLE 52-continued

Plasma Fatty Acid Profiles at Week 4

| | Corn | | | Flax | | |
|---|---|---|---|---|---|---|
| | 0 | 3 | 5 | 0 | 3 | 5 |
| MUFA | 48.71 ± 2.34 | 49.94 ± 1.29 | 49.83 ± 6.95 | 49.66 ± 1.54 | 47.72 ± 1.89 | 49.35 ± 2.10 |
| PUFA | 19.18 ± 2.05 | 18.97 ± 1.13 | 20.37 ± 1.53 | 20.24 ± 1.94 | 20.97 ± 1.52 | 20.21 ± 2.41 |
| SAT | 32.08 ± 1.10 | 31.08 ± 0.45 | 29.78 ± 7.48 | 30.08 ± 0.9 | 31.28 ± 1.54 | 30.41 ± 1.00 |
| n3 | 1.63 ± 0.21$^c$ | 2.22 ± 0.17$^b$ | 2.47 ± 0.25$^b$ | 6.30 ± 0.73$^a$ | 6.50 ± 0.91$^a$ | 6.62 ± 0.57$^a$ |
| n6 | 17.56 ± 1.88$^a$ | 16.75 ± 1.00$^a$ | 17.90 ± 1.32$^a$ | 13.94 ± 1.39$^b$ | 14.47 ± 1.3$^b$ | 13.59 ± 1.87$^b$ |
| n6TOn3 | 10.86 ± 0.92$^a$ | 7.57 ± 0.41$^b$ | 7.26 ± 0.46$^b$ | 2.22 ± 0.2$^c$ | 2.26 ± 0.38$^c$ | 2.05 ± 0.15$^c$ |

$^{a-d}$Values with different superscripts in each row differ according to one-way ANOVA (P < 0.05).

TABLE 53

Plasma Fatty Acid Profiles at Week 6

| | Corn | | | Flax | | |
|---|---|---|---|---|---|---|
| | 0 | 3 | 5 | 0 | 3 | 5 |
| c14:0 | 1.18 ± 0.47 | 1.17 ± 0.28 | 1.08 ± 0.32 | 1.11 ± 0.27 | 1.3 ± 0.31 | 1.19 ± 0.43 |
| C14:1 | 0.5 ± 0.61 | 0.16 ± 0.44 | 0.29 ± 0.41 | 0.15 ± 0.31 | 0.53 ± 1.01 | 0.3 ± 0.39 |
| C16:0 | 22.96 ± 0.84 | 23.21 ± 1.15 | 22.69 ± 1.04 | 21.69 ± 1.15 | 21.81 ± 0.86 | 21.26 ± 0.63 |
| c16:1 | 1.64 ± 0.4 | 1.76 ± 0.12 | 1.65 ± 0.38 | 1.64 ± 0.29 | 1.74 ± 0.37 | 1.78 ± 0.4 |
| C18:0 | 9.81 ± 0.99 | 9.98 ± 0.54 | 9.88 ± 1.29 | 9.41 ± 0.37 | 9.36 ± 0.69 | 9.5 ± 0.81 |
| c18:1n9 | 43.35 ± 3.89 | 43.38 ± 1.95 | 44.14 ± 2.78 | 44.86 ± 2.67 | 42.29 ± 3.63 | 44.02 ± 1.98 |
| C18:2n6 | 16.73 ± 2.45$^a$ | 16.26 ± 0.83$^a$ | 15.8 ± 1.21a | 12.63 ± 1.07$^b$ | 13.41 ± 1.3$^b$ | 13.03 ± 1.63$^b$ |
| C18:3n6 | 0 ± 0 | 0 ± 0 | 0 ± 0 | 0 ± 0 | 0 ± 0 | 0 ± 0 |
| C20:1c11 | 0.08 ± 0.16 | 0 ± 0 | 0.07 ± 0.15 | 0 ± 0 | 0 ± 0 | 0 ± 0 |
| C18:3n3 | 0 ± 0$^b$ | 0 ± 0$^b$ | 0.08 ± 0.17$^b$ | 2.65 ± 0.64$^a$ | 2.72 ± 0.85$^a$ | 2.45 ± 0.5$^a$ |
| C20:2n6 | 0.02 ± 0.05 | 0 ± 0 | 0.01 ± 0.04 | 0 ± 0 | 0 ± 0 | 0 ± 0 |
| C22:0 | 0.29 ± 0.37 | 0.08 ± 0.16 | 0.14 ± 0.15 | 0.22 ± 0.28 | 0.05 ± 0.13 | 0.07 ± 0.14 |
| C20:3n6 | 1.12 ± 0.2$^{ab}$ | 1.21 ± 0.13$^a$ | 1.07 ± 0.17$^b$ | 0.59 ± 0.06$^c$ | 0.7 ± 0.1$^c$ | 0.7 ± 0.09$^c$ |
| C20:5EPA | 0.00 ± 0.00 | 0 ± 0 | 0 ± 0 | 0 ± 0 | 0 ± 0 | 0.03 ± 0.08 |
| C22:6DHA | 1.62 ± 0.31$^c$ | 2.44 ± 0.23$^b$ | 2.51 ± 0.39$^b$ | 4.89 ± 0.81$^a$ | 5.35 ± 0.3$^a$ | 5.29 ± 0.63$^a$ |
| MUFA | 45.75 ± 3.77 | 45.41 ± 1.6 | 46.27 ± 2.76 | 46.7 ± 2.71 | 44.79 ± 2.49 | 46.22 ± 1.97 |
| PUFA | 19.77 ± 2.78$^b$ | 20 ± 0.84$^b$ | 19.61 ± 1.15$^b$ | 20.98 ± 2.47$^{ab}$ | 22.22 ± 1.61$^a$ | 21.57 ± 1.31$^{ab}$ |
| SAT | 34.48 ± 1.75$^a$ | 34.59 ± 1.78$^a$ | 34.13 ± 2.39$^{ab}$ | 32.31 ± 1.37$^b$ | 32.99 ± 2.28$^{ab}$ | 32.21 ± 1.63$^b$ |
| n3 | 1.62 ± 0.31$^c$ | 2.44 ± 0.23$^b$ | 2.59 ± 0.27$^b$ | 7.54 ± 1.37$^a$ | 8.07 ± 0.81$^a$ | 7.76 ± 0.62$^a$ |
| n6 | 18.15 ± 2.56$^a$ | 17.56 ± 0.89$^a$ | 17.02 ± 1.14$^a$ | 13.44 ± 1.17$^b$ | 14.15 ± 1.33$^b$ | 13.8 ± 1.66$^b$ |
| n6TOn3 | 11.42 ± 1.55$^a$ | 7.25 ± 0.9$^b$ | 6.65 ± 0.84$^b$ | 1.82 ± 0.23$^c$ | 1.77 ± 0.24$^c$ | 1.8 ± 0.33$^c$ |

$^{a-d}$Values with different superscripts in each row differ according to one-way ANOVA (P < 0.05).

TABLE 54

Egg Fatty Acid Profiles at Week 0

| | Corn | | | Flax | | |
|---|---|---|---|---|---|---|
| | 0 | 3 | 5 | 0 | 3 | 5 |
| c14:0 | 0 ± 0.01 | 0 ± 0.01 | 0.01 ± 0.01 | 0 ± 0.01 | 0 ± 0 | 0 ± 0.01 |
| C14:1 | 0.1 ± 0.03 | 0.12 ± 0.1 | 0.09 ± 0.02 | 0.1 ± 0.04 | 0.09 ± 0.02 | 0.09 ± 0.03 |
| C16:0 | 19.83 ± 6.97 | 21.66 ± 0.71 | 22.11 ± 0.43 | 21.71 ± 0.5 | 22.45 ± 0.53 | 21.69 ± 0.64 |
| c16:1 | 2.25 ± 0.27 | 2.09 ± 0.19 | 2.05 ± 0.31 | 2.01 ± 0.24 | 2.22 ± 0.25 | 2.03 ± 0.2 |
| C18:0 | 6.96 ± 2.49 | 7.97 ± 0.49 | 8.25 ± 1.09 | 7.98 ± 0.59 | 8.2 ± 0.37 | 8.09 ± 0.35 |
| c18:1n9 | 47.97 ± 1.35 | 48.17 ± 2.1 | 47.9 ± 1.96 | 48.68 ± 0.7 | 47.63 ± 1.54 | 47.98 ± 0.71 |
| C18:2n6 | 17.58 ± 2.84 | 16.22 ± 1.43 | 16.42 ± 1.52 | 16.25 ± 1.05 | 16.18 ± 1.38 | 16.84 ± 1.04 |
| C18:3n6 | 0.1 ± 0.02 | 0.09 ± 0.01 | 0.09 ± 0.01 | 0.09 ± 0.01 | 0.1 ± 0.01 | 0.1 ± 0.02 |
| C20:1c11 | 0.32 ± 0.04 | 0.27 ± 0.07 | 0.29 ± 0.03 | 0.32 ± 0.02 | 0.28 ± 0.03 | 0.29 ± 0.03 |
| C18:3n3 | 0.21 ± 0.04 | 0.19 ± 0.07 | 0.2 ± 0.02 | 0.21 ± 0.04 | 0.21 ± 0.03 | 0.21 ± 0.02 |
| C20:2n6 | 0.08 ± 0.01 | 0.08 ± 0.04 | 0.08 ± 0.01 | 0.08 ± 0.01 | 0.07 ± 0.01 | 0.08 ± 0.01 |
| C20:3n6 | 0.18 ± 0.02 | 0.18 ± 0.03 | 0.18 ± 0.01 | 0.18 ± 0.01 | 0.18 ± 0.03 | 0.18 ± 0.02 |
| C20:4n6 | 0.7 ± 0.09 | 0.68 ± 0.05 | 0.66 ± 0.02 | 0.67 ± 0.03 | 0.69 ± 0.03 | 0.7 ± 0.03 |
| C20:5EPA | 0 ± 0.01 | 0.01 ± 0.02 | 0 ± 0.01 | 0 ± 0.01 | 0 ± 0 | 0 ± 0 |
| C22:6DHA | 1.35 ± 0.21 | 1.36 ± 0.15 | 1.29 ± 0.06 | 1.33 ± 0.08 | 1.31 ± 0.09 | 1.34 ± 0.12 |
| MUFA | 52.77 ± 6.45 | 50.81 ± 2.04 | 50.5 ± 2.15 | 51.28 ± 0.71 | 50.38 ± 1.3 | 50.57 ± 0.61 |
| PUFA | 20.21 ± 3.19 | 18.82 ± 1.53 | 18.92 ± 1.54 | 18.81 ± 1.13 | 18.74 ± 1.46 | 19.44 ± 1.17 |
| SAT | 27.02 ± 9.38 | 30.37 ± 1.61 | 30.58 ± 1.45 | 29.91 ± 0.79 | 30.88 ± 0.63 | 30 ± 0.69 |

TABLE 54-continued

Egg Fatty Acid Profiles at Week 0

| | Corn | | | Flax | | |
|---|---|---|---|---|---|---|
| | 0 | 3 | 5 | 0 | 3 | 5 |
| n3 | 1.56 ± 0.25 | 1.56 ± 0.19 | 1.5 ± 0.06 | 1.55 ± 0.09 | 1.52 ± 0.09 | 1.55 ± 0.14 |
| n6 | 18.65 ± 2.97 | 17.26 ± 1.45 | 17.42 ± 1.53 | 17.27 ± 1.07 | 17.22 ± 1.41 | 17.89 ± 1.05 |
| n6TOn3 | 11.96 ± 0.84 | 11.15 ± 1.46 | 11.61 ± 1.01 | 11.18 ± 0.53 | 11.35 ± 0.88 | 11.59 ± 0.57 |

TABLE 55

Egg Fatty Acid Profiles at Week 1

| | Corn | | | Flax | | |
|---|---|---|---|---|---|---|
| | 0 | 3 | 5 | 0 | 3 | 5 |
| c14:0 | 0 ± 0 | 0 ± 0 | 0 ± 0 | 0 ± 0 | 0 ± 0 | 0 ± 0 |
| C14:1 | 0.09 ± 0.02 | 0.12 ± 0.06 | 0.1 ± 0.03 | 0.15 ± 0.12 | 0.09 ± 0.02 | 0.11 ± 0.03 |
| C16:0 | 22.97 ± 0.44 | 23.33 ± 0.62 | 22.8 ± 0.82 | 20.94 ± 0.56 | 21.47 ± 0.77 | 21.21 ± 0.51 |
| c16:1 | 2.29 ± 0.28 | 2.55 ± 0.34 | 2.3 ± 0.47 | 2.11 ± 0.29 | 2.44 ± 0.23 | 2.54 ± 0.26 |
| C18:0 | 8.16 ± 0.43 | 8.15 ± 0.3 | 8.56 ± 1.26 | 7.14 ± 2.37 | 7.97 ± 0.45 | 7.93 ± 0.29 |
| c18:1n9 | 46.16 ± 1.27$^a$ | 44.86 ± 0.61$^{ab}$ | 45.83 ± 1.85$^{abc}$ | 46.32 ± 1.52$^a$ | 44.51 ± 1.97$^{bc}$ | 44.15 ± 1.5$^c$ |
| C18:2n6 | 17.47 ± 1.48$^a$ | 17.86 ± 0.58$^a$ | 17.05 ± 1.49$^a$ | 14.31 ± 0.87$^b$ | 14.04 ± 1.13$^b$ | 14.42 ± 1.2$^b$ |
| C18:3n6 | 0.14 ± 0.02 | 0.13 ± 0.02 | 0.11 ± 0.01 | 0.08 ± 0.03 | 0.09 ± 0.01 | 0.09 ± 0.02 |
| C20:1c11 | 0.28 ± 0.02 | 0.26 ± 0.02 | 0.28 ± 0.02 | 0.15 ± 0.09 | 0.11 ± 0.08 | 0.13 ± 0.09 |
| C18:3n3 | 0.07 ± 0.05$^b$ | 0.01 ± 0.03$^b$ | 0.03 ± 0.05$^b$ | 4.36 ± 0.65$^a$ | 4.95 ± 1.14$^a$ | 4.91 ± 1.93$^a$ |
| C20:2n6 | 0.08 ± 0.01 | 0.08 ± 0.01 | 0.08 ± 0.01 | 0.06 ± 0.01 | 0.05 ± 0.01 | 0.05 ± 0.01 |
| C20:3n6 | 0.21 ± 0.01 | 0.21 ± 0.02 | 0.23 ± 0.03 | 0.22 ± 0.05 | 0.18 ± 0.02 | 0.19 ± 0.02 |
| C20:4n6 | 0.74 ± 0.05 | 0.72 ± 0.04 | 0.7 ± 0.05 | 0.49 ± 0.07 | 0.48 ± 0.03 | 0.48 ± 0.06 |
| C20:5EPA | 0 ± 0$^b$ | 0.02 ± 0.02$^{cb}$ | 0.04 ± 0.02$^c$ | 0.09 ± 0.03$^b$ | 0.14 ± 0.02$^a$ | 0.16 ± 0.03$^a$ |
| C22:6DHA | 1.1 ± 0.12$^c$ | 1.44 ± 0.11b | 1.62 ± 0.18$^b$ | 3.17 ± 0.3$^a$ | 3.19 ± 0.32$^a$ | 3.35 ± 0.2$^a$ |
| MUFA | 48.9 ± 1.25 | 47.88 ± 0.47 | 48.6 ± 1.96 | 48.82 ± 1.64 | 47.25 ± 1.8 | 47.02 ± 1.55 |
| PUFA | 19.8 ± 1.58$^b$ | 20.47 ± 0.63$^b$ | 19.87 ± 1.54$^b$ | 22.81 ± 0.98$^a$ | 23.14 ± 2.15$^a$ | 23.68 ± 2$^a$ |
| SAT | 31.3 ± 0.67$^a$ | 31.65 ± 0.45$^a$ | 31.54 ± 1.67$^a$ | 28.37 ± 1.74$^c$ | 29.61 ± 0.97$^b$ | 29.3 ± 0.71$^{bc}$ |
| n3 | 1.16 ± 0.14$^b$ | 1.47 ± 0.13$^b$ | 1.7 ± 0.19$^b$ | 7.65 ± 0.86$^a$ | 8.3 ± 1.3$^a$ | 8.44 ± 2.03$^a$ |
| n6 | 18.63 ± 1.49$^a$ | 19 ± 0.59$^a$ | 18.17 ± 1.47$^a$ | 15.16 ± 0.92$^b$ | 14.84 ± 1.17$^b$ | 15.23 ± 1.29$^b$ |
| n6TOn3 | 16.11 ± 1.44$^a$ | 13 ± 1.17$^b$ | 10.78 ± 1.17$^c$ | 2.01 ± 0.34$^d$ | 1.81 ± 0.19$^d$ | 2.01 ± 0.96$^d$ |

$^{a-d}$Values with different superscripts in each row differ according to one-way ANOVA (P < 0.05).

TABLE 56

Egg Fatty Acid Profiles at Week 2

| | Corn | | | Flax | | |
|---|---|---|---|---|---|---|
| | 0 | 3 | 5 | 0 | 3 | 5 |
| c14I0 | 0 ± 0 | 0 ± 0 | 0 ± 0 | 0 ± 0 | 0 ± 0 | 0 ± 0 |
| C14I1 | 0.09 ± 0.02 | 0.09 ± 0.02 | 0.09 ± 0.02 | 0.09 ± 0.02 | 0.09 ± 0.02 | 0.12 ± 0.06 |
| C16I0 | 22.85 ± 0.54 | 22.82 ± 0.81 | 22.82 ± 0.61 | 20.82 ± 0.6 | 21.2 ± 0.68 | 21 ± 0.44 |
| c16I1 | 2.39 ± 0.27 | 2.46 ± 0.22 | 2.6 ± 0.35 | 2.42 ± 0.34 | 2.62 ± 0.33 | 2.72 ± 0.29 |
| C18I0 | 7.82 ± 0.31 | 7.95 ± 0.31 | 7.79 ± 0.32 | 7.5 ± 0.56 | 7.54 ± 0.34 | 7.62 ± 0.36 |
| c18I1n9 | 45.06 ± 1.36$^{ab}$ | 44.57 ± 1.21$^{ab}$ | 45.33 ± 1.07$^a$ | 43.84 ± 0.93$^{bc}$ | 43.27 ± 1.46$^c$ | 43.3 ± 1.47$^c$ |
| C18I2n6 | 18.54 ± 1.59$^a$ | 18.45 ± 1.02$^a$ | 17.41 ± 1.19$^a$ | 14.84 ± 0.66$^b$ | 14.47 ± 1.08$^b$ | 13.91 ± 1.32$^b$ |
| C18I3n6 | 0.13 ± 0.03 | 0.12 ± 0.02 | 0.12 ± 0.02 | 0.09 ± 0.01 | 0.09 ± 0.01 | 0.09 ± 0.02 |
| C20I1c11 | 0.29 ± 0.02 | 0.27 ± 0.01 | 0.29 ± 0.03 | 0.23 ± 0.01 | 0.21 ± 0.03 | 0.2 ± 0.02 |
| C18I3n3 | 0.52 ± 0.08$^b$ | 0.54 ± 0.06$^b$ | 0.5 ± 0.06$^b$ | 5.64 ± 0.62$^a$ | 5.78 ± 1.06$^a$ | 6.21 ± 0.75$^a$ |
| C20I2n6 | 0.09 ± 0.01 | 0.09 ± 0.01 | 0.09 ± 0.01 | 0.06 ± 0.01 | 0.06 ± 0.01 | 0.06 ± 0.01 |
| C20I3n6 | 0.22 ± 0.02 | 0.21 ± 0.01 | 0.21 ± 0.02 | 0.19 ± 0.03 | 0.17 ± 0.02 | 0.18 ± 0.04 |
| C20I4n6 | 0.69 ± 0.05 | 0.63 ± 0.22 | 0.67 ± 0.04 | 0.4 ± 0.02 | 0.42 ± 0.04 | 0.41 ± 0.04 |
| C20I5EPA | 0 ± 0.01$^e$ | 0.04 ± 0.02$^d$ | 0.04 ± 0.02$^d$ | 0.11 ± 0.01$^c$ | 0.14 ± 0.02$^b$ | 0.18 ± 0.03$^a$ |
| C22I6DHA | 1.01 ± 0.11$^e$ | 1.45 ± 0.13$^d$ | 1.69 ± 0.11$^c$ | 3.4 ± 0.17b | 3.59 ± 0.28$^a$ | 3.6 ± 0.26$^a$ |
| MUFA | 47.92 ± 1.42$^a$ | 47.48 ± 1.21$^{ab}$ | 48.42 ± 1.02$^a$ | 46.69 ± 0.89$^b$ | 46.28 ± 1.36$^b$ | 46.45 ± 1.43$^b$ |
| PUFA | 21.21 ± 1.74$^b$ | 21.53 ± 1.16$^b$ | 20.73 ± 1.31$^b$ | 24.77 ± 1.25$^a$ | 24.76 ± 1.74$^a$ | 24.68 ± 1.82$^a$ |
| SAT | 30.87 ± 0.61$^a$ | 30.98 ± 0.79$^a$ | 30.85 ± 0.6a | 28.54 ± 0.79$^b$ | 28.94 ± 0.78$^b$ | 28.87 ± 0.64$^b$ |
| n3 | 1.53 ± 0.15$^d$ | 2.03 ± 0.15$^{cd}$ | 2.24 ± 0.14$^c$ | 9.18 ± 0.74$^b$ | 9.55 ± 1.24$^{ab}$ | 10.03 ± 0.84$^a$ |
| n6 | 19.68 ± 1.6$^a$ | 19.5 ± 1.05$^{ab}$ | 18.49 ± 1.21$^b$ | 15.6 ± 0.68$^c$ | 15.22 ± 1.11$^c$ | 14.65 ± 1.37$^c$ |
| n6Ton3 | 12.88 ± 0.73$^a$ | 9.63 ± 0.52$^b$ | 8.27 ± 0.46$^c$ | 1.71 ± 0.11$^d$ | 1.61 ± 0.21$^d$ | 1.47 ± 0.15$^d$ |

$^{a-d}$Values with different superscripts in each row differ according to one-way ANOVA (P < 0.05).

TABLE 57

Egg Fatty Acid Profiles at Week 3

| | Corn | | | Flax | | |
|---|---|---|---|---|---|---|
| | 0 | 3 | 5 | 0 | 3 | 5 |
| c14:0 | 0 ± 0 | 0 ± 0 | 0 ± 0 | 0 ± 0 | 0 ± 0 | 0 ± 0 |
| C14:1 | 0.11 ± 0.06 | 0.09 ± 0.02 | 0.09 ± 0.02 | 0.09 ± 0.01 | 0.09 ± 0.01 | 0.09 ± 0.02 |
| C16:0 | 23.18 ± 0.93$^a$ | 23.19 ± 0.92$^a$ | 23.37 ± 0.44$^a$ | 21.27 ± 0.7$^b$ | 21.8 ± 0.58$^b$ | 21.48 ± 0.76$^b$ |
| c16:1 | 2.49 ± 0.42 | 2.49 ± 0.31 | 2.71 ± 0.25 | 2.49 ± 0.31 | 2.72 ± 0.18 | 2.83 ± 0.4 |
| C18:0 | 7.63 ± 0.48 | 7.91 ± 0.29 | 7.83 ± 0.22 | 7.49 ± 0.5 | 7.49 ± 0.38 | 7.62 ± 0.39 |
| c18:1n9 | 44.11 ± 1.23$^{ab}$ | 44 ± 1.09$^{abc}$ | 44.83 ± 0.97$^a$ | 43.76 ± 1.15$^{abc}$ | 43.09 ± 1.45$^{bc}$ | 42.86 ± 1.28$^c$ |
| C18:2n6 | 19.2 ± 1.05$^a$ | 18.65 ± 1.07$^a$ | 17.31 ± 1.02$^b$ | 14.38 ± 1.01$^c$ | 14.08 ± 0.71$^c$ | 13.83 ± 1.41$^c$ |
| C18:3n6 | 0.14 ± 0.03 | 0.14 ± 0.02 | 0.12 ± 0.02 | 0.09 ± 0.01 | 0.09 ± 0.01 | 0.09 ± 0.02 |
| C20:1c11 | 0.28 ± 0.02 | 0.25 ± 0.01 | 0.27 ± 0.02 | 0.22 ± 0.01 | 0.19 ± 0.02 | 0.2 ± 0.01 |
| C18:3n3 | 0.57 ± 0.06$^b$ | 0.55 ± 0.04$^b$ | 0.49 ± 0.05$^b$ | 5.69 ± 0.76$^a$ | 5.7 ± 1.06$^a$ | 6.25 ± 0.47$^a$ |
| C20:2n6 | 0.09 ± 0.01 | 0.09 ± 0.01 | 0.08 ± 0.01 | 0.06 ± 0 | 0.05 ± 0.01 | 0.05 ± 0.01 |
| C20:3n6 | 0.22 ± 0.02 | 0.21 ± 0.03 | 0.21 ± 0.02 | 0.18 ± 0.02 | 0.17 ± 0.02 | 0.17 ± 0.02 |
| C20:4n6 | 0.68 ± 0.05 | 0.69 ± 0.04 | 0.69 ± 0.05 | 0.38 ± 0.02 | 0.41 ± 0.04 | 0.4 ± 0.03 |
| C20:5EPA | 0 ± 0.01$^{ae}$ | 0.04 ± 0.01$^{bd}$ | 0.05 ± 0.01$^d$ | 0.11 ± 0.02$^c$ | 0.15 ± 0.01$^b$ | 0.19 ± 0.03$^a$ |
| C22:6DHA | 1 ± 0.1$^d$ | 1.41 ± 0.08$^c$ | 1.65 ± 0.1$^b$ | 3.48 ± 0.15$^a$ | 3.64 ± 0.21$^a$ | 3.6 ± 0.23$^a$ |
| MUFA | 47.07 ± 1.05$^{ab}$ | 46.92 ± 1.07$^a$ | 47.99 ± 0.87$^a$ | 46.64 ± 1.06$^b$ | 46.18 ± 1.38$^b$ | 46.06 ± 1.17$^b$ |
| PUFA | 21.91 ± 1.18$^b$ | 21.76 ± 1.13$^b$ | 20.6 ± 1.09$^b$ | 24.4 ± 1.77$^a$ | 24.33 ± 1.62$^a$ | 24.62 ± 1.59$^a$ |
| SAT | 31.02 ± 0.84$^a$ | 31.31 ± 0.77$^a$ | 31.41 ± 0.48$^a$ | 28.96 ± 0.96$^b$ | 29.48 ± 0.82$^b$ | 29.31 ± 0.78$^b$ |
| n3 | 1.57 ± 0.12$^{cc}$ | 1.99 ± 0.1$^c$ | 2.19 ± 0.11$^c$ | 9.31 ± 0.84$^b$ | 9.52 ± 1.17$^{ab}$ | 10.08 ± 0.58$^a$ |
| n6 | 20.34 ± 1.09$^a$ | 19.77 ± 1.07$^a$ | 18.41 ± 1.06$^b$ | 15.09 ± 1.04$^c$ | 14.81 ± 0.73$^c$ | 14.55 ± 1.46$^c$ |
| n6TOn3 | 13.02 ± 0.63$^a$ | 9.92 ± 0.43$^b$ | 8.42 ± 0.54$^c$ | 1.63 ± 0.1$^d$ | 1.57 ± 0.15$^d$ | 1.45 ± 0.16$^d$ |

$^{a\text{-}d}$Values with different superscripts in each row differ according to one-way ANOVA (P < 0.05).

TABLE 58

Egg Fatty Acid Profiles at Week 4

| | Corn | | | Flax | | |
|---|---|---|---|---|---|---|
| algae | 0 | 3 | 5 | 0 | 3 | 5 |
| c14:0 | 0.39 ± 0.05 | 0 ± 0 | 0 ± 0 | 0 ± 0 | 0 ± 0 | 0 ± 0 |
| C14:1 | 0.06 ± 0.05 | 0.03 ± 0.03 | 0.06 ± 0.01 | 0.02 ± 0.02 | 0.04 ± 0.03 | 0.05 ± 0.03 |
| C16:0 | 25.41 ± 1.78 | 23.06 ± 0.8 | 23.03 ± 0.73 | 21.1 ± 0.6 | 21.66 ± 0.74 | 21.59 ± 0.59 |
| c16:1 | 2.69 ± 0.24 | 2.45 ± 0.25 | 2.51 ± 0.36 | 2.35 ± 0.35 | 2.57 ± 0.27 | 2.72 ± 0.36 |
| C18:0 | 8.71 ± 0.98 | 8.27 ± 0.3 | 8.18 ± 0.34 | 7.95 ± 0.53 | 7.96 ± 0.39 | 8.05 ± 0.28 |
| c18:1n9 | 41.75 ± 3.42 | 46.09 ± 1.02 | 46.35 ± 1.43 | 45.46 ± 1.06 | 44.64 ± 1.86 | 44.87 ± 1.3 |
| C18:2n6 | 18.47 ± 1.57$^a$ | 17.12 ± 1.03$^b$ | 16.79 ± 1.18$^b$ | 13.46 ± 1.07$^c$ | 13.31 ± 0.88$^c$ | 12.87 ± 0.99$^c$ |
| C18:3n6 | 0.15 ± 0.04 | 0.13 ± 0.01 | 0.12 ± 0.02 | 0.07 ± 0.03 | 0.09 ± 0.03 | 0.09 ± 0.04 |
| C20:1c11 | 0.29 ± 0.05 | 0.39 ± 0.07 | 0.31 ± 0.03 | 0.25 ± 0.02 | 0.22 ± 0.02 | 0.22 ± 0.01 |
| C18:3n3 | 0.09 ± 0.14$^b$ | 0.07 ± 0.06$^b$ | 0.11 ± 0.04$^b$ | 5.51 ± 0.61$^a$ | 5.5 ± 1.08$^a$ | 5.5 ± 0.36$^a$ |
| C20:2n6 | 0.09 ± 0.01 | 0.07 ± 0.01 | 0.07 ± 0.01 | 0.05 ± 0 | 0.05 ± 0.01 | 0.05 ± 0 |
| C20:3n6 | 0.23 ± 0.03 | 0.2 ± 0.02 | 0.2 ± 0.02 | 0.17 ± 0.02 | 0.17 ± 0.02 | 0.16 ± 0.02 |
| C20:4n6 | 0.65 ± 0.09 | 0.62 ± 0.06 | 0.61 ± 0.04 | 0 ± 0 | 0 ± 0 | 0 ± 0 |
| C20:5EPA | 0 ± 0$^e$ | 0.01 ± 0.02$^e$ | 0.03 ± 0.02$^d$ | 0.1 ± 0.02$^c$ | 0.13 ± 0.02$^b$ | 0.16 ± 0.03$^a$ |
| C22:6DHA | 0.75 ± 0.06$^c$ | 1.28 ± 0.16$^b$ | 1.4 ± 0.09$^b$ | 3 ± 0.17$^a$ | 3.09 ± 0.26$^a$ | 3.12 ± 0.16$^a$ |
| MUFA | 44.81 ± 3.43$^b$ | 48.97 ± 1.07$^a$ | 49.24 ± 1.14$^a$ | 48.1 ± 1.1$^a$ | 47.49 ± 1.62$^a$ | 47.86 ± 1.3$^a$ |
| PUFA | 20.45 ± 1.6$^b$ | 19.51 ± 1.02$^b$ | 19.33 ± 1.18$^b$ | 22.7 ± 1.44$^a$ | 22.71 ± 1.8$^a$ | 22.31 ± 1.13$^a$ |
| SAT | 34.75 ± 2.72$^a$ | 31.52 ± 0.72$^b$ | 31.43 ± 0.66$^b$ | 29.2 ± 0.81$^c$ | 29.8 ± 0.86$^c$ | 29.83 ± 0.51$^c$ |
| n3 | 0.84 ± 0.1$^c$ | 1.37 ± 0.18b$^c$ | 1.54 ± 0.1$^b$ | 8.61 ± 0.56$^a$ | 8.72 ± 1.2$^a$ | 8.78 ± 0.41$^a$ |
| n6 | 19.6 ± 1.62$^a$ | 18.14 ± 1.03$^b$ | 17.8 ± 1.2$^b$ | 14.08 ± 1.11$^c$ | 13.99 ± 0.89$^c$ | 13.53 ± 1.06$^c$ |
| n6TOn3 | 23.59 ± 3.14$^a$ | 13.53 ± 2.21$^b$ | 11.64 ± 1.21$^c$ | 1.64 ± 0.13$^d$ | 1.62 ± 0.18$^d$ | 1.54 ± 0.15$^d$ |

$^{a\text{-}d}$Values with different superscripts in each row differ according to one-way ANOVA (P < 0.05).

TABLE 59

Egg Fatty Acid Profiles at Week 5

| | Corn | | | Flax | | |
|---|---|---|---|---|---|---|
| | 0 | 3 | 5 | 0 | 3 | 5 |
| c14I0 | 0 ± 0 | 0 ± 0 | 0 ± 0 | 0 ± 0 | 0 ± 0 | 0 ± 0 |
| C14I1 | 0.11 ± 0.03 | 0.1 ± 0.03 | 0.13 ± 0.05 | 0.1 ± 0.03 | 0.12 ± 0.11 | 0.11 ± 0.03 |
| C16I0 | 23.43 ± 0.29 | 23.18 ± 1.01 | 22.99 ± 0.59 | 21.2 ± 0.69 | 21.68 ± 0.7 | 21.53 ± 0.56 |
| c16I1 | 2.45 ± 0.24 | 2.45 ± 0.25 | 2.51 ± 0.3 | 2.4 ± 0.36 | 2.64 ± 0.29 | 2.75 ± 0.3 |
| C18I0 | 7.82 ± 0.45 | 8.04 ± 0.26 | 7.9 ± 0.38 | 7.58 ± 0.56 | 7.62 ± 0.39 | 7.79 ± 0.29 |

TABLE 59-continued

Egg Fatty Acid Profiles at Week 5

| | Corn | | | Flax | | |
|---|---|---|---|---|---|---|
| | 0 | 3 | 5 | 0 | 3 | 5 |
| c18I1n9 | 44.59 ± 0.89$^a$ | 44.57 ± 0.95$^a$ | 44.65 ± 1.49$^a$ | 44.35 ± 1.31$^a$ | 42.5 ± 2.06$^b$ | 43.33 ± 0.85$^{ab}$ |
| C18I2n6 | 18.33 ± 0.91$^a$ | 17.96 ± 0.84$^a$ | 17.86 ± 1.43$^a$ | 13.9 ± 0.81$^{bc}$ | 14.68 ± 0.79$^b$ | 13.68 ± 0.79$^c$ |
| C18I3n6 | 0.14 ± 0.02 | 0.13 ± 0.01 | 0.12 ± 0.02 | 0.08 ± 0.02 | 0.1 ± 0.01 | 0.09 ± 0.02 |
| C20I1c11 | 0.28 ± 0.02 | 0.26 ± 0.01 | 0.28 ± 0.03 | 0.22 ± 0.02 | 0.2 ± 0.02 | 0.2 ± 0.02 |
| C18I3n3 | 0.55 ± 0.05$^b$ | 0.56 ± 0.07$^b$ | 0.52 ± 0.07$^b$ | 5.6 ± 0.53$^a$ | 5.82 ± 1.14$^a$ | 5.91 ± 0.42$^a$ |
| C20I2n6 | 0.1 ± 0.02 | 0.1 ± 0.01 | 0.09 ± 0.01 | 0.07 ± 0.01 | 0.07 ± 0.01 | 0.06 ± 0.01 |
| C20I3n6 | 0.23 ± 0.04 | 0.22 ± 0.02 | 0.23 ± 0.03 | 0.19 ± 0.03 | 0.21 ± 0.04 | 0.17 ± 0.02 |
| C20I4n6 | 0.67 ± 0.04 | 0.62 ± 0.21 | 0.61 ± 0.23 | 0.36 ± 0.03 | 0.31 ± 0.19 | 0.27 ± 0.18 |
| C20I5EPA | 0.01 ± 0.01$^e$ | 0.02 ± 0.02$^e$ | 0.06 ± 0.01$^d$ | 0.12 ± 0.02$^c$ | 0.15 ± 0.02$^b$ | 0.19 ± 0.03$^a$ |
| C22I6DHA | 0.95 ± 0.04$^d$ | 1.46 ± 0.14$^c$ | 1.69 ± 0.11$^b$ | 3.43 ± 0.14$^a$ | 3.48 ± 0.25$^a$ | 3.51 ± 0.17$^a$ |
| MUFA | 47.53 ± 0.98$^a$ | 47.5 ± 0.79$^a$ | 47.68 ± 1.38$^a$ | 47.18 ± 1.21$^a$ | 45.57 ± 1.76$^b$ | 46.5 ± 0.95$^{ab}$ |
| PUFA | 20.98 ± 0.94$^b$ | 21.06 ± 1.02$^b$ | 21.18 ± 1.49$^b$ | 23.8 ± 1.31$^a$ | 24.86 ± 1.71$^a$ | 23.92 ± 1.12$^a$ |
| SAT | 31.49 ± 0.33$^a$ | 31.44 ± 1.05$^a$ | 31.14 ± 0.58$^a$ | 29.02 ± 0.75$^b$ | 29.57 ± 0.91$^b$ | 29.57 ± 0.58$^b$ |
| n3 | 1.51 ± 0.04$^c$ | 2.04 ± 0.15$^b$ | 2.27 ± 0.13$^b$ | 9.18 ± 0.52$^a$ | 9.49 ± 1.21$^a$ | 9.64 ± 0.49$^a$ |
| n6 | 19.47 ± 0.92$^a$ | 19.02 ± 0.94$^a$ | 18.91 ± 1.44$^a$ | 14.62 ± 0.86$^{bc}$ | 15.37 ± 0.97$^b$ | 14.28 ± 0.82$^c$ |
| n6TOn3 | 12.91 ± 0.58$^a$ | 9.36 ± 0.58$^b$ | 8.33 ± 0.63$^c$ | 1.59 ± 0.06$^d$ | 1.64 ± 0.19$^d$ | 1.48 ± 0.09$^d$ |

$^{a-d}$Values with different superscripts in each row differ according to one-way ANOVA (P < 0.05).

TABLE 60

Egg Fatty Acid Profiles at Week 6

| | Corn | | | Flax | | |
|---|---|---|---|---|---|---|
| | 0 | 3 | 5 | 0 | 3 | 5 |
| c14I0 | 0.35 ± 0.02 | 0.35 ± 0.03 | 0.35 ± 0.04 | 0 ± 0 | 0 ± 0 | 0 ± 0 |
| C14I1 | 0.05 ± 0.02 | 0.05 ± 0.02 | 0.05 ± 0.05 | 0.04 ± 0.03 | 0.05 ± 0.01 | 0.05 ± 0.03 |
| C16I0 | 22.74 ± 0.49 | 22.39 ± 0.95 | 22.59 ± 0.75 | 20.77 ± 0.83 | 21.53 ± 0.51 | 21.14 ± 0.46 |
| c16I1 | 2.2 ± 0.29 | 2.23 ± 0.24 | 2.24 ± 0.39 | 2.28 ± 0.4 | 2.52 ± 0.17 | 2.61 ± 0.38 |
| C18I0 | 8.59 ± 0.69 | 9 ± 0.84 | 9.11 ± 1.25 | 8.4 ± 0.86 | 8.54 ± 0.61 | 8.59 ± 0.71 |
| c18I1n9 | 46.64 ± 1.27$^a$ | 45.65 ± 1.28$^{ab}$ | 45.23 ± 1.93$^{abc}$ | 45.83 ± 0.92$^{ab}$ | 44 ± 2$^c$ | 44.34 ± 1.75$^{bc}$ |
| C18I2n6 | 16.91 ± 1.58$^a$ | 16.16 ± 1.03$^a$ | 15.86 ± 1.09$^a$ | 12.41 ± 0.49$^b$ | 12.86 ± 1.09$^b$ | 12.39 ± 1.16$^b$ |
| C18I3n6 | 0.11 ± 0.05 | 0.11 ± 0.04 | 0.1 ± 0.04 | 0.09 ± 0.03 | 0.1 ± 0.02 | 0.09 ± 0.04 |
| C20I1c11 | 0.31 ± 0.03 | 0.3 ± 0.03 | 0.27 ± 0.03 | 0.25 ± 0.04 | 0.24 ± 0.03 | 0.24 ± 0.04 |
| C18I3n3 | 0.04 ± 0.05$^b$ | 0.02 ± 0.04$^b$ | 0.04 ± 0.05$^b$ | 4.96 ± 0.75$^a$ | 5.22 ± 1.08$^a$ | 5.36 ± 0.5$^a$ |
| C20I2n6 | 0.08 ± 0.01 | 0.06 ± 0.02 | 0.07 ± 0.01 | 0.05 ± 0 | 0.05 ± 0.01 | 0.04 ± 0.01 |
| C20I3n6 | 0.2 ± 0.02 | 0.19 ± 0.02 | 0.19 ± 0.02 | 0.17 ± 0.02 | 0.17 ± 0.02 | 0.16 ± 0.02 |
| C20I4n6 | 0.51 ± 0.18$^a$ | 0.52 ± 0.19$^a$ | 0.56 ± 0.03$^a$ | 0.3 ± 0.05$^b$ | 0.33 ± 0.02$^b$ | 0.33 ± 0.02$^b$ |
| C20I5EPA | 0 ± 0$^d$ | 0 ± 0$^d$ | 0.01 ± 0.02$^d$ | 0.09 ± 0.01$^c$ | 0.13 ± 0.02$^b$ | 0.15 ± 0.02$^a$ |
| C22I6DHA | 0.77 ± 0.07$^d$ | 1.12 ± 0.07$^c$ | 1.3 ± 0.11$^b$ | 2.71 ± 0.15$^a$ | 2.79 ± 0.13$^a$ | 2.76 ± 0.16$^a$ |
| MUFA | 49.27 ± 1.23$^a$ | 48.3 ± 1.17a$^b$ | 47.87 ± 1.99$^{ab}$ | 48.46 ± 0.78$^{ab}$ | 46.88 ± 1.94$^b$ | 47.29 ± 1.69$^b$ |
| PUFA | 18.72 ± 1.68$^b$ | 18.29 ± 1.06$^b$ | 18.14 ± 1.09$^b$ | 20.78 ± 1.04$^a$ | 21.65 ± 2.03$^a$ | 21.28 ± 1.5$^{ab}$ |
| SAT | 32 ± 0.89$^b$ | 33.14 ± 1.21$^a$ | 33.69 ± 1.8$^a$ | 30.27 ± 0.81$^c$ | 31.13 ± 1.09$^{cb}$ | 31.03 ± 1.16$^c$ |
| n3 | 0.91 ± 0.37$^b$ | 1.24 ± 0.3$^b$ | 1.35 ± 0.13$^b$ | 7.77 ± 0.71$^a$ | 8.13 ± 1.07$^a$ | 8.27 ± 0.57$^a$ |
| n6 | 17.81 ± 1.54$^a$ | 17.05 ± 1.04$^a$ | 16.79 ± 1.11$^a$ | 13.01 ± 0.47$^b$ | 13.52 ± 1.11$^b$ | 13.01 ± 1.22$^b$ |
| n6TOn3 | 21.05 ± 4.49$^a$ | 14.22 ± 2.48$^b$ | 12.55 ± 1.54$^b$ | 1.68 ± 0.13$^c$ | 1.67 ± 0.13$^c$ | 1.58 ± 0.15$^c$ |

$^{a-d}$Values with different superscripts in each row differ according to one-way ANOVA (P < 0.05).

Example 6—Impacts of Feeding Egg Yolk and Chicken Muscle Produced by Hens Fed Defatted Microalgae (23%

Experiment 1

10 wild type (WT) male mice of age 32-33 days, weighing 16-17 grams. Mice were divided randomly into two groups, "CG" and "EG." Egg yolks which were bio fortified with *Nannochloropsis* algae were used to enrich eggs with omega-3 fatty acids. The EG group received egg yolks of bio fortified eggs, while the CG group received egg yolks of normal eggs. The amount of omega-3 fatty acids in egg yolk given to each mouse was 0.378 mg/mice/day, which is equal to 93.77 mg for a healthy individual.

HED=animal dose in mg/kg×(animal weight in kg/human weight in kg) (Reagan-Shaw et al., "Dose Translation from Animal to Human Studies Revisited," *FASEB* 22:659-661 (2008), which is hereby incorporated by reference in its entirety). A healthy individual needs daily 400 mg of omega-3 fatty acids. Each mouse was given 5 g diet daily. The diet composition of both EG and CG groups is shown in Table 61 below.

TABLE 61

Diet Composition

| Ingredients (g) | % Age of Total Diet | 1Kg |
|---|---|---|
| Yeast | 30 | 300 |
| Sucrose | 58.96 | 589.603 |
| Corn Oil | 2.5 | 25 |
| CaCO3 | 2.68 | 26.8 |

TABLE 61-continued

| Diet Composition | | |
|---|---|---|
| Ingredients (g) | % Age of Total Diet | 1Kg |
| VitMix | 0.9 | 9 |
| MinMix | 4 | 40 |
| | 100% | 1000 g |
| Egg Yolk | 0.9597% | 9.597 g |

Body weight changes were measured after every week. A blood sample was taken after 3 and 4 weeks to analyze lipid profile (TG, TC, NEFA) from plasma. Blood glucose was analyzed from blood. Lipid profile was also analyzed from tissues (liver, kidney, muscles, and adipose tissues) at the end of the study. The duration of the experiment was 4 weeks. At the end of the experiment, mice were killed using $CO_2$ gas. Data was analyzed by applying T-test tail-2 type-2.

Figure 7:
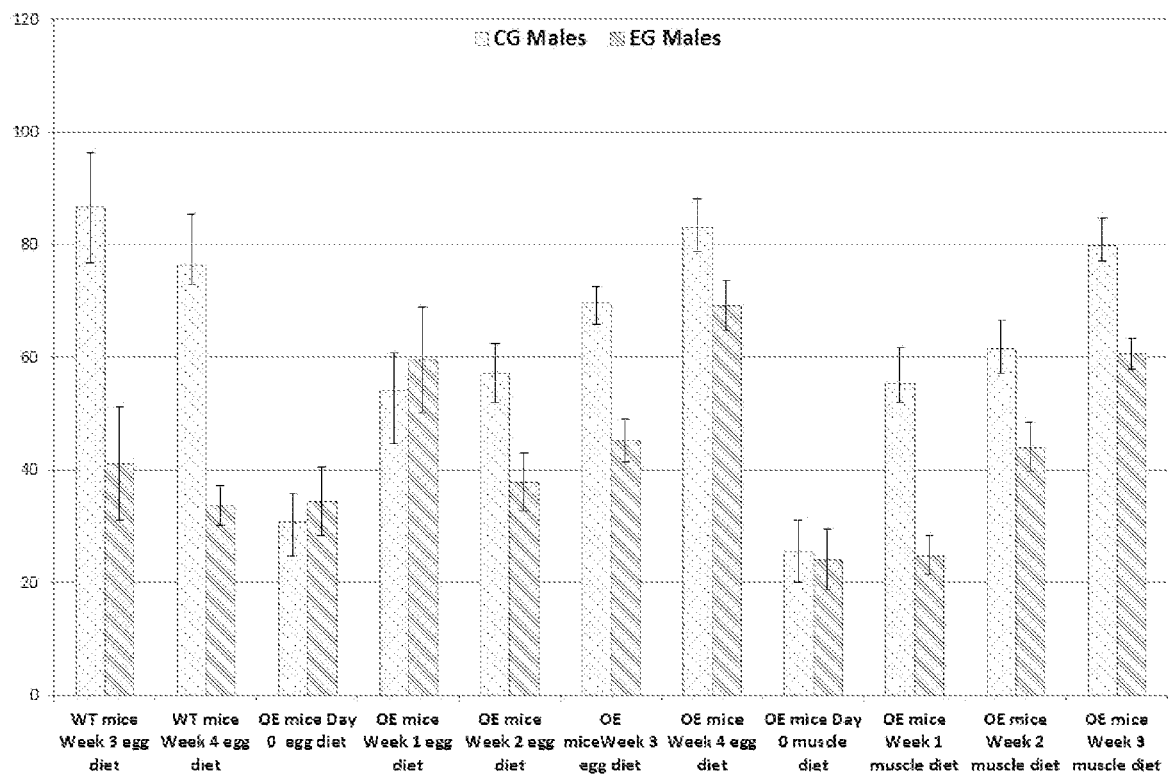
FIG. 7 is a graph showing triglyceride levels in plasma from wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 8:
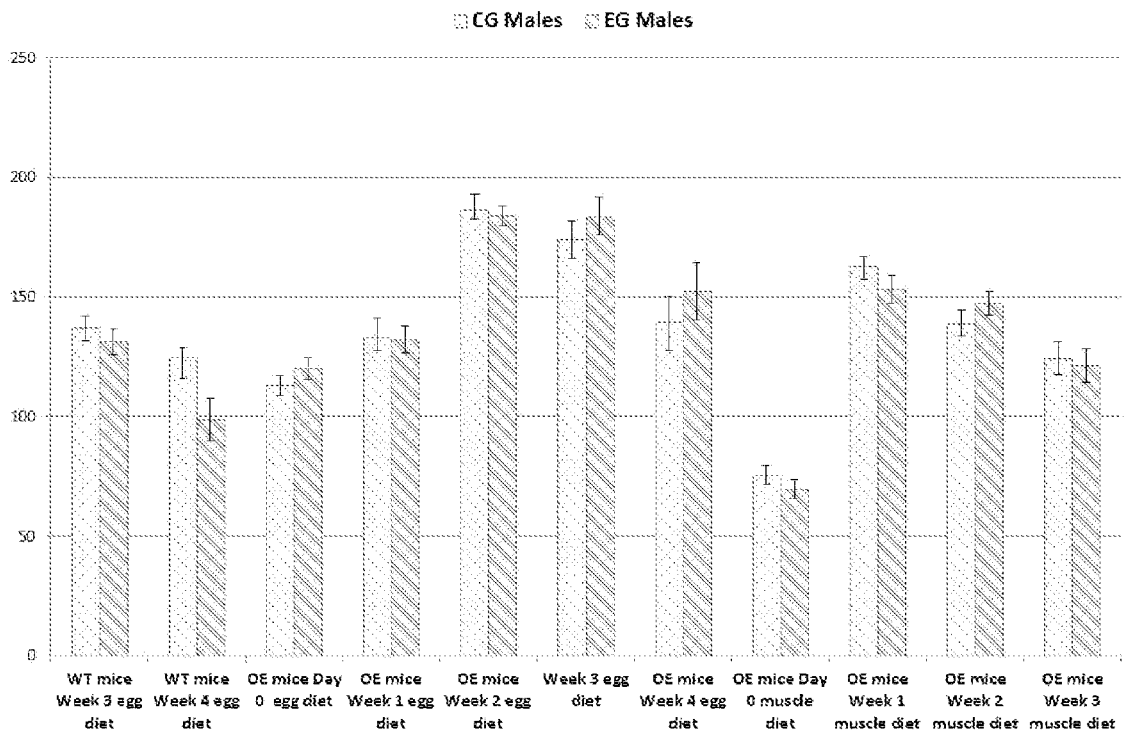
FIG. 8 is a graph showing total cholesterol levels in plasma from wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 11:
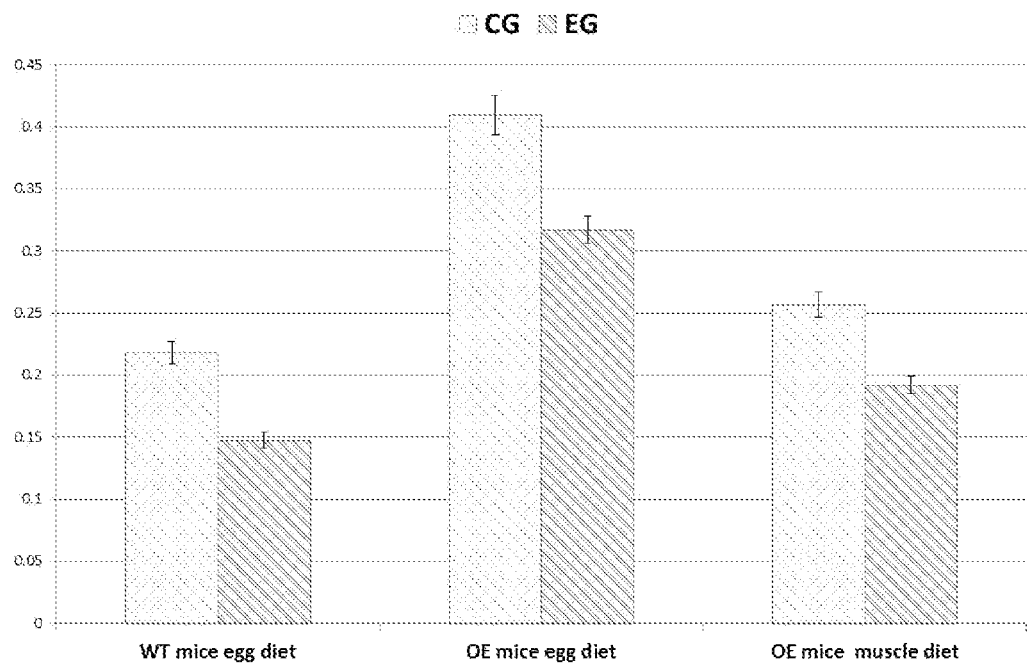
FIG. 11 is a graph showing triglyceride levels in the liver of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 12:
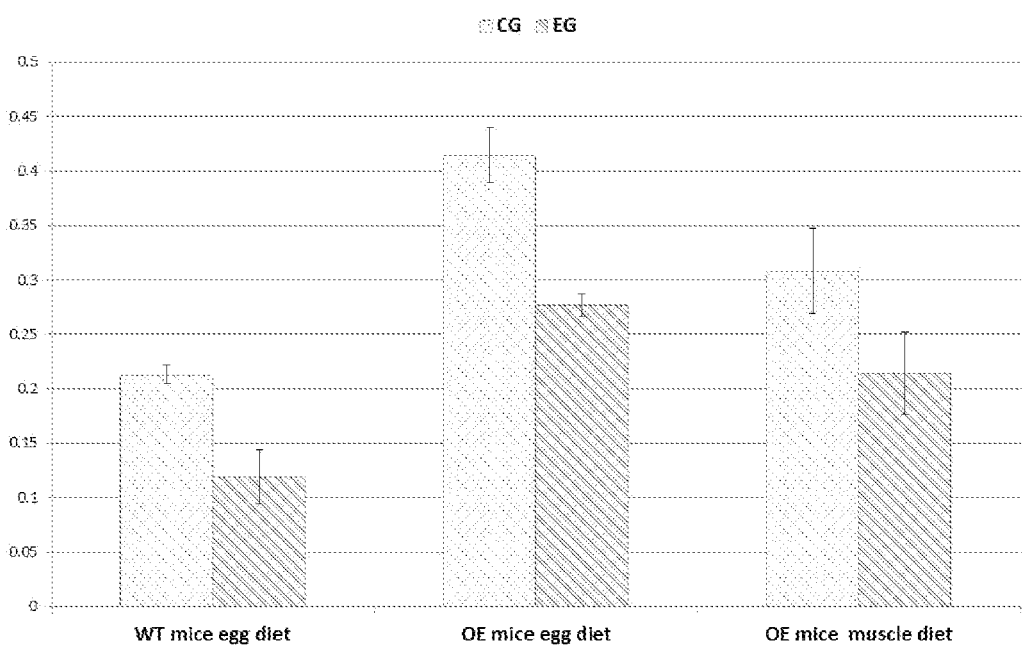
FIG. 12 is a graph showing triglyceride levels from muscles of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 13:
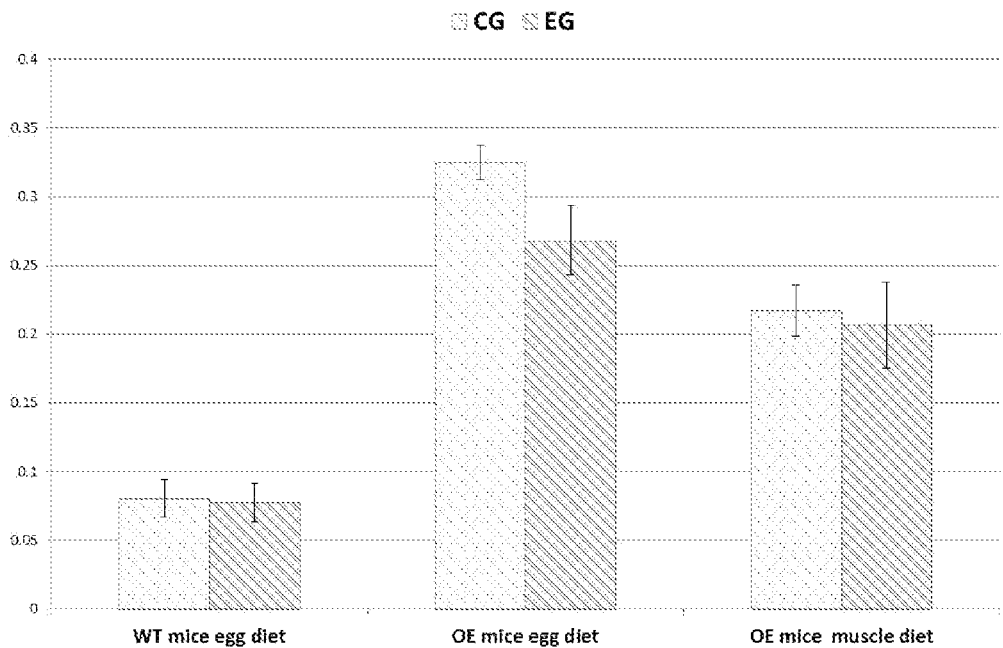
FIG. 13 is a graph showing triglyceride levels from kidney of wildtype (WT) and obsese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 14:
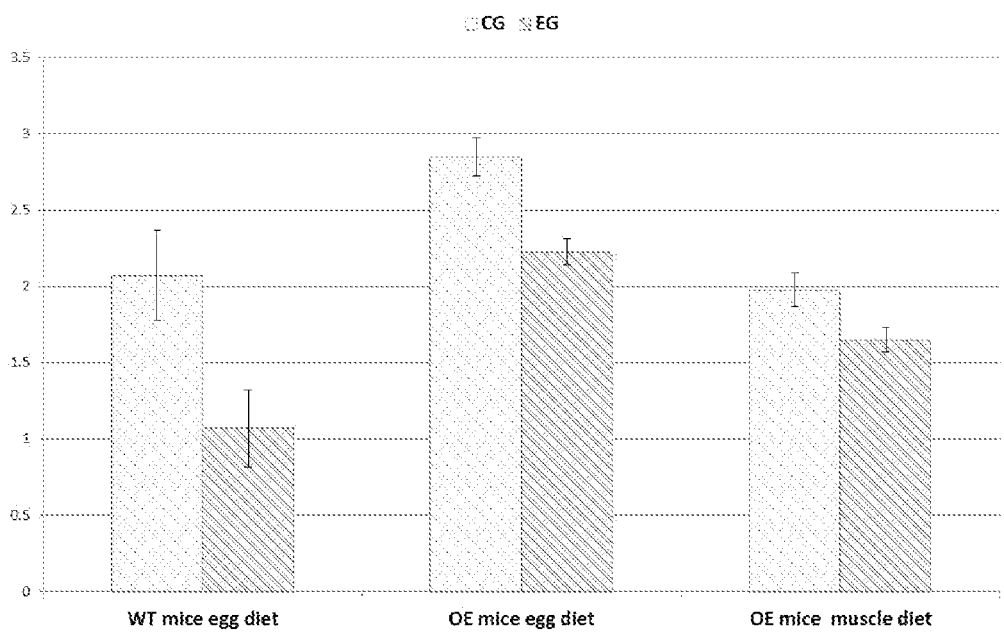
FIG. 14 is a graph showing triglyceride levels from adipose tissues of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 15:
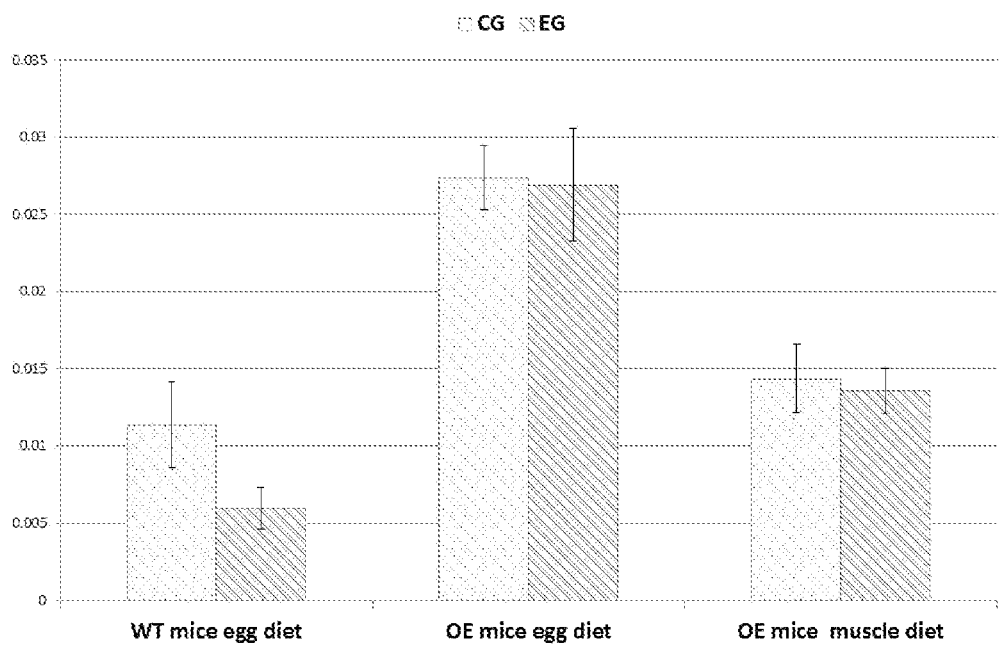
FIG. 15 is a graph showing total cholesterol levels from liver of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 16:
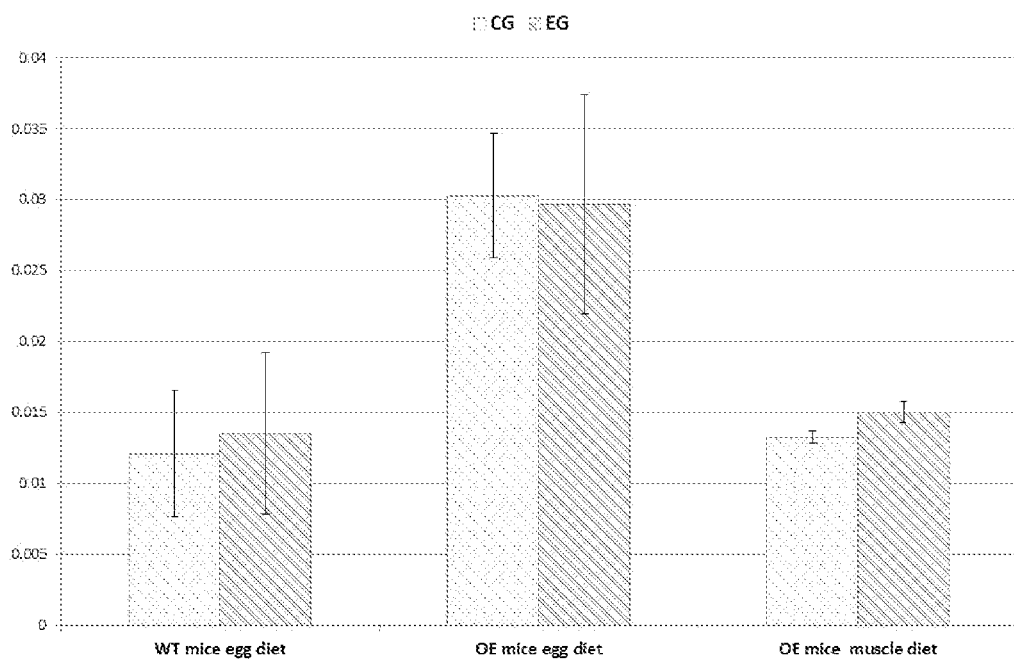
FIG. 16 is a graph showing total cholesterol levels from muscles of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 17:
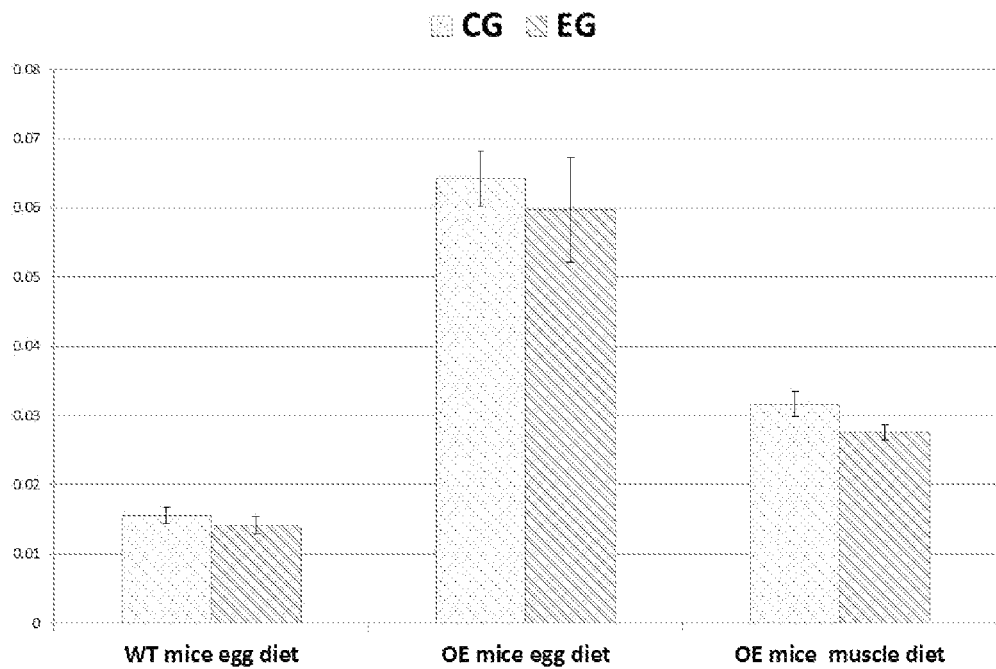
FIG. 17 is a graph showing total cholesterol levels from kidney of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 18:
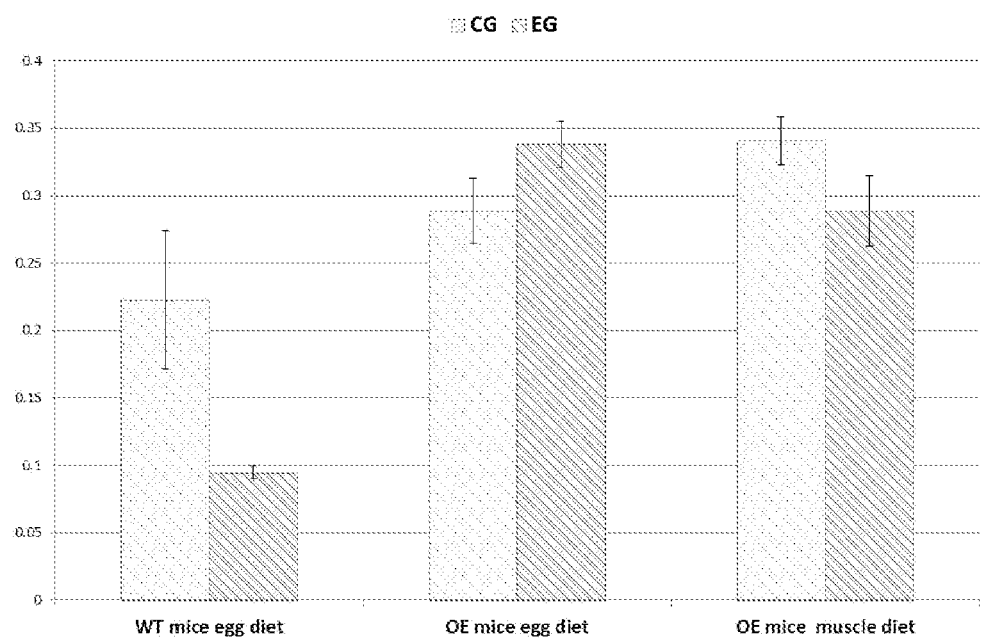
FIG. 18 is a graph showing total cholesterol levels from adipose tissues of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 19:
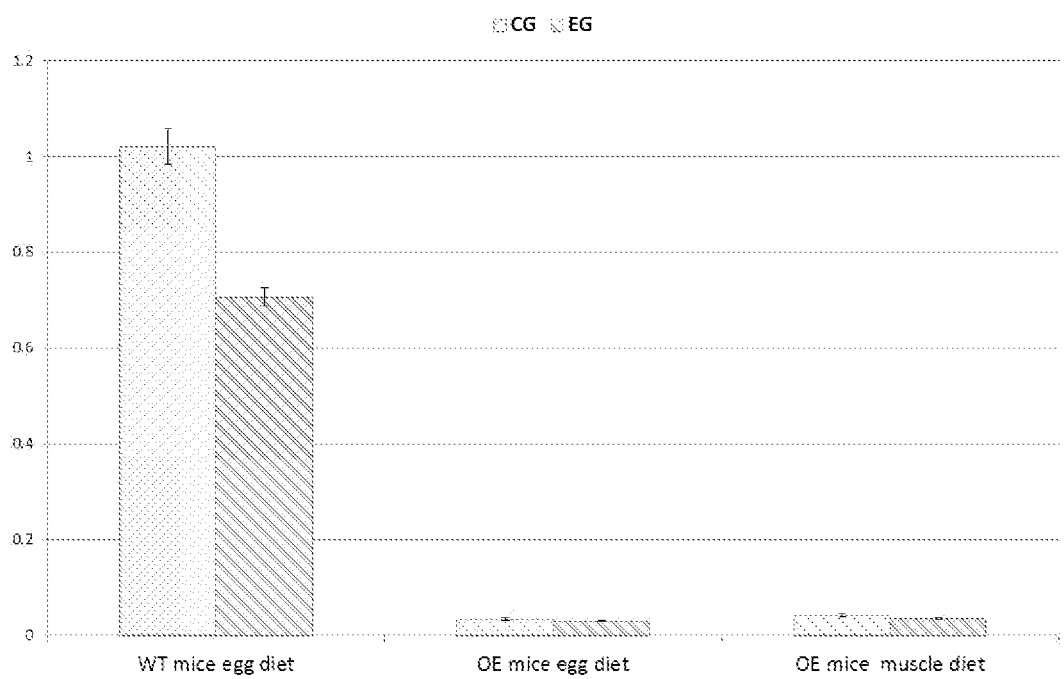
FIG. 19 is a graph showing NEFA from liver of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 20:
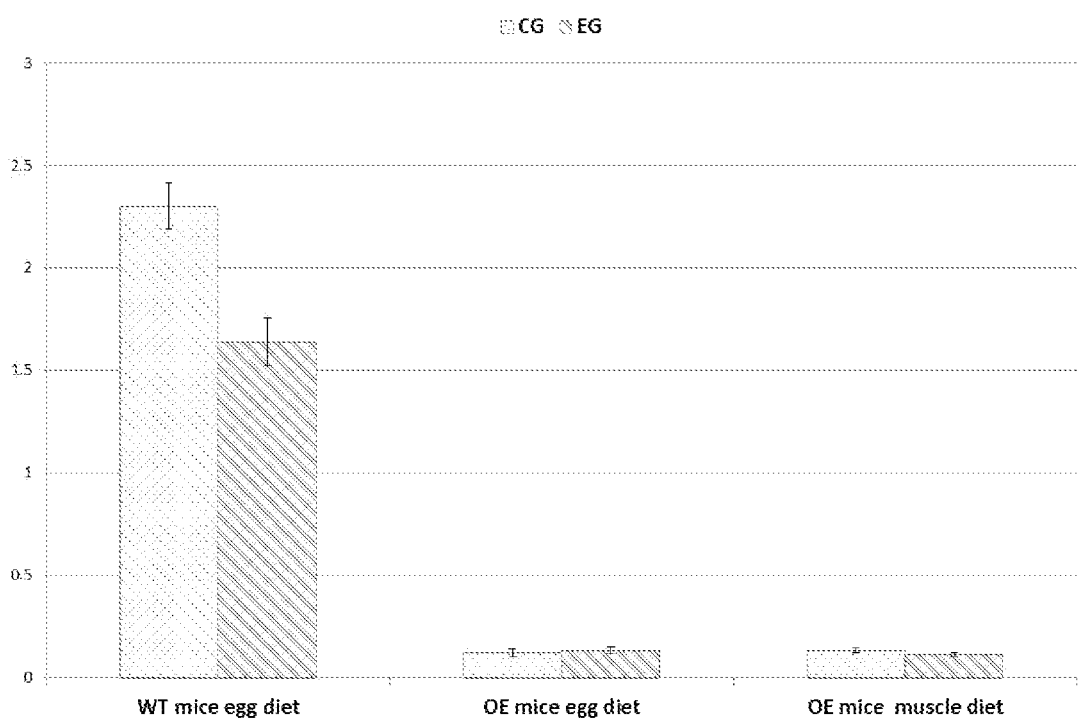
FIG. 20 is a graph showing NEFA from adipose tissues of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 21:
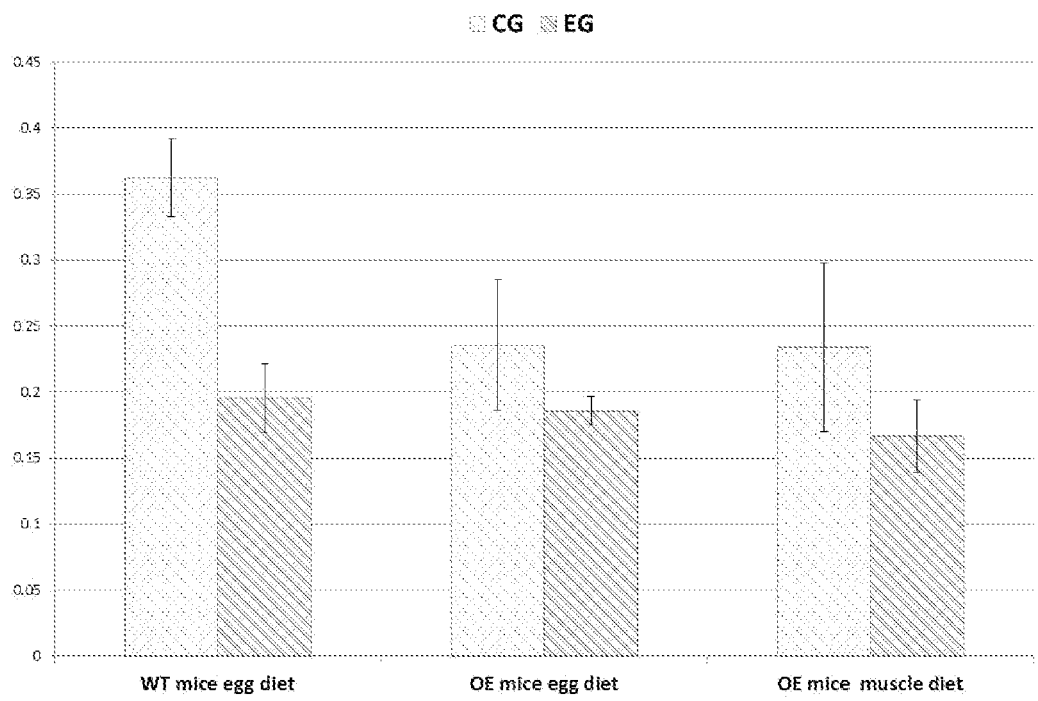
FIG. 21 is a graph showing NEFA from muscles of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 22:
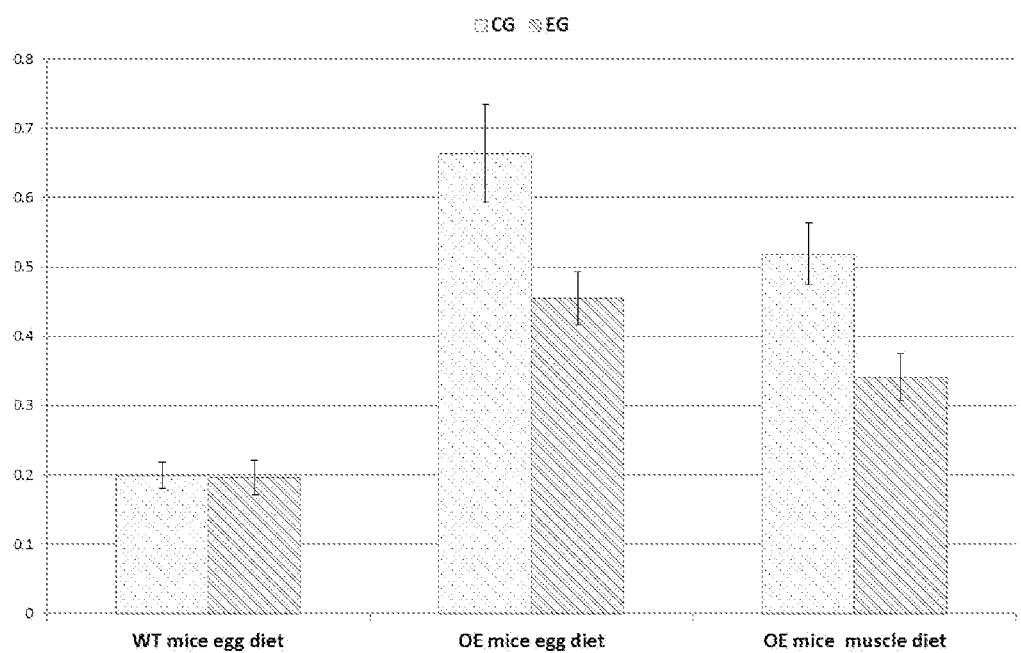
FIG. 22 is a graph showing NEFA from kidney of wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).

A diet of egg yolks of bio fortified eggs resulted in a significant decrease in plasma triglyceride levels (FIG. 7, p=0.001), plasma total cholesterol (FIG. 8, p=0.002), liver triglycerides (FIG. 11, p=0.0002), muscle triglycerides (FIG. 12, p=0.007), adipose tissue triglycerides (FIG. 14, p=0.03), adipose tissue total cholesterol (FIG. 18, p=0.03), liver NEFA (FIG. 19, p=0.01), adipose tissue NEFA (FIG. 20, p=0.003), and muscle NEFA (FIG. 21, p=0.003) in wildtype (WT) mice. Plasma NEFA (FIG. 9), blood glucose levels (FIG. 10), kidney triglycerides (FIG. 13), liver total cholesterol (FIG. 15), muscle total cholesterol (FIG. 16), kidney total cholesterol (FIG. 17), and kidney NEFA (FIG. 22) were not significantly affected.

Experiment 2

14 OE mice weighing 31-42 grams were procured and randomly divided into 2 groups. One group was "CG" (n=7) and the other group was "EG" (n=7). The EG group received egg yolks of bio fortified eggs, while the CG group received egg yolks of normal eggs in their diet.

The diet composition was the same as what was used in Experiment 1. The mice of the same weight were paired, one in CG and one in EG. The amount of omega-3 fatty acids in egg yolk given to each mouse was 0.378 mg/mice/day. Each mouse was given a 5 g diet daily. Body weight changes were measured after every week. Blood samples were taken at the beginning of the study and then after every week to analyze lipid profile from plasma. Glucose was measured from the blood in the tail after every week. Lipid profile was also analyzed from tissues (liver, kidney, muscles, and adipose tissue) at the end of the study. At the end of the experiment, mice were killed using $CO_2$ gas. The duration of the experiment was 4 weeks. Data was analyzed by applying paired T-test tail-1 type-1.

Figure 9:
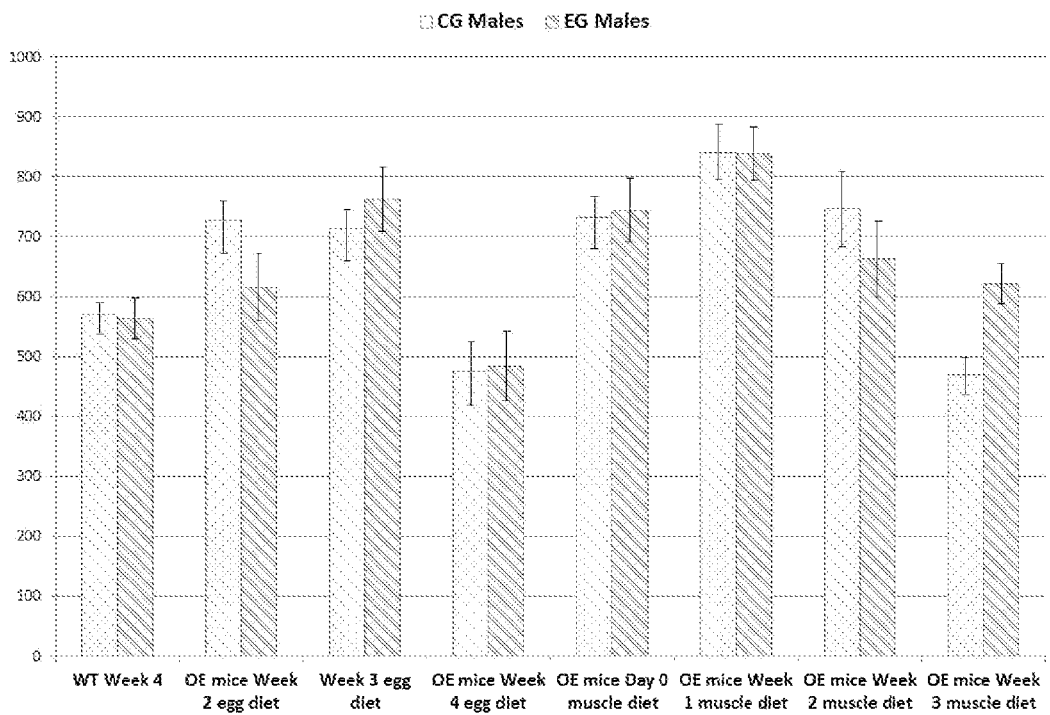
FIG. 9 is a graph showing NEFA in plasma from wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 10:
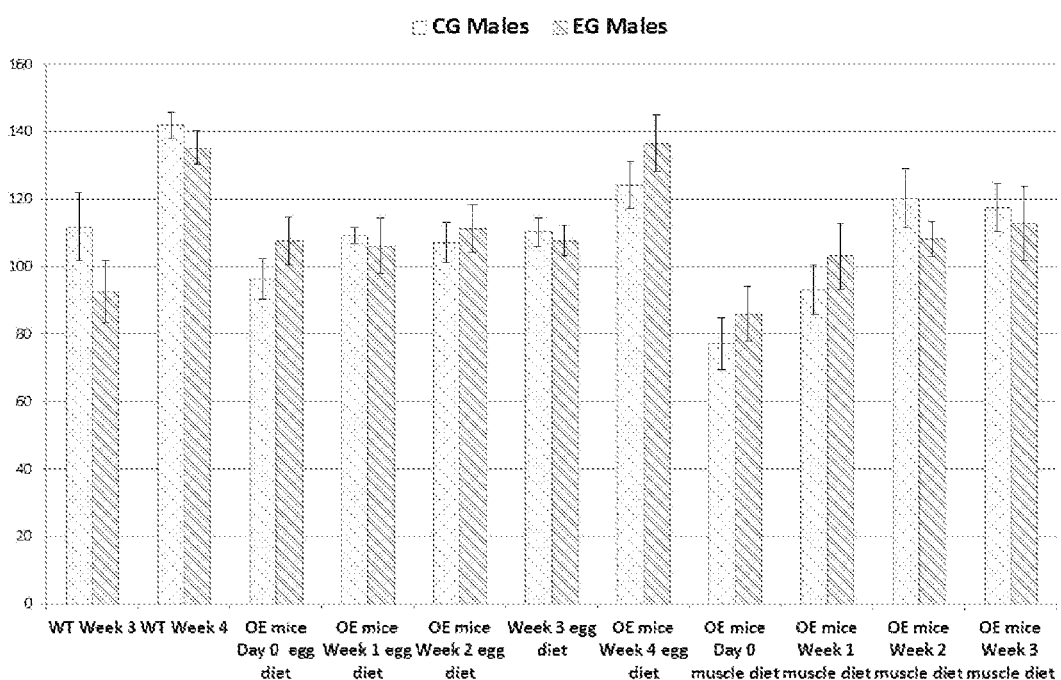
FIG. 10 is a graph showing glucose levels in blood from wildtype (WT) and obese (OE) mice receiving diets of either egg yolks of bio fortified eggs (EG), egg yolks of normal eggs (CG), chicken breast muscles enriched with omega-3 fatty acids (EG), or normal chicken breast muscles (CG).

A diet of egg yolks of bio fortified eggs resulted in a significant decrease in plasma triglyceride levels (FIG. 7, week 2, p=0.05), plasma total cholesterol (FIG. 8, week 4, p=0.012), liver triglycerides (FIG. 11, p=0.001), muscle triglycerides (FIG. 12, p=0.002), adipose tissue triglycerides (FIG. 14, p=0.007), liver NEFA (FIG. 19, p=0.04), and kidney NEFA (FIG. 22, p=0.02) in obese (OE) mice. Blood glucose levels were increased after 4 weeks (FIG. 10). Plasma NEFA (FIG. 9), kidney triglycerides (FIG. 13), liver total cholesterol (FIG. 15), muscle total cholesterol (FIG. 16), kidney total cholesterol (FIG. 17), adipose tissue NEFA (FIG. 20), and muscle NEFA (FIG. 21) were not significantly affected.

Figure 27:
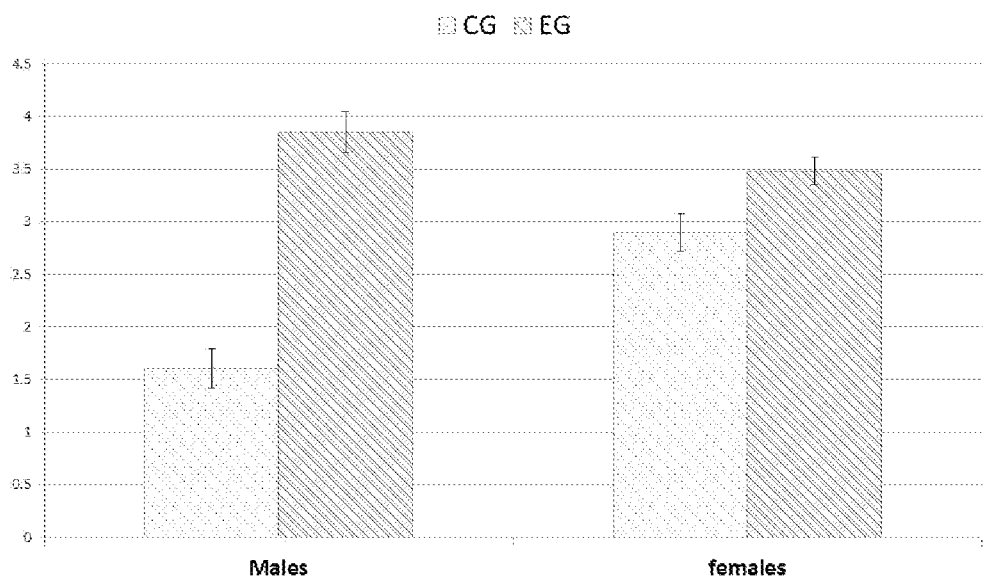
FIG. 27 is a graph showing the DHA retention in the liver of wildtype (WT) mice receiving diets of either egg yolks of bio fortified eggs (EG) or egg yolks of normal eggs (CG).
Figure 28:
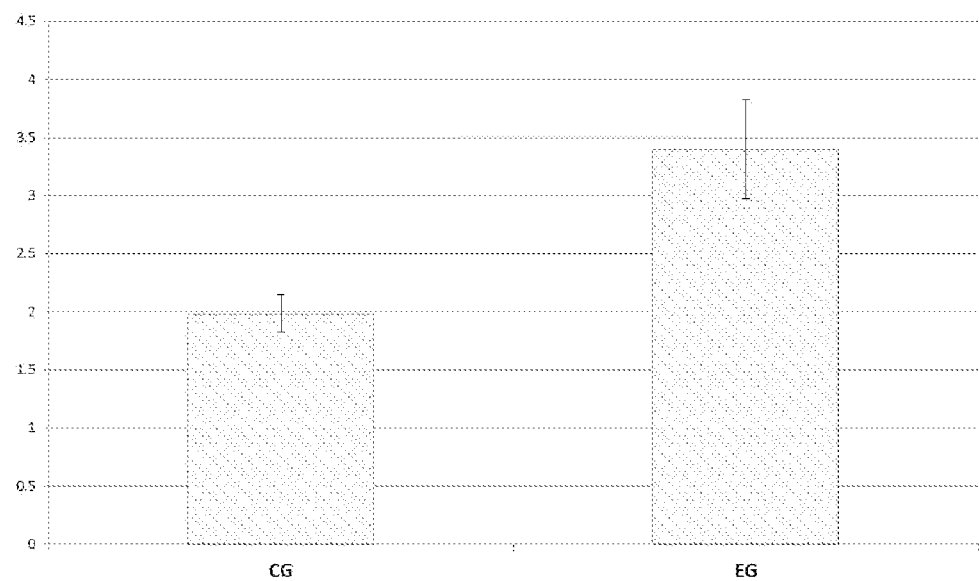
FIG. 28 is a graph showing the DHA retention in the liver of obese (OE) mice receiving diets of either egg yolks of bio fortified eggs (EG) or egg yolks of normal eggs (CG).

Further, a diet of egg yolks of bio fortified eggs resulted DHA retention in the liver of both WT and OE mice (FIGS. 27-28).

Experiment 3

12 OE mice were procured weighing 23-33 grams, and were randomly divided into 2 groups, including "CG" (n=6) and "EG" (n=6). Mice of the same weight were paired, one in CG and one in EG.

EG mice were fed with chicken breast muscles which were enriched with omega-3 fatty acids by feeding chicks *Nannochloropsis* algae, while CG mice received normal chicken breast muscles in diet. The amount of omega-3 fatty acids in chicken breast muscles given to each mouse was 0.126 mg/mice/day. Each mouse was given 5 g diet daily. Body weight changes were measured after every week. Blood samples were taken at the beginning of the study and then after every week to analyze lipid profile from plasma. Glucose was measured from the blood in the tail after every week. Lipid profile was also analyzed from tissues (liver, kidney, muscles, and adipose tissue) at the end of the study. At the end of the experiment, mice were killed using $CO_2$ gas. The duration of the experiment was 3 weeks. Data was analyzed by applying paired T-test tail-1 type-1.

A diet of chicken breast muscles which were enriched with omega-3 fatty acids resulted in a significant decrease in plasma triglyceride levels (FIG. 7, week 2, p=0.02), liver triglycerides (FIG. 11, p=0.0003), adipose tissue triglycerides (FIG. 14, p=0.037), kidney total cholesterol (FIG. 17, p=0.01), adipose tissue total cholesterol (FIG. 18, p=0.03), liver NEFA (FIG. 19, p=0.04), and kidney NEFA (FIG. 22, p=0.007) in obese (OE) mice. Blood glucose levels were not significant affected (FIG. 10). Plasma NEFA levels were significantly increased at week 3 (FIG. 9). Plasma NEFA (FIG. 9), plasma total cholesterol (FIG. 8), muscle triglycerides (FIG. 12), kidney triglycerides (FIG. 13), liver total cholesterol (FIG. 15), muscle total cholesterol (FIG. 16), adipose tissue NEFA (FIG. 20), and muscle NEFA (FIG. 21) were not significantly affected.

Figure 23:
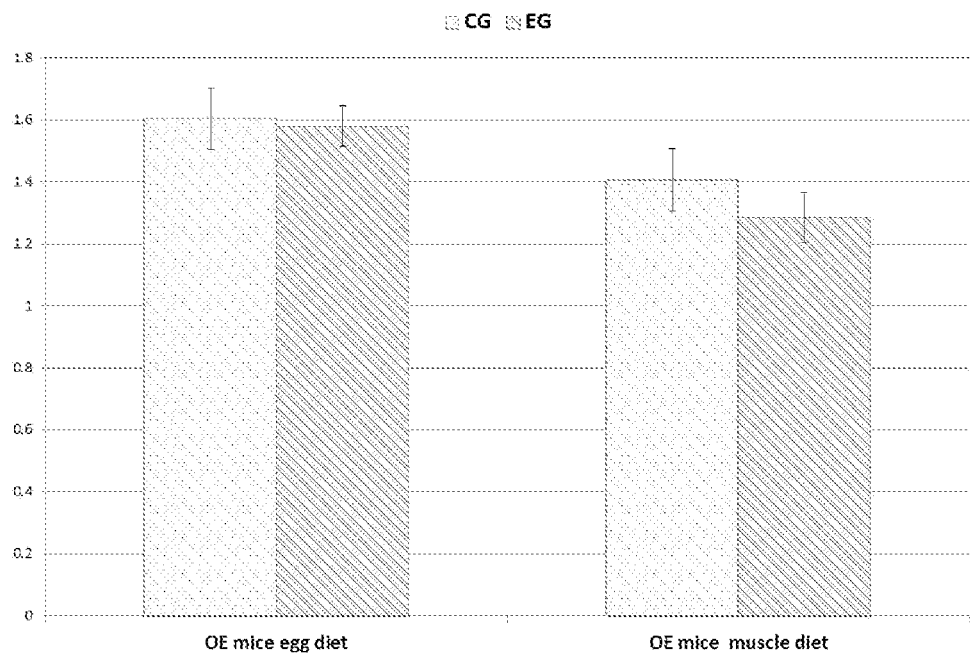
FIG. 23 is a graph showing the liver weight of obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 24:
FIG. 24 is a graph showing mesenteric fat weight of obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 25:
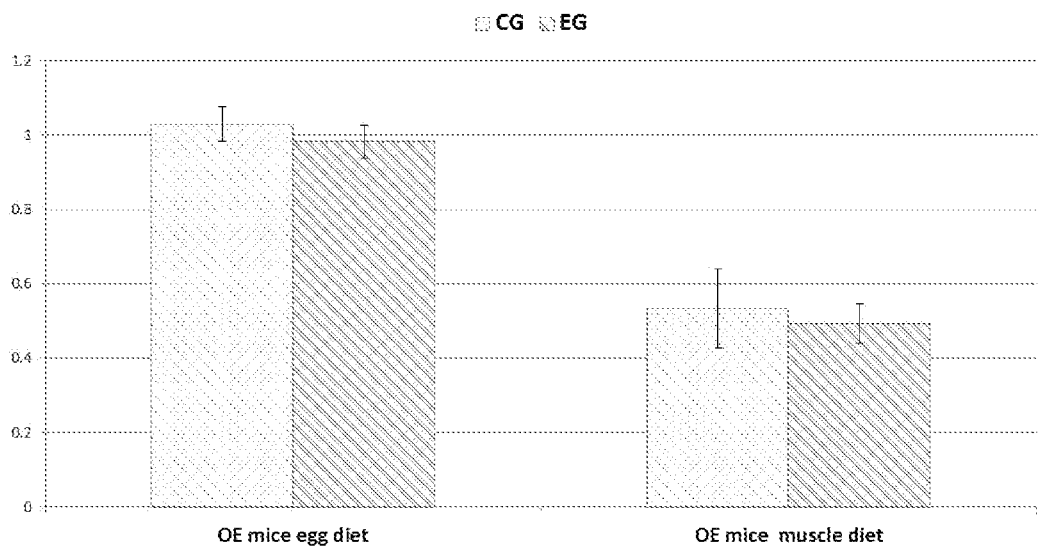
FIG. 25 is a graph showing is a graph showing s epididymal fat weight of obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 26:
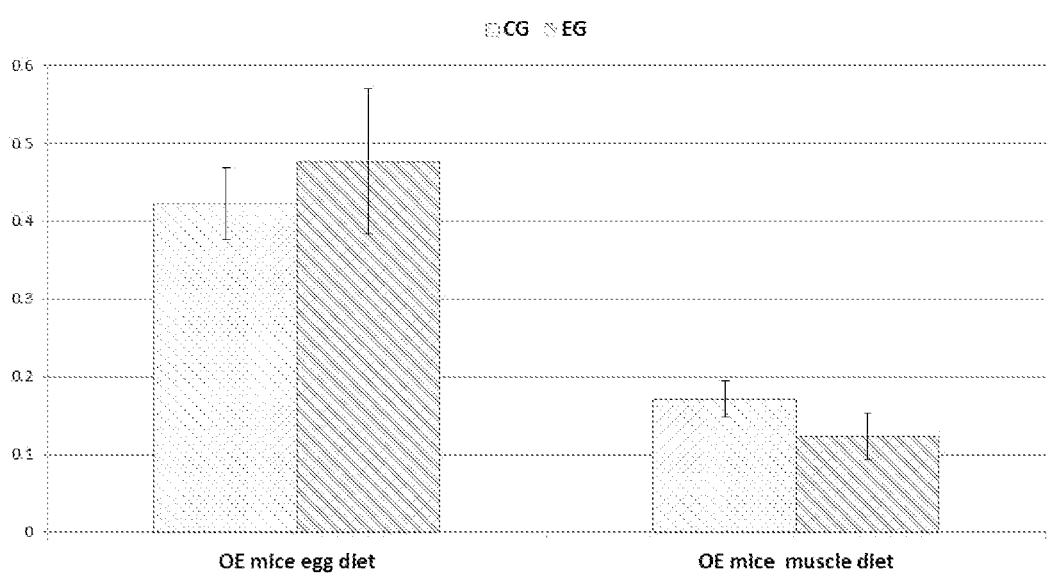
FIG. 26 is a graph showing retroperitoneal fat weight of obese (OE) mice receiving diets of either egg yolks of bio fortified eggs (EG), egg yolks of normal eggs (CG), chicken breast muscles enriched with omega-3 fatty acids (EG), or normal chicken breast muscles (CG).
Figure 29:
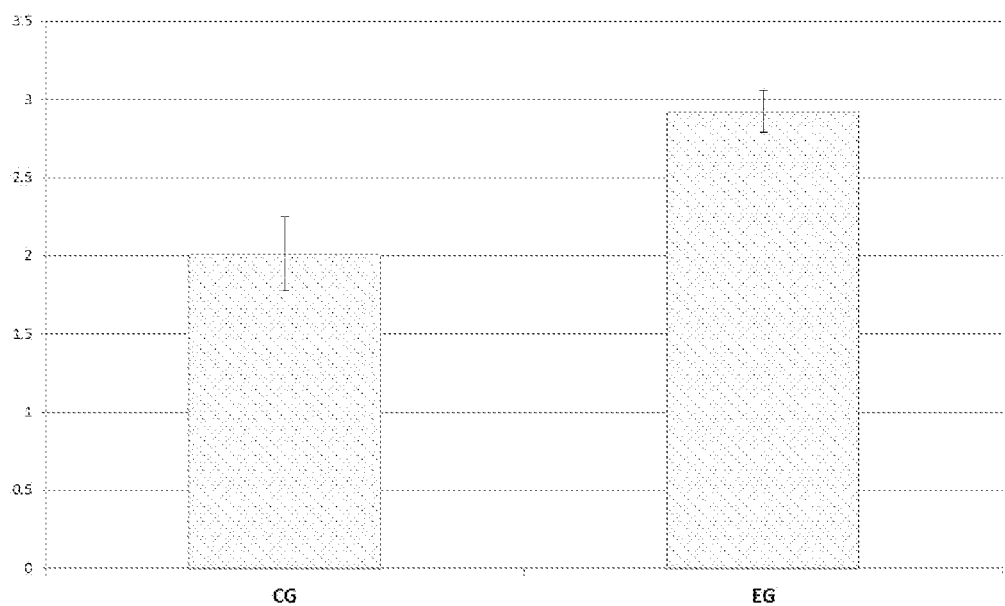
FIG. 29 is a graph showing the DHA retention in the liver of obese (OE) mice receiving diets of either chicken breast muscles enriched with omega-3 fatty acids (EG) or normal chicken breast muscles (CG).

This diet also resulted in a decreased liver weight (FIG. 23), mesenteric fat weight (FIG. 24), and no change in either epididymal fat weight (FIG. 25) or retroperitoneal fat weight (FIG. 26). Further, DHA was also retained in the liver (FIG. 29).

Discussion

The results of these experiments show that microalgae feeding-produced eggs/muscle/tissue enriched with EPA/DHA can be digested, utilized, and retained in the body with a high efficiency. Further, these products can significantly decrease blood and tissue triglycerides consistently in normal wild type or obese mice, which can be used to prevent and treat fatty liver, obesity, and other triglyceride-related disorders.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of producing a poultry egg with elevated amounts of n-3 fatty acids, said method comprising:
feeding poultry an effective amount of defatted microalgae under conditions effective for the poultry to produce an egg comprising about 300 to about 550 mg of n-3 fatty acids.

2. The method of claim 1, wherein the defatted microalgae is selected from species of microalgae selected from *Nannochloropsis* or *Desmodesmus*.

3. The method of claim 1, wherein the defatted microalgae comprises about 0.1% to about 50% of oil content compared to non-defatted microalgae.

4. The method of claim 1, wherein the egg contains at least about 80 mg or more of a combination of docosahexanoic acid (DHA) and eicosapentaenoic acid (EPA).

5. The method of claim 1, wherein the egg has a ratio of n-3:n-6 fatty acids greater than that of eggs produced by poultry not fed defatted microalgae under the conditions and decreased n-9 fatty acids compared to that of eggs produced by poultry not fed defatted microalgae under the conditions.

6. The method of claim 1, wherein the poultry is fed defatted microalgae at the amount of about 1% to about 23% on a weight/weight basis of the poultry's total diet.

7. The method of claim 1, further comprising feeding the poultry a non-microalgae source of n-3 fatty acids.

8. The method of claim 7, wherein the non-microalgae source of n-3 fatty acids is flaxseed or flaxseed oil.

9. The method of claim 8, wherein the flaxseed or flaxseed oil is fed to the poultry at an amount of about 0.5% to about 5% on a weight/weight basis of the poultry's total diet.

10. The method of claim 1, wherein the poultry is a chicken.

* * * * *